United States Patent
Curtin et al.

(10) Patent No.: US 6,294,573 B1
(45) Date of Patent: *Sep. 25, 2001

(54) REVERSE HYDROXAMATE INHIBITORS OF MATRIX METALLOPROTEINASES

(75) Inventors: Michael L. Curtin, Pleasant Prairie, WI (US); Yujia Dai, Gurnee, IL (US); Steven K. Davidsen, Libertyville, IL (US); Joseph F. Dellaria, Jr., Lindenhurst, IL (US); Alan S. Florjancic, Lafayette, CO (US); Jianchun Gong; Yan Guo, both of Gurnee, IL (US); Howard R. Heyman, Chicago, IL (US); James H. Holms, Gurnee, IL (US); Michael R. Michaelides, Libertyville, IL (US); Jamie R. Stacey, Racine, WI (US); Douglas H. Steinman, Morton Grove, IL (US); Carol K. Wada, Gurnee, IL (US); Lianhong Xu, San Mateo, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/492,567

(22) Filed: Jan. 27, 2000

Related U.S. Application Data

(63) Continuation-in-part of application No. 09/239,087, filed on Jan. 27, 1999, which is a continuation-in-part of application No. 09/129,360, filed on Aug. 5, 1998, now abandoned.
(60) Provisional application No. 60/055,103, filed on Aug. 6, 1997.

(51) Int. Cl.[7] .......................... C07C 255/37; A61K 31/16

(52) U.S. Cl. .......................... 514/471; 514/389; 514/425; 514/521; 514/522; 514/630; 548/319.5; 548/477; 549/321; 558/404; 558/417; 564/219

(58) Field of Search ............................. 564/219; 558/404, 558/417; 549/321; 548/319.5, 477; 544/389, 425, 471, 521, 522, 630

(56) References Cited

U.S. PATENT DOCUMENTS

| | | | |
|---|---|---|---|
| 4,859,706 | 8/1989 | Buersinghaus et al. | 514/624 |
| 4,981,865 | 1/1991 | Belliotti et al. | 514/480 |
| 5,605,923 | 2/1997 | Christensen, IV et al. | 514/417 |

FOREIGN PATENT DOCUMENTS

| | | |
|---|---|---|
| 0196184 | 3/1986 | (EP) . |
| 0780386 | 6/1997 | (EP) . |
| 9402448 | 2/1994 | (WO) . |
| 9533731 | 12/1995 | (WO) . |
| 9718188 | 5/1997 | (WO) . |
| 9838179 | 9/1998 | (WO) . |
| 9906361 | 2/1999 | (WO) . |

OTHER PUBLICATIONS

Biochemistry, vol. 31 (1992), pp. 11231–11235, Ye et al., "Purification and Characterization of the Human Stromelysin Catalytic Domain Expressed in *Escherichia coli*".

Analytical Biochemistry, vol. 147 (1985), pp. 437–440, Weingarten et al., "Spectrophotometric Assay for Vertebrate Collagenase".

K. M. Mohler et al., "Protection against a lethal dose of endotoxin by an inhibitor of tumor necrosis factor processing", Letters to Nature, vol. 370, Jul. 21, 1994, pp. 218–220.

A.J. H. Gearing et al., Processing of tumor necrosis factor–α by metalloproteinases, Letters to Nature, vol. 370, Aug. 18, 1994, pp. 555–557.

G. M. McGeehan et al., "Regulation of tumor necrosis factor–α processing by a metalloproteinase inhibitor", Letters to Nature vol. 370, Aug. 18, 1994, pp. 558–560.

S. M. Berge et al., "Pharmaceutical Salts", Journal of Pharmaceutical Sciences, vol. 66, No. 1, Jan. 1997, pp. 1–19.

T. Higuchi & V. Stella, "Pro–drugs as Novel Drug Delivery Systems", vol. 14 of the A.C.S. Symposium Series.

Edward B. Roche, ed., "Bioreversible Carriers in Drug Design—Theory and Application", American Pharmaceutical Association and Pergamon Press, 1987.

D. B. Dess et al., "A Useful 12–1–15 Triacetoxyperiodinane (the Dess–Martin Periodinane) for the Selective Oxidation of Primary or Secondary Alcohols and a Variety of Realted 12–1–5 Species", J. Am. Chem. Soc., 1991, 113, 7277–7287.

Green, "Protective Groups min Organic Synthesis", John Wiley & Sons, New York (1981).

S.F. Wnuk, et al., "Nucleic Acid Related Compounds. 67.", Canadian Journal of Chemistry, vol. 69, No. 12, pp. 2104–2111.

*Primary Examiner*—Robert Gerstl
(74) *Attorney, Agent, or Firm*—B. Gregory Donner; Gregory W. Steele

(57) ABSTRACT

Compounds having the formula

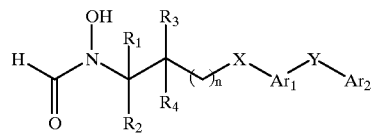

are matrix metalloproteinase inhibitors. Also disclosed are matrix metalloproteinase-inhibiting compositions and methods of inhibiting matrix metalloproteinase in a mammal.

17 Claims, No Drawings

REVERSE HYDROXAMATE INHIBITORS OF MATRIX METALLOPROTEINASES

CROSS REFERENCE TO RELATED APPLICATIONS

This application is a continuation-in-part of pending U.S. patent application Ser. No. 09/239,087, filed Jan. 27, 1999, which is a continuation-in-part of of U.S. patent application Ser. No. 09/129,360, filed Aug. 5, 1998, now abandoned, which is a continuation-in-part of Provisional U.S. patent application Ser. No. 60/055,103 filed Aug. 6, 1997, now abandoned.

TECHNICAL FIELD

This invention relates to compounds having activity to inhibit matrix metalloproteinases, to pharmaceutical compositions comprising these compounds and to a medical method of treatment. More particularly, this invention concerns reverse hydroxamate-containing compounds which inhibit matrix metalloproteinases, pharmaceutical compositions comprising these compounds and a method of inhibiting matrix metalloproteinases.

BACKGROUND OF THE INVENTION

The matrix metalloproteinases (MMP's) are a class of extracellular enzymes including collagenase, stromelysin and gelatinase which are believed to be involved in the tissue destruction which accompanies a large number of disease states varying from arthritis to cancer.

Typical connective tissue cells are embedded within an extracellular matrix of high molecular weight proteins and glycoproteins. In healthy tissue, there is a continual and delicately-balanced series of processes which include cell division, matrix synthesis and matrix degradation. In certain pathological conditions, an imbalance of these three processes can lead to improper tissue restructuring. In arthritis, for example, joint mobility can be lost when there is improper remodeling of load-bearing joint cartilage. With cancer, lack of coordination of cell division and the two processes of matrix synthesis and degradation may lead to conversion of transformed cells to invasive phenotypes in which increased matrix turnover permits tumor cells to penetrate basement membranes surrounding capillaries which, in turn, may lead to subsequent metastasis.

There has been heightened interest in discovering therapeutic agents which bind to and inhibit MMP's. The discovery of new therapeutic agents possessing this activity will lead to new drugs having a novel mechanism of action for combating disease states involving tissue degenerative processes including, for example, rheumatoid arthritis, osteoarthritis, osteopenias such as osteoporosis, periodontitis, gingivitis, corneal, epidermal or gastric ulceration, and tumor growth and metastasis or invasion.

SUMMARY OF THE INVENTION

In its principle embodiment, the present invention provides a matrix metalloproteinase inhibitory compound of formula (I),

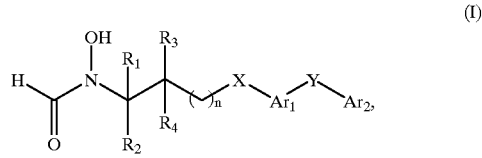

or a pharmaceutically acceptable salt or prodrug thereof, wherein n is zero;

$R_1$ and $R_3$ are independently selected from the group consisting of
(1) hydrogen, and
(2) alkyl of one to six carbon atoms;

$R_2$ and $R_4$ are independently selected from the group consisting of
(1) hydrogen,
(2) alkyl of one to six carbon atoms,
(3) alkenyl of one to six carbon atoms,
(4) alkynyl of one to six carbon atoms,
(5) alkoxyalkyl, wherein the alkoxyalkyl can be optionally substituted with hydroxy or silyloxy,
(6) alkoxycarbonylalkyl, wherein the alkylene and alkyl groups are independently of one to six carbon atoms,
(7) haloalkyl of one to six carbon atoms,
(8) hydroxyalkyl, wherein the alkylene group is of one to six carbon atoms,
(9) -(alkylene)-$S(O)_p$-alkyl, wherein the alkylene is of one to six carbon atoms, p is zero to two, and the alkyl is of one to six carbon atoms,
(10) phenyl,
(11) phenylalkoxyalkyl, wherein the alkylene and alkyl groups are independently of one to six carbon atoms,
(12) phenylalkyl, wherein the alkylene group is of one to six carbon atoms,
(13) phenoxyalkyl, wherein the alkylene group is of one to six carbon atoms,
(14) -(alkylene)-$N(R_5)SO_2$-phenyl, wherein the alkylene is of one to six carbon atoms, and wherein $R_5$ is selected from the group consisting of
(a) hydrogen, and
(b) alkyl of one to six carbon atoms;
(15) (heterocycle)oxyalkyl, wherein the alkylene group is of one to six carbon atoms,
(16) -(alkylene)-$S(O)_p$-heterocycle, wherein the alkylene group is of one to six carbon atoms,
(17) -(alkylene)-heterocycle, wherein the alkylene group is of one to six carbon atoms,
(18) -(alkylene)-$NR_6R_7$, wherein the alkylene group is of one to six carbon atoms,
(19) -heterocycle,
(20) -(alkylene)-$S(O)_p$-$NR_6R_7$,
(21) -cycloalkyl, wherein the cycloalkyl can be optionally substituted with dioxolanyl,
(22) (cycloalkyl)alkyl, wherein the cycloalkyl can be optionally substituted with dioxolanyl,
(23) -carbonyl-$NR_6R_7$,
(24) -(alkylene)-$S(O)_p$-phenyl,
(25) -(alkylene)-$N(R_5)SO_2$-alkyl, wherein the alkylene is of one to six carbon atoms, and
(26) -(alkylene)-carbonyl-$NR_6R_7$;

wherein for (15)–(17) and (19), the heterocycle is selected from the group consisting of (a) pyridyl,
(b) pyrazinyl,
(c) pyridazinyl,
(d) furyl,
(e) thienyl,
(f) isoxazolyl,
(g) oxazolyl,
(h) thiazolyl,
(i) isothiazolyl, (j) 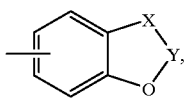

(k) 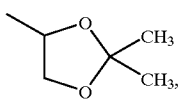

(l) 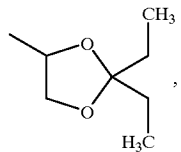

(m) 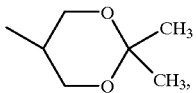

(n) 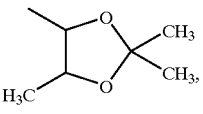

(o) 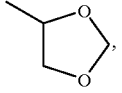

(p) 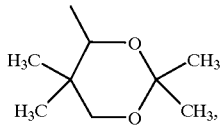

(q) tetrahydropyranyl,
(r) pyrrolidinyl,
(s) tetrahydrothiopyranyl, wherein the sulfur atom can be optionally oxidized,
(t) oxazolidinonyl,
(u) tetrahydrofuranyl,
(v) dihydrofuranonyl,
(w) piperidinyl,
(x) morpholinyl, and
(y) thiazolidinonyl;

wherein for (10)–(17), (19), and (24), the phenyl, the phenyl parts of phenylalkoxyalkyl, phenylalkyl, -(alkylene)-N($R_5$)$SO_2$-phenyl, phenoxyalkyl, and -(alkylene)-S(O)$_p$-phenyl, and the heterocycle, the heterocycle parts of (heterocycle)oxyalkyl, -(alkylene)-heterocycle and -(alkylene)-S(O)$_p$-heterocycle are optionally substituted with one, two, or three substituents independently selected from the group consisting of (a) alkyl of one to six carbon atoms,
(b) alkoxy of one to six carbon atoms,
(c) alkoxyalkyl, wherein the alkyl group and the alkylene group are independently of one to six carbon atoms,
(d) halo,
(e) haloalkyl of one to six carbon atoms,
(f) hydroxy,
(g) hydroxyalkyl of one to six carbon atoms,
(h) -(alkylene)-heterocycle, wherein the alkylene group is of one to six carbon atoms,
(i) -(alkylene)-phenyl, wherein the alkylene group is of one to six carbon atoms,
(j) -N($R_5$)$SO_2$-alkyl, wherein the alkyl group is of one to six carbon atoms,
(k) phenyl, wherein the phenyl is optionally substituted with 1, 2, 3, 4, or 5 substituents independently selected from the group consisting of
  (i) cyano,
  (ii) nitro, and
  (iii) halo;
(l) —C(O)O$R_5$,
(m) —C(O)N$R_x R_y$, wherein $R_x$ and $R_y$ are independently selected from the group consisting of
  (i) alkyl of one to six carbon atoms,
  (ii) phenyl, and
  (iii) phenylalkyl, wherein the alkyl group is of one to six carbon atoms;
  wherein for (ii) and (iii), the phenyl and the phenyl part of phenylalkyl are optionally substituted with substituents independently selected from the group consisting of halo and alkoxy of one to six carbon atoms, and
(n) —$SO_2$-alkyl,
(o) alkanoyl of one to ten carbons,
(p) dioxolanyl; and
(q) -(alkylene)-C(O)O$R_5$; and wherein for (18), (20), (23), and (26), $R_6$ and $R_7$ are independently selected from the group consisting of
(a) hydrogen,
(b) alkyl of one to six carbon atoms,
(c) cycloalkyl of three to eight carbon atoms,
(d) cycloalkylalkyl, wherein the cycloalkyl group is of three to eight carbon atoms, and the alkylene group is of one to ten carbon atoms,
(e) alkanoyl of one to ten carbon atoms, wherein the alkanoyl group can be optionally substituted with alkoxycarbonyl,
(f) phenyl, and
(g) phenylalkyl, wherein the alkylene group is of three to ten carbon atoms;

wherein for (f) and (g), the phenyl and the phenyl part of phenylalkyl are optionally substituted with one or two substituents independently selected from the group consisting of
(i) alkyl of one to six carbon atoms,
(ii) alkoxy of one to six carbon atoms,
(iii) perfluoroalkyl of one to six carbon atoms,
(iv) halo,
(v) haloalkyl of one to six carbon atoms,
(vi) hydroxyalkyl, and
(vii) alkanoyl of one to six carbon atoms; or $R_6$ and $R_7$, taken together with the nitrogen atom to which they are attached, define a group selected from the group consisting of
(1) morpholinyl,
(2) thiomorpholinyl, (3) thiomorpholinyl sulfone,
(4) pyrrolidinyl,
(5) piperazinyl,
(6) piperidinyl,
(7) succinimidyl,
(8) maleimidyl,
(9) glutarimidyl,
(10) phthalimidyl,
(11) naphthalimidyl,

(12) 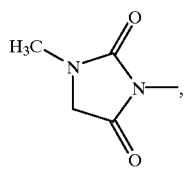

(13) 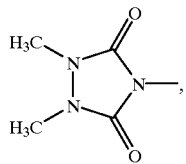

(14) 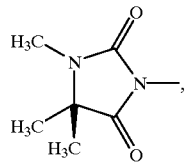

(15) 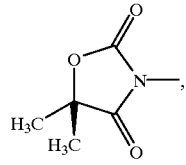

(16) 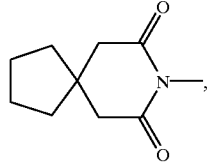

(17) 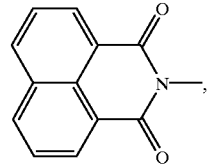

(18) 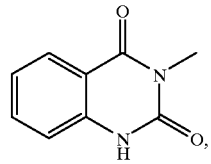

(19) 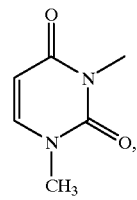

(20) 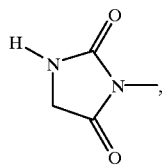

(21) 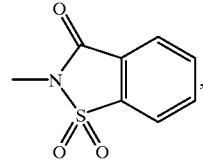

(22) 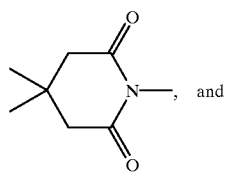, and

(23) 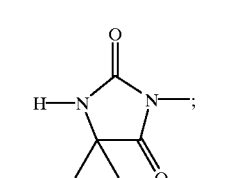;

wherein for (1)–(23), the groups defined by $R_6$ and $R_7$, together with the nitrogen atom to which they are attached, are optionally substituted with one or two substituents independently selected from the group consisting of
(a) halo,
(b) alkyl of one to six carbon atoms,
(c) alkoxy, wherein the alkyl part of the alkoxy is of one to six carbon atoms,
(d) phenoxy,
(e) phenylalkyl, wherein the alkyl group is of one to six carbon atoms,
(f) benzyloxy,
(g) alkanoyl of one to ten carbons, and
(h) —$SO_2$-alkyl; or
$R_1$ and $R_2$, taken together with the carbon atom to which they are attached form a ring selected from the group consisting of
(1) spiroalkyl of three to eight carbon atoms, wherein the spiroalkyl can be optionally substituted with dioxolanyl or —$CO_2R_5$,
(2) tetrahydropyranyl,
(3) tetrahydrothiopyranyl, wherein the sulfur group can be optionally oxidized,
(4) piperidinyl, wherein the nitrogen group can be optionally substituted with alkanoyl or —$SO_p$-alkyl, (5) dioxanyl, wherein the dioxanyl can be optionally substituted with alkyl, and dihydrobenzodioxepinyl; or $R_3$ and $R_4$, taken together with the carbon atom to which they are attached, form a spiroalkyl group of three to eight carbon atoms; or $R_1$ and $R_3$ taken together with the carbon atoms to which they are attached are a 5, 6, or 7-membered carbocyclic ring;

X is selected from the group consisting of
(1) —O—,
(2) —$NR_5SO_2$—,
(3) —$S(O)_p$—; and
(4) —C(O)—;

wherein each group is drawn with its left-hand end being the end which attaches to the alkylene group and its right-hand end being the end which attaches to $Ar_1$;

$Ar_1$ is phenyl which is optionally substituted with one or two substituents independently selected from the group consisting of
(a) alkyl of one to six carbon atoms,
(b) perfluoroalkyl of one to six carbon atoms,
(c) halo,
(d) haloalkyl of one to six carbon atoms,
(e) alkoxy of one to six carbon atoms,
(f) hydroxy,
(g) hydroxyalkyl of one to six carbon atoms,
(h) alkoxyalkyl, wherein the alkyl and alkylene groups are independently of one to six carbon atoms, and
(i) nitro;

Y is selected from the group consisting of
(1) a covalent bond,
(2) —O—,
(3) alkylene of two to four carbon atoms,
(4) piperidineneyl,
(5) alkenylene of two carbon atoms,
(6) alkynylene of two carbon atoms,
(7) —$S(O)_p$—, and
(8) —C(O)—; and $Ar_2$ is an aryl group selected from the group consisting of
(1) phenyl,
(2) pyridyl,
(3) pyrazinyl,
(4) pyridazinyl,
(5) furyl,
(6) thienyl,
(7) isoxazolyl,
(8) oxazolyl,
(9) thiazolyl, and
(10) isothiazolyl;

wherein the aryl group is optionally substituted with one, two, or three substituents independently selected from the group consisting of
(a) alkyl of one to six carbon atoms,
(b) alkoxy of one to six carbon atoms,
(c) alkoxy of one to six carbon atoms substituted with alkoxy of one to six carbon atoms,
(d) -alkyl-$CO_2R_5$,
(e) -alkyl-$NR_xR_y$,
(f) alkoxyalkyl, wherein the alkyl group is of one to six carbon atoms, and the alkylene group is of one to six carbon atoms,
(g) cyano,
(h) cyanoalkyl of one to six carbon atoms,
(i) halo,
(j) haloalkyl of one to six carbon atoms,
(k) hydroxy,
(l) hydroxyalkyl of one to six carbon atoms,
(m) hydroxyalkyl, wherein the alkyl group is of one to six carbon atoms,
(n) thioalkoxy of one to six carbon atoms,
(o) thioalkoxyalkyl, wherein the alkyl group is of one to six carbon atoms, and the alkylene group is of one to six carbon atoms,
(p) phenylalkoxy, wherein the alkylene group is of one to six carbon atoms,
(q) phenoxy,
(r) phenoxyalkyl, wherein the alkylene group is of one to six carbon atoms,
(s) (heterocycle)oxy,
(t) (heterocycle)oxyalkyl, wherein the alkylene group is of one to six carbon atoms,
(u) perfluoroalkyl of one to six carbon atoms,
(v) perfluoroalkoxy, wherein the perfluoroalkyl part is of one to six carbon atoms,
(w) sulfinylalkyl, wherein the alkyl part is of one to six carbon atoms,
(x) sulfonylalkyl, wherein the alkyl part is of one to six carbon atoms,
(y)

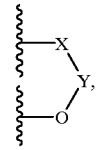

wherein X is selected from the group consisting of —$CH_2$—, —$CH_2O$— and —O—, and Y is selected from the group consisting of —C(O)— and —$(C(R")_2)_v$—, where R" is hydrogen or alkyl of one to four carbon atoms, and v is 1–3, and (z) —$N(R_5)SO_2R_{5'}$, wherein $R_5$ is defined previously and $R_{5'}$ is selected from the group consisting of
(i) hydrogen and
(ii) alkyl of one to six carbon atoms, and
(iii) —$SO_2N(R_5)(R_{5'})$;

wherein for (s) and (t), the heterocycle part of (heterocycle)oxy, and (heterocycle)oxyalkyl are selected from the group consisting of
(i) pyridyl,
(ii) pyrazinyl,
(iii) pyridazinyl,
(iv) furyl,
(v) thienyl,
(vi) isoxazolyl,
(vii) oxazolyl,
(viii) thiazoloyl,
(ix) isothiazolyl;

wherein for (s) and (t), the heterocycle part of (heterocycle)oxy and (heterocycle)oxyalkyl are optionally substituted with one or two substituents independently selected from the group consisting of
(i) alkyl of one to six carbon atoms,
(ii) alkoxy of one to six carbon atoms,
(iii) perfluoroalkyl of one to six carbon atoms,
(iv) halo,
(v) cyano,
(vi) cyanoalkyl, wherein the alkyl is of one to six carbon atoms,
(vii) haloalkyl of one to six carbon atoms, and
(viii) alkanoyl of one to six carbon atoms;

wherein for (q) and (r), the phenyl part of phenoxy and phenoxyalkyl are optionally substituted with one or two substituents independently selected from the group consisting of
(i) alkyl of one to six carbon atoms,
(ii) alkoxy of one to six carbon atoms,
(iii) perfluoroalkyl of one to six carbon atoms,
(iv) halo,
(v) cyano,
(vi) cyanoalkyl, wherein the alkyl is of one to six carbon atoms,
(vii) haloalkyl of one to six carbon atoms, and
(viii) alkanoyl of one to six carbon atoms.

In another embodiment, the present invention provides pharmaceutical compositions which comprise a therapeutically effective amount of compound of formula I in combination with a pharmaceutically acceptable carrier.

In yet another embodiment, the present invention provides a method of inhibiting matrix metalloproteinases in a host mammal in need of such treatment comprising administering to a mammal in need of such treatment a therapeutically effective amount of a compound of formula I.

DETAILED DESCRIPTION OF THE INVENTION DEFINITION OF TERMS

As used throughout this specification and the appended claims, the following terms have the meanings specified:

The term "alkyl," as used herein, represents a monovalent group derived from a straight or branched chain saturated hydrocarbon by the removal of a single hydrogen atom and is exemplified by methyl, ethyl, n- and iso-propyl, n-, sec-, iso- and tert-butyl, neopentyl, and the like. The alkyl groups of this invention can be optionally substituted.

The term "alkanoyl," as used herein, represents an alkyl group, as defined above, attached to the parent molecular group through a carbonyl group and is exemplified by formyl, acetyl, propionyl, butanoyl, and the like. The alkanoyl groups of this invention can be optionally substituted.

The term "alkenyl," as used herein, represents monovalent straight or branched chain groups containing a carbon-carbon double bond derived from an alkene by the removal of one hydrogen atom and is exemplified by ethenyl, 1-propenyl, 2-propenyl, 2-methyl-1-propenyl, 1-butenyl, 2-butenyl, and the like. The alkenyl groups of this invention can be optionally substituted.

The term "alkoxy," as used herein, represents an alkyl group attached to the parent molecular group through an oxygen atom. The alkyl part of the alkoxy group can be substituted with additional alkoxy groups. Alkoxy groups are exemplified by methoxy, isopropoxy, tert-butoxy, 2-methoxyethoxy, and the like. The alkoxy groups of this invention can be optionally substituted.

The term "alkoxyalkyl" as used herein, represents an alkyl group to which is attached an alkoxy group. The alkoxyalkyl groups of this invention can be optionally substituted.

The term "alkoxycarbonyl," as used herein, represents an ester group, i.e. an alkoxy group attached to the parent molecular group through a carbonyl group, and is exemplified by methoxycarbonyl, ethoxycarbonyl, and the like. The alkoxycarbonyl groups of this invention can be optionally substituted.

The term "alkoxycarbonylalkyl," as used herein, represents an alkyl group, as defined above, substituted by a alkoxycarbonyl group. The alkoxycarbonylalkyl groups of this invention can be optionally substituted.

The term "alkylene," as used herein, represents a saturated divalent hydrocarbon group derived from a straight or branched chain saturated hydrocarbon by the removal of two hydrogen atoms and is exemplified by methyene, ethylene, isopropylene, and the like. The alkylene groups of this invention can be optionally substituted.

The term "alkynyl," as used herein, represents monovalent straight or branched chain groups of two to six carbon atoms containing a carbon-carbon triple bond derived from an alkyne by the removal of one hydrogen atom and is exemplified by ethynyl, 1-propynyl, and the like. The alkynyl groups of this invention can be optionally substituted.

The term "benzyloxy," as used herein, represents phenyl-($CH_2$)—O—. The benzyloxy groups of this invention can be optionally substituted.

The term "cyano," as used herein, represents a —CN group.

The term "cyanoalkyl," as used herein, represents a cyano group attached to the parent molecular moiety through an alkyl group. The cyanoalkyl groups of this invention can be optionally substituted.

The term "cycloalkyl," as used herein represents a monovalent saturated cyclic hydrocarbon group and is exemplified by cyclopropyl, cyclobutyl, cyclopentyl, cyclohexyl, cycloheptyl, bicyclo[2.2.1]heptyl, and the like. The cycloalkyl groups of this invention can be optionally substituted.

The term "cycloalkylalkyl," as used herein, represents a cycloalkyl group attached to the parent molecular group through an alkylene group. The cycloalkylalkyl groups of this invention can be optionally substituted.

The term "dioxolanyl," as used herein, represents {—O—($CH_2$)$_2$—O—}, both oxygens of which are attached to the same carbon atom of the parent group to form a spirocyclic moiety.

The term "halo," as used herein, represents F, Cl, Br, and I.

The term "haloalkyl," as used herein, represents an alkyl group substituted by one, two, three or four halogen atoms and is exemplified by chloromethyl, bromoethyl, chlorodifluoromethyl, and the like. The haloalkyl groups of this invention can be optionally substituted.

The term "heterocycle," as used herein, represents a five-, six- or seven-membered ring containing one, two or three heteroatoms independently selected from the group consisting of nitrogen, oxygen and sulfur. The five-membered ring has zero to two double bonds and the six- and seven-membered rings have zero to three double bonds. Hererocycles include indolyl, quinolyl, isoquinolyl, tetrahydroquinolyl, benzofuryl, benzothienyl, pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiomorpholino sulfone, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, triazolyl, tetrazolyl, oxadiazolyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl, succinimidyl, maleimidyl, glutarimidyl, phthalimidyl, naphthalimidyl, and the like.

The heterocycle groups of this invention can be optionally substituted.

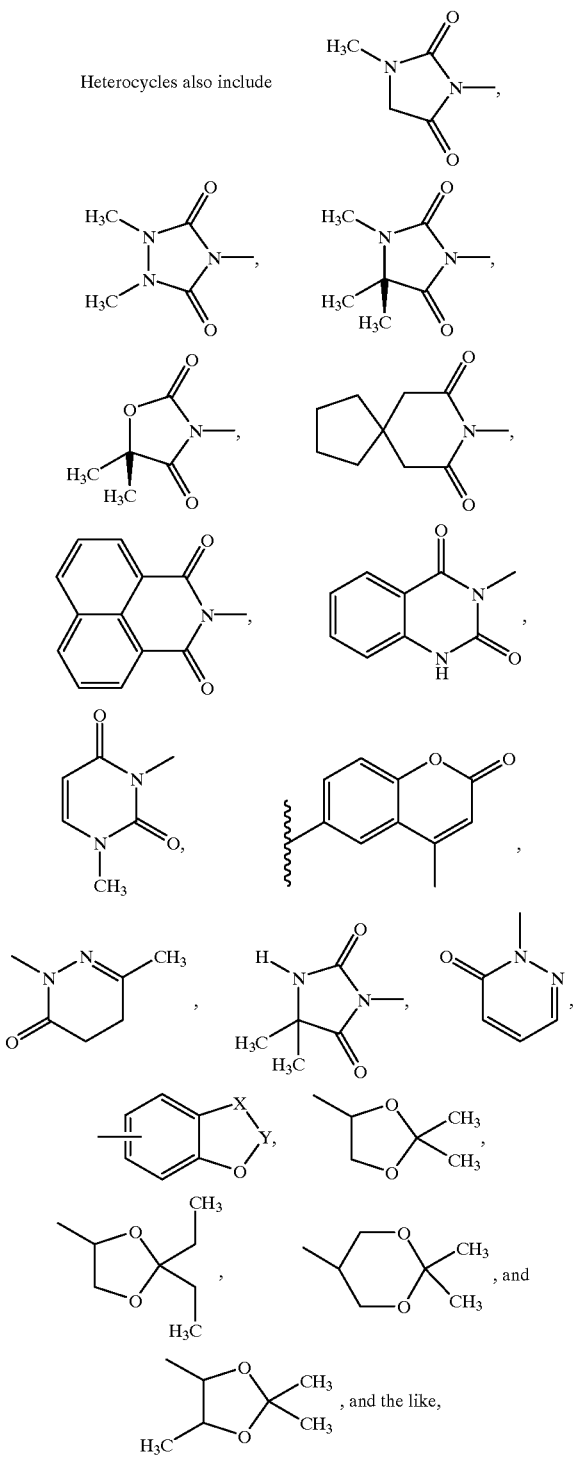

wherein X is selected from —CH$_2$—, —CH$_2$O— and —O—, and Y is selected from —C(O)— and —(C(R")$_2$)$_v$—, where R" is hydrogen or alkyl of one to four carbons, and v is 1–3.

The term "(heterocycle)oxy," as used herein, represents a heterocycle group attached to the parent molecular moiety through oxygen. The (heterocycle)oxy groups of this invention can be optionally substituted.

The term "(heterocycle)oxyalkyl," as used herein, represents a (heterocycle)oxy group attached to the parent molecular group through an alkyl group. The (heterocycle)oxyalkyl groups of this invention can be optionally substituted.

The term "hydroxy" as used herein, represents an —OH group.

The term "hydroxyalkyl," as used herein, represents an alkyl group, as defined above, substituted by one to three hydroxy groups, with the proviso that no more than one hydroxy group may be attached to a single carbon atom of the alkyl group and is exemplified by hydroxymethyl, dihydroxypropyl, and the like. The hydroxyalkyl groups of this invention can be optionally substituted.

The term "nitro," as used herein, refers to —NO$_2$.

The term "perfluoroalkyl," as used herein, represents an alkyl group, as defined herein, wherein each hydrogen radical bound to the alkyl group has been replaced by a fluoride radical. Perfluoroalkyl groups are exemplified by trifluoromethyl, pentafluoroethyl, and the like. The perfluoroalkyl groups of this invention can be optionally substituted.

The term "perfluoroalkoxy," as used herein, refers to a perfluoroalkyl group, as defined herein, attached to the parent molecular group through an oxygen atom. The perfluoroalkoxy groups of this invention can be optionally substituted.

The term "pharmaceutically acceptable salt," as use herein, represents those salts which are, within the scope of sound medical judgement, suitable for use in contact with the tissues of humans and lower animals without undue toxicity, irritation, allergic response and the like and are commensurate with a reasonable benefit/risk ratio. Pharmaceutically acceptable salts are well known in the art. For example, S. M Berge, et al. describe pharmaceutically acceptable salts in detail in J. Pharmaceutical Sciences, 1977, 66:1–19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "phenoxy," as used herein, represents a phenyl group attached to the parent molecular group through an oxygen atom. The phenoxy groups of this invention can be optionally substituted.

The term "phenoxyalkyl," as used herein, represents a phenoxy group attached to the parent molecular group through an alkyl group. The phenoxyalkyl groups of this invention can be optionally substituted.

The term "phenyl," as used herein, represents a 6-membered, monocyclic, aromatic carbocyclic ring. The phenyl groups of this invention can be optionally substituted.

The term "phenylalkyl," as used herein, represents an phenyl group attached to the parent molecular group through an alkylene group and is exemplified by benzyl, phenethyl, and the like. The phenylalkyl groups of this invention can be optionally substituted.

The term "phenylalkoxy," as used herein, represents a phenyl group attached to the parent molecular group through an alkoxy group. The phenylalkoxy groups of this invention can be optionally substituted.

The term "phenylalkoxyalkyl" as used herein, represents a phenylalkoxy group, as defined above, attached to the parent molecular group through an alkyl group. The phenylalkoxyalkyl groups of this invention can be optionally substituted.

The term "piperidineneyl," as used herein, represents a divalent group derived from piperidine by the removal of two hydrogen atoms. The piperidineneyl groups of this invention can be optionally substituted.

The term "prodrug," as used herein, represents compounds which are rapidly transformed in vivo to the parent compound of the above formula, for example, by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference. Prodrugs of the compounds of the present invention are, within the scope of sound medical judgement, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "silyloxy," as used herein, represents —OSiR$_8$R$_9$R$_{10}$, wherein R$_8$, R$_9$, and R$_{10}$ are independently selected from the group consisting of alkyl and aryl.

The term "spiroalkyl," as used herein, represents an alkylene diradical, both ends of which are bonded to the same carbon atom of the parent group to form a spirocyclic group. The spiroalkyl groups of this invention can be optionally substituted.

The term "sulfinyl," as used herein, refers to an —S(O)— group.

The term "sulfinylalkyl," as used herein, refers to an alkyl group, as defined herein, attached to the parent mplecular group through a sulfinyl group.

The term "sulfonyl," as used herein, refers to an —SO$_2$— group.

The term "sultonylalkyl," as used herein, refers to an alkyl group, as defined herein, attached to the parent mplecular group through a sulfonyl group. The sulfonylalkyl groups of this invention can be optionally substituted.

The term "thioalkoxy," as used herein, represents an alkyl group attached to the parent molecular group through a sulfur atom. The thioalkoxy groups of this invention can be optionally substituted.

Compounds of the present invention may exist as stereoisomers, wherein asymmetric or chiral centers are present. These compounds are designated by the symbols "R" or "S," depending on the configuration of subsitiuents around the chiral carbon atom. The present invention contemplates various stereoisomers and mixtures thereof. Stereoisomers include enantiomers and diastereomers, and mixtures of enantiomers or diastereomers are designated (±). Individual stereoisomers of compounds of the present invention may be prepared synthetically from commercially availa ble starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

PREFERRED EMBODIMENTS

Preferred compounds of the present invention have formula (I), wherein

R$_1$, R$_3$ and R$_4$ are H;

X is selected from the group consisting of
  (1) —O—,
  (2) —C(O)—,
  (3) —S(C)$_p$—, wherein p is 2, and
  (4) —NR$_5$SO$_2$—;

Ar$_1$ is phenyl;

Y is selected from the group consisting of a
  (1) covalent bond and
  (2) —O—; and n is zero;

More preferred compounds of the present invention have formula (I), wherein

R$_1$, R$_3$ and R$_4$ are H;

X is —O— and —S(O)$_p$—;

Ar$_1$ is phenyl;

Y is ay covalent bond or —O—; and n is zero.

Preferred compounds falling within the scope of formula (I) include but are not limited to:

(±)-N-[1-[[(4'-cyano-[1,1'-biphenyl]-4-yl)oxy]methyl]-2-phenoxyethyl]-N-hydroxyformamide;

(±)-N-[1-[[(4'-cyano-[1,1'-biphenyl]-4-yl)oxy]methyl]-2-(phenylthio)ethyl]-N-hydroxyformamide;

(±)-N-[1-[[(4'-cyano-[1,1'-biphenyl]-4-yl)oxy]methyl]-2-(2,3-dihydro-1,3-dioxo-1H-isoindol-2-yl)ethyl]-N-hydroxyformamide;

(±)-N-[1-[[(4'-cyano-[1,1'-biphenyl]-4-yl)oxy]methyl]-2-(3,4,4-trimethyl-2,5-dioxoimidazolidin-1-yl)ethyl]-N-hydroxyformamide;

(±)-N-[1-[[(4'-cyano-[1,1'-biphenyl]-4-yl)oxy]methyl]-3-(3,4,4-trimethyl-2,5-dioxoimidazolidin-1-yl)propyl]-N-hydroxyformamide;

(±)-N-[1-[[[3'-(cyanomethyl)-[1,1'-biphenyl]-4-yl]oxy]methyl]pentyl]-N-hydroxyformamide;

(±)-N-[1-[[(4'-cyano-[1,1'-biphenyl]-4-yl)oxy]methyl]-3-methylbutyl]-N-hydroxyformamide;

(±)-N-[1-[[(4'-cyano-[1,1'-biphenyl]-4-yl)oxy]methyl]-2-methylbutyl]-N-hydroxyformamide;

(±)-N-[1-[[(4'-cyano-[1,1'-biphenyl]-4-yl)oxy]methyl]pentyl]-N-hydroxyformamide;

(±)-N-[1-[[(4'-cyano-[1,1'-biphenyl]-4-yl)oxy]methyl]-2-(4-methylphenyl)ethyl]-N-hydroxyformamide;

(±)-N-[2-[(4'-cyano-[1,1'-biphenyl]-4-yl)oxy]-1-(4-fluorophenyl)ethyl]-N-hydroxyformamide;

(±)-N-[1-[[(4'-cyano-[1,1'-biphenyl]-4-yl)oxy]methyl]-2-(4-fluorophenyl)ethyl]-N-hydroxyformamide;

(±)-N-[1-[[(4'-cyano-[1,1'-biphenyl]-4-yl)oxy]methyl]ethyl]-N-hydroxyformamide;

(±)-N-[2-[(4'-cyano-[1,1'-biphenyl]-4-yl)oxy]ethyl]-N-hydroxyacetamide (±)-N-[2-[(4'-cyano-[1,1'-biphenyl]-4-yl)oxy]ethyl]-N-hydroxyformamide;

(±)-N-[1-[4-[(2E-phenylethenyl)phenoxy]methyl]-2-(3,4,4-trimethyl-2,5-dioxo-1-imidazolidinyl)ethyl]-N-hydroxyformamide;

(±)-N-[1-[[4-(2-furanyl)phenoxy]methyl]-2-(3,4,4-trimethyl-2,5-dioxo-1-imidazolidinyl)ethyl]-N-hydroxyformamide;

(±)-N-[1-[[(4'-butoxy[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[(4'-fluoro[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[(3,4,4-trimethyl-2,5-dioxo-1-imidazolidinyl)methyl]-2-[[4'-(trifluoromethyl)[1,1'-biphenyl]-4-yl]oxy]ethyl]-N-hydroxyformamide;

(±)-N-[1-[[(4'-methoxy[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[(4'-methyl[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[(4'-butoxy[1,1'-biphenyl]-4-yl)oxy]methyl]-2-(4,4-dimethyl-2,5-dioxo-1-imidazolidinyl)ethyl]-N-hydroxyformamide;

(±)-N-[1-[(4,4-dimethyl-2,5-dioxo-1-imidazolidinyl)methyl]-2-[(4'-ethoxy[1,1-biphenyl]-4-yl)oxy]ethyl]-N-hydroxyformamide;

(±)-N-[1-[[4-(1,3-benzodioxol-5-yl)phenoxy]methyl]-2-(4,4-dimethyl-2,5-dioxo-1-imidazolidinyl)ethyl]-N-hydroxyformamide;

(±)-N-[1-[[(4'-butoxy[1,1'-biphenyl]-4-yl)oxy]methyl]-2-(3-methy-2,5-dioxo-1-imidazolidinyl)ethyl]-N-hydroxyformamide;

(±)-N-[1-[[4-(3-thienyl)phenoxy]methyl]-2-(3,4,4-trimethyl-2,5-dioxo-1-imidazolidinyl)ethyl]-N-hydroxyformamide;

(±)-N-[1-[[([1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[(3'-chloro-4'-fluoro[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[(2'-methyl[1,1'-biphenyl]-4-yl)oxy]methyl]-2-(3,4,4-trimethy-2,5-dioxo-1-imidazolidinyl)ethyl]-N-hydroxyformamide;

(±)-N-[1-[[(4'-cyanol[1,1'-biphenyl]-4-yl)oxy]methyl]-2-(2,5-dioxo-1-imidazolidinyl)ethyl]-N-hydroxyformamide;

(±)-N-[1-[[(4'-cyanol[1,1'-biphenyl]-4-yl)oxy]methyl]-2-(1,1-dioxido-3-oxo-1,2-benzisothiazol-2(3H)-yl)ethyl]-N-hydroxyformamide;

(±)-N-[1-[(4,4-dimethyl-2,5-dioxo-1-imidazolidinyl)methyl]-2-[[4'-(trifluoromethoxy)[1,1'-biphenyl]-4-yl]oxy]ethyl]-N-hydroxyformamide;

(±)-N-[1-[[4-(4-phenyl-1-piperidinyl)phenoxy]methyl]-2-(3,4,4-trimethyl-2,5-dioxo-1-imidazolidinyl)ethyl]-N-hydroxyformamide;

(±)-N-[1-[(4,4-dimethyl-2,5-dioxo-1-imidazolidinyl)methyl]-2-[[4'-(trifluoromethyl)[1,1'-biphenyl]-4-yl]oxy]ethyl]-N-hydroxyformamide;

(±)-N-[1-[[(3'-cyano[1,1'-biphenyl]-4-yl)oxy]methyl]-2-[methyl[(4-methylphenyl)sulfonyl]amino]ethyl]-N-hydroxyformamide;

(±)-N-[1-[[(4'-cyano[1,1'-biphenyl]-4-yl)oxy]methyl]-2-[4,4-dimethyl-2,5-dioxo-3-(3-pyridinylmethyl)-1-imidazolidinyl]ethyl]-N-hydroxyformamide;

(±)-N-[2-[(4'-cyano[1,1'-biphenyl]-4-yl)oxy]-1-methylpropyl]-N-hydroxyformamide;

(±)-N-[1-[[(3'-cyano[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[[4'-(methylthio)[1,1'-biphenyl]-4-yl]oxy]methyl]-2-(3,4,4-trimethyl-2,5-dioxo-1-imidazolidinyl)ethyl]-N-hydroxyformamide;

(±)-N-[1-[4-[[4-(trifluoromethyl)phenoxy]phenoxy]methyl]-2-(3,4,4-trimethyl-2,5-dioxo-1-imidazolidinyl)ethyl]-N-hydroxyformamide;

(±)-N-[1-[[[4'-(trifluoromethoxy)[1,1'-biphenyl]-4-yl]oxy]methyl]-2-(3,4,4-trimethy-2,5-dioxo-1-imidazolidinyl)ethyl]-2-N-hydroxyformamide;

(±)-N-[1-[[[4'-(methylsulfonyl)[1,1'-biphenyl]-4-yl]oxy]methyl]-2-(3,4,4-trimethy-2,5-dioxo-1-imidazolidinyl)ethyl]-N-hydroxyformamide;

(±)-N-[1-[[[3'-(cyanomethyl))-4'-methoxyl[1,1'-biphenyl]-4-yl]oxy]methyl]-2-(3,4,4-trimethy-2,5-dioxo-1-imidazolidinyl)ethyl]-N-hydroxyformamide;

(±)-N-[1-[[[3'-(cyanomethyl)[1,1'-biphenyl]-4-yl]oxy]methyl]-3-(4,4-dimethyl-2,5-dioxo-1-imidazolidinyl)propyl]]-N-hydroxyformamide;

(±)-N-[1-[[(4'-butoxy[1,1'-biphenyl]-4-yl)sulfonyl]methyl]-2-(4,4-dimethyl-2,5-dioxo-1-imidazolidinyl)ethyl]-N-hydroxyformamide;

(±)-N-[1-[[(4'-cyano[1,1'-biphenyl]-4-yl)oxy]methyl]-3-(4,4-dimethyl-2,5-dioxo-1-imidazolidinyl)propyl]-N-hydroxyformamide;

(±)-N-[1-[[[4'-(methylsulfonyl)[1,1'-biphenyl]-4-yl]oxy]methyl]-2-(4,4-dimethyl-2,5-dioxo-1-imidazolidinyl)ethyl]-N-hydroxyformamide;

(±)-N-[1-[[(3'-cyano[1,1'-biphenyl]-4-yl)oxy]methyl]-2-(2,5-dioxo-1-pyrrolidinyl)ethyl]-N-hydroxyformamide;

(±)-N-[1-[[(4'-cyano[1,1'-biphenyl]-4-yl)oxy]methyl]-2-(4,4-dimethyl-2,6-dioxo-1-piperidinyl)ethyl]-N-hydroxyformamide;

(±)-N-[1S-[[(4'-cyano[1,1'-biphenyl]-4-yl)oxy]methyl]-2-(2,5-dioxo-1-pyrrolidinyl)ethyl]-N-hydroxyformamide;

(±)-N-[1R-[[(4'-cyano[1,1'-biphenyl]-4-yl)oxy]methyl]-2-(2,5-dioxo-1-pyrrolidinyl)ethyl]-N-hydroxyformamide;

(±)-N-[1-[[(4'-cyano[1,1'-biphenyl]-4-yl)oxy]methyl]-2-(3-ethyl-3-methyl-2,5-dioxo-1-pyrrolidinyl)ethyl]-N-hydroxyformamide;

N-[4-[4-[[(4-chlorophenoxy)phenyl]sulfonyl]methyl]tetrahydro-2H-pyran-4-yl]-N-hydroxyformamide;

(±)-N-[1-[[(4'-cyano[1,1'-biphenyl]-4-yl)oxy]methyl]-2-[[(2-methoxycarbonyl)-phenyl]thio]ethyl]-N-hydroxyformamide;

(±)-N-[1-[[(4'-cyano[1,1'-biphenyl]-4-yl)oxy]methyl]-5-[(4-methyl-2-oxo-2H-1-benzopyran-6-yl)oxy]pentyl]-N-hydroxyformamide;

(±)-N-[1-[[(4'-cyano[1,1'-biphenyl]-4-yl)oxy]methyl]-4-[(4-methyl-2-oxo-2H-1-benzopyran-6-yl)oxy]butyl]-N-hydroxyformamide;

(±)-N-[1-[[(4'-cyano[1,1'-biphenyl]-4-yl)oxy]methyl]-4-[(4-methyl-2-oxo-2H-1-benzopyran-7-yl)oxy]butyl]-N-hydroxyformamide;

(±)-N-[1-[[(4'-cyano[1,1'-biphenyl]-4-yl)oxy]methyl]-5-[(4-methyl-2-oxo-2H-1-benzopyran-7-yl)oxy]pentyl]-N-hydroxyformamide;

(±)-N-[1-[[(4'-cyano [1,1'-biphenyl]-4-yl)oxy]methyl]-2-(5,5-dimethyl-2,4-diox-3-oxazolidinyl)ethyl]-N-hydroxyformamide;

(±)-N-[1-[[(4'-cyano[1,1'-biphenyl]-4-yl)sulfonyl]methyl]-2-(3,4,4-trimethy-2,5-dioxo-1-imidazolidinyl)ethyl]-N-hydroxyformamide;

(±)-N-[1-[[(4'-cyano[1,1'-biphenyl]-4-yl)oxy]methyl]-2-(3-methyl-2,5-dioxo-1-imidazolidinyl)ethyl]-N-hydroxyformamide;

(±)-N-[1-[[(4'-cyano[1,1'-biphenyl]-4-yl)sulfonyl]methyl]-2-(4,4-dimethyl-2,5-dioxo-1-imidazolidinyl)ethyl]-N-hydroxyformamide;

(±)-N-[1-[[(4'-chloro-[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[(3'-cyanomethyl-[1,1'-biphenyl]-4-y)oxy]methyl]-2-(3,5,5-trimethyl-2,4-dioxo-1-imidazolidinyl)propyl]-N-hydroxyformamide;

(±)-N-[1-[[(4'-cyano-[1,1'-biphenyl]-4-y)oxy]methyl]-2-isopropylthioethyl]-N-hydroxyformamide;

(±)-N-[1-[[(3'-cyanomethyl-[1,1'-biphenyl]-4-y)oxy]methyl]-2-(3,4,4-trimethyl-2,5-dioxo-1-imidazolidinyl)ethyl]-N-hydroxyformamide;

(±)-N-[1-[[(4'-cyano-[1,1'-biphenyl]-4-yl)oxy]methyl]-2-(3-ethyl-4,4-dimethyl-2,5-dioxo-1-imidazolidinyl)ethyl]-N-hydroxyformamide;

(±)-N-[1-[[(4'-cyano-[1,1'-biphenyl]-4-yl)oxy]methyl]-2-(3-benzyl-4,4-dimethyl-2,5-dioxo-1-imidazolidinyl)ethyl]-N-hydroxyformamide;

(±)-N-[1-[[(4'-cyano-[1,1'-biphenyl]-4-y)oxy]methyl]-2-(3,5,5-trimethyl-2,4-dioxo-1-imidazolidinyl)ethyl]-N-hydroxyformamide;

(±)-N-[1-[[4'-methoxy[1,1'-biphenyl]-4-yl)sulfonyl]methyl]ethyl]-N-hydroxyformamide;

(±)-N-[1-[[(4'-chloro[1,1'-biphenyl]-4-yl)sulfonyl]methyl]ethyl]-N-hydroxyformamide;

(±)-N-[1-[[[4-(1,3-benzodioxol-5-yl)phenyl]sulfonyl]methyl]ethyl]-N-hydroxyformamide;

(±)-N-[1-[[[4-(4-chlorophenoxy)phenyl]sulfonyl]methyl]ethyl]-N-hydroxyformamide;

(±)-N-[1-[[(4'-methoxy[1,1'-biphenyl]-4-yl)sulfonyl]methyl]propyl]-N-hydroxyformamide;

(±)-N-[1-[1,1-dimethyl-2-[(4'-(trifluoromethyl)[1,1'-biphenyl]-4-yl]sulfonyl]ethyl]-N-hydroxyformamide;

(±)-N-[1-[(phenylmethoxy)methyl]-2-[[4'-(trifluoromethyl)[1,1'-biphenyl]-4-yl]sulfonyl]ethyl]-N-hydroxyformamide;

(±)-N-[1-(hydroxymethyl)-2-[[(4'-(trifluoromethyl)[1,1'-biphenyl]-4-yl]sulfonyl]ethyl]-N-hydroxyformamide;

(±)-N-[1-[(4,4-dimethyl-2,5-dioxo-1-imidazolidinyl)methyl]-2-[[4'-(trifluoromethyl)[1,1'-biphenyl]-4-yl]thio]ethyl]-N-hydroxyformamide;

(±)-N-[1-[(4,4-dimethyl-2,5-dioxo-1-imidazolidinyl)methyl]-2-[[4'-(trifluoromethyl)[1,1'-biphenyl]-4-yl]sulfonyl]ethyl]-N-hydroxyformamide;

(±)-N-[1-[(2,5-dioxo-1-imidazolidinyl)methyl]-2-[[4'-(trifluoromethoxy)[1,1'-biphenyl]-4-yl]oxy]ethyl]-N-hydroxyformamide;

(±)-N-[1-[[[4'-(trifluoromethyl)[1,1'-biphenyl]-4-yl]sulfonyl]methyl]-2-(3,4,4-trimethyl-2,5-dioxo-1-imidazolidinyl)ethyl]-N-hydroxyformamide;

(±)-N-[1-[[(4'-butyl[1,1'-biphenyl]-4-yl)oxy]methyl]-2-(3-methy-2,5-dioxo-1-imidazolidinyl)ethyl]-N-hydroxyformamide;

(±)-N-[1-[(3-methy-2,5-dioxo-1-imidazolidinyl)methyl]-2-[[4'-(trifluoromethoxy)[1,1'-biphenyl]-4-yl]oxy]ethyl]-N-hydroxyformamide;

(±)-N-[4-[4-[(4'-chloro[1,1'-biphenyl]-4-yl)sulfonyl]methyl]tetrahydro-2H-pyran-4-yl]-N-hydroxyformamide;

(±)-N-[1-[[[4-(4-chlorophenoxy)phenyl]sulfonyl]methyl]-2-(4,4-dimethyl-2,5-dioxo-1-imidazolidinyl)ethyl]-N-hydroxyformamide;

(±)-N-[1-[[[4-(4-chlorophenoxy)phenyl]sulfonyl]methyl]-2-(3,4,4-trimethyl-2,5-dioxo-1-imidazolidinyl)ethyl]-N-hydroxyformamide;

(±)-N-[1-[[(4-butyl[1,1'-biphenyl]-4-yl)sulfonyl]methyl]-2-(3,4,4-trimethyl-2,5-dioxo-1-imidazolidinyl)ethyl]-N-hydroxyformamide;

(±)-N-[1-[[(4'-butyl[1,1'-biphenyl]-4-yl)oxy]methyl]-2-(4,4-dimethyl-2,5-imidazolidinyl)ethyl]-N-hydroxyformamide;

(±)-N-[1-[[[3'-(cyanomethyl)[1,1'-biphenyl]-4-yl]oxy]methyl]-2-(4,4-dimethyl-2,5-dioxo-1-imidazolidinyl)ethyl]-N-hydroxyformamide;

(±)-N-[1-[4-(2-thienyl)phenoxy]methyl]-2-[1-(3,4,4-trimethyl-2,5-dioxo-1-imidazolidinyl)ethyl]-N-hydroxyformamide;

(±)-N-[1-[[(3-nitro[1,1'-biphenyl]-4-yl)oxy]methyl]-2-(3,4,4-trimethyl-2,5-dioxo-1-imidazolidinyl)ethyl]-N-hydroxyformamide;

(±)-N-[1-[[(4'-methyl[1,1'-biphenyl]-4-yl)oxy]methyl]-2-[[3-(methylsulfonyl)-amino]phenyl]ethyl]-N-hydroxyformamide;

(±)-N-[1-[[[3-(diethylamino)carbonyl]phenyl]methyl]-2-[(4'-methyl[1,1'-biphenyl]-4-yl)oxy]ethyl]-N-hydroxyformamide; (±)-N-[1-[[(4'-cyano[1,1'-biphenyl]-4-yl)oxy]methyl]-2-[(4'-cyano[1,1'-biphenyl]-4-yl)oxy]ethyl]-N-hydroxyformamide;

(±)-N-[1-[[(4'-cyano[1,1'-biphenyl]-4-yl)oxy]methyl]-2-(4,4-dimethyl-2,5-dioxo-1-imidazolidinyl)ethyl]-N-hydroxyformamide;

(±)-N-[1-[(4,4-dimethyl-2,5-dioxo-1-imidazolidinyl)methyl]-2-[[4'-(2-methoxyethoxy)[1,1'-biphenyl]-4-yl]oxy]ethyl]-N-hydroxyformamide;

(±)-N-[1-[(4,4-dimethyl-2,5-dioxo-1-imidazolidinyl)methyl]-2-[(4'-propoxy[1,1'-biphenyl]-4-yl)oxy]ethyl]-N-hydroxyformamide;

(±)-N-[1-[(4,4-dimethyl-2,5-dioxo-1-imidazolidinyl)methyl]-2-[(4'-pentyloxy[1,1'-biphenyl]-4-yl)oxy]ethyl]-N-hydroxyformamide;

(±)-N-[1-[[[3'-(cyanomethyl)[1,1'-biphenyl]-4-yl]sulfonyl]methyl]-3-(4,4-dimethyl-2,5-dioxo-1-imidazolidinyl)propyl]-N-hydroxyformamide;

(±)-N-[1-[[[4'-(trifluoromethoxy)[1,1'-biphenyl]-4-yl]sulfonyl]methyl]-2-(3,4,4-trimethy-2,5-dioxo-1-imidazolidinyl)ethyl]-N-hydroxyformamide;

(±)-N-[1-[[(4'-cyano[1,1'-biphenyl]-4-yl)sulfonyl]methyl]-2-(3-methy-2,5-dioxo-1-imidazolidinyl)ethyl]-N-hydroxyformamide;

(±)-N-[1-[[[3'-(cyanomethyl)[1,1'-biphenyl]-4-yl]
sulfonyl]methyl]-2-(3,4,4-trimethyl-2,5-dioxo-1-
imidazolidinyl)ethyl]-N-hydroxyformamide;

(±)-N-[1-[[(4'-cyano[1,1"-biphenyl]-4-yl)oxy]methyl]-2-
(1,6-dihydro-3-methyl-6-oxo-1-pyridazinyl)ethyl]-N-
hydroxyformamide;

(±)-N-[1-[[(4'-cyano[1,1'-biphenyl]-4-yl)sulfonyl]
methyl]-2-(4,4-dimethyl-2,5-dioxo-1-imidazolidinyl)
ethyl]-N-hydroxyformamide;

(±)-N-[1-[[[4-(4-fluorophenoxy)phenyl]sulfonyl]
methyl]-2-(4,4-dimethyl-2,5-dioxo-1-imidazolidinyl)
ethyl]-N-hydroxyformamide;

(±)-N-[1-[[4-(4-pyridinyl)phenoxy]methyl]-2-(3,4,4-
trimethy-2,5-dioxo-1-imidazolidinyl)ethyl]-N-
hydroxyformamide;

(S)-N-[1-[(4,4-dimethyl-2,5-dioxo-1-imidazolidinyl)
methyl]-2-[[4'-(trifluoromethoxy)[1,1'-biphenyl]-4-yl]
oxy]ethyl]-N-hydroxyformamide;

(R)-N-[1-[(4,4-dimethyl-2,5-dioxo-1-imidazolidinyl)
methyl]-2-[[4'-(trifluoromethoxy)[1,1'-biphenyl]-4-yl]
oxy]ethyl]-N-hydroxyformamide;

N-[1-[[[4'-(trifluoromethoxy))[1,1'-biphenyl]-4-yl]oxy
methyl]-3-(4,4-dimethyl-2,5-dioxo-1-imidazolidinyl)
propyl]-N-hydroxyformamide;

N-[1-[4-[(4-pyridinylthio)phenoxy]methyl]-2-(4,4-
dimethyl-2,5-dioxo-1-imidazolidinyl)ethyl]-N-
hydroxyformamide;

N-[1-[[[(4-chlorophenoxy)phenyl]sulfonyl]methyl]-3-(4,
4-dimethyl-2,5-dioxo-1-imidazolidinyl)propyl]-N-
hydroxyformamide;

N-[1-[[(4'-cyano[1,1"-biphenyl]-4-yl)oxy]methyl]-2-(1,
6-dihydro-6-oxo-1-pyridazinyl)ethyl]-N-
hydroxyformamide;

N-[1-[[[4'-(aminosulfonyl)[1,1'-biphenyl]-4-yl]oxy]
methyl]-2-(3,4,4-trimethyl-2,5-dioxo-1-
imidazolidinyl)ethyl]-N-hydroxyformamide;

N-[1-[[[4'-(trifluoromethoxy)[1,1'-biphenyl]-4-yl]
sulfonyl]methyl]-2-(4,4-dimethyl-2,5-dioxo-1-
imidazolidinyl)ethyl]-N-hydroxyformamide;

N-[1-[4-[(4-pyridinyloxy)phenyl]sulfonyl]]ethyl]-N-
hydroxyformamide;

N-[1-[[[(4-cyanophenoxy)phenyl]sulfonyl]methyl]-2-(4,
4-dimethyl-2,5-dioxo-1-imidazolidinyl)ethyl]-N-
hydroxyformamide;

N-[1-[[4-[[4-(trifluoromethoxy)phenoxy]phenyl]
sulfonyl]methyl]-3-(4,4-dimethyl-2,5-dioxo-1-
imidazolidinyl)propyl]-N-hydroxyformamide;

N-[1-[[4-[[4-(trifluoromethoxy)phenoxy]phenyl]
sulfonyl]methyl]-2-(4,4-dimethyl-2,5-dioxo-1-
imidazolidinyl)ethyl]-N-hydroxyformamide;

(±)-N-hydroxy-N-[1-(3-pyridinyl)-2-[[4'-
(trifluoromethyl)[1,1'-biphenyl]-4-yl]-sulfonyl]ethyl]
formamide;

(±)-N-hydroxy-N-[1-(hydroxymethyl)-2-[[4-[(4-
chlorophenoxy)phenyl]sulfonyl]-ethyl]formamide;

(±)-N-hydroxy-N-[1-methyl-2-[[4'-(trifluoromethyl)[1,1'-
biphenyl]-4-yl]sulfonyl]ethyl]formamide;

(±)-N-hydroxy-N-[1-(2-pyridinyl)-2-[[4'-
(trifluoromethyl)[1,1'-biphenyl]-4-yl]-sulfonyl]ethyl]
formamide;

(±)-N-[1-[(4,4-dimethyl-2,6-dioxo-1-piperidinyl)
methyl]-2-[[4'-(trifluoromethyl)[1,1'-biphenyl]-4-yl]
sulfonyl]ethyl]-N-hydroxyformamide;

(±)-N-hydroxy-N-[3-hydroxy-1-[[[4'-(trifluoromethyl)[1,
1'-biphenyl]-4-yl]sulfonyl]methyl]propyl]formamide;

(±)-N-hydroxy-N-[1-(methoxymethyl)-2-[[4'-
(trifluoromethyl)[1,1'-biphenyl]-4-yl]sulfonyl]ethyl]
formamide;

()-N-[1-(1,3-benzodioxol-5-yl)-2-[[4'-(trifluoromethyl)
[1,1'-biphenyl]-4-yl]sulfonyl]-ethyl]-N-
hydroxyfonnamide;

(±)-N-hydroxy-N-[4-hydroxy-1-[[[4'-(trifluoromethyl)[1,
1'-biphenyl]-4-yl]sulfonyl]methyl]butyl]formamide;

(±)-N-hydroxy-N-[1-[4-(methoxymethoxy)phenyl]-2-
[[4'-(trifluoromethyl)[1,1'-biphenyl]-4-yl]sulfonyl]
ethyl]formamide;

(±)-N-hydroxy-N-[1-(1-methyl-1H-pyrrol-2-yl)-2-[[4-[4-
(trifluoromethoxy)phenoxy]phenyl]sulfonyl]ethyl]
formamide;

(±)-N-hydroxy-N-[1-phenyl-2-[[4-[4-(trifluoromethoxy)
phenoxy]phenyl]sulfonyl]ethyl]formamide;

(±)-N-hydroxy-N-[1-(2-thienyl)-2-[[4-[4-
(trifluoromethoxy)phenoxy]phenyl]sulfonyl]ethyl]
formamide;

(±)-N-[1-(2-furanyl)-2-[[4-[4-(trifluoromethoxy)
phenoxy]phenyl]sulfonyl]ethyl]-N-
hydroxyformamide;

(±)-N-[1-(5,5-dimethyl-2,4-dioxo-3-oxazolidinyl)-2-[[4'-
(trifluoromethoxy)[1,1'-biphenyl]-4-yl]sulfonyl]ethyl]-
N-hydroxyformamide;

(±)-N-hydroxy-N-[1-(methoxymethyl)-2-[[4-[4-
(trifluoromethoxy)phenoxy]phenyl]sulfonyl]ethyl]
formamide;

(S)-N-hydroxy-N-[1-[(phenylmethoxy)methyl]-2-[[4'-
(trifluoromethoxy)[1,1'-biphenyl]-4-yl]oxy]ethyl]
formamide;

(S)-N-hydroxy-N-[1-(hydroxymethyl)-2-[[4'-
(trifluoromethoxy)[1,1'-biphenyl]-4-yl]oxy]ethyl]
formamide;

(±)-N-hydroxy-N-[1-(hydroxymethyl)-2-[[4-[4-
(trifluoromethoxy)phenoxy]phenyl]sulfonyl]ethyl]
formamide;

[S-(R*,S*)]-N-[1-(2,2-dimethyl-1,3-dioxol-4-yl)-2-[[4-
[4-(trifluoromethoxy)-phenoxy]phenyl]sulfonyl]
ethyl]-N-hydroxyformamide;

[S-(R*,R*)]-N-[1-(2,2-dimethyl-1,3-dioxol-4-yl)-2-[[4-
[4-(trifluoromethoxy)-phenoxy]phenyl]sulfonyl]
ethyl]-N-hydroxyformamide;

[S-(R*,R*)]-N-[(2,3-dihydroxy)-1-[[[4-[4-
(trifluoromethoxy)phenoxy]phenyl]-sulfonyl]methyl]
propyl]-N-hydroxyformamide;

(±)-N-[1-[(dimethylamino)methyl]-2-[[4-[4-
(trifluoromethoxy)phenoxy]phenyl]-sulfonyl]ethyl]-N-
hydroxyformamide;

[S-(R*,R*)]-N-[2-[(4'-chloro[1,1'-biphenyl]-4-yl)
sulfonyl]-1-(2,2-dimethyl-1,3-dioxol-4-yl)ethyl]-N-
hydroxyformamide;

(±)-N-[1-[(1,1-dioxido-3-oxo-1,2-benzisothiazol-2(3H)-
yl)methyl]-2-[[4'-(trifluoromethoxy)[1,1'-biphenyl]-4-
yl]oxy]ethyl]-N-hydroxyformamide;

[R-(R*,R*)]-N-[1-(2,2-dimethyl-1,3-dioxol-4-yl)-2-[[4-
[4-(trifluoromethoxy)phenoxy]phenyl]sulfonyl]ethyl]-
N-hydroxyformamide;

[R-(S*,R*)]-N-[1-(2,2-dimethyl-1,3-dioxol-4-yl)-2-[[4-
[4-(trifluoromethoxy)phenoxy]phenyl]sulfonyl]ethyl]-
N-hydroxyformamide;

[S-(R*,R*)]-N-[1-(2,2-diethyl-1,3-dioxol-4-yl)-2-[[4-[4-(trifluoromethoxy)phenoxy]phenyl]sulfonyl]ethyl]-N-hydroxyformamide;

(±)-N-hydroxy-N-[1-(hydroxymethyl)-2-[[4'-(methylsulfonyl)[1,1'-biphenyl]-4-yl]sulfonyl]ethyl] formamide;

(±)-N-[1-[[4-[(1,3-benzodioxol-5-yl)phenyl]sulfonyl] methyl]-2-hydroxyethyl]-N-hydroxyformamide;

(±)-N-hydroxy-N-[1-(hydroxymethyl)-2-[[4'-(methylthio)[1,1'-biphenyl]-4-yl]-sulfonyl]ethyl] formamide;

(±)-N-hydroxy-N-[1-(hydroxymethyl)-2-[[4'-(trifluoromethoxy)[1,1'-biphenyl]-4-yl]sulfonyl]ethyl] formamide;

(±)-N-hydroxy-N-[1-(hydroxymethyl)-2-[(4'chloro[1,1'-biphenyl]-4-yl)sulfonyl]ethyl]formamide;

(±)-N-[1-[(2,5-dioxo-3,4,4-trimethyl-1-imidazolidinyl) methyl]-2-[[4-[4-(trifluoromethyl)phenoxy]phenyl] sulfonyl]ethyl]-N-hydroxyformamide;

(±)-N-hydroxy-N-[1-(hydroxymethyl)-2-[[[4-(methylsulfonyl)phenoxy]phenyl]sulfonyl]ethyl] formamide;

(±)-N-[1-methyl-3-(4'-chloro[1,1'-biphenyl]-4-yl)-3-oxopropyl]-N-hydroxyformamide;

(±)-N-[1-[(2,5-dioxo-3,4,4-trimethyl-1-imidazolidinyl) methyl]-2-[[4-(4-butylphenoxy)phenyl]sulfonyl] ethyl]-N-hydroxyformamide;

(±)-N-[3-[(2,5-dioxo-3,4,4-trimethyl-1-imidazolidinyl)-1-[[4-[4-(trifluoromethyl)phenoxy]phenyl]sulfonyl] methyl]propyl]-N-hydroxyformamide;

(±)-N-[1-[(2,5-dioxo-3,4,4-trimethyl-1-imidazolidinyl) methyl]-2-[[4-[4-(trifluoromethoxy)phenoxy]phenyl] sulfonyl]ethyl]-N-hydroxyformamide;

(±)-N-[1-[[4-[(4-chlorophenoxy)phenyl]sulfonyl] methyl]-3-[(2,5-dioxo-3,4,4-trimethyl-1-imidazolidinyl)methyl]propyl]-N-hydroxyformamide;

(±)-N-[2-[4-(4'-cyano[1,1'-biphenyl]-4-yl)oxy] cyclohexyl]-N-hydroxyformamide;

(±)-N-[2-[4-[4'-(trifluoromethoxy)[1,1'-biphenyl]-4-yl) oxy]cyclohexyl]-N-hydroxyformamide;

(±)-1-[[[[4-(4-chlorophenoxy)phenyl]sulfonyl]methyl]-2-(3-methyl-6-oxo-1(6H)-pyridazinyl)ethyl]-N-hydroxyformamide;

(±)-N-hydroxy]-1-[(6-oxo-1(6H)-pyridazinyl)methyl]-2-[[4'-(trifluoromethoxy)[1,1'-biphenyl]-4-yl]oxy]ethy] formamide;

(±)-N-[1-[(1,6-dihydro-3-methyl-2,6-dioxo-1(6H)-pyrimidinyl)methyl]-2-[[4-[4-(trifluoromethoxy) phenoxy]phenyl]sulfonyl]ethyl]-N-hydroxyformamide;

(±)-N-[1-[(2,5-dioxo-3,4,4-trimethyl-1-imidazolidinyl) methyl]-2-[[4-(4-bromophenoxy)phenyl]sulfonyl] ethyl]-N-hydroxyformamide;

(±)-N-[1-[(2,5-dioxo-4,4-dimethyl-1-imidazolidinyl) methyl]-2-methyl-2-[[4'-(trifluoromethoxy)[1,1'-biphenyl]-4-yl]oxy]propyl]-N-hydroxyformamide;

(±)-N-[1-[[4-[(4-chlorophenoxy)phenyl]sulfonyl] methyl]-2-(1,6-dihydro-3-methyl-2,6-dioxo-1(6H)-pyrimidinyl)ethyl]-N-hydroxyformamide;

(±)-N-hydroxy-N-[1-[(3-methyl-6-oxo-1(6H)-pyridazinyl)methyl]-2-[[4-[4-(trifluoromethoxy) phenoxy]phenyl]sulfonyl]ethyl]formamide;

(±)-N-hydroxy-N-[1-(1-methyl-1H-indol-4-yl)-[2-[[4-(trifluoromethoxy)phenoxy]phenyl]sulfonyl]]ethyl] formamide;

(±)-N-hydroxy-N-[1-(1-methyl-1H-indol-2-yl)-2-[[4-[4-(trifluoromethoxy)phenoxy]phenyl]sulfonyl]]ethyl] formamide;

()-N-[1-(4-chlorophenyl)-2-[[[4-(trifluoromethoxy) phenoxy]phenyl]sulfonyl]ethyl]-N-hydroxyformamide;

(±)-N-hydroxy-N-[2-[[[4-(trifluoromethoxy)phenoxy] phenyl]sulfonyl]-1-[4-(trifluoromethyl)phenyl]ethyl] formamide;

()-N-[1-[(2,5-dioxo-3,4,4-trimethyl-1-imidazolidinyl) methyl]-2-[[4-[4-(trifluoromethoxy)phenoxy]phenyl] sulfonyl]ethyl]-N-hydroxyformamide;

(±)-N-hydroxy-N-[1-[[(2-thienylthio)methyl]-2-[[4-(trifluoromethoxy)phenoxy]phenyl]sulfonyl]ethyl] formamide;

(±)-N-hydroxy-N-[1-[[[(4-methylphenyl)sulfonyl] methylamino]methyl]-2-[[[4-(trifluoromethoxy) phenoxy]phenyl]sulfonyl]ethyl]formamide;

(±)-N-hydroxy-N-[[[2-(methoxyethoxy)methyl]-1-[[4-(trifluoromethoxy)phenoxy]phenyl]sulfonyl]ethyl] formamide;

(±)-N-[1-[(1,6-dihydro-3-methyl-2,6-dioxo-1(6H)-pyrimidinyl)methyl]-2-[[(4-phenoxyphenyl]sulfonyl] ethyl]-N-hydroxyformamide;

(±)-N-hydroxy-N-[1-(4-hydroxyphenyl)-2-[[4'-(trifluoromethyl)[1,1'-biphenyl]-4-yl]sulfonyl]ethyl] formamide;

(±)-N-hydroxy-N-[1-(2,2-dimethyl-1,3-dioxan-5-yl)-2-[[4-(trifluoromethoxy)phenoxy]phenyl]sulfonyl]ethyl] formamide;

(±)-N-hydroxy-N-[3-hydroxy-2-(hydroxymethyl)-1-[[[[4-(trifluoromethoxy)phenoxy]phenyl]sulfonyl] methyl]propyl]formamide;

(±)-N-hydroxy-N-[1-(hydroxymethyl)-2-[[[(4-chlorophenyl)thio]phenyl]sulfonyl]ethyl]formamide;

(±)-N-hydroxy-N-[1-(4-morpholinylmethyl)-2-[[[4-(trifluoromethoxy)phenoxy]phenyl]sulfonyl]ethyl] formamide;

(±)-N-hydroxy-N-[4-hydroxy-[1-[[[4-(trifluoromethoxy) phenoxy]phenyl]sulfonyl]methyl]butyl]formamide;

(±)-N-[1-[(1H-isoindole-1,3(2H)-dione)methyl]-2-[[4-(4-chlorophenoxy)phenyl]sulfonyl]ethyl]-N-hydroxyformamide;

(±)-N-[1-[(2,5-dioxo-3,4,4-trimethyl-1-imidazolidinyl) methyl]-2-[[4-(4-cyanophenoxy)phenyl]sulfonyl] ethyl]-N-hydroxyformamide;

(±)-N-hydroxy-N-[1-(2-pyridinyl)-2-[[4'-(trifluoromethoxy)[1,1'-biphenyl]-4-yl]sulfonyl]ethyl] formamide;

(±)-N-[1-[[[(4-chlorophenoxy)phenyl]sulfonyl]methyl]-4-hydroxybutyl]-N-hydroxyformamide;

(±)-N-[1-[[[(4-trifluoromethoxyphenoxy)phenyl] sulfonyl]methyl]-3-hydroxypropyl]-N-hydroxyformamide;

(±)-N-hydroxy-N-[1-[(4-trifluoromethoxyphenoxy) methyl]-2-[[4-[4-(trifluoromethoxy)phenoxy]phenyl] sulfonyl]ethyl]formamide;

[S-(R*,R*)]-N-hydroxy-N-[1-(2,2-dimethyl-1,3-dioxol-4-yl)-2-[4-[(4-phenyl-1-piperidinyl)phenyl]sulfonyl] ethyl]formamide;

(±)-N-hydroxy-N-[1-(4-trifluoromethoxyphenyl)-2-[[4-[4-(trifluoromethoxy)phenoxy]phenyl]sulfonyl]ethyl] formamide;

[S-(R*,R*,R*)]-N-[1-(2,2,5-trimethyl-1,3-dioxol-4-yl)-2-[[4-[4-(trifluoromethoxy)phenoxy]phenyl]sulfonyl]ethyl]-N-hydroxyformamide;

(±)-N-hydroxy-N-[1-(2-trifluoromethylphenyl)-2-[[4-[4-(trifluoromethoxy)phenoxy]phenyl]sulfonyl]ethyl]formamide;

(±)-N-hydroxy-N-[1-(4-fluorophenyl)-2-[[4-[4-(trifluoromethoxy)phenoxy]phenyl]sulfonyl]ethyl]formamide;

(±)-N-hydroxy-N-[1-(cyclohexyl)-2-[[4-[4-(trifluoromethoxy)phenoxy]phenyl]sulfonyl]ethyl]formamide;

(−)-(S)-N-[1-[[[4-(4-chlorophenoxy)phenyl]sulfonyl]methyl]-2-(3,4,4-trimethyl-2,5-dioxo-1-imidazolidinyl)ethyl]-N-hydroxyformamide;

(±)-N-hydroxy-N-[1-[[[4-[4-(trifluorophenoxy)phenyl]sulfonyl]methyl]-2-(3,4,5-trimethoxyphenyl)ethyl]formamide;

3-(cyanomethyl)-4'-({3-(4,4-dimethyl-2,5-dioxo-1-imidazolidinyl)-2-[formyl(hydroxy)amino]propyl}sulfonyl)-1,1'-biphenyl; hydroxy{3-(4-morpholinyl)-1-[({4-[4-(trifluoromethoxy)phenoxy]phenyl}sulfonyl)methyl]propyl}formamide;

4-({3-(4,4-dimethyl-2,5-dioxo-1-imidazolidinyl)-2-[formyl(hydroxy)amino]propyl}sulfonyl)-4'-fluoro-1,1-biphenyl;

4-({3-(4,4-dimethyl-2,5-dioxo-1-imidazolidinyl)-2-[formyl(hydroxy)amino]propyl}sulfonyl)-4'-(methylsulfanyl)-1,1-biphenyl;

4-({3-(4,4-dimethyl-2,5-dioxo-1-imidazolidinyl)-2-[formyl(hydroxy)amino]propyl}sulfonyl)-4'-(methoxy)-1,1-biphenyl;

4-fluoro-4'-({2-[formyl(hydroxy)amino]-4-hydroxybutyl}sulfonyl-1,1'-biphenyl;

4-chloro-4'-({2-[formyl(hydroxy)amino]-4-hydroxybutyl}sulfonyl-1,1'-biphenyl;

4-fluoro-4'-({2-[formyl(hydroxy)amino]-4-hydroxypentyl}sulfonyl-1,1'-biphenyl;

4-chloro-4'-({2-[formyl(hydroxy)amino]-4-hydroxypentyl}sulfonyl-1,1'-biphenyl;

4-chloro-4'-({3-(4,4-dimethyl-2,6-dioxo-1-piperididnyl)-2-[formyl(hydroxy)amino]propyl}sulfonyl)-1,1-biphenyl;

ethyl 5-({3-[4'-fluoro[1,1'-biphenyl]-4-yl)sulfonyl]-2-[formyl(hydroxy)amino]propyl}amino)-3,3-dimethyl-5-oxopentanoate;

4-({3-(4,4-dimethyl-2,6-dioxo-1-piperidinyl)-2-[formyl(hydroxy)amino]propyl}sulfonyl)-4'-fluoro-1,1'-biphenyl;

hydroxy[3-(4-morpholinyl)-1-({[4'-(trifluoromethyl)[1,1'-biphenyl]-4-yl]sulfonyl}methyl)propyl]formamide;

4-chloro-4'-{[2-[formyl(hydroxy)amino]-4-(4-morpholinyl)butyl]sulfonyl}-1,1'-biphenyl;

4-chloro-4'-{[2-[formyl(hydroxy)amino]-4-(1-piperidinyl)butyl]sulfonyl}-1,1'-biphenyl;

hydroxy{3-(1-piperidinyl)-1-[({4-[4-(trifluoromethoxy)phenoxy]phenyl}sulfonyl)methyl]propyl}formamide;

4-chloro-4'-{[2-[formyl(hydroxy)amino]-3-(1-piperidinyl)propyl]sulfonyl}-1,1'-biphenyl;

hydroxy{2-(1-piperidinyl)-1-[({4-[4-(trifluoromethoxy)phenoxy]phenyl}sulfonyl)methyl]ethyl}formamide;

3-(4-acetyl-1-piperazinyl)-1-[({4-[4-(trifluoromethoxy)phenoxy]phenyl}sulfonyl)methyl]propyl(hydroxy)formamide;

hydroxy{3-(4-thiomorpholinyl)-1-[({4-[4-(trifluoromethoxy)phenoxy]phenyl}sulfonyl)methyl]propyl}formamide;

hydroxy{3-(4-methyl-1-piperazinyl)-1-[({4-[4-(trifluoromethoxy)phenoxy]phenyl}sulfonyl)methyl]propyl}formamide;

hydroxy{2-tetrahydro-2H-pyran-4-yl-1-[({4-[4-(trifluoromethoxy)phenoxy]phenyl}sulfonyl)methyl]ethyl}formamide;

hydroxy[(1R)-1-(2R)-1-(methylsulfonyl)pyrrolidinyl]-2-({4-[4-(trifluoromethoxy)phenoxy]phenyl}sulfonyl)ethyl]formamide;

hydroxy[(1S)-1-(2R)-1-(methylsulfonyl)pyrrolidinyl]-2-({4-[4-(trifluoromethoxy)phenoxy]phenyl}sulfonyl)ethyl]formamide;

2-(1,1-dioxidotetrahydro-2H-thiopyran-4-yl)-1-[({4-[4-(trifluoromethoxy)phenoxy]phenyl}sulfonyl)methyl]ethyl(hydroxy)formamide;

hydroxy{2-[4-(methylsulfonyl)-1-piperazinyl]-1-[({4-[4-(trifluoromethoxy)phenoxy]phenyl}sulfonyl)methyl]ethyl}formamide;

hydroxy{3-[4-(methylsulfonyl)-1-piperazinyl]-1-[({4-[4-(trifluoromethoxy)phenoxy]phenyl}sulfonyl)methyl]propyl}formamide;

2-[4-(2,2-dimethylpropanoyl)-1-piperazinyl]-1-[({4-[4-(trifluoromethoxy)phenoxy]phenyl}sulfonyl)methyl]ethyl(hydroxy)formamide;

2,2-dimethyl-1-[({4-[4-(trifluoromethoxy)phenoxy]phenyl}sulfonyl)methyl]propyl(hydroxy)formamide;

1-cyclopropyl-2-({4-[4-(trifluoromethoxy)phenoxy]phenyl}sulfonyl)ethyl(hydroxy)formamide;

2-(1,4-dioxaspiro[4.5]dec-8-yl)-1-[({4-[4-(trifluoromethoxy)phenoxy]phenyl}sulfonyl)methyl]ethyl(hydroxy)formamide;

hydroxy[1-[(4S)-2-oxo-1,3-oxazolidin-4-yl]-2-({4-[4-(trifluoromethoxy)phenoxy]phenyl}sulfonyl)ethyl]formamide;

hydroxy[(1S)-1-[(2R)-tetrahydro-2-furanyl]-2-({4-[4-(trifluoromethoxy)phenoxy]phenyl}sulfonyl)ethyl]formamide;

hydroxy[(1R)-1-[(2R)-tetrahydro-2-furanyl]-2-({4-[4-(trifluoromethoxy)phenoxy]phenyl}sulfonyl)ethyl]formamide;

hydroxy[1-[(4S)-3-methyl-2-oxo-1,3-oxazolidin-4-yl]-2-({4-[4-(trifluoromethoxy)phenoxy]phenyl}sulfonyl)ethyl]formamide;

hydroxy[1-[(2R)-5-oxotetrahydro-2-furanyl]-2-({4-[4-(trifluoromethoxy)phenoxy]phenyl}sulfonyl)ethyl]formamide;

hydroxy[1-[1-(methylsulfonyl)-4-piperidinyl]-2-({4-[4-(trifluoromethoxy)phenoxy]phenyl}sulfonyl)ethyl]formamide;

hydroxy[1-(1-isobutyryl-4-piperidinyl)-2-({4-[4-(trifluoromethoxy)phenoxy]phenyl}sulfonyl)ethyl]formamide;

hydroxy{2-(4-morpholinylsulfonyl)-1-[({4-[4-(trifluoromethoxy)phenoxy]phenyl}sulfonyl)methyl]ethyl}formamide;

hydroxy{2-methyl-2-(4-morpholinylsulfonyl)-1-[({4-[4-(trifluoromethoxy)phenoxy]phenyl}sulfonyl)methyl]propyl}formamide;

hydroxy{8-[({4-[4-(trifluoromethoxy)phenoxy]phenyl}sulfonyl)methyl]-1,4-dioxaspiro[4.5]dec-8-yl}formamide;

1,1-dimethyl-2-({4-[4-(trifluoromethoxy)phenoxy]
    phenyl}sulfonyl)ethyl(hydroxy)formamide;
hydroxy{2-(2-thienyl)-1-[({4-[4-(trifluoromethoxy)
    phenoxy]phenyl}sulfonyl)methyl]ethyl}formamide;
(1S)-1-[(4S)-2,2-dimethyl-1,3-dioxolan-4-yl]-2-{[4-(4-
    methoxyphenoxy)phenyl]sulfonyl}ethyl(hydroxy)
    formamide;
1,2,3-trideoxy-2-[formyl(hydroxy)amino]-4,5-O-(1-
    methylethylidene)-1-({4-[4-(trifluoromethoxy)
    phenoxy]phenyl}sulfonyl)-D-threo-pentitol;
(1S)-2-{[4-(4-chlorophenoxy)phenyl]sulfonyl}-1-[(4S)-
    2,2-dimethyl-1,3-dioxolan-4-yl]ethyl(hydroxy)
    formamide;
2-[formyl(hydroxy)amino]-N,N-dimethyl-3-({4-[4-
    (trifluoromethoxy)phenoxy]phenyl}sulfonyl)
    propanamide;
hydroxy{2-(4-morpholinyl)-2-oxo-1-[({4-[4-
    (trifluoromethoxy)phenoxy]phenyl}sulfonyl)methyl]
    ethyl}formamide;
N-[2-[formyl(hydroxy)amino]-3-({4-[4-
    (trifluoromethoxy)phenoxy]phenyl}sulfonyl)propyl]-
    N-methylmethanesulfonamide;
(1S)-1-[(4S)-2,2-dimethyl-1,3-dioxolan-4-yl]-2-({4-[4-
    (trifluoromethyl)phenoxy]phenyl}sulfonyl)ethyl
    (hydroxy)formamide;
(1S)-1-[(4S)-2,2-dimethyl-1,3-dioxolan-4-yl]-2-({4-[4-
    (methylphenoxy]phenyl}sulfonyl)ethyl(hydroxy)
    formamide;
4-({(2S)-2-[(4S)-2,2-dimethyl-1,3-dioxolan-4-yl]-2-
    [formyl(hydroxy)amino]ethyl}sulfonyl)-4'-
    (trifluoromethyl)-1,1'-biphenyl;
methyl 4-[3-[formyl(hydroxy)amino]-4-({4-[4-
    (trifluoromethoxy)phenoxy]phenyl}sulfonyl)butyl]
    benzoate;
4-[3-[formyl(hydroxy)amino]-4-({4-[4-
    (trifluoromethoxy)phenoxy]phenyl}sulfonyl)butyl]
    benzoic acid;
hydroxy{3-[4-(hydroxymethyl)phenyl]-1-[({4-[4-
    (trifluoromethoxy)phenoxy]phenyl}sulfonyl)methyl]
    propyl}formamide;
2-{[4-(4-chlorophenoxy)phenyl]sulfonyl}-1-{[(4-
    chlorophenyl)sulfonyl]methyl}ethyl(hydroxy)
    formamide;
hydroxy{(1S)-4-hydroxy-1-[({4-[4-(trifluoromethoxy)
    phenoxy]phenyl}sulfonyl)methyl]butyl}formamide;
hydroxy{(1R)-2-({4-[4-(trifluoromethoxy)phenoxy]
    phenyl}sulfonyl)-1-[(4S)-3,5,5-trimethyl-2-oxo-1,3-
    thiazolidin-4-yl]ethyl}formamide;
hydroxy{1-[({4-[4-(trifluoromethoxy)phenoxy]
    phenyl}sulfonyl)methyl]cyclopentyl}formamide;
(1R)-1-[(4S)-5,5-dimethyl-2-oxo-1,3-thiazolidin-4-yl]-2-
    ({4-[4-(trifluoromethoxy)phenoxy]phenyl}sulfonyl)
    ethyl(hydroxy)formamide;
1,1-dioxido-4-[({4-[4-(trifluoromethoxy)phenoxy]
    phenyl}sulfonyl)methyl]tetrahydro-2H-thiopyran-4-yl
    (hydroxy)formamide;
(1S)-2-((4-(4-chlorophenoxy)phenyl)sulfonyl)-1-((4,4-
    dimethyl-2,5-dioxo-1-imidazolidinyl)methyl)ethyl
    (hydroxy)formamide;
(1S)-2-(4,4-dimethyl-2,5-dioxo-1-imidazolidinyl)-1-
    (((4'-(trifluoromethyl)(1,1'-biphenyl)-4-yl)sulfonyl)
    methyl)ethyl(hydroxy)formamide;
hydroxy(4-(((4-(4-(trifluoromethoxy)phenoxy)phenyl)
    sulfonyl)methyl)tetrahydro-2H-pyran-4-yl)formamide;
(1S)-2-(2,5-dioxo-1-imidazolidinyl)-1-(((4-(4-
    (trifluoromethoxy)phenoxy)phenyl)sulfonyl)methyl)
    ethyl(hydroxy)formamide;
1-acetyl-4-(((4-(4-(trifluoromethoxy)phenoxy)phenyl)
    sulfonyl)methyl)-4-piperidinyl(hydroxy)formamide;
hydroxy(1-(methylsulfonyl)-4-(((4-(4-(trifluoromethoxy)
    phenoxy)phenyl)sulfonyl)methyl)-4-piperidinyl)
    formamide;
2,2-dimethyl-5-(((4-(4-(trifluoromethoxy)phenoxy)
    phenyl)sulfonyl)methyl)-1,3-dioxan-5-yl(hydroxy)
    formamide;
(1S)-1-((4S)-1,3-dioxolan-4-yl)-2-((4-(4-
    (trifluoromethoxy)phenoxy)phenyl)sulfonyl)ethyl
    (hydroxy)formamide;
4-(((2S)-2-((4S)-2,2-dimethyl-1,3-dioxolan-4-yl)-2-
    (formyl(hydroxy)amino)ethyl)sulfonyl)-4'-(2-
    methoxyethoxy)-1,1'-biphenyl;
(1S)-1-((4S)-2,2-dimethyl-1,3-dioxolan-4-yl)-2-((4-(4-
    (2-methoxyethoxy)phenoxy)phenyl)sulfonyl)ethyl
    (hydroxy)formamide;
hydroxy(4-(4-morpholinyl)-4-oxo-1-(((4-(4-
    (trifluoromethoxy)phenoxy)phenyl)sulfonyl)methyl)
    butyl)formamide;
1,2,4-trideoxy-2-(formyl(hydroxy)amino)-4,4-dimethyl-
    3,5-O-(1-methylethylidene)-1-((4-(4-
    (trifluoromethoxy)phenoxy)phenyl)sufonyl)-D-threo-
    pentitol;
hydroxy((2R)-2-phenyl-1-(((4-(4-(trifluoromethoxy)
    phenoxy)phenyl)sulfonyl)methyl)propyl)formamide;
2-(2-((tert-butyl(dimethyl)silyl)oxy)ethoxy)-1-(((4-(4-
    (trifluoromethoxy)phenoxy)phenyl)sulfonyl)methyl)
    ethyl(hydroxy)formamide;
hydroxy(2-(2-hydroxyethoxy)-1-(((4-(4-
    (trifluoromethoxy)phenoxy)phenyl)sulfonyl)methyl)
    ethyl)formamide;
(1S)-2-(4,4-dimethyl-2,5-dioxo-1-imidazolidinyl)-1-
    (((4'-methoxy(1,1'-biphenyl)-4-yl)oxy)methyl)ethyl
    (hydroxy)formamide;
(1S)-2-(4,4-dimethyl-2,5-dioxo-1-imidazolidinyl)-1-
    (((4'-methyl(1,1'-biphenyl)-4-yl)oxy)methyl)ethyl
    (hydroxy)formamide;
4-(((2S)-2-(formyl(hydroxy)amino)-3-(3,4,4-trimethyl-2,
    5-dioxo-1-imidazolidinyl)propyl)oxy)-4'-
    (trifluoromethoxy)-1,1'-biphenyl;
hydroxy((1S,2S)-2-(4-isobutylphenyl)-1-(((4-(4-
    (trifluoromethoxy)phenoxy)phenyl)sulfonyl)methyl)
    propyl)formamide;
hydroxy(3-hydroxy-2,2-dimethyl-1-(((4-(4-
    (trifluoromethoxy)phenoxy)phenyl)sulfonyl)methyl)
    propyl)formamide;
1,2,3-trideoxy-2-(formyl(hydroxy)amino)-4,5-O-(1-
    methylethylidene)-1-((4-(4-(trifluoromethoxy)
    phenoxy)phenyl)sulfonyl)-D-erythro-pentitol;
hydroxy(3-(((4-(4-(trifluoromethoxy)phenoxy)phenyl)
    sulfonyl)methyl)-3,4-dihydro-2H-1,5-benzodioxepin-
    3-yl)formamide;
ethyl 4-(formyl(hydroxy)amino)-4-(((4-(4-
    (trifluoromethoxy)phenoxy)phenyl)sulfonyl)methyl)
    cyclohexanecarboxylate;
4-(formyl(hydroxy)amino)-4-(((4-(4-(trifluoromethoxy)
    phenoxy)phenyl)sulfonyl)methyl)
    cyclohexanecarboxylic acid;
hydroxy(4-hydroxy-1-methyl-1-(((4-(4-
    (trifluoromethoxy)phenoxy)phenyl)sulfonyl)methyl)
    butyl)formamide;

4-cyano-4'-(((4-(formyl(hydroxy)amino)tetrahydro-2H-pyran-4-yl)methyl)sulfonyl)-1,1'-biphenyl;

hydroxy(4-(((4'-(trifluoromethyl)(1,1'-biphenyl)-4-yl)sulfonyl)methyl)tetrahydro-2H-pyran-4-yl)formamide;

(1R)-1-((4S)-5,5-dimethyl-2-oxo-1,3-thiazolidin-4-yl)-2-((4-(4-(trifluoromethoxy)phenoxy)phenyl)sulfonyl)ethyl(hydroxy)formamide;

hydroxy(2-(1-piperidinyl sulfonyl)-1-(((4-(4-(trifluoromethoxy)phenoxy)phenyl)sulfonyl)methyl)ethyl)formamide;

hydroxy(2-(1-pyrrolidinylsulfonyl)-1-(((4-(4-(trifluromethoxy)phenoxy)phenyl)sulfonyl)methyl)ethyl)formamide;

4-((3-(1,4-dioxaspiro[4.5]dec-8-yl)-2-formyl(hydroxy)amino)propyl)sulfonyl)-4'-fluoro-1,1'-biphenyl;

2-(formyl(hydroxy)amino)-N,N-dimethyl-3-((4-(4-(trifluoromethoxy)phenoxy)phenyl)sulfonyl)-1-propanesulfonamide;

2-(1,4-dioxa-8-azaspiro[4.5]dec-8-ylsulfonyl)-1-(((4-(4-(trifluoromethoxy)phenoxy)phenyl)sulfonyl)methyl)ethyl(hydroxy)formamide;

1-(1,4-dioxaspiro[4.5]dec-8-yl)-2-((4-(4-(trifluoromethoxy)phenoxy)phenyl)sulfonyl)ethyl(hydroxy)formamide;

3-(cyanomethyl)-4'-(((4-(formyl(hydroxy)amino)tetrahydro-2H-pyran-4-yl)methyl)sulfonyl)-1,1'-biphenyl;

2-(formyl(hydroxy)amino)-N-(4-(hydroxymethyl)phenyl)-N-methyl-3-((4-(4-(trifluoromethoxy)phenoxy)phenyl)sulfonyl)-1-propanesulfonamide;

N,N-diethyl-2-(formyl(hydroxy)amino)-3-((4-(4-(trifluoromethoxy)phenoxy)phenyl)sulfonyl)-1-propanesulfonamide;

methyl(3-(2-(formyl(hydroxy)amino)-3-((4-(4-(trifluoromethoxy)phenoxy)phenyl)sulfonyl)propyl)phenyl)acetate;

(3-(2-(formyl(hydroxy)amino)-3-((4-(4-(trifluoromethoxy)phenoxy)phenyl)sulfonyl)propyl)phenyl)acetic acid; and 1,2-dideoxy-2-(formyl(hydroxy)amino)-3,4-O-(1-methylethylidene)-1-((4-(4-(trifluoromethoxy)phenoxy)phenyl)sulfonyl)-L-threo-pentitol.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection or for rectal administration.

The pharmaceutical compositions of this invention can be administered to humans and other animals orally, rectally, parenterally, intracisternally, intravaginally, intraperitoneally or topically (such as powders, ointments or drops), bucally or as an oral or nasal spray. The term "parenteral" administration, as used herein, refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms may be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form may be brought about by the inclusion of agents (such as aluminum monostearate and gelatin) which delay absorption.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable mediajust prior to use.

Solid dosage forms for oral administration include capsules, tablets, pills, powders and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and may also be of a composition such that they release the active ingredient(s) only, or preferentially, in a certain part of the intestinal tract, optionally or in delayed fashion. Examples of embedding compositions which can be used include polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents such as ethoxylated isostearyl alcohols, polyoxyethylene sorbitol and sorbitan esters, microcrystalline cellulose, aluminum metahydroxide, bentonite, agar-agar, and tragacanth and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which may be required. Opthalmic formulations, eye ointments, powders and solutions are also contemplated as being within the scope of this invention. Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg, of active compound per kilogram of body weight per day when administered orally to a mammalian patient. If desired, the effective daily dose may be divided into multiple doses for purposes of administration, e.g. two to four separate doses per day.

Determination of Stromelysin Inhibition

The efficacy of the compounds of this invention as matrix metalloproteinase inhibitors was determined by measuring the inhibition of stromelysin. The inhibition of stromelysin by the compounds of this invention was determined as follows: Recombinant truncated stromelysin (human sequence) produced in E. coli was prepared by expression and purification of the protein as described by Ye et al. (Biochemistry, 1992, 31, 11231–11235, which is incorporated herein by reference). The enzyme was assayed by its cleavage of the thiopeptide ester substrate Ac-Pro-Leu-Gly-[2-mercapto- 4-methylpentanoyl]-Leu-Gly-OEt as described by Weingarten and Feder (Anal. Biochem., 1985, 147, 437–440 (1985), which is incorporated herein by reference) as a substrate of vertebrate collagenase. The reported conditions were modified to allow assays to be carried out in a microtiter plate. Upon hydrolysis of the thioester bond, the released thiol group reacted rapidly with 5,5'-dithio-bis(2-nitrobenzoic acid) (DTNB) to produce a yellow color which was measured by a microtiter plate reader set at 405 nm. The rates of cleavage of the substrate by stromelysin in the presence or absence of inhibitors were measured in a 30 minute assay at ambient temperature. Solutions of the compounds in DMSO were prepared, and these were diluted at various concentrations into the assay buffer (50 mM MES/NaOH pH 6.5 with 10 mM $CaCl_2$ and 0.2% Pluronic F-68), which was also used for dilution of the enzyme and substrate. The potency of the compounds [$IC_{50}$] was calculated from the inhibition/inhibitor concentration data. The compounds of this invention inhibited stromelysin as shown by the data for representative examples in Table 1.

TABLE 1

| Example | $IC_{50}$ (nM) |
| --- | --- |
| 1 | 130 |
| 2 | 36 |
| 3 | 21 |
| 4 | 9.1 |
| 5 | 17 |
| 6 | 30 |
| 7 | 120 |
| 8 | 170 |
| 9 | 100 |
| 10 | 1,500 |
| 11 | 300 |
| 12 | 180 |

TABLE 1-continued

| Example | IC$_{50}$ (nM) |
|---|---|
| 13 | 310 |
| 14 | 4,000 |
| 15 | 620 |

Preparation of Compounds of this Invention

The compounds and processes of the present invention will be better understood in connection with the following synthetic schemes which are merely illustrative of the methods by which the compounds of the invention may be prepared and are not intended to limit the scope of the invention as defined in the appended claims. Representative procedures are outlined in the following Schemes 1–5.

Abbreviations

Abbreviations which have been used in the descriptions of the schemes and the examples that follow are: THF for tetrahydrofuran; DMF for N,N-dimethylformamide; rt 0for room temperature; TBDMSC1 for tert-butyldimethylsilyl chloride; h for hour; decomp. for decomposition; sat. for saturated; LAH for lithiumaluminum chloride; min for minutes; aq. for aqueous; and m-CPBA for meta-chloroperbenzoic acid.

As shown in Scheme 1, deprotonation of the phenolic moiety of 1 with a base, preferably sodium or potassium hydride, and alkylation of the resulting anion with an excess, preferably a two to four-fold excess, of an electrophile, preferably epibromohydrin or epichlorohydrin, provided the alkylated epoxide 2. An excess of a second nucleophile, preferably a two to four-fold excess, was deprotonated with a base such as sodium or potassium hydride and condensed with 2 to provide alcohol 3 which was treated with bis-Boc-hydroxylamine under Mitsunobu conditions to provide the bis-Boc protected hydroxylamine 6. Removal of the Boc-protecting groups with acid, preferably HCl in dioxane or trifluoroacetic acid in methylene chloride, and neutralization of the amine salt with a base, preferably sodium bicarbonate, provided an exposed hydroxylamine moiety which was treated with a formylating agent, preferably formicacetyl anhydride, in solvents such as THF or dichloromethane to provide hydroxamic acid 7.

Alternatively, 2 was converted to the corresponding iodoketone 4 by a two-step procedure which comprised (a) treatment of the epoxide with triphenylphosphine and an iodinating agent, preferably iodine, in an inert solvent such as dichloromethane to provide the corresponding iodoalcohol followed by (b) oxidation to the corresponding iodoketone 4 with a mild oxidizing agent, preferably Dess-Martin periodinane (Dess, D. B.; Martin, J. C., J. Am. Chem. Soc. 1991, 113, 7277–7287, which is incorporated herein by reference). Introduction of $R_1$ was accomplished by alkylation of the desired phenol or benzenenethiol derivative with 4 in the presence of base, preferably potassium carbonate, in a polar solvent such as DMF. The resulting ketone was converted to the corresponding oxime 5 by treatment with hydroxylamine hydrochloride in a hydroxylic solvent, preferably ethanol, with a catalytic amount of base, preferably pyridine. When $R_1$ contained sulfur, the alcohol was oxidized to the corresponding ketone using Dess-Martin periodinane in an inert solvent such as dichloromethane then converted to 5 as described above. Treatment of 5 with a reducing agent, preferably boranepyridine complex, in a hydroxylic solvent, preferably ethanol, and adding excess aqueous hydrochloric acid provided the corresponding hydroxylamine which was formylated as described above to provide 7. Depending on the nature of $R_1$ group, protection and subsequent deprotection of other reactive groups was required to successfully complete the described synthetic sequences. Commonly used protecting groups are disclosed in Greene, "Protective Groups In Organic Synthesis," (John Wiley & Sons, New York (1981)), which is incorporated herein by reference.

Scheme 1

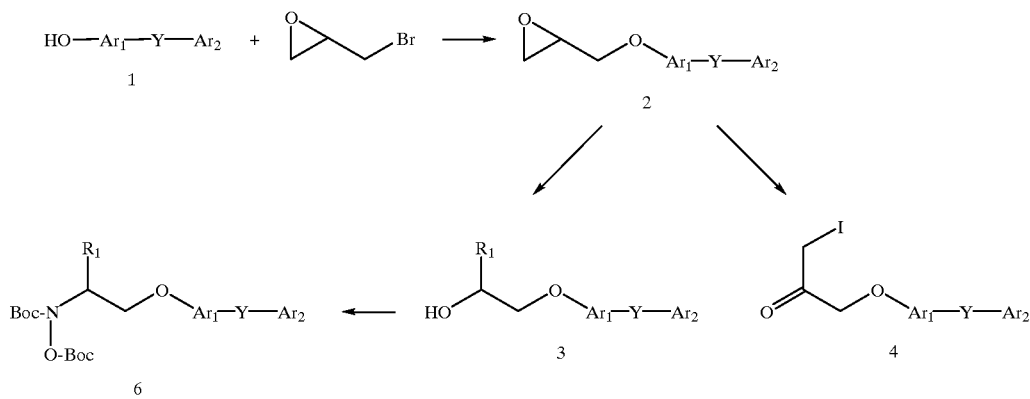

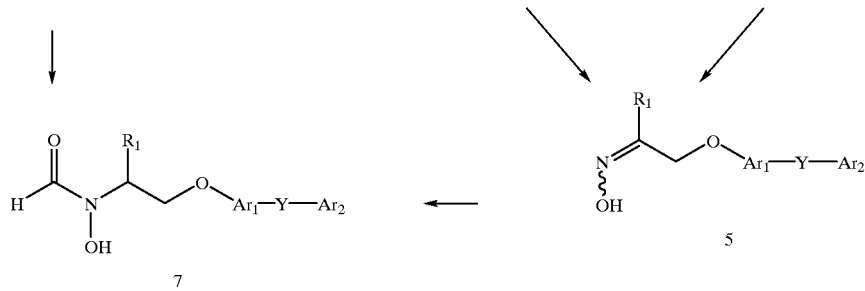

Scheme 2 shows an alternate preparation of intermediate 5. Alkylation of 1 with ethyl bromoacetate was accomplished in the presence of base, preferably potassium carbonate, in a polar solvent, preferably DMF, to provide 8, which was subsequently hydrolyzed to 9 by treatment with aqueous base, preferably lithium hydroxide in a solvent mixture, preferably water and dioxane. Amide 10 was prepared by coupling N,O-dimethylhydroxylamine hydrochloride to 9 with a coupling agent, preferably bis(2-oxo-3-oxazolidinyl)phosphinic chloride (BOP-Cl). Treatment of 10 with $R_1$-MgX, wherein X is Br or Cl, at reduced temperature, preferably −78° C. in an inert solvent, preferably THF, provided ketone 11, which was converted to 5, and finally to 7, as described in Scheme 1.

be utilized to convert 14 into the hydroxamic acid by employing HO-$Ar_1$-Y-$Ar_2$ in place of $R_1$-H. Heterocyclic derivatives of $R_1$-H, preferably those having appropriate pKa's, such as the hydantoin in this scheme, were condensed with the desired olefinic alcohol under Mitsunobu conditions to provide the corresponding N-alkenylheterocycle 12. Treatment of 12 with an alkylating agent, preferably methyl iodide, in the presence of base, preferably sodium hydride, provided N-methyl alkenylheterocycle 13, which was epoxidized with meta-chloroperbenzoic acid (MCPBA) in dichloromethane to provide 14. The reaction sequence described in Scheme 1 was then used to convert 14 to hydroxamic acid 5.

Scheme 2

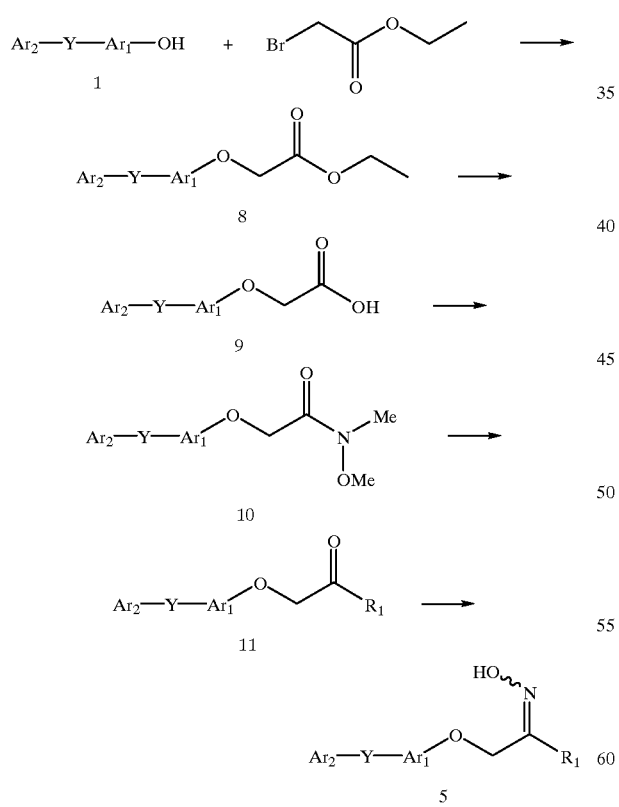

Scheme 3

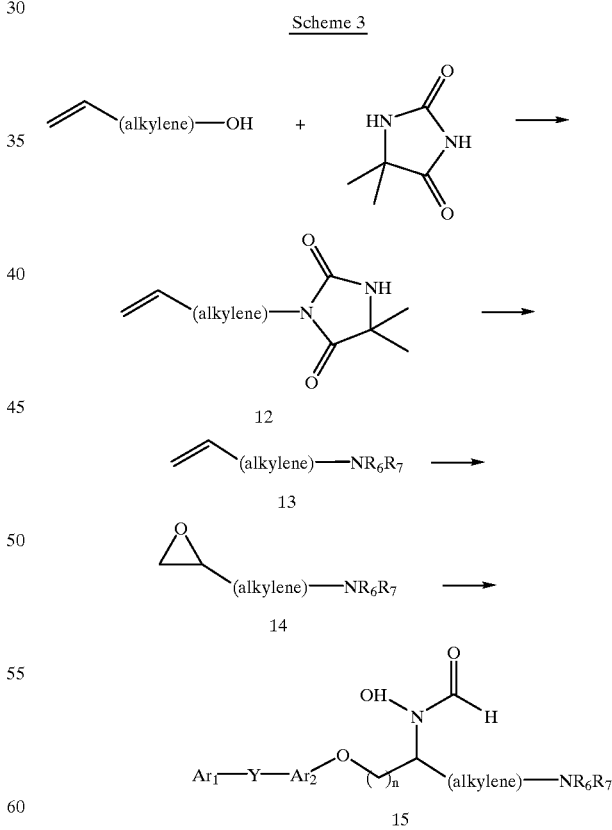

Scheme 3 shows the synthesis of compounds where the introduction of the phenolic and $R_1$ groups was reversed. This route intersects with the route described in Scheme 1 at epoxide 14, and the chemistry described in Scheme 1 may wherein the alkylene group is of one to six carbon atoms, n is 1, and $R_6$ and $R_7$ together with the nitrogen aton to which they are attached, form

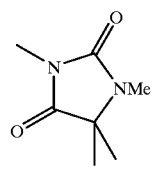

Scheme 4 shows an alternate synthesis of the hydantoin substituted compounds 22 and 23. Alkylation of 16 with a substituted hydantoin 17 in the presence of base, preferably potassium carbonate provides the enol ether 18. Treatment of 18 with a brominating agent such as NBS in acetone, gives the the bromoketone 19 which can then be alkylated with either aryl thiols (20, X=S) or substituted phenols (20, X=O) to afford the ketones 21. Ketones 21, wherein Y is a covalent bond could also be prepared from 19 in a two step procedure, first alkylating with either bromo thiophenols (20a, X=S) or bromophenols (20a, H=O), then coupling the aryl bomides 10a with an appropriate aryl boronic acid following the Suzuki protocol, or an appropriate arul stannane. The reaction sequence described in scheme 1 can then be used to convert 21 into the hydroxamic acids 22. The compounds wherein X=S can be converted to the sulfones 23 via oxidation with an appropriate oxidant such as m-chloroperbenzoic acid or oxone.

Scheme 4

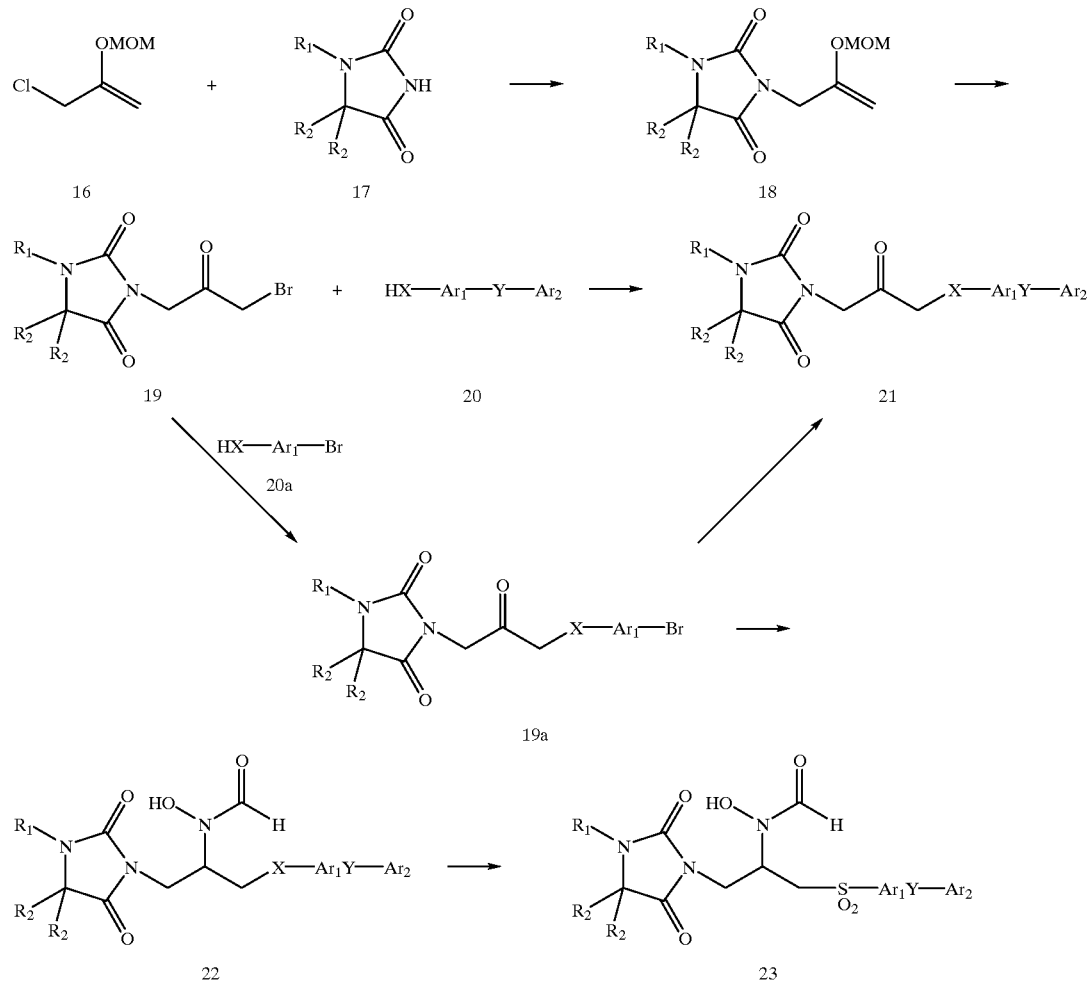

Scheme 5 shows an alternate synthesis of the sulfones 29. Deprotonation of the sulfone 25 with a base such as LDA followed by addition to a ketone or aldehyde 24 gives an alcohol which can be dehydrated either by reaction with acid, such as toluene sulfonic acid or by a stepwise 2 step procedure: first convering the alcohol into a leaving group, such as mesylate via treatment with mesyl chloride and triethyl amine, then eliminating with a base, preferably 1,8-diazabicyclo[5.4.0]undec-7-ene. Reaction of the olefin with an O-protected hydroxylamime preferably O-benzyl gives the adduct 28. Formylation as previously described in scheme 1 followed by removal of the protecting group, preferably under hydrogenation conditions for the compounds wherin P is benzyl affords the sulfone 29. The sulfone 28 can also be prepared directly via the deprotonation of sulfone 25, with a base such as n-BuLi and subsequent addition, preferably in the presence of boron trifluoride etherate, to a O-protected oxime 30.

($Na_2SO_4$), filtered, and concentrated to provide 1.65 g of a golden oil which was purified on silica gel with 10% ethyl acetate/hexanes (500 mL) and 20% ethyl acetate/hexanes to provide 1.19 g (75%) of the title compound.

MS ($DCI/NH_3$) m/e 168 $(M+NH_4)^+$ and 185 $(M+NH_4+NH_3)^+$.

EXAMPLE 1B (±)-1-(4-(4'-Carbonitrilephenyl)phenoxy)-3-phenoxy-2-propanol

A suspension of sodium hydride (0.18 g, 4.39 mmol) in THF (4 mL) was treated sequentially with a solution of 4'-hydroxy-4-biphenylcarbonitrile (0.78 g, 3.99 mmol) in THF (4 mL), Example 1A (0.60 g, 3.99 mmol) in THF (2 mL) then DMF (6 mL), refluxed for 1 hour, cooled, treated with 20% aqueous potassium hydrogen sulfate and partitioned between ethyl acetate and brine. The organic layer Scheme 5

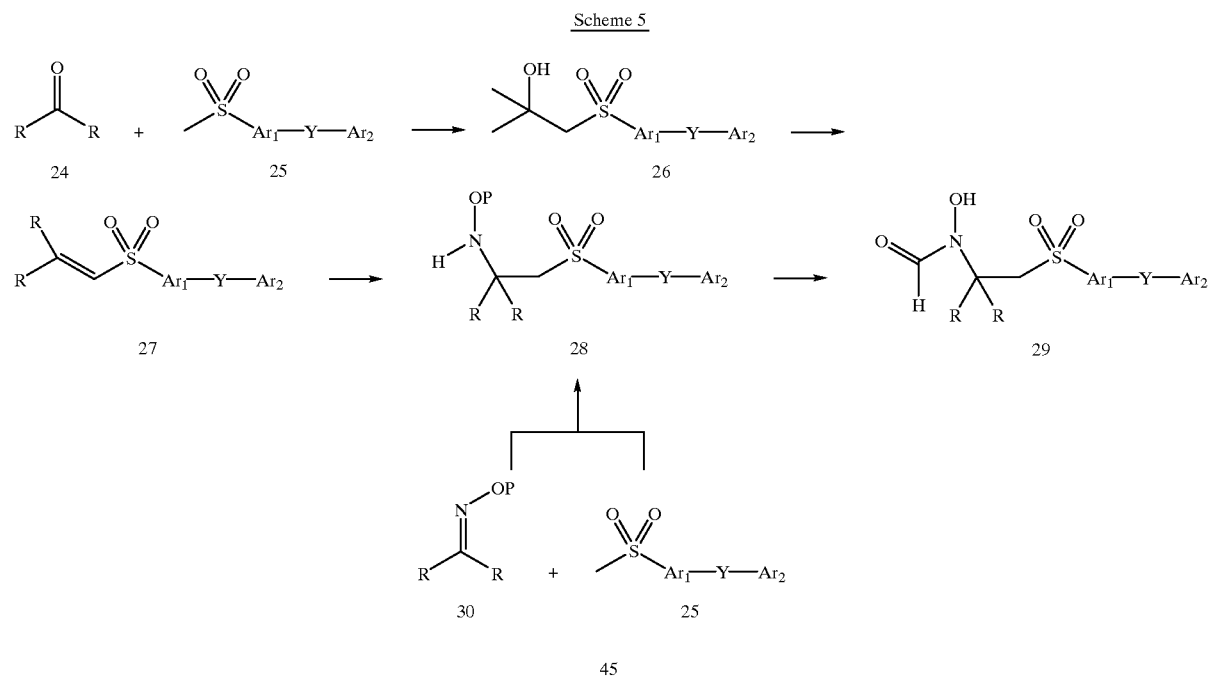

The foregoing may be better understood by reference to the following examples which illustrate the methods by which the compounds of the invention may be prepared and are not intended to limit the scope of the invention as defined in the appended claims.

EXAMPLE 1

(±)-N-[1-[[(4'-cyano-[1,1'-biphenyl]-4-yl)oxy]methyl]-2-phenoxyethyl]-N-hydroxyformamide

EXAMPLE 1A (±)-3-Phenoxypropan-[1,2]oxirane

A suspension of sodium hydride (0.47 g, 11.7 mmol) in THF (20 mL) was treated sequentially with a solution of phenol (1.00 g, 10.6 mmol) in THF (20 mL) then epibromohydrin (2.73 mL, 31.8 mmol) in a single portion, refluxed for 2 hours, cooled, treated with 20% aqueous potassium hydrogen sulfate then partitioned between ethyl acetate and brine. The organic layer was washed sequentially with saturated aqueous sodium bicarbonate and brine, dried was washed with saturated aqueous sodium bicarbonate, 15% aqueous sodium hydroxide and brine, dried ($Na_2SO_4$), filtered, and concentrated to provide 1.04 g of a yellow oil which was purified on silica gel with 25–30% ethyl acetate/hexanes to provide 0.42 g (22%) of the title compound.

MS ($DCI/NH_3$) m/e 363 $(M+NH_4)^+$ and 380 $(M+NH_4+NH_3)^+$.

EXAMPLE 1C (±)-N,O-bis(t-butlyoxycarbonyl)-1-(4-(4'-carbonitrilephenyl)phenoxy)-3-phenoxy-prop-2-yl-N-hydroxylamine A solution of Example 1B (0.41 g, 1.19 mmol), triphenylphosphine (0.40 g, 1.54 mmol), and di-Boc-hydroxylamine (0.33 g, 1.42 mmol) in THF (5 mL) was treated dropwise with diethylazodicarboxylate (0.24 mL, 1.54 mmol), stirred at ambient temperature for 1 hour and concentrated. The resulting oil was redissolved in dichloromethane (30 mL) and concentrated under vacuum (2 cycles) to remove any excess THF then purified on silica gel with 15% ethyl acetate/hexanes to provide 0.50 g (75%) of the title compound as a colorless foam.

MS (DCI/NH$_3$) m/e 578 (M+NH$_4$)$^+$.

EXAMPLE 1D (±)-1-(4-(4'-Carbonitrilephenyl)phenoxy)-3-phenoxy-prop-2-yl-N-hydroxylamine A solution of Example 1C (0.45 g; 0.80 mmol) in dichloromethane (3 mL) was treated with trifluoroacetic acid (6 mL), stirred for 15 minutes at ambient temperature, poured into excess saturated aqueous sodium bicarbonate and extracted with ethyl acetate. The resulting organic extracts were washed with brine, dried (Na$_2$SO$_4$), filtered, and concentrated to provide 0.70 g of a brown oil which was purified on silica gel with 50% ethyl acetate/hexanes to provide 0.23 g (81%) of deprotected hydroxylamine as a light yellow foam.

EXAMPLE 1E (±)-N-[1-[[(4'-cyano-[1,1'-biphenyl]-4-yl)oxy]methyl-]2-phenoxyethyl]-N-hydroxyformamide A solution of Example 1D (0.15 g, 0.41 mmol) in dichloromethane (2 mL) was cooled to −10° C. and treated with a solution of formicacetyl anhydride (38 mg, 0.43 mmol) in dichloromethane (1 mL), stirred for 15 minutes, diluted with ether and washed sequentially with saturated aqueous sodium bicarbonate, 10% aqueous hydrochloric acid, saturated aqueous sodium bicarbonate and brine, dried (Na$_2$SO$_4$), filtered, and concentrated to provide 0.17 g of a brown, glassy oil which was purified on silica gel with 97.5% (40% ethyl acetate/hexanes)/2.5% methanol to provide 67 mg (42%) of light brown foam which was recrystallized from ethyl acetate/hexanes/acetone to provide the title compound as light pink, clumpy crystals.

mp 133–135° C.; $^1$H NMR (300 MHz, CDCl$_3$) δ 8.15 (br s; 1H), 8.07 (s; 1H), 7.69 (AB; 1H; J=9 Hz), 7.62 (AB; 1H; J=9 Hz), 7.54 (d; 1H; J=9 Hz), 7.32 (dd; 1H; J=6.5, 8.0 Hz), 6.97–7.06 (m; 3H), 6.92 (d; 2H; J=7.5 Hz), 4.24–4.47 (m; 5H); MS (DCI/NH$_3$) m/e 345 (M+NH$_4$-HCONHOH)$^+$; Anal. calcd for C$_{23}$H$_{20}$N$_2$O$_4$: C, 71.12; H, 5.19; N, 7.21. Found: C, 71.04; H, 5.16; N, 7.01.

EXAMPLE 2

(±)-N-[1-[[(4'-cyano-[1,1'-biphenyl]-4-yl)oxy]methyl]-2-(phenylthio)ethyl]-N-hydroxyformamide

EXAMPLE 2A (±)-3-(4-(4'-Carbonitrilephenyl)phenoxy)propan-[1,2]oxirane

The title compound was prepared following the procedure from Example 1A but using 4'-hydroxy-4-biphenylcarbonitrile (10.0 g, 51.2 mmol) in place of phenol. Purification by trituration with ether provided 9.13 g (71%) the title compound as a chalky solid.

mp 115–116° C.; MS (DCI/NH$_3$) m/e 269 (M+NH$_4$)$^+$ and 286 (M+NH$_4$+NH$_3$)$^+$.

EXAMPLE 2B (±)-1-(4-(4'-Carbonitrilephenyl)phenoxy)-3-thiophenoxy-2-propanol A solution of Example 2A (0.90 g), triethylamine (1.75 mL), and benzenethiol (1.10 mL) in absolute ethanol (14 mL) was heated at reflux for 1 hour, cooled and partitioned between ethyl acetate and 10% aqueous sodium hydroxide. The organic layer was washed sequentially with 10% aqueous hydrochloric acid, saturated aqueous sodium bicarbonate and brine, dried (Na$_2$SO$_4$), filtered, and concentrated to provide 1.27 g of a thick golden oil which was purified by recrystallization from ethyl acetate/hexanes/methanol to provide the title compound as colorless, clumpy crystals.

mp 105–106° C.; MS (DCI/NH$_3$) m/e 379 (M+NH$_4$)$^+$.

EXAMPLE 2C (±)-1-(4-(4'-Carbonitrilephenyl)phenoxy)-3-thiophenoxy-2-propanone A suspension of the Dess-Martin periodinane in dichloromethane (25 mL) was treated with Example 2B (2.02 g) in dichloromethane (15 mL), stirred at ambient temperature for 0.5 hours and partitioned between ethyl acetate and saturated aqueous sodium bicarbonate. The organic layer was washed sequentially with saturated aqueous sodium thiosulfate, saturated aqueous sodium bicarbonate and brine, dried (Na$_2$SO$_4$), filtered, and concentrated to provide 2.27 g of a clumpy, orange solid which was purified on silica gel with 30% ethyl acetate/hexanes to provide 1.90 g of the title compound as a chalky, light yellow solid.

MS (DCI/NH$_3$) m/e 377 (M+NH$_4$)$^+$.

EXAMPLE 2D (±)-1-(4-(4'-Carbonitrilephenyl)phenoxy)-3-thiophenoxy-2-propanone oxime A solution of Example 2C (2.02 g) in methanol (20 mL) and THF (10 mL) was treated sequentially with 10 drops of pyridine then hydroxylaminehydrochloride (0.78 g), heated at reflux for 1 hour, cooled and partitioned between ethyl acetate and saturated aqueous sodium bicarbonate. The organic layer was washed sequentially with water and brine, dried (Na$_2$SO$_4$), filtered, and concentrated to provide 1.90 g of the title compound as a chalky yellow solid which was used without further purification.

MS (DCI/NH$_3$) m/e 375 (M+H)$^+$ and 392 (M+NH$_4$)$^+$.

EXAMPLE 2E (±)-N-(4-(4'-carbonitrilephenyl)phenoxy)-3-thiophenoxyprop-2-yl)hydroxylamine A solution of Example 2D (1.90 g) in THF (10 mL) was treated sequentially with absolute ethanol (20 mL), borane-pyridine (1.5 mL) then dropwise with 6N aqueous hydrochloric acid, stirred for 1 hour at ambient temperature, poured into excess saturated aqueous sodium bicarbonate and extracted with ethyl acetate. The combined organic extracts were washed with brine, dried (Na$_2$SO$_4$), filtered, and concentrated to provide 2.25 g of an orange oil which was purified on silica gel with 30% ethyl acetate/hexanes to provide 1.26 g of the title compound as a light gold oil.

MS (DCI/NH$_3$) m/e 377 (M+H)$^+$ and 394 (M+NH$_4$)$^+$.

EXAMPLE 2F (±)-N-[1-[[(4'-cyano-[1,1'-biphenyl]-4-yl)oxy]methyl]-2-(phenylthio)ethyl]-N-hydroxyformamide A solution of compound 2E (1.24 g) in THF (10 mL) was cooled to −23° C. and treated with a solution of formicacetylanhydride (280 µL) in THF (2 mL), stirred for 15 minutes, diluted with ether. The organic layer was washed sequentially with saturated aqueous sodium bicarbonate, 10% aqueous hydrochloric acid, saturated aqueous sodium bicarbonate and brine, dried ($Na_2SO_4$), filtered, and concentrated to provide 1.27 g of a glassy orange oil which was purified on silica gel with 97.5% (40% ethyl acetate/hexanes)/2.5% methanol to provide 300 mg of the title compound as a light orange foam.

$^1$H NMR (300 MHz, $CDCl_3$) δ 7.95 (br s; 1H), 7.90 (s; 1H), 7.70 (AB; 1H; J=7.5 Hz), 7.62 (AB; 1H; J=7.5 Hz), 7.51 (d; 1H; J=9 Hz), 7.20–7.43 (m; 5H), 6.95 (d; 2H; J=9 Hz), 4.33 (dd; 1H; J=8.5,10.5 Hz), 4.17 (dd; 1H; J=4.5,10.5 Hz), 4.0 (m; 1H), 3.36 (dd; 1H; J=8.5,14 Hz), 3.28 (dd; 1H; J=6,14 Hz); MS (DCI/$NH_3$) m/e 422 (M+$NH_4$)$^+$. Anal. calcd for $C_{23}H_{20}N_2O_3S$: C, 68.30; H, 4.98; N, 6.73. Found: C, 68.19; H, 4.86; N, 6.73.

EXAMPLE 3

(±)-N-[1-[[(4'-cyano-[1,1'-biphenyl]-4-yl)oxy]
methyl]-2-(2,3-dihydro-1,3-dioxo-1H-isoindol-2-yl)
ethyl]-N-hydroxyformamide

EXAMPLE 3A (±)-3-(4-(4'-Carbonitrilephenyl)phenoxy)-3-iodo-2-propanol

A solution of iodine (1.54 g, 6.0 mmol) in dichloromethane (20 mL) was treated with triphenylphosphine (1.58 g, 6.0 mmol), stirred for 5 minutes, treated with 3-(4'-carbonitrilephenyl)phenoxy)propan-(1,2) oxirane (1.0 g, 4.0 mmol) in a single portion, stirred at ambient temperature for 30 minutes, treated with water and partitioned between ethyl acetate and brine. The organic layer was dried ($Na_2SO_4$), filtered, and concentrated to provide 3 g of crude product which was purified on silica gel with 30% ethyl acetate/hexanes to provide 1.38 g (91%) of the title compound.

MS (DCI/$NH_3$) m/e 397 (M+$NH_4$)$^+$ and 414 (M+$NH_4$+$NH_3$)$^+$.

EXAMPLE 3B 3-(4-(4'-Carbonitrilephenyl)phenoxy)-1-iodopropan-2-one

The title compound was prepared as in Example 2C but using Example 3A (1.0 g, 2.63 mmol) in place of 3-(4-(4'-carbonitrilephenyl)phenoxy)-1-thiophenoxypropan-2-ol. Purification on silica gel with 20% ethyl acetate/hexanes provided 0.65 g (66%) of the title compound.

MS (DCI/$NH_3$) m/e 395 (M+$NH_4$)$^+$ and 412 (M+$NH_4$+$NH_3$)$^+$.

EXAMPLE 3C 1-(4-(4'-Carbonitrilephenyl)phenoxy)-3-phthaloylpropan-2-one

A solution of Example 3B (1.38 g; 3.66 mmol) in DMF (20 mL) was treated with potassium phthalimide (1.02 g; 5.50 mmol), stirred at ambient temperature for 10 minutes, treated with water and partitioned between ethyl acetate and brine. The organic layer was dried ($Na_2SO_4$), filtered, and concentrated to provide 1.1 g of crude product which was purified on silica gel with ethyl acetate to provide 0.98 g (67%) of the title compound.

MS (DCI/$NH_3$) m/e 414 (M+$NH_4$)$^+$.

EXAMPLE 3D (±)-N-[1-[[(4'-cyano-[1,1'-biphenyl]-4-yl)oxy]
methyl]-2-(2,3-dihydro-1,3-dioxo-1H-isoindol-2-yl)
ethyl]-N-hydroxyformamide The title compound was prepared according to Example 2D but using Example 3C (0.56 g, 1.41 mmol) in place of 1-(4-(4'-carbonitrilephenyl)phenoxy)-3-thiophenoxypropan-2-one to provide the corresponding oxime which was reduced according to Example 2E using 1-(4-(4'-carbonitrilephenyl)phenoxy)-3-phthaloylpropan-2-one oxime in place of 1-(4-(4'-carbonitrilephenyl)phenoxy)-3-thiophenoxypropan-2-one oxime. The resulting hydroxylamine was formylated according to Example 2F but using 1-(4-(4'-carbonitrilephenyl)phenoxy)-3-phthaloyl-2-propylhydroxylamine in place of 1-(4-(4'-carbonitrilephenyl)phenoxy)-3-thiophenoxy-2-propylhydroxylamine. Purification on silica gel with 60% ethyl acetate/hexanes provided 0.185 g (30%) of the title compound.

mp 199–202° C.; $^1$H NMR (300 MHz, $CDCl_3$) δ 10.06 (s; 0.5H), 9.67 (s; 0.5H), 8.32 (s; 0.5H), 7.99 (s; 0.5H), 7.88 (m; 8H), 7.72 (m; 2H), 7.02 (m; 3H), 4.96 (m; 0.5H), 4.52 (m; 0.5H), 4.25 (m; 2H), 3.78–4.00 (m; 2H); MS (DCI/$NH_3$) m/e 459 (M+$NH_4$)$^+$; Anal. calcd for $C_{25}H_{19}N_3O_5$: C, 67.96; H, 4.304; N, 9.51. Found: C, 67.43; H, 4.34; N, 9.04.

EXAMPLE 4

(±)-N-[1-[[(4'-cyano-[1,1'-biphenyl]-4-yl)oxy]
methyl]-2-(3,4,4-trimethyl-2,5-dioxoimidazolidiny-1-yl)ethyl]-N-hydroxyformamide

EXAMPLE 4A (±)-1-(4-(4'-Carbonitrilephenyl)phenoxy)-3-((5,5-dimethyl)hydantoin-3-yl)-2-propanol A solution of 5,5-dimethylhydantoin (0.26 g, 1.99 mmol) in THF (20 mL) was treated with potassium tert-butoxide (1.99 mL, 1.99 mmol), stirred for 5 minutes, treated with 3-(4'-carbonitrilephenyl)phenoxy)-(1,2) oxirane (0.50 g, 1.99 mmol) in a single portion, stirred at 70° C. for 6 hours, treated with excess saturated aqueous ammonium chloride and partitioned between ethyl acetate and brine. The organic layer was dried ($Na_2SO_4$), filtered, and concentrated to provide a yellow solid which was purified on silica gel with ethyl acetate to provide 0.70 g (93%) of the title compound.

MS (DCI/$NH_3$) m/e 397 (M+$NH_4$)$^+$.

EXAMPLE 4B (±)-1-(4-(4'-Carbonitrilephenyl)phenoxy)-3-(3-(5,5-dimethyl)hydantoin)-2-(t-butyldimethylsilyloxy)
propane A solution of Example 4A (0.40 g, 1.06 mmol) in dichloromethane (20 mL) was treated with tert-butyldimethylsilyl chloride (0.24 g, 1.60 mmol) and imidazole (0.1 g, 1.6 mmol), stirred at ambient temperature for 30 minutes, treated with water and partitioned between ethyl acetate and brine. The organic layer was dried ($Na_2SO_4$), filtered, and concentrated to provide a solid which was purified on silica gel with 50% ethyl acetate/hexanes to provide 0.50 g (95%) of the title compound.

MS (DCI/$NH_3$) m/e 511 (M+$NH_4$)$^+$.

EXAMPLE 4C (±)-1-(4'-Cyano-[1,1'-biphenyl]-4-yl)oxy)-3-(3,4,4-trimethyl-2,5-dioxo-1-imidazolidin-1-yl)-2-t-butyldimethylsilyloxypropane A solution of 4B (0.60 g, 1.20 mmol) in THF (20 mL) was treated with sodium hydride (0.035 g, 1.40 mmol) then

EXAMPLE 4D (±)-1-(4'-Cyano-[1,1'-biphenyl]-4-yl)oxy)-3-(3,4,4-trimethyl-2,5-dioxo-1-imidazolidin-1-yl)-2-propanol A solution of Example 4C in THF (30 mL) was treated with tetrabutylammonium fluoride (1M in THF, 2.0 mL, 2.0 mmol), stirred at ambient temperature for 30 minutes, treated with water and partioned between ethyl acetate and brine. The organic layer was dried ($Na_2SO_4$), filtered, and concentrated to provide crude product which was purified on silica gel with ethyl acetate to provide 0.47 g (100%) of the title compound.

MS ($DCI/NH_3$) m/e 411 $(M+NH_4)^+$.

EXAMPLE 4E 1-(4'-Cyano-[1,1'-biphenyl]-4-yl)oxy)-3-(3,4,4-trimethyl-2,5-dioxoimidazolidin-1-yl)-2-propanone Example 4D (0.59 g, 1.50 mmol) was processed according to the procedure in Example 2C. Purification of the crude product on silica gel with 50% ethyl acetate/hexanes provided 0.58 g (98%) of the title compound.

MS ($DCI/NH_3$) m/e 409 $(M+NH_4)^+$.

EXAMPLE 4F (±)-[1-(4'-Cyano-[1,1'-biphenyl]-4-yl)oxy)-3-(3,4,4-trimethyl-2,5-dioxoimidazolidin-1-yl)-prop-2-yl] hydroxylamine Example 4E (0.57 g, 1.46 mmol) was processed according to the procedures in Examples 2D and 2E. Purification of the crude product on silica gel with 60% ethyl acetate/hexanes provide 0.31 g (52%) of the title compound.

MS ($DCI/NH_3$) m/e 409 $(M+H)^+$.

EXAMPLE 4G (±)-N-[1-[[(4'-cyano-[1,1'-biphenyl]-4-yl)oxy]methyl]-2-(3,4,4-trimethyl-2,5-dioxoimidazolidin-1-yl)ethyl]-N-hydroxyformamide Example 4F was processed according to the procedure in Example 2F. Purification of the crude product on silica gel with 60% ethyl acetate/hexanes provided 0.19 g (60%) of the title compound.

mp 65–67° C.; MS ($DCI/NH_3$) m/e 437 $(M+H)^+$ and 454 $(M+NH_4)^+$. $^1H$ NMR (300 MHz, $CDCl_3$) δ 9.90 (s; 0.5H), 9.58 (s; 0.5H), 8.32 (s; 0.5H), 7.92 (s; 0.5H), 7.85 (m; 4H), 7.72 (d; 2H; J=5.6 Hz), 7.02 (dd; 2H; J=5.5, 2.5 Hz), 4.86 (m; 0.5H), 4.42 (m; 0.5H), 4.08–4.02 (m; 2H), 3.82–3.70 (m; 1H), 3.55–4.05 (m; 1H), 2.8 (s; 1.5H), 2.78 (s; 1.5H), 1.5 (s; 3H), 1.48 (s; 3H); Anal. calcd for $C_{23}H_{24}N_4O_5$: C, 63.23; H, 5.50; N, 12.83. Found: C, 62.96; H, 5.55; N, 12.45.

EXAMPLE 5

(±)-N-[1-[[(4'-cyano-[1,1'-biphenyl]-4-yl)oxy]methyl-3-(3,4,4-trimethyl-2,5-dioxoimidazolidiny-1-yl)propyl]-N-hydroxyformamide

EXAMPLE 5A 1-(Prop-2-enyl)-4,4-dimethyl-2,5-dioxoimidazolidine

A solution of 3-buten-1-ol (1 g, 13.9 mmol), triphenylphosphine (4.73 g, 18 mmol) and 5,5-dimethylhydantoin (2.1 g, 16.7 mmol) in THF (50 mL) was treated dropwise with diethylazodicarboxylate (3.13 g, 18.0 mmol), stirred at ambient temperature for 1 hour, treated with water and partitioned between ethyl acetate and brine. The organic layer was dried ($Na_2SO_4$), filtered, and concentrated to provide crude product which was purified on silica gel with 50% ethyl acetate/hexanes to provide 2.5 g (100%) of the title compound.

EXAMPLE 5B 1-(Prop-2-enyl)-3,4,4-trimethyl-2,5-dioxoimidazolidine

A solution of Example 5A (2.3 g, 12.6 mmol) in THF (50 mL) was treated with sodium hydride (0.45 g, 18.9 mmol) then iodomethane (2.7 g, 18.9 mmol) in a single portion, refluxed for 2 hours, cooled, treated with water, and partitioned between ethyl acetate and brine. The organic layer was dried ($Na_2SO_4$), filtered, and concentrated to provide 3.5 g of a yellow solid which was purified on silica gel with 50% ethyl acetate/hexanes to provide 2.4 g (98%) of the title compound.

MS ($DCI/NH_3$) m/e 214 $(M+NH_4)^+$.

EXAMPLE 5C (±)-1-((1',2'Oxiranyl)propyl)-3,4,4-trimethyl-2,5-dioxoimidazolidine A solution of Example 5B (3.0 g, 15.3 mmol) in dichloromethane (50 mL) was treated with m-chloroperbenzoic acid (4.4 g), stirred at ambient temperature for 2 hours, treated with saturated aqueous sodium carbonate and partitioned between ethyl acetate and brine. The organic layer was dried ($Na_2SO_4$), filtered, and concentrated to a solid which was purified on silica gel with 70% ethyl acetate/hexanes to provide 1.5 g (46%) of the title compound.

MS ($DCI/NH_3$) m/e 213 $(M+1)^+$ and 230 $(M+NH_4)^+$.

EXAMPLE 5D (±)-1-(2-Hydroxy-3-iodo-propyl)-3,4,4-trimethyl-2,5-dioxoimidazolidine A solution of iodine (0.29 g, 1.88 mmol) in dichloromethane (20 mL) was treated with triphenylphosphine (0.3 g, 1.88 mmol), stirred for 5 minutes, treated with Example 5C (0.2 g, 0.94 mmol) in a single portion, stirred at ambient temperature for 30 minutes, treated with water and partitioned between ethyl acetate and brine. The organic layer was dried ($Na_2SO_4$), filtered, and concentrated to provide a yellow solid which was purified on silica gel with 75% ethyl acetate/hexanes to provide 0.26 g (80%) of the title compound.

MS ($DCI/NH_3$) m/e 342 $(M+H)^+$ and 358 $(M+NH_4)^+$.

EXAMPLE 5E 1-(3-Iodo-propan-2-onyl)-3,4,4-trimethyl-2,5-dioxoimidazolidine

Example 5D was processed according to the procedure in Example 2C. Purification the crude product on silica gel with 60% ethyl acetate/hexanes provided 0.3 g (96%) of the title compound.

MS ($DCI/NH_3$) m/e 339 $(M+H)^+$ and 356 $(M+NH_4)^+$.

EXAMPLE 5F (±)-1-(3-[(4'-Cyano-[1,1'-biphenyl]-4-yl)oxy]-propan-2-on-1-yl)-3,4,4-trimethyl-2,5-dioxoimidazolidine A solution of 4'-hydroxy-4-biphenylcarbonitrile (0.38 g, 1.9 mmol) in THF (50 mL) was treated with potassium carbonate (0.5 g) then Example 5E (0.44 g, 1.30 mmol), refluxed for 7 hours, cooled, treated with 10% aqueous HCl and partitioned between ethyl acetate and brine. The organic layer was dried ($Na_2SO_4$), filtered, and concentrated to provide a yellow solid which was purified on silica gel with 75% ethyl acetate/hexanes to provide 0.52 g (99%) of the title compound.

MS (DCI/$NH_3$) m/e 423 (M+$NH_4$)$^+$.

EXAMPLE 5G (±)-1-(3-[(4'-Cyano-[1,1'-biphenyl]-4-yl)oxy]-propan-2-oximino-1-yl)-3,4,4-trimethyl-2,5-dioxoimidazolidine Example 5F was processed according to the procedure in Example 2D. The crude product was purified on silica gel with 75% ethyl acetate/hexanes to provide 0.68 g (1.60 mmol; 100%) of the title compound.

MS (DCI/$NH_3$) m/e 439 (M+$NH_4$)$^+$.

EXAMPLE 5H (±)-N-[1-[[(4'-cyano-[1,1'-biphenyl]-4-yl)oxy]methyl]-3-(3,4,4-trimethyl-2,5-dioxo-1-imidazolidinyl)propyl]-N-hydroxyformamide Example 5G was processed according to the procedures in Examples 2E and 2F. Purification of the crude product on silica gel with 75% ethyl acetate/hexanes provided 0.408 g (56%) of the title compound.

mp 68–70° C.; $^1$H NMR (300 MHz, $CDCl_3$) δ 9.99 (s; 0.5H), 9.46 (s; 0.5H), 8.35 (s; 0.5H), 7.92 (s; 0.5H), 7.92 (d; 2H; J=5.6 Hz), 7.85 (d; 2H; J=5.6 Hz), 7.70 (d; 2H; J=5.6 Hz), 7.05 (d; 2H; J=5.6 Hz), 4.52 (m; 0.5H), 4.18–3.95 (m; 3.5H), 3.46 (m; 2H), 2.82 (s; 1.5H), 2.79 (s; 1.5H), 2.02–1.72 (m; 1H), 1.32 (s; 6H); MS (DCI/$NH_3$) m/e 468 (M+$NH_4$)$^+$; Anal. calcd for $C_{24}H_{26}N_4O_5$: C, 63.93; H, 5.77; N, 12.43. Found: C, 63.38; H, 5.99; N, 11.97.

EXAMPLE 6

(±)-N-[1-[[[3'-(cyanomethyl)-[1,1'-biphenyl]-4-yl]oxy]methyl]pentyl]-N-hydroxyformamide

EXAMPLE 6A 4-((t-Butyldimethyl)silyloxy)phenyl boronic acid

A solution of (4-bromophenoxy)trimethylsilane (69 g, 20.9 mmol) in THF (60 mL) was treated with n-butyllithium at −78° C., stirred for 15 minutes, treated with triisopropyl borate, stirred at −78° C. for 10 minutes, warmed to ambient temperature, stirred for another 30 minutes, treated with water and partitioned between ethyl acetate and brine. The organic layer was dried ($MgSO_4$), filtered, and concentrated to provide 4.79 g (91%) of the title compound.

EXAMPLE 6B

4'-Hydroxy-3-biphenylcarbonitrilemethane

A mixture of Example 6A (4.8 g, 19.0 mmol), 3-bromophenyl acetonitrile (3.1 g, 16.0 mmol), cesium carbonate (7.8 g, 24.0 mmol) and tetrakis(triphenylphosphine)-palladium(0) (0.55 g, 0.48 mmol) was treated via syringe with DMF (30 mL) under positive nitrogen pressure, stirred at 100° C. for 10 h, treated with water and partitioned between ethyl acetate and brine. The organic layer was dried ($MgSO_4$), filtered, and concentrated to provide a brown oil which was purified on silica gel with 50% ethyl acetate/hexanes to provide 3.3 g (82%) of the title compound.

MS (DCI/$NH_3$) m/e 227 (M+$NH_4$)$^+$.

EXAMPLE 6C

Ethyl 2-(4-(3'-carbonitrilemethyphenyl)phenoxy)acetate

A solution of 6B (0.5 g, 2.4 mmol) in THF (20 mL) was treated with potassium cabonate (0.5 g) and ethyl bromoacetate (0.6 g, 3.6 mmol), refluxed for 3 hours, cooled, treated with 10% aqueous HCl and partitioned between ethyl acetate and brine. The organic layer was dried ($Na_2SO_4$), filtered, and concentrated to provide a yellow solid which was purified on silica gel with 50% ethyl acetate/hexanes to provide 0.48 g (68%) of the title compound.

$^1$H NMR (300 MHz, $CDCl_3$) δ 7.52 (m; 4H), 7.40 (m; 1H), 7.36 (m; 1H), 7.0 (m; 2H), 4.65 (s; 2H), 4.30 (q; 2H; J=4.8 Hz), 3.80 (s; 2H), 1.32 (t; 3H; J=4.8 Hz).

EXAMPLE 6D 2-(4-(3'-Carbonitrilemethylphenyl)phenoxy)acetic acid

A solution of 6C (0.47 g, 1.6 mmol) in 1,4-dioxane (20 mL) and water (10 mL) was treated with lithium hydroxide (0.5 g), stirred at ambient temperature for 30 minutes, treated with 10% aqueous HCl and partitioned between ethyl acetate and brine. The organic layer was dried ($Na_2SO_4$), filtered, and concentrated to provide a yellow solid which was purified on silica gel with 50% ethyl acetate/hexanes to provide 0.37 g (83%) of the title compound.

$^1$H NMR (300 MHz, $CDCl_3$) δ 7.60 (m; 4H), 7.46 (m; 1H), 7.32 (m; 1H), 7.02 (m; 2H), 4.72 (s; 2H), 4.08 (s; 2H).

EXAMPLE 6E

N,O-dimethyl-2-(4-(3'-carbonitrilemethylphenyl)phenoxy)acetyl hydroxylamine

A solution of 6D (0.35 g, 1.3 mmol), triethylamine (0.5 mL) and bis(2-oxo-3-oxazolidinyl)-phosphinic chloride (0.78 g, 2.6 mmol) in dichloromethane (20 mL) was treated with N,O-dimethyl-hydroxylamine hydrochloride (0.25 g, 2.6 mmol), stirred at ambient temperature for 2 hours, treated with water and partitioned between ethyl acetate and brine. The organic layer was dried ($Na_2SO_4$), filtered, and concentrated to provide a yellow solid which was purified on silica gel with 50% ethyl acetate/hexanes to provide 0.28 g (69%) of the title compound.

$^1$H NMR (300 MHz, $CDCl_3$) δ 7.59 (m; 4H), 7.46 (m; 1H), 7.32 (m; 1H), 7.02 (m; 2H), 4.96 (s; 2H), 4.08 (s; 2H), 3.78 (s; 3H), 3.15 (s; 3H).

EXAMPLE 6F 1-(4-(3'-Carbonitrilemethylphenyl)phenoxy)-2-hexanone

A solution of 6E (0.27 g, 0.85 mmol) in THF (10 mL) was treated with n-butylmagnesium bromide (1 mL, 2.0 mmol) at −78° C., stirred at −78° C. for 1 h, treated with water and partitioned between ethyl acetate and brine. The organic layer was dried ($Na_2SO_4$), filtered, and concentrated to provide a yellow solid which was purified on silica gel with 25% ethyl acetate/hexanes to provide 0.15 g (59%) of the title compound.

$^1$H NMR (300 MHz, CDCl$_3$) δ 7.52 (m; 4H), 7.42 (m; 1H), 7.28 (m; 1H), 6.98 (m; 2H), 4.60 (s; 2H), 3.82 (s; 2H), 2.62 (t; 2H; J=5.5 Hz), 1.64 (m; 2H); 1.38 (m, 2H), 0.92 (t; 3H; J=4.8 Hz).

EXAMPLE 6G (±)-N-[1-[[[3'-(cyanomethyl)-[1,1'-biphenyl]-4-yl]oxy]methyl]pentyl]-N-hydroxyformamide Example 6F (0.15 g, 0.50 mmol) was processed according to the procedures described in Examples 2D–F (inclusive). Purification of the crude final product on silica gel with 40% ethyl acetate/hexanes provided 0.07 g (41%) of the title compound.

mp 99–101° C.; MS (DCI/NH$_3$) m/e 352 (M+NH$_4$)$^+$. $^1$H NMR (300 MHz, CDCl$_3$) δ 8.58 (brs; 0.5H), 8.04 (brs; 0.5H), 8.0 (s; 1H), 7.48 (m; 4H), 7.42 (m; 1H), 7.26 (m; 1H), 6.98 (m; 2H), 4.05 (t; 1H; J=5.6 Hz), 3.8–4.0 (m; 2H), 3.80 (s; 2H), 1.92 (m; 1H0, 1.60 (m; 2H), 1.38 (m; 3H), 0.98 (t; 3H; J=4.8 Hz). Anal. calcd for C$_{21}$H$_{24}$N$_2$O$_3$: C, 71.50; H, 6.81; N, 7.94. Found: C, 71.44; H, 6.90; N, 7.80.

EXAMPLE 7

(±)-N-[1-[[(4'-cyano-[1,1'-biphenyl]-4-yl)oxy]methyl]-3-methylbutyl]-N-hydroxyformamide 4'-hydroxy-4-biphenylcarbonitrile (1.0 g, 5.12 mmol) was processed according to the procedures described in Examples 6C–G (inclusive), but substituting isobutylmagnesium bromide for the n-butylmagnesium bromide used in Example 6F. Purification of the crude final product on silica gel with 30% ethyl acetate/hexanes provided 0.036 g of the title compound.

mp 112–113° C.; MS (DCI/NH$_3$) m/e 356 (M+NH$_4$)$^+$. $^1$H NMR (300 MHz, CDCl$_3$) δ 7.95 (s; 1H), 7.70 (d; 2H; J=5.6 Hz), 7.62 (d; 2H; J=5.8), 7.52 (d; 2H; J=5.8 Hz), 6.98 (d; 2H; J=5.8 Hz), 4.25 (m; 1H), 3.92–4.05 (m; 2H), 1.95 (m; 1H), 1.75 (m; 1H), 1.35 (m; 1H), 1.00 (d; 3H; J=4.8 Hz), 0.98 (d; 3H; J=4.8 Hz). Anal. calcd for C$_{20}$H$_{22}$N$_2$O$_3$: C, 70.92; H, 6.50; N, 8.27. Found: C, 70.91; H, 6.68; N, 8.13.

EXAMPLE 8

(±)-N-[1-[[(4'-cyano-[1,1'-biphenyl]-4-yl)oxy]methyl]-2-methylbutyl]-N-hydroxyformamide The title compound was prepared following the sequence of steps described in Example 7 but substituting sec-butylmagnesium chloride for isobutylmagnesium bromide. Purification of the crude final product on silica gel with 30% ethyl acetate/hexanes provided 0.10 g of the title compound.

mp 96–98° C.; MS (DCI/NH$_3$) m/e 356 (M+NH$_4$)$^+$. $^1$H NMR (300 MHz, CDCl$_3$) δ 7.95 (s; 1H), 7.70 (d; 2H; J=5.6 Hz), 7.62 (d; 2H; J=5.8), 7.52 (d; 2H; J=5.8 Hz), 6.98 (d; 2H; J=5.8 Hz), 4.32 (m; 1H), 4.15 (m; 2H), 3.65 (m; 1H), 1.98 (m; 1H), 1.62 (m; 1H), 1.02 (m; 3H), 0.98 (m; 3H;). Anal. calcd for 0.8 H$_2$O+C$_{20}$H$_{22}$N$_2$O$_3$: C, 68.03; H, 6.69; N, 7.90. Found: C, 68.60; H, 6.58; N, 7.23.

EXAMPLE 9

(±)-N-[1-[[(4'-cyano-[1,1'-biphenyl]-4-yl)oxy]methyl]pentyl]-N-hydroxyformamide

The title compound was prepared following the sequence of steps described in Example 7 but substituting n-butylmagnesium bromide for isobutylmagnesium bromide. Purification of the crude final product on silica gel with 30% ethyl acetate/hexanes provided 0.210 g of the title compound.

mp 105–108° C.; MS (DCI/NH$_3$) m/e 356 (M+NH$_4$)$^+$. $^1$H NMR (300 MHz, CDCl$_3$) δ 7.95 (s; 1H), 7.70 (d; 2H; J=5.6 Hz), 7.62 (d; 2H; J=5.8), 7.52 (d; 2H; J=5.8 Hz), 6.98 (d; 2H; J=5.8 Hz), 4.25 (m; 1H), 3.99–3.82 (m; 2H), 1.92 (m; 1H), 1.60 (m; 2H), 1.40 (m; 3H), 0.98 (t; 3H; J=4.3 Hz). Anal. calcd for 0.5C$_6$H$_6$+C$_{20}$H$_{22}$N$_2$O$_3$: C, 73.13; H, 6.62; N, 7.42. Found: C, 73.18; H, 6.65; N, 7.39.

EXAMPLE 10

(±)-N-[1-[[(4'-cyano-[1,1'-biphenyl]-4-yl)oxy]methyl]-2-(4-methylphenyl)ethyl]-N-hydroxyformamide The title compound was prepared following the sequence of steps described in Example 7 but substituting 4-methylbenzylmagnesium bromide for isobutylmagnesium bromide. Purification of the crude final product on silica gel with 30% ethyl acetate/hexanes provided 0.24 g of the title compound.

mp 173–175° C.; MS (DCI/NH$_3$) m/e 404 (M+NH$_4$)$^+$. $^1$H NMR (300 MHz, CDCl$_3$) δ 7.70 (d; 2H; J=5.6 Hz), 7.68 (s; 1H), 7.62 (d; 2H; J=5.8), 7.52 (d; 2H; J=5.8 Hz), 7.12 (s; 4H), 6.98 (d; 2H; J=5.8 Hz), 4.35 (m; 1H), 4.12–3.98 (m; 2H), 3.15 (m; 1H), 2.94 (m; 1H), 1.35 (s; 3H). Anal. calcd for C$_{24}$H$_{22}$N$_2$O$_3$: C, 74.52; H, 5.69; N, 7.24. Found: C, 73.95; H, 5.79; N, 7.06.

EXAMPLE 11

(±)-N-[2-[(4'-cyano-[1,1'-biphenyl]-4-yl)oxy]-1-(4-fluorophenyl)ethyl]-N-hydroxyformamide The title compound was prepared following the sequence of steps described in Example 7, but substituting 4-fluorophenylmagnesium bromide for isobutylmagnesium bromide. Purification of the crude final product on silica gel with 30% ethyl acetate/hexanes provided 0.285 g of the title compound.

mp 194–196° C.; MS (DCI/NH$_3$) m/e 394 (M+NH$_4$)$^+$; $^1$H NMR (300 MHz, CDCl$_3$) δ 9.70 (brs; 1H), 8.42 (s; 0.5H), 8.28 (s; 0.5H), 7.86 (m; 4H), 7.72 (d; 2H; J=5.6 Hz), 7.55 (m; 2H), 7.25 (m; 2H), 7.12 (d; 2H; J=5.8 Hz), 5.72 (brs; 0.5H), 5.35 (brs; 0.5H), 4.60 (m; 1H), 4.36 (m; 1H); Anal. calcd for C$_{22}$H$_{17}$N$_2$O$_3$F: C, 70.14; H, 4.45; N, 7.44. Found: C, 70.19; H, 4.25; N, 7.30.

EXAMPLE 12

(±)-N-[-[[(4'-cyano-[1,1'-biphenyl]-4-yl)oxy]methyl]-2-(4-fluorophenyl)ethyl]-N-hydroxyformamide The title compound was prepared following the sequence of steps described in Example 7 but substituting 4-fluorobenzylmagnesium bromide for isobutylmagnesium bromide. Purification of the crude final product on silica gel with 30% ethyl acetate/hexanes provided 0.22 g of the title compound.

MS (DCI/NH$_3$) m/e 408 (M+NH$_4$)$^+$; $^1$H NMR (300 MHz, CDCl$_3$) δ 8.35 (brs; 1H), 7.65 (m; 5H), 7.52 (d; 2H; J=5.6 Hz), 7.20 (m; 2H), 6.98 (m; 4H), 4.35 (m; 1H), 4.15–3.98 (m; 2H), 3.18 (dd; 1H; J=6.0, 9.0 Hz), 2.95 (dd; 1H; J=3.0, 9.0 Hz); Anal. calcd for C$_{23}$H$_{19}$N$_2$O$_3$F: C, 70.69; H, 4.87; N, 7.17. Found: C, 70.38; H, 4.96; N, 6.98.

EXAMPLE 13

(±)-N-[1-[[(4'-cyano-[1,1'-biphenyl]-4-yl)oxy]methyl]ethyl]-N-hydroxyformamide

EXAMPLE 13A (4-(4'-Carbonitrilephenyl)phenoxy)propan-2-one

A solution of 4-(4'-carbonitrilephenyl)phenol (4.86 g, 24.9 mmol) in DMF (100 mL) was treated with potassium carbonate (13.8 g, 99.6 mmol), heated at 50° C. for 10 minutes, treated in a single portion with chloroacetone (2.48 mL, 30 mmol), stirred for 4 hours at ambient temperature and partitioned between 3:1 ether:hexanes and saturated aqueous sodium carbonate. The organic layer was dried (MgSO$_4$), filtered, and concentrated under vacuum to ⅓ of its original volume to cause precipitation of product from solution. The solution was treated with more ether and stored at −20° C. for 17 hours. The title compound (2.01 g, 32%) was collected by filtration and dried under vacuum.

MS (DCI/NH$_3$) m/e 251 (M)$^+$, 269 (M+NH$_4$)$^+$ and 286 (M+NH$_4$+NH$_3$)$^+$.

EXAMPLE 13B (±)-N-[1-[[(4'-cyano-[1,1'-biphenyl]-4-yl)oxy]methyl]ethyl]-N-hydroxyformamide The title compound was obtained following the procedures in Examples 2D–F (inclusive) but substituting Example 13A (2.00 g, 7.96 mmol) for Example 2C. Purification of the crude final product on silica gel with 5% methanol/dichloromethane provided 325 mg of the title compound.

mp 141–144° C.; $^1$H NMR (300 MHz, d$_6$-DMSO) δ 9.88 and 9.45 (br s; 1H), 8.02 and 8.33 (s; 1H), 7.90 (AB; 2H; J=7.5 Hz), 7.84 (AB; 2H; J=7.5 Hz), 7.61 (d; 2H; J=9 Hz), 7.06 (d; 2H; J=9 Hz), 4.67 (m; 0.32H), 3.92–4.25 (m; 2.68H), 1.23 and 1,18 (d; 3H; J=6 Hz); MS (DCI/NH$_3$) m/e 314 (M+NH$_4$)$^+$; Anal. calcd for C$_{17}$H$_{16}$N$_2$O$_3$: C, 68.90; H, 5.44; N, 9.45. Found: C, 68.61; H, 5.55; N, 9.21.

EXAMPLE 14

N-[2-[(4'-cyano-[1,1'-biphenyl]-4-yl)oxy]ethyl]-N-hydroxyacetamide

EXAMPLE 14A 2-(4-(4'-Carbonitrilephenyl)phenoxy)-bromoethane

A solution of 4-(4'-carbonitrilephenyl)phenol (3.00 g, 24.8 mmol) in DMF (20 mL) was treated with potassium carbonate (8.24 g, 99.4 mmol) and 1,2-dibromoethane (6.42 mL, 124 mmol), heated at 50° C. for 19 hours and partitioned between 3:1 ether:hexanes and water. The organic layer was separated and the aqueous layer was extracted with 3:1 ether:hexanes. The combined organic layers were dried (MgSO$_4$), filtered, and concentrated. Purification of the crude product on silica gel with 50% dichloromethane/hexanes) provided a white solid which was recrystallized from ether/pentane to provide 1.25 g (17%) of the title compound as colorless needles.

MS (DCI/NH$_3$) m/e 301/303 (M)$^+$, 319/321 (M+NH$_4$)$^+$ and 336/338 (M+NH$_4$+NH$_3$)$^+$.

EXAMPLE 14B

N,O-bis(t-butyloxycarbonyl)-2-[(4-(4'-carbonitrilephenyl)phenoxy)ethyl-N-hydroxylamine A solution of N,O-bis(t-butyloxycarbonyl)-N-hydroxylamine (443 mg, 1.9 mmol) in DMF (15 mL) was treated with a 60% oil dispersion of sodium hydride (76 mg, 1.9 mmol), stirred at ambient temperature for 15 minutes, treated with Example 13A (0.54 g, 1.79 mmol), stirred for 4 hours at ambient temperature and partitioned between 1:1 ether:hexanes and saturated aqueous ammonium chloride. The organic layer was separated, and the aqueous layer was extracted with 1:1 ether:hexanes. The combined organic layers were dried (MgSO$_4$), filtered, and concentrated. Purification on silica gel with 10% ethyl acetate/hexanes provided 0.65 g (80%) of the title compound as colorless viscous oil.

MS (DCI/NH$_3$) m/e 472 (M+NH$_4$)$^+$.

EXAMPLE 14C

2-[(4-(4'-Carbonitrilephenyl)phenoxy)ethyl-N-hydroxylamine hydrochloride

Example 14B (0.64 g, 1.41 mmol) was treated with 4N hydrochloric acid in dioxane (10 mL) and stirred at ambient temperature for 2.5 hours, during which time a colorless precipitate formed. The precipitate was collected by filtration, washed with dioxane, and dried to afford the HCl salt of the title compound as a colorless solid (0.22 g, 56%).

EXAMPLE 14D

N,O-bis(acetyl)-2-[(4-(4'-carbonitrilephenyl)phenoxy)ethyl-N-hydroxlamine

A solution of Example 14C (27 mg, 0.093 mmol) in THF at 0° C. was treated with triethylamine (32 μL, 0.23 mmol), stirred for 1 hour at 0° C., treated dropwise with acetyl chloride (16 μL), stirred for 1 hour at 0° C. and 18 hours at ambient temperature and partitioned between 1N aqueous hydrochloric acid and ether. The organic layer was separated, and the aqueous layer was extracted with ethyl acetate. The combined organic layers were dried (MgSO$_4$), filtered, and concentrated. Purification of the residue on silica gel with 2% acetone/dichloromethane provided 29 mg (83%) of the title compound.

MS (DCI/NH$_3$) m/e (M+NH$_4$)$^+$.

EXAMPLE 14D

N-[2-[(4'-cyano-[1,1'-biphenyl]-4-yl)oxy]ethyl]-N-hydroxyacetamide

A solution of Example 14D (29 mg, 0.077 mmol) in THF (5 mL) and ethanol (2 mL) was cooled to 0° C., treated with aqueous lithium hydroxide (0.31 mL of 1.0 N lithium hydroxide), stirred at 0° C. for 10 minutes and at ambient temperature for 1.5 hours and partitioned between water and ethyl acetate. The organic layer was separated and the aqueous layer was extracted with ether. The combined organic layers were washed with 1N aqueous hydrochloric acid, dried (MgSO$_4$), filtered, and concentrated to a semi-solid which was purified by trituration with ethyl acetate to provide 19.7 mg (86%) of the title compound as a colorless solid.

mp 174–175° C.; $^1$H NMR (300 MHz, d$_6$-DMSO) δ 9.90 (br s; 1H), 7.88 (AB; 2H; J=7.5 Hz), 7.84 (AB; 2H; J=7.5 Hz), 7.71 (d; 2H; J=8.5 Hz), 7.07 (d; 2H; J=8.5 Hz), 4.20 (t; 2H; J=7.5, 7.5 Hz), 3.89 (t; 2H; J=7.5, 7.5 Hz), 2.02 (s; 3H); MS (DCI/NH$_3$) m/e 297 (M+H)$^+$ and 314 (M+NH$_4$)$^+$; Anal. calcd for C$_{17}$H$_{16}$N$_2$O$_3$(0.25H$_2$O): C, 67.87; H, 5.52; N, 9.31. Found: C, 67.65; H, 5.55; N, 9.12.

EXAMPLE 15

N-[2-[(4'-cyano-[1,1'-biphenyl]-4-yl)oxy]ethyl]-N-hydroxyformamide

A solution of Example 14C (78 mg, 0.27 mmol) in THF (2.0 mL) was treated with triethylamine (75 μL, 0.54 mmol)

and then dropwise with formicacetyl anhydride (41 mg, 0.30 mmol) in THF (0.5 mL), stirred for 2 hours at ambient temperature and partitioned between ethyl acetate and 1N aqueous hydrochloric acid. The organic layer was separated and the aqueous layer was extracted with ethyl acetate. The combined organic layers were dried (MgSO$_4$), filtered, and concentrated. Purification by chromatography on silica gel with 0.2% acetic acid/ethyl acetate and subsequent recrystallization from cold methanol provided 14.7 mg (19%) of the title compound.

mp 142–145° C.; $^1$H NMR (300 MHz, d$_6$-DMSO) δ 10.17 and 9.74 (br s; 1H), 8.34 and 7.98 (br s; 1H), 7.88 (AB; 2H; J=7.5 Hz), 7.84 (AB; 2H; J=7.5 Hz), 7.73 (d; 2H; J=8.5 Hz), 7.07 (d; 2H; J=8.5 Hz), 4.14–4.26 (m; 2H), 3.77–3.88 (m; 2H); MS (DCI/NH$_3$) m/e 300 (M+NH$_4$)$^+$; Anal. calcd for C$_{16}$H$_{14}$N$_2$O$_3$(0.125H$_2$O): C, 67.54; H, 5.05; N, 9.84. Found: C, 67.59; H, 5.32; N, 9.53.

EXAMPLE 16

N-[1-[4-[(2E-phenylethenyl)phenoxy]methyl]-2-(3,4,4-trimethyl-2,5-dioxo-1-imidazolidinyl)ethyl]-N-hydroxyformamide

EXAMPLE 16A 3-(3,4,4-trimethyl-2,5-dioxoimidazolidin-1-yl)-2-methoxymethyloxy-prop-1-ene A mixture of 1,5,5 trimethylhydantoin (7.0 g, 49.2 mmol), powdered potassium carbonate (8.16 g, 59 mmol) and 2-methoxymethyloxy-allyl chloride (7.65 g, 56 mmol) in dry DMF (100 mL) was heated to 100° C. with stirring for 1.5 h. The reaction mixture was cooled, fliltered and the filtrate was concentrated, then partitioned between ethyl acetate and water. The organic extract was washed twice with water, brine, dried and concentrated, then purified via silica gel chromatography eluting with 50% ethyl acetate: hexane to give 10.58 g (89%) of the title compound.

MS (DCI/NH$_3$) m/e 243 (M+H)$^+$ and 260 (M+NH$_4$)$^+$.

EXAMPLE 16B 1-bromo-3-(3,4,4-trimethyl-2,5-dioxoimidazolidin-1-yl)propan-2-one A 0° C. solution of example 16A (10.58 g, 43.7 mmol) in acetone (200 mL) was treated sequentially with a solution of potassium carbonate (0.58 g, 4.2 mmol) in water (60 mL) and N-bromo succinimide (8.56 g, 48 mmol) and the resulting mixture was stirred with the ice bath in place. An additional 2 portions of 1.5 g of N-bromo succinimide were added after 1 and 2 h respectively. The ice bath was then removed and the reaction was allowed to stir for an additional 10 min, then was concentrated and extracted twice with ethyl acetate. The combined extracts were washed with aq. 0.5 M NaHSO3, 1M NaHCO3, water, brine, dried, filtered, and concentrated. The residue was purified via silica gel chromatography eluting with 50% ethyl acetate: hexane to give 7.39 g (61%) of the title compound.

MS (DCI/NH$_3$) m/e 277/279 (M+H)$^+$ and 294/296 (M+NH$_4$)$^+$.

EXAMPLE 16C 1-(4'-bromophenyloxy)-3-(3,4,4-trimethyl-2,5-dioxoimidazolidin-1-yl)-2-propanone To a suspension of 4-bromophenol (3.99 g, 23.0 mmol) and cesium carbonate (7.45 g, 22.9 mmol) in DMF (150 mL) was added a solution of bromoketone 16B (3 g, 11.5 mmol) in DMF (5 mL), drop-wise over 30 minutes. The suspension held at rt for 16 h, diluted with ethyl acetate (500 mL) and the organics washed with water, brine and dried over magnesium sulfate, filtered, and concentrated in vacuo. Flash chromatography (hexane/ethyl acetate 1:1) gave 2.55 g of 16C as a white solid.

EXAMPLE 16D

To a warm (100° ) solution of 16C (0.5 g, 1.35 mmol) and tributyl(phenylethynyl)tin (0.64 g, 1.62 mmol, Aldrich) in toluene (25 mL) was added a catalytic amount of Pd(PPh$_3$)$_4$. The reaction was brought to reflux and held for 7 h. The resulting black solution was diluted with ethyl acetate (125 mL) and the organics washed with 1M NaOH, brine, dried over magnesium sulfate, filtered, and concentrated in vacuo. Flash chromatography (gradient elution; hexane/ethyl acetate 4:1 to 1:1) gave 0.24 g of the desired compound after trituration with diethyl ether.

EXAMPLE 16E

N-[1-[4-[(2E-phenylethenyl)phenoxy]methyl]-2-(3,4,4-trimethyl-2,5-dioxo-1-imidazolidinyl)ethyl]-N-hydroxyformamide The title compound was prepared in the same manner as example 2D,E,F substituting 16D for 2C.

$^1$H NMR (300 MHz, d$_6$-DMSO) δ 9.90 (s, 0.5H), 9.58 (s, 0.5H), 8.31 (s, 0.5H), 7.9 (s, 0.5H), 7.57–7.54 (m, 6H), 7.38–7.33 (m, 2H), 7.26–7.08 (m, 6H), 6.94–6.90 (m, 2H), 4.80–4.60 (m, 0.5H), 4.55–4.40 (m, 0.5H), 4.16–4.04 (m, 4H), 3.76–3.73 (m, 2H), 3.61–3.57 (2, 2H), 2.79 (s, 6H), 1.28 (s, 12H); MS (ESI) m/e M–H (436), M+H (438); Anal. Calcd for: C$_{24}$H$_{27}$N$_3$O$_5$.H$_2$O: C, 63.28; H, 6.41; N, 9.22. Found: C, 63.06; H, 5.97; N, 8.94.

EXAMPLE 17

N-[1-[[4-(2-furanyl)phenoxy]methyl]-2-(3,4,4-trimethyl-2,5-dioxo-1-imidazolidinyl)ethyl]-N-hydroxyformamide Prepared in the same manner as example 16 substituting 2-(tributylstannyl)furan for tributyl(phenylethynyl)tin in example 16D.

$^1$H NMR (300 MHz, d$_6$-DMSO) δ 9.86 (s, 0.5H), 9.53 (s, 0.5H), 8.30 (s, 0.5H), 7.91 (s, 0.5H), 7.67–7.61 (m, 6H), 6.96–6.94 (m, 4H), 6.79–6.74 (d, 2H, J=3.4 Hz), 6.55–6.54 (m, 2H), 4.80–4.60 (m, 0.5H), 4.45–4.30 (m, 0.5H), 4.17–3.98 (m, 6H), 3.76–3.70 (m, 2H), 3.62–3.56 (m, 2H), 2.79 (s, 6H), 1.28 (s, 12H); MS (ESI) m/e M+H (402), M–H (400), M+NH$_4$ (419); Anal. Calcd for: C$_{20}$H$_{23}$N$_3$O$_6$: C, 59.84; H, 5.77; N, 10.46. Found: C, 59.83; H, 5.90; N, 10.12.

EXAMPLE 18

N-[1-[[(4'-butoxy[1,1'-biphenyl]-4-yl)oxy]methyl]-2-(3,4,4-trimethyl-2,5-dioxo-1-imidazolidinyl)ethyl]-N-hydroxyformamide

EXAMPLE 18A 1-(4'-butyloxy-[1,1'-biphenyl]-4-yl)oxy)-3-(3,4,4-trimethyl-2,5-dioxoimidazolidin-1-yl)-2-propanone To a warm (75° ) solution of example 16C (0.1 g, 0.27 mmol) and 4-butoxyphenylboronic acid (0.08 g, 0.41 mmol) in DME (2 mL) was added a 1M Na$_2$CO$_3$ solution (0.4 mL)

followed by a catalytic amount of PdCl$_2$(dppf). The reaction was held at 100° for 2 h, diluted with ethyl acetate (25 mL), washed with sat'd ammonium chloride, water, brine, dried over magnesium sulfate, filtered, and concentrated in vacuo. Flash chromatography (20% ethyl acetate in methylene chloride) gave 0.105 g of 5 as a white solid.

EXAMPLE 18B

N-[1-[[(4-butoxy[1,1'-biphenyl]-4-yl)oxy]methyl]-2-(3,4,4-trimethyl-2,5-dioxo-1-imidazolidinyl)ethyl]-N-hydroxyformamide Prepared in the same manner as example 2D,E,F substituting 18A for 2C.

$^1$H NMR (300 MHz, d$_6$-DMSO) δ 9.87 (s, 0.5H), 9.55 (s, 0.5H), 8.31 (s, 0.5H), 7.91 (s, 0.5H), 7.55–7.50 (m, 8H), 6.98–6.95 (m, 8H), 4.80–4.60 (m, 0.5H), 4.50–4.35 (m, 0.5H), 4.16–4.06 (m, 4H), 4.01–3.96 (t, 4H, J=7.0, 5.9 Hz), 3.76–3.70 (m, 2H), 3.62–3.59 (m, 2H), 2.80 (s, 6H), 1.72–1.65 (m, 4H), 1.48–1.40 (m, 4H), 1.29 (s, 12H), 0.96–0.91 (t, 6H, J=7.1, 7.5 Hz); MS (ESI) m/e M+H (484), M+NH$_4$ (506); Anal. Calcd for: C$_{26}$H$_{33}$N$_3$O$_6$: C, 64.57; H, 6.87; N, 8.68. Found: C, 64.70; H, 7.04; N, 8.50.

EXAMPLE 9

N-[1-[[(4'-fluoro[1,1'-biphenyl]-4-yl)oxy]methyl]-2-(3,4,4-trimethyl-2,5-dioxo-1-imidazolidinyl)ethyl]-N-hydroxyformamide

EXAMPLE 19A 3-(3,4,4-trimethyl-2,5-dioxo-1-imidazolidinyl)-propan-[1,2]oxirane The title compound was prepared following the procedures described for example 5A and 5C, but using allyl alcohol in place of 3-buten-1-ol.

EXAMPLE 19B

N-[1-[[(4'-fluoro [1,1'-biphenyl]-4-yl)oxy]methyl]-2-(3,4,4-trimethyl-2,5-dioxo-1-imidazolidinyl)ethyl]-N-hydroxyformamide Prepared according to the sequence of reaction described in examples 5D through 5H, substituting 19A for 5C in example 5D and 4-(4'-fluorophenyl)-phenol for 4'-hydroxy-4-biphenyl carbonitrile in example 5F.

$^1$H NMR (300 MHz, d$_6$-DMSO) δ 9.86 (S, 0.5H), 9.54 (S, 0.5H), 8.31 (S, 0.5H), 7.91 (S, 0.5H), 7.67–7.57 (M, 6H), 7.27–7.22 (M, 3H), 7.01–6.97 (M, 3H), 4.96–4.70 (M, 0.5H), 4.50–4.40 (M, 0.5H), 4.18–4.08 (M, 3H), 3.77–3.73 (M, 2H), 2.79 (S, 6H), 1.28 (S, 12H). MS (ESI) m/e 430 (M+H), 428 (M−H); Anal. Calcd for: C$_{22}$H$_{24}$N$_3$O$_5$F.0.5H$_2$O: C, 60.26; H, 5.74; N, 9.58. Found: C, 60.48; H, 5.66; N, 8.72.

EXAMPLE 20

N-[1-[(3,4,4-trimethyl-2,5-dioxo-1-imidazolidinyl)methyl]-2-[[4'-(trifluoromethyl)[1,1'-biphenyl]-4-yl]oxy]ethyl]-N-hydroxyformamide Prepared according to the sequence of reaction described in examples 5D through 5H, substituting 19A for 5C in example 5D and substituting 4-(4'-Trifluoromethylphenyl)phenol for 4'-hydroxy-4-biphenyl carbonitrile in example 5F.

$^1$H NMR (300 MHz, d$_6$-DMSO) δ 9.80 (S, 0.5H), 9.58 (S, 0.5H), 8.32 (S, 0.5H), 7.92 (S, 0.5H), 7.87–7.84 (D, 4H, J=8.1 Hz), 7.79–7.76 (D, 4H, J=8.8 Hz), 7.72–7.69 (d, 4H, J=8.4 Hz), 7.06–7.02 (m, 4H), 4.80–4.60 (m, 0.5H), 4.45–4.40 (m, 0.5H), 4.20–4.12 (m, 4H), 3.78–3.74 (m, 2H), 3.63–3.62 (m, 2H), 2.08 (s, 6H), 1.30 (s, 12H); MS (ESI) m/e M−H (478), M+H (480); Anal. Calcd for: C$_{23}$H$_{24}$N$_3$O$_5$F$_3$.0.5H$_2$O: C, 56.55; H, 5.15; N, 8.60. Found: C, 56.52; H, 5.07; N, 8.43.

EXAMPLE 21

N-[1-[[(4'-methoxy[1,1'-biphenyl]-4-yl)oxy]methyl]-2-(3,4,4-trimethyl-2,5-dioxo-1-imidazolidinyl)ethyl]-N-hydroxyformamide Prepared according to the sequence of reaction described in examples 5D through 5H, substituting 19A for 5C in example 5D and substituting 4-(4'-methoxyphenyl)phenol for 4'-hydroxy-4-biphenyl carbonitrile in example 5F.

$^1$H NMR (300 MHz, d$_6$-DMSO) δ 9.89 (s, 0.5H), 9.57 (s, 0.5H), 8.31 (s, 0.5H), 7.91 (s, 0.5H), 7.56–7.53 (d, 8H, J=8.8 Hz), 7.01–6.94 (m, 8H), 4.80–4.60 (m, 0.5H), 4.44–4.35 (m, 0.5H), 4.17–3.95 (m, 4H), 3.74–3.71 (m, 2H), 3.63–3.58 (m, 2H), 2.79 (s, 6H), 1.28 (s, 12H); MS (ESI) m/e M+H (442); Anal. Calcd for: C$_{23}$H$_{26}$N$_3$O$_6$.0.25H$_2$O: C, 62.08; H, 6.00; N, 9.44. Found: C, 62.25; H, 6.30; N, 8.94.

EXAMPLE 22

N-[1-[[(4'-methyl[1,1'-biphenyl]-4-yl)oxy]methyl]-2-(3,4,4-trimethyl-2,5-dioxo-1-imidazolidinyl)ethyl]-N-hydroxyformamide Prepared according to the sequence of reaction described in examples 5D through 5H, substituting 19A for 5C in example 5D and substituting 4-(4'-methylphenyl)phenol for 4'-hydroxy-4-biphenyl carbonitrile in example 5F.

$^1$H NMR (300 MHz, d$_6$-DMSO) δ 9.89 (s, 0.5H), 9.57 (s, 0.5H), 8.31 (s, 0.5H), 7.92 (s, 0.5H), 7.59–7.56 (d, 4H, J=8.8 Hz), 7.52–7.49 (d, 4H, J=8.1 Hz), 7.24–7.22 (d, 4H, J=7.7 Hz), 7.00–6.97 (m, 4H), 4.80–4.60 (m, 0.5H), 4.40–4.35 (m, 0.5H), 4.40–4.1 (m, 4H), 3.80–3.55 (m, 2H), 3.60–3.50 (m, 2H), 2.79 (s, 6H), 2.32 (s, 6H), 1.28 (s, 12H); MS (ESI) m/e 424 (M−H), 426 (M+H); Anal. Calcd for: C$_{23}$H$_{27}$N$_3$O$_5$.0.25H$_2$O: C, 64.24; H, 6.44; N, 9.77. Found: C, 64.30; H, 6.55; N, 9.36.

EXAMPLE 23

N-[1-[[(4'-butoxy[1,1'-biphenyl]-4-yl)oxy]methyl]-2-(4,4-dimethy-2,5-dioxo-1-imidazolidinyl)ethyl]-N-hydroxyformamide

EXAMPLE 23A 1-bromo-3-(4,4-dimethyl-2,5-dioxoimidazolidin-1-yl)propan-2-one

The title compound was prepared following the procedure desribed in examples 16A and 16B, except substituting 5,5 dimethylhydantoin for 1,5,5 trimethylhydantoin in example 16A.

EXAMPLE 23B

N-[1-[[(4'-butoxy[1,1'-biphenyl]-4-yl)oxy]methyl]-2-(4,4-dimethy-2,5-dioxo-1-imidazolidinyl)ethyl]-N-hydroxyformamide Prepared according to the procedures of example 16C and 16E, substituting example 23A for 16B and 4-(4'-Butyloxyphenyl)phenol for 4-bromophenol in example 16C.

¹H NMR (300 MHz, d₆-DMSO) δ 9.86 (s, 0.5H), 9.55 (s, 0.5H), 8.36 (s, 0.5H), 8.34 (s, 0.5H), 8.32 (s, 0.5H), 7.94 (s, 0.5H), 7.55–7.51 (m, 8H), 6.99–6.96 (m, 8H), 4.85–4.80 (m, 0.5H), 4.40–4.36 (m, 0.5H), 4.20–4.06 (mm, 2H), 4.01–3.97 (m, 4H), 3.78–3.71 (m, 2H), 3.60–3.51 (m, 2H), 1.73–1.66 (m, 6H), 1.48–1.38 (m, 4H), 1.25 (s, 12H), 0.96–0.86 (m, 6H); MS (ESI) m/e M–H (468); Anal. Calcd for: $C_{25}H_{30}ON_3O_6$: C, 63.95; H, 6.65; N, 8.94. Found: C, 63.89; H, 6.91; N, 8.63.

EXAMPLE 24

N-[1-[(4,4-dimethy-2,5-dioxo-1-imidazolidinyl)methyl]-2-[(4'-ethoxy[1,1'-biphenyl]-4-yl)oxy]ethyl]-N-hydroxyformamide Prepared according to the procedures of example 23B, except substituting 4-(4'-ethoxyphenyl)phenol for 4-(4'-Butyloxyphenyl)phenol.

¹H NMR (300 MHz, d₆-DMSO) δ 9.84 (s, 0.5H), 9.52 (s, 0.5H), 8.37 (s, 0.5H), 8.32 (s, 2H), 7.92 (s, 0.5H), 7.55–7.52 (m, 8H), 6.98–6.95 (d, 4H, J=8.8 Hz), 4.90–4.80 (m, 0.5H), 4.45–4.30 (m, 0.5H), 4.19–3.98 (m, 8H), 3.74–3.67 (m, 2H), 3.59–3.53 (m, 2H), 1.36–1.25 (m, 18H); MS (ESI) m/e M–H (440), M+H (442); Anal. Calcd for: $C_{23}H_{27}N_3O_6.0.5H_2O$: C, 61.32; H, 6.26; N, 9.32. Found: C, 61.12; H, 6.35; N, 9.32.

EXAMPLE 25

N-[1-[[4-(1,3-benzodioxol-5-yl)phenoxy]methyl]-2-(4,4-dimethy-2,5-dioxo-1-imidazolidinyl)ethyl]-N-hydroxyformamide Prepared according to the procedures of example 23B, except substituting 4-(3',4'-methylenedioxyphenyl)-phenol for 4-(4'-Butyloxyphenyl)phenol.

¹H NMR (300 MHz, d₆-DMSO) δ 9.84 (s, 0.5H), 9.52 (s, 0.5H), 8.37–8.31 (m, 3H), 7.91 (s, 0.5H), 7.55–7.52 (d, 4H, J=8.5 Hz), 7.19 (s, 2H), 7.09–7.06 (m, 2H), 6.97–6.93 (d, 6H), J=10.2 Hz), 6.03 (s, 4H), 4.70–4.60 (m, 0.5H), 4.45–4.30 (m, 0.5H), 4.16–3.96 (s, 6H), 3.73–3.57 (m, 5H), 1.27 (s, 12H); MS (ESI) m/e M+H (442), M–H (440); Anal. Calcd for: $C_{22}H_{23}N_3O_7.0.50H_2O$: C, 58.66; H, 5.37; N, 9.32. Found: C, 58.70; H, 5.80; N, 8.79.

EXAMPLE 26

N-[1-[[(4'-butoxy[1,1'-biphenyl]-4-yl)oxy]methyl]-2-(3-methy-2,5-dioxo-1-imidazolidinyl)ethyl]-N-hydroxyformamide

EXAMPLE 26A 1-bromo-3-(3-methyl-2,5-dioxoimidazolidin-1-yl)propan-2-one

The title compound was prepared following the procedure desribed in examples 16A and 16B, except substituting 1-methylhydantoin for 1,5,5 trimethylhydantoin in example 16A.

EXAMPLE 26B

N-[1-[[(4'-butoxy[1,1'-biphenyl]-4-yl)oxy]methyl]-2-(3-methy-2,5-dioxo-1-imidazolidinyl)ethyl]-N-hydroxyformamide Prepared according to the procedures of example 16C and 16E, substituting example 26A for 16B and 4-(4'-Butyloxyphenyl)phenol for 4-bromophenol in example 16C.

¹H NMR (300 MHz, d₆-DMSO) δ 9.97 (s, 0.5H), 9.60 (s, 0.5H), 8.34 (s, 0.5H), 7.97 (s, 0.5H), 7.55–7.50 (m, 8H), 6.99–6.91 (m, 8H), 4.86–4.82 (m, 0.5H), 4.33–4.31 (m, 0.5H), 4.18–4.12 (m, 2H), 3.99–3.94 (m, 4H), 2.85 (s, 6H), 1.82–1.68 (m, 4H), 1.50–1.38 (m, 6H), 0.96–0.91 (m, 6H); MS (ESI) m/e M–H (454); Anal. Calcd for: $C_{24}H_{29}N_3O_6.0.25C_4H_5O$: C, 63.51; H, 6.44; N, 8.88. Found: C, 63.59; H, 6.46; N, 8.68.

EXAMPLE 27

N-[1-[[4-(3-thienyl)phenoxy]methyl]-2-(3,4,4-trimethyl-2,5-dioxo-1-imidazolidinyl)ethyl]-N-hydroxyformamide Prepared according to the procedures of example 16C and 16E, substituting 4-(4'-(3-thienyl)phenyl)phenol for 4-bromophenol in example 16C.

¹H NMR (300 MHz, d₆-DMSO) δ 9.90 (s, 0.5H), 9.57 (s, 0.5H), 8.31 (s, 0.5H), 7.91 (s, 0.5H), 7.75–7.74 (m, 2H), 7.67–7.60 (m, 6H), 7.52–7.49 (m, 2H), 6.96–6.92 (m, 4H), 4.80–4.6 (m, 0.5H), 4.50–4.4 (m, 0.5H), 4.19–3.98 (m, 6H), 3.81–3.70 (m, 2H), 3.61–3.56 (m, 2H), 2.79 (s, 6H), 1.29 (s, 12H); Anal. Calcd for: $C_{20}H_{23}N_3O_5S$: C, 57.54; H, 5.55; N, 10.06. Found: C, 57.72; H, 5.84; N, 9.76.

EXAMPLE 28

N-[1-[[([1,1'-biphenyl]-4-yl)oxy]methyl]-2-(3,4,4-trimethyl-2,5-dioxo-1-imidazolidinyl)ethyl]-N-hydroxyformamide Prepared according to the procedures of example 16C and 16E, substituting 4-phenyl-phenol for 4-bromophenol in example 16C.

¹H NMR (300 MHz, d₆-DMSO) δ 9.90 (S, 0.5H), 9.57 (S, 0.5H), 8.30 (S, 0.5H), 7.92 (S, 0.5H), 7.62–7.60 (D, 8H, J=8.1 Hz), 7.45–7.40 (t, 4H, J=5.8, 7.8 Hz), 7.33–7.28 (t, 2H, J=7.1, 6.9 Hz), 7.02–6.97 (m, 4H), 4.80–4.60 (m, 0.5H), 4.45–4.40 (m, 0.5H), 4.18–4.01 (m, 4H), 3.77–3.70 (m, 2H), 3.63–3.6 (m, 2H), 2.80 (s, 6H), 1.28 (s, 12H); MS (ESI) m/e M–H (410), M+H (412); Anal. Calcd for: $C_{22}H_{25}N_3O_5.0.25H_2O$: C, 63.25; H, 6.17; N, 10.10. Found: C, 63.94; H, 6.41; N, 9.60.

EXAMPLE 29

N-[1-[[(3'-chloro-4'-fluoro[1,1'-biphenyl]-4-yl)oxy]methyl]-2-(3,4,4-trimethyl-2,5-dioxo-1-imidazolidinyl)ethyl]-N-hydroxyformamide Prepared according to the procedures of example 16C and 16E, substituting 4-(4'-fluoro-3'-chloro-phenyl)phenol for 4-bromophenol in example 16C.

¹H NMR (300 MHz, d₆-DMSO) δ 9.90 (s, 0.5H), 9.57 (s, 0.5H), 8.31 (s, 0.5H), 7.92 (s, 0.5H), 7.84–7.82 (m, 2H), 7.65–7.61 (m, 6H), 7.49–7.43 (t, 2H, J=9.2, 8.8 Hz), 7.02–6.96 (m, 4H), 4.80–4.60 (m, 0.5H), 4.43–4.40 (m, 0.5H), 4.21–4.06 (m, 4H), 3.82–3.70 (m, 2H), 3.62–3.59 (m, 2H), 2.79 (s, 6H), 1.28 (s, 12H); MS (ESI) m/e M–H (462), M+H (464); Anal. Calcd for: $C_{22}H_{23}N_3O_5ClF.0.25H_2O$: C, 56.41; H, 5.05; N, 8.97. Found: C, 56.78; H, 5.24; N, 8.55.

EXAMPLE 30

N-[1-[[(2'-methyl[1,1'-biphenyl]-4-yl)oxy]methyl]-2-(3,4,4-trimethy-2,5-dioxo-1-imidazolidinyl)ethyl]-N-hydroxyformamide Prepared according to the procedures of example 16C and 16E, substituting 4-(3'-methyl-phenyl)phenol for 4-bromophenol in example 16C.

$^1$H NMR (300 MHz, d$_6$-DMSO) δ 9.90 (s, 0.5H), 9.57 (s, 0.5H), 8.32 (s, 0.5H), 7.93 (s, 0.5H), 7.28–7.14 (mm, 12H), 6.99–6.64 (m, 4H), 4.90–4.80 (m, 0.5H), 4.42–4.40 (m, 0.5H), 4.22–4.04 (m, 6H), 3.82–3.74 (m, 2H), 3.62–3.58 (m, 2H), 2.80 (s, 6H), 2.20 (s, 6H), 1.29 (s, 12H); MS (ESI) m/e M+H (426), M−H (424); Anal. Calcd for: C$_{23}$H$_{27}$N$_3$O$_5$.0.25H$_2$O: C, 64.24; H, 6.44; N, 9.77. Found: C, 64.50; H, 6.69; N, 9.31.

EXAMPLE 31

N-[1-[[(4'-cyanol[1,1'-biphenyl]-4-yl)oxy]methyl]-2-(2,5-dioxo-1-imidazolidinyl)ethyl]-N-hydroxyformamide

EXAMPLE 31A 3-(4-(4'-Carbonitrilephenyl)phenoxy)-1-bromopropan-2-one

The title compound was prepared according to the procedure described in examples 16A and 16B, but substituting 4-(4'-cyanophenyl)-phenol for 1,5,5-trimethyl hydantoin in example 16A.

EXAMPLE 31B

N-[1-[[(4'-cyanol[1,1'-biphenyl]-4-yl)oxy]methyl]-2-(2,5-dioxo-1-imidazolidinyl)ethyl]-N-hydroxyformamide Prepared according to the procedures of example 16C and 16E, substituting example 31A for 16B and hydantoin for 4-bromophenol in example 16C.

$^1$H NMR (300 MHz, DMSO-d$_6$) δ 3.6–3.8 (m, 2H), 3.92 (d, 2H, J=8.4 Hz), 4.10–4.25 (m, 2H), 4.3–4.4 (m, 0.5H), 4.8–4.9 (m, 0.5H), 7.0–7.1 (m, 2H), 7.74 (d, 2H, J=9.0 Hz), 7.84 (d, 2H, J=8.4 Hz), 7.89 (d, 2H, J=8.4 Hz), 7.98 (s, 0.5H), 8.1–8.2 (m, 1H), 8.35 (s, 0.5H), 9.57 (br s, 0.5H), 9.53 (br s, 0.5H); MS (ESI+) 395 (M+H); Anal. Calcd for C$_{20}$H$_{18}$N$_4$O$_5$.0.2H$_2$O.0.4EtOAc: C, 59.88; H, 5.03; N, 12.93. Found: C, 59.80; H, 4.81; N, 12.74.

EXAMPLE 32

N-[1-[[(4'-cyanol[1,1'-biphenyl]-4-yl)oxy]methyl]-2-(1,1-dioxido-3-oxo-1,2-benzisothiazol-2(3H)-yl)ethyl]-N-hydroxyformamide Prepared according to the procedures of example 16C and 16E, substituting example 31A for 16B and saccharin for 4-bromophenol in example 16C.

$^1$H NMR (300 MHz, DMSO-d$_6$) δ 3.9–4.2 (m, 2H), 4.2–4.3 (m, 2H), 4.45–4.55 (m, 0.5H), 5.0–5.1 (m, 0.5H), 7.0–7.1 (m, 2H), 7.74 (d, 2H, J=8.4 Hz), 7.85 (d, 2H, J=8.7 Hz), 7.88 (d, 2H, J=8.4 Hz), 8.0–8.2 (m, 3.5H), 8.3–8.4 (m, 1.5H), 9.78 (s, 0.5H), 10.14 (s, 0.5H), MS (ESI−) 476 (M−H); Anal. Calcd for C$_{24}$H$_{19}$N$_3$O$_6$S.1.1H$_2$O: C, 57.97; H, 4.30; N, 8.45. Found: C, 58.01; H, 3.96; N, 8.16.

EXAMPLE 33

N-[1-[(4,4-dimethy-2,5-dioxo-1-imidazolidinyl)methyl]-2-[[4'-(trifluoromethoxy)[1,1'-biphenyl]-4-yl]oxy]ethyl]-N-hydroxyformamide Prepared according to the procedures of example 23B, except substituting 4-(4'-trifluoromethoxyphenyl)-phenol for 4-(4'-Butyloxyphenyl)-phenol.

$^1$H NMR (300 MHz, DMSO-d$_6$) δ 1.27 (s, 6H), 3.5–3.8 (m, 2H), 4.0–4.3 (m, 2H), 4.4–4.5 (m, 0.5H), 4.8–4.9 (m, 0.5H), 7.0–7.2 (m, 2H), 7.42 (d, 2H, J=7.8 Hz), 7.64 (d, 2H, J=8.4 Hz), 7.75 (d, 2H, J=8.7 Hz), 7.93 (s, 0.5H), 8.33 (s, 0.5H), 8.35 (s, 0.5H), 8.40 (s, 0.5H), 9.56 (s, 0.5H), 9.87 (s, 0.5H); MS (ESI+) 482 (M+H); Anal. Calcd for C$_{22}$H$_{21}$N$_3$O$_6$F$_3$: C, 54.88; H, 4.60; N, 8.72. Found: C, 55.22; H, 4.87; N, 8.36.

EXAMPLE 34

N-[1-[[4-(4-phenyl-1-piperidinyl)phenoxy]methyl]-2-(3,4,4-trimethyl-2,5-dioxo-1-imidazolidinyl)ethyl]-N-hydroxyformamide Prepared according to the procedures of example 16C and 16E, substituting the 4-phenyl-N-phenyl piperidine (prepared as in Warner-Lambert patent WO 97/19068), for 4-bromophenol in example 16C.

$^1$H NMR (300 MHz, DMSO-d$_6$) δ 1.27 (s, 3H), 1.28 (s, 3H), 1.7–1.9 (m, 4H), 2.55–2.75 (m, 3H), 2.78 (s, 1.5H), 2.79 (s, 1.5H), 3.5–3.8 (m, 4H), 3.9–4.1 (m, 2H), 4.3–4.4 (m, 0.5H), 4.7–4.8 (m, 0.5H), 6.81 (d, 2H, J=8.7 Hz), 6.93 (d, 2H, J=9.0 Hz), 7.15–7.25 (m, 1H), 7.25–7.35 (m, 4H), 7.89 (s, 0.5H), 8.30 (s, 0.5H), 9.54 (s, 0.5H), 9.86 (s, 0.5H); MS (ESI+) 495 (M+H); Anal. Calcd for C$_{27}$H$_{34}$N$_4$O$_5$: C, 65.56; H, 6.92; N, 11.32. Found: C, 65.35; H, 7.24; N, 10.93.

EXAMPLE 35

N-[1-[(4,4-dimethy-2,5-dioxo-1-imidazolidinyl)methyl]-2-[[4'-(trifluoromethyl)[1,1'-biphenyl]-4-yl]oxy]ethyl-N-hydroxyformamide Prepared according to the procedures of example 23B, except substituting 4-(4'-trifluoromethylphenyl)phenol for 4-(4'-Butyloxyphenyl)phenol.

$^1$H NMR (300 MHz, DMSO-d$_6$) δ 1.28 (s, 6H), 3.5–3.8 (m, 2H), 4.1–4.3 (m, 2H), 4.4–4.5 (m, 0.5H), 4.8–4.9 (m, 0.5H), 7.0–7.2 (m, 2H), 7.72 (d, 2H, J=8.4 Hz), 7.78 (d, 2H, J=8.4 Hz), 7.86 (d, 2H, J=8.4 Hz), 7.93 (s, 0.5H), 8.33 (s, 0.5H), 8.35 (s, 0.5H), 8.40 (s, 0.5H), 9.56 (s, 0.5H), 9.87 (s, 0.5H); MS (ESI+) 466 (M+H); Anal. Calcd for C$_{22}$H$_{22}$N$_3$O$_5$F$_3$.0.6H$_2$O: C, 55.49; H, 4.91; N, 8.82. Found: C, 55.55; H, 4.66; N, 8.77.

EXAMPLE 36

N-[1-[[(3'-cyano[1,1'-biphenyl]-4-yl)oxy]methyl]-2-[methyl[(4-methylphenyl)sulfonyl]amino]ethyl]-N-hydroxyformamide Prepared according to the procedures of example 16C and 16E, substituting example 31A for 16B and N-methyl-(p-tolyl)sulfonamide for 4-bromophenol in example 16C.

$^1$H NMR (300 MHz, DMSO-d$_6$) δ 2.41 (s, 3H), 2.70 (s, 1.5H), 2.73 (s, 1.5H), 3.05–3.35 (m, 2H), 4.0–4.2 (m, 2H), 4.3–4.4 (m, 0.5H), 4.8–4.9 (m, 0.5H), 7.06 (d, 2H, J=8.7 Hz), 7.46 (d, 2H, J=8.1 Hz), 7.65–7.8 (m, 4H), 7.85 (d, 2H, J=8.7 Hz), 7.89 (d, 2H, J=8.7 Hz), 8.04 (s, 0.5H), 8.40 (s, 0.5H), 9.71 (s, 0.5H), 10.0 (s, 0.5H); MS (ESI+) 480 (M+H); Anal. Calcd for C$_{25}$H$_{25}$N$_3$O$_5$S: C, 62.61; H, 5.25; N, 8.76. Found: C, 62.52; H, 5.27; N, 7.98.

EXAMPLE 37

N-[1-[[(4'-cyano[1,1'-biphenyl]-4-yl)oxy]methyl]-2-[4,4-dimethy-2,5-dioxo-3-(3-pyridinylmethyl)-1-imidazolidinyl]ethyl]-N-hydroxyformamide

EXAMPLE 37A 3-(3-pyridinylmethyl))-2,5-dioxo-4,4-dimethylimidazolidine

The title compound was prepared following the prosedures described in examples 68A, 68B and 69B, except substituting 3-picolyl chloride for methyl iodide in example 68B.

EXAMPLE 37B

N-[1-[[(4'-cyano[1,1'-biphenyl]-4-yl)oxy]methyl]-2-[4,4-dimethy-2,5-dioxo-3-(3-pyridinylmethyl)-1-imidazolidinyl]ethyl]-N-hydroxyformamide The title compound was prepared according to the procedures of example 16C and 16E, substituting example 31A for 16B and 37A for 4-bromophenol in example 16C.

$^1$H NMR (300 MHz, DMSO-$d_6$) δ 1.25 (s, 6H), 3.6–3.7 (m, 1H), 3.8–3.9 (m, 1H), 4.1–4.3 (m, 2H), 4.4–4.5 (m, 0.5H), 4.56 (s, 2H), 4.85–4.95 (m, 0.5H), 7.0–7.1 (m, 2H), 7.35 (dd, 1H, J=8.1,4.8 Hz), 7.7–7.8 (m, 3H), 7.86 (d, 2H, J=8.4 Hz), 7.90 (d, 2H, J=8.4 Hz), 7.96 (s, 0.5H), 8.34 (s, 0.5H), 8.45–8.50 (narrow m, 1H), 8.60 (s, 1H), 9.64 (s, 0.5H), 9.97 (s, 0.5H); MS (ESI (+)) 514 (M+H); Anal. Calcd for $C_{28}H_{27}N_5O_5 \cdot 1.7H_2O$: C, 61.80; H, 5.63; N, 12.87. Found: C, 61.77; H, 5.08; N, 12.48.

EXAMPLE 38

N-[2-[(4'-cyano[1,1'-biphenyl]-4-yl)oxy]-1-methylpropyl]-N-hydroxyformamide

The title compound was prepared according to the procedures of example 16C and 16E, substituting 3-bromo-2-butanone for 16B and 4-(4'-cyanophenyl)phenol for 4-bromophenol in example 16C.

$^1$H NMR (300 MHz, DMSO-$d_6$) δ 1.1–1.3 (m, 6H), 3.8–4.0 (m, 1H), 4.3–4.7 (m, 1H), 7.0–7.1 (m, 2H), 7.6–7.7 (m, 2H), 7.8–7.9 (m, 4H), 8.02 (s, 0.5H), 8.28 (s, 0.25H), 8.33 (s, 0.25H), 9.43 (s, 0.25H), 9.60 (s, 0.25H), 9.85 (s, 0.25H), 9.95 (s, 0.25H). MS (ESI+) 311 (M+H). Anal. Calcd for $C_{18}H_{18}N_2O_3 \cdot 0.2H_2O$: C, 68.86; H, 5.91; N, 8.92. Found: C, 68.73; H, 5.79; N, 8.58.

EXAMPLE 39

N-[1-[[(3'-cyano[1,1'-biphenyl]-4-yl)oxy]methyl]-2-(3,4,4-trimethyl-2,5-dioxo-1-imidazolidinyl)ethyl]-N-hydroxyformamide

EXAMPLE 39A

3'-cyano-4-hydroxy biphenyl

A 250 mL flask was charged with 2.21 g (2.7 mmol) [1,1'-Bis(diphenylphosphino)ferrocene]dichloropalladium (II).$CH_2Cl_2$ and 6.26 g (2.73 mmol) 3-iodobenzonitrile, 6.0 g (3.95 mmol) 4-methoxyphenylboronic acid and 12.45 g (8.20 mmol) cesium fluoride added as solids followed by addition of 180 mL 1,2-dimethoxyethane. The flask was flushed with $N_2$ and the suspension heated to reflux which was maintained for 3 hours. the cooled reaction mixture was filtered through a pad of 300 g flash silica gel and the pad was washed with 1 L ethyl acetate. The ethyl acetate was concentrated and the residue purified by flash chromatography eluting with 10% hexanes/90% ethyl acetate to give 3.3 g of the desired product (58% yield). This material was dissolved in 50 mL anhydrous CH2Cl2 and the solution cooled in a dry ice-acetone bath and a solution of boron tribromide (40 mL, 4 mmol) was added dropwise under inert atmosphere. The reaction solution was then stirred at room temperature overnight. The reaction solution was cooled in an ice bath and 5 mL of $H_2O$ added dropwise followed by the addition of 20 mL 1N HCl. The mixture was stirred for 1 hour and the resulting suspension was filtered and the filtrate transferred to a separatory funnel and the organic layer separated off and set aside. the filtered solid was washed with $H_2O$ and ethyl acetate and filtered and the filtrate transferred to the separatory funnel and the organic layer combined with the previous organic layer, dried over Na2SO4, filtered and the filtrate concentrated to a 3.05 g of a white solid (99% yield).

EXAMPLE 39B

N-[1-[[(3'-cyano[1,1'-biphenyl]-4-yl)oxy]methyl]-2-(3,4,4-trimethyl-2,5-dioxo-1-imidazolidinyl)ethyl]-N-hydroxyformamide Prepared according to the procedures of example 16C and 16E, substituting 3'-cyano-4-hydroxy biphenyl for 4-bromophenol in example 16C.

mp: 130–132° C.; $^1$H NMR (DMSO-δ 6) δ 9.86 (s, ½H), 9.48–9.63 (c, ½H), 8.33 (s, ½H), 8.09 (s, 1H), 7.97 (d, 1H, J=4.5 Hz), 7.93 (s, ½H), 7.75 (d, 1H, J=4.5 Hz), 7.70 (d, 2H, J=6.0 Hz), 7.63 (t, 1H, J=4.5 Hz), 7.00–7.07 (c, 2H), 4.83–4.90 (c, ½H), 4.60–4.67 (c, ½H); ESI(+): 409 (M-27), 437 (M+H), 454 (M+NH$_4$), 459 (M+Na); Anal. Calcd for: $C_{23}H_{24}N_4O_5 \cdot 0.25C_4H_8O_2$: C, 62.87; H, 5.71; N, 12.21. Found: C, 62.68; H, 5.55; N, 12.27.

EXAMPLE 40

N-[1-[[[4'-(methylthio)[1,1'-biphenyl]-4-yl]oxy]methyl]-2-(3,4,4-trimethyl-2,5-dioxo-1-imidazolidinyl)ethyl]-N-hydroxyformamide Prepared according to the procedures of example 16C and 16E, substituting 4'-thiomethyl-4-hydroxy biphenyl for 4-bromophenol in example 16C.

mp 172–174. $^1$H NMR (DMSO-δ 6) δ 9.48–9.96 (BS, 1H), 8.34 (S, ½H), 7.94 (S, ½H), 7.54–7.63 (C, 4H), 7.29–7.34 (C, 2H), 6.97–7.03 (C, 2H), 4.82–4.92 (C, ½H), 4.39–4.47 (C, ½H), 4.07–4.25 (C, 2H), 3.73–3.85 (C, 1H), 3.59–3.68 (C, 1H), 2.80 (S, 1.5H), 2.79 (S, 1.5H) MS (ESI(-)) 456 ((M–H)), 913 ((2M–H)) Calcd: 458.175 Found: 458.1747; Anal. Calcd for: $C_{23}H_{27}N_3O_5S$ C, 60.37; H, 5.95; N, 9.19; S; 7.01 Found: C, 60.29; H, 5.82; N, 9.08; S; 6.98.

EXAMPLE 41

N-[1-[4-[[4-(trifluoromethyl)phenoxyl]phenoxymethyl]-2-(3,4,4-trimethyl-2,5-dioxo-1-imidazolidinyl)ethyl]-N-hydroxyformamide Prepared according to the procedures of example 16C and 16E, substituting 4-(4'-trifluoromethylphenoxy)phenol for 4-bromophenol in example 16C.

mp 121–123 $^1$H NMR (DMSO-δ 6) δ 9.46–9.97 (C, 1H), 8.33 (S, ½H), 7.94 (S, ½H), 7.71 (S, 1H), 7.69 (S, 1H), 7.04–7.14 (C, 4H), 6.97–7.03 (C, 2H), 4.81–4.91 (C, ½H), 4.39–4.47 (C, ½H), 4.14–4.22 (C, 1H), 4.04–4.13 (C, 1H), 2.81 (S, 1.5H), 2.80 (S, 1.5H), 1.30 (S, 1.5H); MS (ESI(-)) 494 (M–H), 530 (M+Cl), 989 (2M–H), 1011 (2M+Na2H) Calcd: 496.169, Found: 496.1696; Anal. Calcd for: $C_{23}H_{24}F_3N_3O_6$ Theory: C, 55.75; H, 4.88; N, 8.48; F, 11.50. Found: C, 55.68; H, 4.92; N, 8.40; F, 11.24.

EXAMPLE 42

N-[1-[[[4'-(trifluoromethoxy)[1,1'-biphenyl]-4-yl]oxy]methyl]-2-(3,4,4-trimethy-2,5-dioxo-1-imidazolidinyl)ethyl]-2-N-hydroxyformamide Prepared according to the procedures of example 16C and 16E, substituting 4'-trifluoromethoxy-4-hydroxy biphenyl for 4-bromophenol in example 16C.

mp 129.3–130° C.; ¹H NMR, 400 Mz (DMSO-d6): δ 9.46–9.84 (c, 1H), 8.26 (s, ½H), 7.87 (s, ½H), 7.67 (s, 1H), 7.65 (s, 1H), 7.57 (s, 1H), 7.55 (s, 1H), 7.34 (s, 1H), 7.32 (s, 1H), 6.94–6.97 (c, 2H), 4.78–4.82 (c, ½H), 4.34–4.38 (c, ½H), 4.02–4.17 (c, 2H), 3.67–3.77 (c, 1H), 3.53–3.60 (c, 1H), 2.73 (s, 1.5H), 2.72 (s, 1.5H), 1.22 (s, 3H), 1.21 (s, 3H); MS (ESI(-)): 494 (M-H), 530 (M+Cl), 989 (2M-H), 1011 (2M+Na-2H) Calcd.: 496.1695 Found: 496.1680; Anal. Calcd. for $C_{23}H_{24}F_3N_3O_6$ Theory: C, 55.75; H, 4.88; N, 8.48; F, 11.50. Found: C, 55.69; H, 4.94; N, 8.23; F, 11.71.

EXAMPLE 43

N-[1-[[[4'-(methylsulfonyl)[1,1'-biphenyl]-4-yl]oxy] methyl]-2-(3,4,4-trimethy-2,5-dioxo-1-imidazolidinyl)ethyl]-N-hydroxyformamide Prepared according to the procedures of example 48A, 48B and 48C, substituting 16B for 23A for 4-bromophenol in example 48A.

mp 174–175° C.; ¹H NMR, 400 MHz (DMSO-d6): δ 9.47–9.98 (c, 1H), 8.35 (s, ½H), 7.92–8.00 (c, 4.5H), 7.77 (s, 1H), 7.75 (s, 1H), 7.07–7.10 (c, 2H), 4.85–4.94 (c, ½H), 4.42–4.50 (½H), 4.13–4.30 (c, 2H), 3.76–3.86 (c, 1H), 3.63–3.69 (c, 1H), 3.39 (s, 3H), 2.83 (s, 1.5H), 2.82 (s, 1.5H), 1.32 (s, 3H), 1.31 (s, 3H); MS [ESI(-)]: 488(M-H), 977(2M-H), 999(2M+Na-2H) [ESI(+)]: 490 (M+H), 507 (M+NH$_4$), 512 (M+Na); Anal. calcd. for $C_{23}H_{28}.5N_3O_7.75S$: Theory: C, 54.91; H, 5.71; N, 8.35; S, 6.37; Found C, 54.85; H, 5.76; N, 8.00; S, 6.31.

EXAMPLE 44

N-[1-[[[3'-(cyanomethyl)-4'-methoxyl[1,1'-biphenyl]-4-yl]oxy]methyl]-2-(3,4,4-trimethy-2,5-dioxo-1-imidazolidinyl)ethyl]-N-hydroxyformamide Prepared according to the procedures of example 16C and 16E, substituting 4-(3'-cyanomethyl-4'-methoxyphenyl)phenol for 4-bromophenol in example 16C.

¹H NMR (300 MHz, DMSO-d6) δ; 1.275, 1.290 (6H), 2.788, 2.800 (3H), 3.566–3.641 (m, 1H), 3.708–3.821 (m, 1H), 4.047–4.214 (m, 2H), 4.399–4.416 (m, 0.5H), 4.846 (m, 0.5H), 6.973–7.013 (2H), 7.110–7.140 (1H), 7.543–7.608 (m, 4H), 7.291 (s, 0.5H), 8.319 (s, 0.5H), 9.576 (s, 0.5H), 9.904 (s, 0.5H); MS (ESI) m/e 481 (M+H)⁺, 498 (M+NH$_4$)⁺, 479 (M-H)⁻; Anal. calcd for $C_{25}H_{28}N_4O_6.0.5MeOH$: C, 61.68; H, 6.08; N, 11.28. Found: C, 62.07; H, 6.21; N, 10.91.

EXAMPLE 45

N-[1-[[[3'-(cyanomethyl)[1,1'-biphenyl]-4-yl]oxy] methyl]-3-(4,4-dimethyl-2,5-dioxo-1-imidazolidinyl)propyl]]-N-hydroxyformamide The title compouns was prepared according to the procedures of example 5, except avoiding the methylation step in example 5B and substituting 4-(3'-cyanomethylphenyl)phenol for 4'-hydroxy-4-biphenylcarbonitrile in example 5F.

¹H NMR (300 MHz, DMSO-d6) δ 1.27 (s, 6H), 1.70–2.00 (m, 2H), 3.37–3.47 (m, 2H), 3.96–4.08 (s+m, 5H), 7.00–7.03 (d, 2H, 8.4 Hz), 7.28–7.31 (d, 1H, 8.7 Hz), 7.426–7.477 (t, 1H, 7.5 Hz), 7.56–7.61 (m, 4H), 7.915 (s, 0.73H), 8.28–8.34 (1.27H), 9.55 (s, 0.75H), 9.96 (s, 0.25H); MS (ESI) m/e 451 (M+H)⁺, 468 (M+NH$_4$)⁺, 449 (M-H)⁻; Anal. calcd for $C_{25}H_{28}N_4O_6.MeOH$: C, 62.22; H, 6.26; N, 11.61. Found: C, 62.25; H, 5.95; N, 11.57.

EXAMPLE 46

N-[1-[[(4'-butoxy[1,1'-biphenyl]-4-yl)sulfonyl] methyl]-2-(4,4-dimethy-2,5-dioxo-1-imidazolidinyl) ethyl]-N-hydroxyformamide

EXAMPLE 46A 1-(4-bromophenylthio)-3-(4,4-dimethyl-2,5-dioxoimidazolidin-1-yl)-2-propanone A solution of 4-bromothiophenol (2.15 g, 11.4 mmol) in DMF (50 mL) at ambient temperature was treated with cesium carbonate (5.57 g, 17.1 mmol) for 20 minutes, treated in a single portion with example 23A (2.5 g, 9.5 mmol), stirred for 1 hours at ambient temperature and diluted with water, extracted with ethyl acetate, the combined extracts were washed with water and brine, dried (Na$_2$SO$_4$), filtered, concentrated and purified on silica gel with 20 to 35 to 50% ethyl acetate/hexane to provide 3.17 g (90%) of the titled compound as a white solid.

MS (APCI) m/e 371, 373 (M+H)⁺, 388, 390 (M+NH$_4$)⁺, 369, 371 (M-H), 405, 407 (M+Cl)⁻.

EXAMPLE 46B

1-[(4'-butoxy[1,1'-biphenyl]-4-yl)thio]-3-(4,4-dimethyl-2,5-dioxoimidazolidin-1-yl)-2-pronanone A solution of example 46A (700 mg, 1.89 mmol) in DME (20 mL) at ambient temperature was treated with 4-n-butoxybenzeneboronic acid (549 mg, 2.83 mmol), tetrakis-(triphenylphosphine)-palladium (218 mg, 0.189 mmol) and 1M sodium carbonate (3.54 mL, 3.54 mmol), the reaction vessel was sealed and heated at 90° C. for 6 hours, diluted with ethyl acetate, washed with sequentially saturated ammonium chloride solution, water and brine, dried (Na$_2$SO$_4$), filtered, concentrated and purified on silica gel with 30 to 50% ethyl acetate/dichloromethane to provide 650 mg (78%) of the title compound as a yellow solid.

MS (APCI) m/e 441 (M+H)⁺, 458 (M+NH$_4$)⁺, 439 (M-H), 475 (M+Cl)⁻.

EXAMPLE 46C

N-[1-[[(4'-butoxy[1,1'-biphenyl]-4-yl)thio]methyl]-2-(4,4-dimethy-2,5-dioxo-1-imidazolidinyl)ethyl]-N-hydroxyformamide The title compound was prepared from 46B following the procedures described in example 2D, 2E, 2F.

¹H NMR (300 MHz, DMSO-d6) δ; 0.919–0.967 (t, 3H, J=7.2 Hz), 1.225–1.237 (s+s, 6H), 1.389–1.512 (m, 2H), 1.666–1.760 (m, 2H), 3.110–3.192 (m, 2H), 3.528–3.735 (m, 2H), 3.987–4.030 (t, 2H, J=6.3 Hz), 4.030 (m, 0.5H), 4.750 (m, 0.5H), 6.991–7.020 (d, 2H, J=9 Hz), 7.383–7.417 (dd, 2H, J=1.8, 8.4 Hz), 7.561–7.601 (4H), (1.5H), 9.56 (s, 7.767 (s, 0.5H), 8.299 (s, 1H), 8.337 (s, 0.5H), 9.457 (br s, 0.5H), 9.695 (br s, 0.5H); MS (ESI) m/e 484 (M-H)⁻; High resolution MS(FAB) Calc. m/z for m.⁺485.1984, observed m/z 485.1980.

EXAMPLE 46D

N-[1-[[(4'-butoxy[1,1'-biphenyl]-4-yl)sulfonyl] methyl]-2-(4,4-dimethy-2,5-dioxo-1-imidazolidinyl) ethyl]-N-hydroxyformamide A solution of example 46C (127 mg, 0.262 mmol) in methanol (2 mL), and PH 7 buffer (1 mL) at 0° C. was treated with oxone (402 mg, 0.655 mmol) for 30 minutes then ambient temperature for 1 hour, neutralized with saturated sodium bicarbonate, extracted with dichloromethane, combined extracts were washed with brine, dried ($Na_2SO_4$), filtered, and concentrated. The crude mixture was purified on silica gel with 50% ethyl acetate/hexane then 10% methanol/dichloromethane to provide 82 mg (60%) of the title compound as an white solid.

$^1$H NMR (300 MHz, DMSO-d6) δ; 0.92–0.97 (t, 3H, 7.5 Hz), 1.20, 1.22 (s+s, 6H), 1.42–1.52 (m, 2H), 1.68–1.77 (m, 2H), 3.41–3.72 (m, 3.5H), 4.02–4.06 (t, 2H, 6.6 Hz), 4.52 (m, 0.5H), 4.89 (m, 0.5H), 7.05–7.08 (d, 2H, 8.4 Hz), 7.70–7.74 (2H), 7.91 (s, 3.5H), 8.10 (s, 0.5H), 8.32–8.35 (d, 1H, 9.6 Hz), 9.48 (s, 0.5H), 9.62 (s, 0.5H); MS (ESI) m/e 518 (M+H)$^+$, 535 (M+NH$_4$)$^+$, 516 (M−H)$^−$, 552 (M+Cl)$^−$; Anal. calcd for $C_{25}H_{28}N_4O_6$·$0.25H_2O$: C, 57.51; H, 6.08; N, 8.04. Found: C, 57.78; H, 6.18; N, 7.84.

EXAMPLE 47

N-[1-[[(4'-cyano[1,1'-biphenyl]-4-yl)oxy]methyl]-3-(4,4-dimethyl-2,5-dioxo-1-imidazolidinyl)propyl]-N-hydroxyformamide

EXAMPLE 47A 1-bromo-4-(3,4,4-trimethy-2,5-dioxoimidazolidin-1-yl)butan-2-one To a suspension of CuBr2 (1.91 g, 8.5 mmol) and lithium bromide (1.48 g, 17 mmol) in THF (10 mL) was added a solution of 1.06 g (5.3 mmol) of 1-((1',2'Oxiranyl)propyl-4,4-dimethyl-2,5-dioxoimidazolidine (prepared from example 5A following the procedure of example 5C) in 15 mL of THF. The reaction mixture was stirred for 2 h at room temperature, then partitioned between ethyl acetate and ph7 buffer.The organic extract was washed with brine, dried and concentrated. The residue was filtered through a plug of silice eluting with ethyl acetate, and the filtrate was concentrated to give a white solid, which was dissolved in acetone (25 mL), cooled to 0° C., then treated with 2.5 mL of 8M Jones reagent and stirred at room temperature for 3 h. The reaction was quenched with 2 mL isopropanol, then partitioned between ethyl acetate and water. The organic extract was washed with brine, dried, filtered, and concentrated. The residue was filtered through a plug of silice eluting with ethyl acetate, and the filtrate was concentrated to give the title compound.

EXAMPLE 47B

N-[1-[[(4'-cyano[1,1'-biphenyl]-4-yl)oxy]methyl]-3-(4,4-dimethyl-2,5-dioxo-1-imidazolidinyl)propyl]-N-hydroxyformamide The title compound was prepared according to the procedures of example 16C and 16E, exept substituting 47A for 16B and 4'-hydroxy-4-biphenylcarbonitrile for 4-bromophenol in example 16C.

mp 202–204° C.; $^1$H NMR (300 MHz, DMSO-d6) δ; 1.272 (6H), 1.70–2.00 (m, 2H), 3.38–3.46 (t, 2H, J=6 Hz), 3.92–4.18 (m, 2.5H), 4.46–4.57 (m, 0.5H), 7.03–7.06 (d, 2H, J=8.7 Hz), 7.695–7.724 (d, 2H, J=8.7 Hz), 7.82–7.92 (m, 6.5H), 8.26–8.35 (1.5H), 9.75 (s), 9.96 (s, 1H); MS (ESI) m/e 437 (M+H)$^+$, 454 (M+NH$_4$)$^+$, 459 (M−H)$^−$; Anal. calcd for $C_{25}H_{28}N_4O_6$·$0.25H_2O$: C, 62.64; H, 5.60; N, 12.70. Found: C, 62.55; H, 5.47; N, 12.65

EXAMPLE 48

N-[1-[[[4'-(methylsulfonyll)[1,1'-biphenyl]-4-yl]oxy]methyl]-2-(4,4-dimethyl-2,5-dioxo-1-imidazolidinyl)ethyl]-N-hydroxyformamide

EXAMPLE 48A 1-(4'-(thiomethyl)[1,1 '-biphenyl]-4-yl)oxy)-3-(4,4-dimethyl-2,5-dioxoimidazolidin-1-yl)-2-propanone A solution of 4'-hydroxy-4-biphenylmethylsulfide (1.18 g, 5.47 mmol) in DMF (25 mL) at ambient temperature was treated with cesium carbonate (2.23 g, 6.84 mmol) for 20 minutes, treated in a single portion with 23A (1.2 g, 4.56 mmol), stirred for 2 hours at ambient temperature and diluted with water, extracted with ethyl acetate, the combined extracts were washed with water and brine, dried ($Na_2SO_4$), filtered, concentrated and purified on silica gel with 50 to 80% ethyl acetate/hexane to provide 1.0 g (55%) of the title compound as a white solid.

MS (APCI) m/e 399 (M+H)$^+$, 416 (M+NH$_4$)$^+$, 397 (M−H)$^−$, 433 (M+Cl)$^−$.

EXAMPLE 48B

N-[1-[[[4'-(thiomethyl)[1,1'-biphenyl]-4-yl]oxy]methyl]-2-(4,4-dimethyl-2,5-dioxo- 1-imidazolidinyl)ethyl]-N-hydroxyformamide The title compound was prepared from 48A following the procedures described in example 2D, 2E, 2F.

MS (ESI) m/e 444 (M+H)$^+$, 461 (M+NH$_4$)$^+$, 466 (M+Na)$^+$, 442 (M−H)$^−$.

EXAMPLE 48C

N-[1-[[[4'-(methylsulfonyll)[1,1'-biphenyl]-4-yl]oxy]methyl]-2-(4,4-dimethyl-2,5-dioxo-1-imidazolidinyl)ethyl]-N-hydroxyformamide A solution of example 48B (440 mg, 0.993 mmol) in methanol (100 mL) and water (50 mL) at 0° C. was treated with oxone (1.27 g, 2.06 mmol) and sodium bicarbonate (174 mg, 2.06 mmol) for 1 hour then ambient temperature for 1.5 hour, diluted with water, extracted with dichloromethane, combined extracts were washed with brine, dried ($Na_2SO_4$), filtered and concentrated. The crude mixture was purified on silica gel with 80% ethyl acetate/ hexane then 10% methanol/dichloromethane then recrystallized from dichloromethane/hexane to provide 375 mg (79%) of the title compound as an off-white solid.

$^1$H NMR (300 MHz, DMSO-d6) δ; 1.26–1.27 (s+s, 6H), 3.24 (s, 3H), 3.53–3.80 (m, 2H), 4.08–4.24 (m, 2H), 4.37–4.48 (m, 0.5H), 4.80–4.92 (m, 0.5H), 7.04–7.08 (dd, 2H, J=3, 8.4 Hz), 7.72–7.75 (d, 2H, J=8.7 Hz), 7.89–8.00 (4.5H), 8.33–8.40 (1.5H), 9.56 (s, 0.5H), 9.88 (s, 0.5H); MS (ESI) m/e 476 (M+H)$^+$, 493(M+NH$_4$)$^+$, 474 (M−H)$^−$, 510 (M+Cl)$^−$.

EXAMPLE 49

N-[1-[[(3'-cyano[1,1'-biphenyl]-4-yl)oxy]methyl]-2-(2,5-dioxo-1-pyrrolidinyl)ethyl]-N-hydroxyformamide

EXAMPLE 49A 1-(4'-Cyano-[1,1'-biphenyl]-4-yl)oxy)-3-(2,5-dioxopyrrolidin-1-yl)-2-propanone The title compound was prepared as in Example 3C, except using potassium succinimide (0.10 g, 0.95 mmol) in place of potassium phthalimide. Purification by trituration with ethyl acetate provided 0.19 g (68%) of the title compound as a white solid.

MS (APCI) m/e 383 (M+Cl)$^+$.

EXAMPLE 49B (±)-[1-(4'-Cyano-[1,1'-biphenyl]-4-yl)oxy)-3-(2,5-dioxopyrrolidin-1-yl)-prop-2-yl]hydroxylamine The title compound was prepared from 49A using the procedure described in Example 2D and 2E.

EXAMPLE 49C

N-[1-[[(3'-cyano[1,1'-biphenyl]-4-yl)oxy]methyl]-2-(2,5-dioxo-1-pyrrolidinyl)ethyl]-N-hydroxyformamide The title compound was prepared from 49B using the procedure described in Example 2F. mp 128° C.;

$^1$H NMR (300 MHz, d6-DMSO) δ 10.01 (s, 0.5H), 9.63 (s, 0.5H), 8.34 (s, 0.5H), 7.98 (s, 0.5H), 7.90–7.82 (m, 4H), 7.73 (d, 2H, J=8.8 Hz), 7.06–6.89 (m, 2H), 4.90–4.78 (m, 0.5H), 4.37–4.24 (m, 0.5H), 4.22–4.04 (m, 2H), 3.74–3.60 (m, 2H), 2.65–2.61 (m, 4H); MS (ESI) m/e 394 (M+H)$^+$, 411(M+NH$_4$)$^+$, 392 (M−1)$^+$; Anal. Calcd for: C$_{21}$H$_{19}$N$_3$O$_5$.H$_2$O: C, 61.30; H, 5.14; N, 10.21. Found: C, 61.20; H, 5.03; N, 10.03.

EXAMPLE 50

N-[1-[[(4'-cyano[1,1'-biphenyl]-4-yl)oxy]methyl]-2-(4,4-dimethyl-2,6-dioxo-1-piperidinyl)ethyl]-N-hydroxyformamide The title compound was prepared as in Example 49, except using potassium-3,3-dimethylglutarimide (0.16 g, 1.1 mmol) in place of potassium succinimide. mp 121° C.;

$^1$H NMR (d6-DMSO) δ 9.88–9.78 (s, 0.5H), 9.60–9.52 (s, 0.5H), 8.31 (s, 0.5H), 7.95 (s, 0.5H), 7.90–7.82 (m, 4H), 7.73 (d, 2H, J=8.9 Hz), 7.02 (d, 2H, J=8.8 Hz), 4.88–4.77 (s, 1H), 4.30–3.78 (m, 4H), 2.56 (s, 4H), 0.98 (s, 6H); MS (ESI) 436 (M+H)$^+$, 458 (M+Na)$^+$, 434 (M−H)$^+$.

EXAMPLES 51 AND 52

N-[1S-[[(4'-cyano[1,1'-biphenyl]-4-yl)oxy]methyl]-2-(2,5-dioxo-1-pyrrolidinyl)ethyl]-N-hydroxyformamide N-[1R-[[(4'-cyano[1,1'-biphenyl]-4-yl)oxy]methyl]-2-(2,5-dioxo-1-pyrrolidinyl)ethyl]-N-hydroxyformamide

EXAMPLES 51A AND 52A

A solution of Example 49B (0.2 g, 0.55 mmol), D-Mannose diacetonide (0.13 g, 0.50 mmol), and acetic acid (0.03 mL, 0.50 mmol) in CHCl$_3$ (5 mL) were heated at reflux for 16 h, cooled, and partitioned between CH$_2$Cl$_2$ and saturated aqueous sodium bicarbonate. The organic layer was washed sequentially with water and brine, dried (MgSO$_4$), filtered, and concentrated. Purification by HPLC provided the two enantiomers 51A (31%) and 52A (16%).

EXAMPLE 51B

A solution of 51A in MeOH (1 mL) and HCl(conc) (0.5 mL) was stirred at ambient temperature for 15 min, treated with saturated aqueous sodium bicarbonate, and partitioned between ethyl acetate and water. The organic layer was dried (MgSO$_4$), filtered, and concentrated to provide 0.014 g (79%) of the corresponding hydroxyl amine, which was then formylated as in Example 2F.

EXAMPLE 52B

The title compound was prepared according to Example 51B but using Example 52A in place of Example 51A.

EXAMPLE 53

N-[1-[[(4'-cyano[1,1'-biphenyl]-4-yl)oxy]methyl]-2-(3-ethyl-3-methyl-2,5-dioxo-1-pyrrolidinyl)ethyl]-N-hydroxyformamide The title compound was prepared as in Example 49, except using potassium-3-methyl-3-ethyl succinimide (0.22 g, 1.53 mmol) in place of potassium succinimide.

$^1$H NMR (d6-DMSO) δ 9.99–9.94 (br, 0.5H), 9.64–9.58 (br, 0.5H), 8.31 (d, 0.5H, J=1.8 Hz), 7.93 (d, 0.5H, J=2.9 Hz), 7.87 (q, 4H, J=4.1 Hz), 7.74 (d, 2H, J=8.9 Hz), 7.04 (dd, 2H, J=8.8, 2.6 Hz), 4.93–4.81 (m, 0.5H), 4.44–4.33 (m, 0.5H), 4.24–4.05 (m, 2H), 3.85–3.71 (m, 1H), 3.62–3.53 (m, 1H), 2.69–2.38 (m, 2H), 1.64–1.46 (m, 2H), 1.18 (d, 3H, J=4.4 Hz), 0.85–0.75 (m, 3H); MS (ESI) 436 (M+H)$^+$, 434 (M−H)$^+$, 458 (M+Na)$^+$, 453 (M+NH4)$^+$; Anal. Calcd for: C$_{24}$H$_{25}$N$_3$O$_5$: C, 66.19; H, 5.78; N, 9.64. Found: C, 66.07; H, 5.85; N, 9.37.

EXAMPLE 54

N-[4-[4-[[(4-chlorophenoxy)phenyl]sulfonyl]methyl]tetrahydro-2H-pyran-4-yl]-N-hydroxyformamide

EXAMPLE 54A

The title compound was prepared as in Example 2D but using 5,6-dihydro-2H-pyran-2-one (4.3 g, 43 mmol) in place of 1-(4-(4'-carbonitrilephenyl)phenoxy)-3-thiophenoxypropan-2-one and O-Benzyl hydroxylamine in place of hydroxylamine to provide the corresponding oxime. Purification on silica gel with 1% methanol/dichloromethane provided 8.5 g (96%) of the title compound as a clear liquid. MS (ESI) 207 (M+H)$^+$

EXAMPLE 54B

N-[4-[4-[[(4-chlorophenoxy)phenyl]sulfonyl]methyl]tetrahydro-2H-pyran-4-yl]-N-benzyloxy amine To a solution of phenoxyphenyl-4-chloro-4'-methylsulfone (0.76 g, 2.7 mmol)(preparation desribed in *J. Med. Chem.* 29, 427–433, 1986) at −78° C. was added n-BuLi (1.1 mL, 2.7 mmol). After stirring at −78° C. for 15 minures, BF$_3$.OEt$_2$ was added, followed by Example 54A. After 1 h, the reaction mixture was partitioned between with water and ethyl acetate, dried (MgSO$_4$), filtered, and concentrated. Recrystallization with ethyl acetate provided 0.41 g (35%) of the desired compound as a white solid.

MS (ESI) 488 (M+H)$^+$, 510 (M+Na)$^+$.

EXAMPLE 54C

N-[4-[4-[[(4-chlorophenoxy)phenyl]sulfonyl]methyl]tetrahydro-2H-pyran-4-yl]-N-benzyloxyformamide A solution of 54B (0.05 g, 0.10 mmol) in CH$_2$Cl$_2$ (2 mL) was treated with formic-p-methoxyphenyl anhydride, stirred at ambient temperature for 16 h, treated with H2O, and partitioned between ethyl acetate and brine. The organice layer was dried (MgSO$_4$), filtered, and concentrated. Purification on silica gel with 10% ethyl acetate/dichloromethane provided 0.017 g (32%) of the desired compound as a white solid MS (ESI) 516 (M+H)$^+$, 533 (M+NH$_4$)$^+$, 538 (M+Na)$^+$.

EXAMPLE 54D

N-[4-[4-[[(4-chlorophenoxy)phenyl]sulfonyl]methyl]tetrahydro-2H-pyran-4-yl]-N-hydroxyformamide A solution of 54C (0.017 g, 0.033 mmol) and Pd black (0.006 g) in dioxane (2 mL) and acetic acid (2 mL) was stirred under H$_2$ for 20 min, treated with NaHCO$_3$, partitioned between ethyl acetate and water. The organic layer was dried (MgSO$_4$), filtered, and concentrated. Purification on silica gel with 2% MeOH/dichloromethane provided 0.002 g (14%) of the desired compound.

$^1$H NMR (d6-DMSO) δ 9.50–9.45 (br, 1H), 8.19 (s, 1H), 7.90–7.86 (m, 2H), 7.53–7.50 (m, 2H), 7.22–7.18 (m, 4H), 3.70–3.58 (m, 4H), 3.55–3.44 (m, 2H), 2.22–2.07 (m, 2H), 2.07–1.91 (m, 2H); MS (ESI) 424 (M–H)$^+$, 426 (M+H)$^+$, 448 (M+Na)$^+$.

EXAMPLE 55

N-[1-[[(4'-cyano[1,1'-biphenyl]-4-yl)oxy]methyl]-2-[[(2-methoxycarbonyl)phenyl]-thio]ethyl]-N-hydroxyformamide The title compound was prepared following the procedure from Example 2B, C, D, E, F but using methyl thiosalicylate (600 mg, 2.39 mmol) in place of thiophenol in example 2B. Mixture of two rotamers: $^1$H NMR (300 MHz, d$_6$-DMSO) δ 10.11 (s, 1H), 9.73 (s, 1H), 8.41 (s, 1H), 7.95 (s, 1H), 7.90–7.83 (m, 10 H), 7.75–7.71 (m, 4H), 7.59–7.55 (m, 4H), 7.31–7.26 (m, 2H), 7.09–7.05 (m, 4H), 4.75 (m, 1H), 4.2804.24 (m, 4H0, 4.18 (m, 1H), 3.83 (s, 3H), 3.82 (s, 3H), 3.31–3.18 (m, 4H); MS (ESI) m/e 463 (M+1)$^+$; Anal. calcd for C$_{25}$H$_{22}$N$_2$O$_5$S: C, 64.92; H, 4.79; N, 6.06. Found: C, 64.69; H, 4.63; N, 5.92.

EXAMPLE 56

N-[1-[[(4'-cyano[1,1'-biphenyl]-4-yl)oxy]methyl]-5-[(4-methyl-2-oxo-2H-1-benzopyran-6-yl)oxy]pentyl]-N-hydroxyformamide

EXAMPLE 56A

6-(4-methyl-2-oxo-2H-1-benzopyran-6-yl)oxy]-hex-1-ene

The title compound was prepared following the procedure from Example 5A but using 6-hydroxy-4-methylcoumarin (500 mg, 2.84 mmol) in place of 5,5-dimethylhydantoin and 5-hexen-1-ol in place of 3-buten-1-ol. Purification on silica gel with 20% ethyl acetate/hexanes provided 560 mg (76%) of the title compound.

$^1$H NMR (300 MHz, d$_6$-DMSO) δ 7.34 (dd, 1H), 7.24–7.20 (m, 2H), 6.40 (d, 1H), 5.90–5.77 (m, 1H), 5.04 (dq, 1H), 4.98 (dq, 1H), 4.06 (t, 2H), 2.43 (d, 3H), 2.10 (q, 2H), 1.75 (dt, 2H), 1.53 (dt, 2H).

EXAMPLE 56B

N-[1-[[(4'-cyano[1,1'-biphenyl]-4-yl)oxy]methyl]-5-[(4-methyl-2-oxo-2H-1-6-yl)oxy]pentyl]-N-hydroxyformamide The title compound was prepared following the procedures from Example 5C, 1B, 2C, 2D, 2E and 2F but using 56A (500 mg, 1.94 mmol) in place of 5B in example 56B. Purification on silica gel with 50% ethyl acetate/hexanes provided 400 mg (75%) of the title compound.

Mixture of two rotamers: $^1$H NMR (300 MHZ, d$_6$-DMSO) δ 9.89 (s, 1H), 9.51 (s, 1H), 8.42 (s, 1H), 8.03 (s, 1H), 7.86 (m, 8H), 7.73–7.70 (m, 4H), 7.34 (d, 2H), 7.24–7.21 (m, 4H), 7.08–7.04 (m, 4H), 6.40 (s, 2H), 4.60 (s, 1H), 4.18–3.99 (m, 9H), 2.43 (s, 6H), 1.86–1.54 (m, 12H); MS (ESI) m/e 513 (M+1)$^+$; Anal. calcd for C$_{30}$H$_{28}$N$_2$O$_6$: C, 70.30; H, 5.51; N, 5.47. Found: C, 70.52; H, 5.85; N, 5.20.

EXAMPLE 57

N-[1-[[(4'-cyano[1,1'-biphenyl]-4-yl)oxy]methyl]-4-[(4-methyl-2-oxo-2H-1-benzopyran-6-yl)oxy]butyl]-N-hydroxyformamide The title compound was prepared following the procedure from Example 56 but using 4-penten-1-ol in place of 5-hexen-1-ol in example 56A.

Mixture of two rotamers: $^1$H NMR (300 MHZ, d$_6$-DMSO) δ 9.94 (s, 1H), 9.55 (s, 1H0, 8.44 (s, 1H), 8.06 (s, 1H), 7.86 (m, 8H), 7.73–7.70 (m, 4H), 7.35 (d, 2H), 7.26–7.22 (m, 4H), 7.08–7/05 (m, 4H), 6.40 (s, 2H), 4.65 (m, 1H), 4.17–4.04 (m, 9H), 2.44 (s, 6H), 1.77 (m, 8H); MS (ESI) m/e 499 (M+1)$^+$; Anal. calcd for C$_{29}$H$_{26}$N$_2$O$_6$.0.75H$_2$O: C, 68.03; H, 5.41; N, 5.47. Found: C, 68.21; H, 5.25; N, 5.28.

EXAMPLE 58

N-[1-[[(4'-cyano[1,1'-biphenyl]-4-yl)oxy]methyl]-4-[(4-methyl-2-oxo-2H-1-benzopyran-7-yl)oxy]butyl]-N-hydroxyformamide The title compound was prepared following the procedure from Example 56 but using 7-hydroxy-4-methylcoumarin (500 mg, 2.8 mmol) in place of 6-hydroxy-4-methylcoumarin and 4-penten-1-ol in place of 5-hexen-1-ol in example 56A.

Mixture of two rotamers: $^1$H NMR (300 MHZ, d$_6$-DMSO) δ 9.95 (s, 1H), 9.55 (s, 1H), 9.44 (s, 1H), 8.05 (s, 1H), 7.90–7.82 (m, 8H), 7.73–7.67 (m, 6H), 7.08–7.04 (m, 4H), 7.01–6.95 (m, 4H), 6.21 (s, 2H), 4.64 (m, 1H), 4.20–4.01 (m, 9H), 2.40 (s, 6H), 1.80–1.74 (m, 8H); MS (ESI) m/e 499 (M+1)$^+$; Anal. calcd for C$_{29}$H$_{26}$N$_2$O$_6$: C, 69.87; H, 5.26; N, 5.62. Found: C, 69.51; H, 5.33; N, 5.40.

EXAMPLE 59

N-[1-[[(4'-cyano[1,1'-biphenyl]-4-yl)oxy]methyl]-5-[(4-methyl-2-oxo-2H-1-benzopyran-7-yl)oxy]pentyl]-N-hydroxyformamide The title compound was prepared following the procedure from Example 56 but using 7-hydroxy-4-methylcoumarin (500 mg, 2.8 mmol) in place of 6-hydroxy-4-methylcoumarin in example 56A.

Mixture of two rotamers: $^1$H NMR (300 MHZ, d$_6$-DMSO) δ 9.89 (s, 1H0, 9.50 (s, 1H0, 8.42 (s, 1H), 8.03 (s, 1H), 7.90–7.82 (m, 8H), 7.73–7.66 (m, 6H), 7.08–7.03 (m, 4H), 6.98–6.94 (m, 2H0, 6.21 (s, 2H), 4.60 (m, 1H), 4.15–3.98 (m, 9H), 2.40 (s, 6H), 1.84–1.40 (m, 12H); MS (ESI) m/e 513 (M+1)$^+$; Anal. calcd for C$_{30}$H$_{28}$N$_2$O$_6$: C, 70.30; H, 5.51; N, 5.47. Found: C, 70.35; H, 5.52; N, 5.17.

EXAMPLE 60

N-[1-[[(4'-cyano[1,1'-biphenyl]-4-yl)oxy]methyl]-2-(5,5-dimethy-2,4-dioxo-3-oxazolidinyl)ethyl]-N-hydroxyformamide The title compound was prepared as in Example 49, except using 5,5-dimethyloxazolidinine-2,4-dione (300 mg, 0.8 mmol) in place of succinimide.

Mixture of two rotamers: $^1$H NMR (300 MHZ, d$_6$-DMSO) δ 10.08 (s, 1H), 9.70 (s, 1H), 8.35 (s, 1H), 7.98 (s, 1H), 7.90–7.83 (m, 8H), 7.74 (d, 4H), 7.06 (d, 4H), 4.90 (m, 1H), 4.47 (m, 1H), 4.24–4.16 (m, 4H), 3.85 (d, 1H), 3.80 (d, 1H), 3.69–3.65 (m, 1H), 3.64–3.61 (m, 1H), 1.49 (s, 6H), 1.48 (s, 6H); MS (ESI) m/e 441 (M+18)$^+$.

EXAMPLE 61

N-[1-[[(4'-cyano[1,1'-biphenyl]-4-yl)sulfonyl]methyl]-2-(3,4,4-trimethy-2,5-dioxo-1-imidazolidinyl)ethyl]-N-hydroxyformamide

EXAMPLE 61A

1-[(4'-cyano[1,1'-biphenyl]-4-yl)thio]-3-(3,4,4-trimethyl-2,5-dioxoimidazolidin-1-yl)-2-propanone A solution of 4'-thiol-4-biphenylcarbonitrile (150 mg, 0.71 mmol) in 6 mL of DMF at −5° C. was treated with potassium carbonate (89 mg, 0.645 mmol) and 1-bromo-3-(3,4,4-trimethyl-2,5-dioxo-1-imidazolidin-1-yl)-2-propanone (179 mg, 0.645 mmol), stirred 1 h at −5° C., quenched with saturated NH$_4$Cl, extracted with ethyl acetate, washed with brine, dried over Na$_2$SO$_4$, filtered, and concentrated to a solid. Purification on silica gel with 1:1 ethyl acetate/hexanes provided 200 mg (75%) of the title compound.

$^1$H NMR (300 MHZ, d$_6$-DMSO) δ 7.94–7.87 (m, 4H), 7.72 (d, 2H), 7.43 (d, 2H), 4.55 (s, 2H), 4.27 (s, 2H), 2.80 (s, 3H), 1.32 (s, 6H).

EXAMPLE 61B

N-[1-[[(4'-cyano[1,1'-biphenyl]-4-yl)thio]methyl]-2-(3,4,4-trimethy-2,5-dioxo-1-imidazolidinyl)ethyl]-N-hydroxyformamide The title compound was prepared from 61A following the procedures from Example 2D, 2E and 2F.

Mixture of two rotamers: $^1$H NMR (300 MHZ, d$_6$-DMSO) δ 9.76 (s, 1H), 9.51 (s, 1H), 8.29 (s, 1H), 7.93–7.87 (m, 8H), 7.75–7.72 (m, 5H), 7.50–7.44 (m, 4H), 4.60 (m, 1H), 4.10 (m, 1H), 3.80–3.60 (m, 4H), 3.25–3.15 (m, 4H), 2.77 (s, 6H), 1.25 (s, 12H).

EXAMPLE 61C

N-[1-[[(4'-cyano[1,1'-biphenyl]-4-yl)sulfonyl]methyl]-2-(3,4,4-trimethy-2,5-dioxo-1-imidazolidinyl)ethyl]-N-hydroxyformamide A solution of 61B (81 mg, 0.18 mmol) in 4:1 THF/H$_2$O at 0° C. was treated with OXONE (140 mg) and NaHCO$_3$ (33 mg), stirred at 0° C. for 30 min then 23° C. for 1 h, quenched with H$_2$O, extracted with ethyl acetate, washed with brine, dried over Na$_2$SO$_4$, filtered, and concentrated to a white solid. Purification on silica gel with 2% methanol/dichloromethane provided 43 mg (49%) of the title compound.

Mixture of two rotamers: $^1$H NMR (300 MHZ, d$_6$-DMSO) δ 9.71 (s, 1H), 9.54 (s, 1H), 8.09 (s, 1H), 8.07–7.96 (m, 16H), 7.74 (s, 1H), 4.90 (m, 1H), 4.54 (m, 1H), 3.74–3.60 (m, 4H), 3.55–3.44 (m, 4H), 2.74 (s, 3H), 2.74 (s, 3H), 1.24–1.22 (m, 12H); MS (ESI) m/e 485 (M+1)$^+$; Anal. calcd for C$_{23}$H$_{24}$N$_4$O$_6$S: C, 57.01; H, 4.99; N, 11.56. Found: C, 56.86; H, 5.21; N, 11.28.

EXAMPLE 62

N-[1-[[(4'-cyano[1,1'-biphenyl]-4-yl)oxy]methyl]-2-(3-methyl-2,5-dioxo-1-imidazolidinyl)ethyl]-N-hydroxyformamide The title compound was prepared as in Example 49, except using 1-methylhydantoin in place of succinimide.

Mixture of two rotamers: $^1$H NMR (300 MHZ, d$_6$-DMSO) δ 9.97 (s, 1H), 9.61 (s, 1H), 8.35 (s, 1H), 7.98 (s, 1H), 7.90–7.83 (m, 8H), 7.73 (d, 4H), 7.03 (d, 2H), 7.01 (d, 2H), 4.88–4.84 (m, 1H), 4.39–4.35 (m, 1H), 4.22–4.08 (m, 4H), 3.97 (s, 2H), 3.94 (s, 2H), 3.75–3.57 (m, 4H), 2.86 (s, 3H), 2.85 (s, 3H); MS (ESI) m/e 409 (M+1)$^+$; Anal. calcd for C$_{21}$H$_{20}$N$_4$O$_5$: C, 61.76; H, 4.94; N, 13.72. Found: C, 61.47; H, 5.00; N, 13.39.

EXAMPLE 63

N-[1-[[(4'-cyano[1,1'-biphenyl]-4-yl)sulfonyl]methyl]-2-(4,4-dimethy-2,5-dioxo-1-imidazolidinyl)ethyl]-N-hydroxyformamide The title compound was prepared following the procedure from Example 61 but using 1-bromo-3-(4,4-dimethyl-2,5-dioxo-1-imidazolidin-1-yl)-2-propanone in place of 1-bromo-3-(3,4,4-trimethyl-2,5-dioxo-1-imidazolidin-1-yl)-2-propanone in example 61A. Mixture of two rotamers: $^1$H NMR (300 MHZ, d$_6$-DMSO) δ 9.66 (s, 1H0, 9.51 (s, 1H), 8.38 (s, 1H), 8.34 (s, 1H), 8.10 (s, 1H), 8.07–7.96 (s, 16H), 7.74 (s, 1H), 4.94–4.86 (m, 1H), 4.58–4.50 (m, 1H), 3.80–3.37 (m, 8H), 1.23–1.20 (m, 12H); MS (ESI) m/e 488 (M+18)$^+$; Anal. calcd for C$_{22}$H$_{22}$N$_4$O$_6$S: C, 56.16; H, 4.71; N, 11.91. Found: C, 56.12; H, 5.00; N, 11.59.

EXAMPLE 64

(±)-N-[1-[[(4'-chloro-[1,1'-biphenyl]-4-yl)oxy]methyl]-2-(3,4,4-trimethyl-2,5-dioxo-1-imidazolidinyl)ethyl]-N-hydroxyformamide

EXAMPLE 64A

1-[4"-chloro-1',1"-biphenyl]-4'-yl)oxy]-3-(3,4,4-trimethyl-2,5-dioxoimidazolidin-1yl)-propan-2-one A solution of Example 16B (0.81 g, 2.93 mmol), 4-chloro-4'-hydroxybiphenyl (0.50 g, 2.44 mmol), and potassium carbonate (0.35 g, 2.57 mmol) in dry DMF (50 mL) was stirred at ambient temperature for 1.5 hour and partitioned between ethyl acetate and water. The aqueous layer was drawn off and extracted with ethyl acetate (1×). The combined organic extracts were diluted with an equal volume of hexanes and washed sequentially with water (3×) and brine (2×), dried (Na$_2$SO$_4$), filtered, and concentrated to provide 0.89 g of a waxy clumpy solid which was purified by purified on silica gel with 40% ethyl acetate/dichloromethane to provide 0.46 g (47%) of the title compound as a colorless solid.

mp 165–166° C.; MS (DCI/NH$_3$) m/e 379 (M+NH$_4$)$^+$.

EXAMPLE 64B (±)-N-[1-[[(4'-chloro-[1,1'-biphenyl]-4-yl)oxy]methyl]-2-(3,4,4-trimethyl-2,5-dioxo-1-imidazolidinyl)ethyl]-N-hydroxyformamide The ketone from Example 64B was sequentially converted to the corresponding oximes, hydroxylamine, and the final compound as described in Examples 2D, 2E, and 2F The title compound was purified on silica gel with 2.5% methanol/dichlormethane to provide the title compound as a colorless solid which was recrystallized from ethyl acetate/hexanes.

mp 124–125° C.; MS (DCI/NH$_3$) m/e 446 (M+H)$^+$ and 463 (M+NH$_4$)$^+$; $^1$H NMR (300 MHz, CDCl$_3$) δ 9.90 (s; 0.5H), 9.58 (s; 0.5H), 8.32 (s; 0.5H), 7.92 (s; 0.5H), 7.65 (d; 2H; J=9 Hz), 7.61 (d; 2H; J=9 Hz), 7.47 (d; 2H; J=9 Hz), 6.99 (d; 1H; J=9 Hz), 6.97 (d; 1H; J=9 Hz), 4.86 (m; 0.5H), 4.42 (m; 0.5H), 4.08–4.23 (m; 2H), 3.82–3.70 (m; 1H), 3.55–3.65 (m; 1H), 2.80 (s; 1.5H), 2.78 (s; 1.5H), 1.30 (s; 3H), 1.28 (s; 3H); Anal. calcd for C$_{22}$H$_{24}$N$_3$O$_5$Cl: C, 59.26; H, 5.42; N, 9.42. Found: C, 59.54; H, 5.61; N, 9.13.

EXAMPLE 65

(+)-N-[1-[[(3'-cyanomethyl-[1,1'-biphenyl]-4-y)oxy]methyl]-2-(3,5,5-trimethyl-2,4-dioxo-1-imidazolidinyl)propyl]-N-hydroxyformamide

EXAMPLE 65A 1-(3-[(3'-cyanomethyl-[1,1'-biphenyl]-4-yl)oxy]-propan-2-on-1-yl)-3,4,4-trimethyl-2,5-dioxoimidazolidine The title compound was prepared as in Example 5F but using 4'-hydroxy-3-biphenylcarbonitrilemethane (0.95 g, 2.80 mmol) in place of 4'-hydroxy-4-biphenylcarbonitrile. Purification on silica gel with 100% ethyl acetate provided 0.78 g of title compound.

MS (DCI/NH$_3$) m/e 437 (M+NH$_4$)$^+$.

EXAMPLE 65B (+)-N-[1-[[(3'-cyanomethyl-[1,1'-biphenyl]-4-y)oxy]methyl]-2-(3,4,4-trimethyl-2,5-dioxo-1-imidazolidinyl)propyl]-N-hydroxyformamide Example 65A (0.78 g, 1.87 mmol) was processed sequentially according to the precedures in Example 2D, 2E, and 2F without purification of the intermediates. Purification on silica gel with 100% ethyl acetate provided 500 mg (1.08 mmol) of the title compound.

$^1$H NMR (300 MHz, DMSO) δ 9.99 (s, 0.5H), 9.58 (s, 0.5H), 8.36 (s, 0.5H), 7.92 (s, 0.5H), d 7.60 (m, 4H), 7.46 (t, 1H J=8 Hz), 7.30 (d, 1H; J=8 Hz), 7.02 (d, 2H; J=8 Hz), 4.50 (m, 0.5H), 4.18 (m, 0.5H), 4.12 (s, 2H), 4.10 (m, 2H), 3.45 (m, 2H), 2.80 (s, 3H), 1.92 (m, 1H), 1.80 (m, 1H), 1.30 (s, 6H); MS (DCI/NH$_3$) m/e 482 (M+NH$_4$)$^+$.

EXAMPLE 66

(+)-N-[1-[[(4'-cyano-[1,1'-biphenyl]-4-y)oxy]methyl]-2-isopropylthioethyl]-N-hydroxyformamide

EXAMPLE 66A (+)-1-[(4'-cyano-[1,1'-biphenyl]-4-y)oxy]-3-isopropylthio-2-propanol A solution of isopropylthiol (0.48 g, 6.4 mmol) in THF (20 mL) was treated with K$_2$CO$_3$ (0.5 g, 3.6 mmol). After 30 minutes, 3-[(4'-cyano-[1,1'-biphenyl]-4-y)oxy]-(1,2) oxirane (0.8 g, 3.19 mmol) was added in a single portion. The resulting solution was stirred at 70° C. for 3 hours, quenched by adding excess aqueous sodium bicarbonate solution and partitioned between ethyl acetate and brine. The organic layer was dried (Na$_2$SO$_4$), filtered, and the product was purified on silica gel with 50% ethyl acetate/hexanes to provide 0.9 g (2.75 mmol, 86%) of the title compound.

MS (DCI/NH$_3$) m/e 345 (M+NH$_4$)$^+$ and 362 (M+NH$_4$+NH$_3$)$^+$.

EXAMPLE 66B (+)-N-[1-[[(4'-cyano-[1,1'-biphenyl]-4-y)oxy]methyl]-2-isopropylthioethyl]-N-hydroxyformamide Example 66A was processed according to the procedures in Example 2C, 2D, 2E, and 2F providing the title compound as a light orange foam.

$^1$H NMR (300 MHz, DMSO) δ 9.99 (s: 0.5H), 9.60 (s: 0.5H), 8.42 (s: 0.5H), 8.04 (s:0.5H), d 7.85 (m; 4H), 7.75 (d; 2H J=9 Hz), 7.05 (d; 2H; J=9 Hz), 4.63 (m; 1H), 4.17 (m; 3H), 3.0 (m; 1H), 2.79 (m; 1H), 1.22 (dd; 6H; J=7.50 Hz); MS (DCI/NH$_3$) m/e 388 (M+NH$_4$)$^+$.

EXAMPLE 67

(+)-N-[1-[[(3'-cyanomethyl-[1,1'-biphenyl]-4-y)oxy]methyl]-2-(3,4,4-trimethyl-2,5-dioxo-1-imidazolidinyl)ethyl]-N-hydroxyformamide

EXAMPLE 67A (+)-1-[4-(3'-cyanoemethylphenyl)phenoxy]-3-(3,4,4-trimethyl-2,5-dioxo-1-imidazolidinyl)-2-propanol The title compound was prepared as in Example 4A but using 4'-hydroxy-3-biphenylcarbonitrilemethane (170 mg, 0.64 mmol) and 3,5,5-trimethylhydantoin (37 mg, 0.96 mmol) in place of 4'-hydroxy-4-biphenylcarbonitrile and 5,5-dimethylhydantoin. Purification on silica gel with 100% ethyl acetate provided 130 g of title compound. MS (DCI/NH$_3$) m/e 415 (M+NH$_4$)$^+$.

EXAMPLE 67B (+)-N-[1-[[(3'-cyanomethyl-[1,1'-biphenyl]-4-y)oxy]methyl]-2-(3,4,4-trimethyl-2,5-dioxo-1-imidazolidinyl)ethyl]-N-hydroxyformamide Example 67A was processed according to the procedures in Example 2C, 2D, 2E, and 2F providing the title compound.

$^1$H NMR (300 MHz, DMSO) δ 9.86 (s: 0.5H), 9.58 (s: 0.5H), 8.34 (s: 0.5H), 7.92 (s:0.5H), d 7.60 (m; 4H), 7.46 (t; 1H J=8 Hz), 7.30 (d; 1H; J=8 Hz), 7.02 (d; 2H; J=8 Hz), 4.85 (m; 0.5H), 4.42 (m; 0.5H), 4.10 (m; 2H), 4.12 (s; 2H), 3.68 (m; 1H), 3.62 (m; 1H), 2.80 (s; 3H), 1.30 (s: 6H); MS (DCI/NH$_3$) m/e 468 (M+NH$_4$)$^+$.

EXAMPLE 68

(+)-N-[1-[[(4'-cyano-[1,1'-biphenyl]-4-yl)oxy]methyl]-2-(3-ethyl-4,4-dimethyl-2,5-dioxo-1-imidazolidinyl)ethyl]-N-hydroxyformamide

EXAMPLE 68A 4,4-dimethyl-2,5-dioxo-N-(4-methoxoybenzyl)imidazolidine

A solution of 4,4-dimethyl-2,5-dioxoimidazolidine (17.0 g, 133 mmol), 4-methoxybenzyl chloride (30.0 g, 192 mmol), and potassium carbonate (27.5 g, 200 mmol) in dry DMF (600 mL) was heated at 80° C. under nitrogen for 3 h. The volume was reduced under high vacuum to about ¼ of the original volume and the resulting solution was partitioned between ethyl acetate and water. The aqueous layer was drawn off and extracted with ethyl acetate (2×). The combined organic extracts were washed sequentially with water (2×) and brine (2×), dried (Na$_2$SO$_4$), filtered and concentrated under vacuum to provide 32.97 g of a solid. Pure title compound was obtained by recrystallization from ethyl acetate and hexanes to provide 24.5 g (74%) of a colorless solid.

mp 109–111° C.; MS (DCI/NH$_3$) m/e 249 (M+H)$^+$ and 266 (M+NH$_4$)$^+$.

EXAMPLE 68B

3-Ethyl-1-(4'-methoxybenzyl)-2,5-dioxo-4,4-dimethylimidazolidine

A solution of 4,4-dimethyl-2,5-dioxo-N-(4-methoxoybenzyl)imidazolidine (3.5 g, 14.1 mmol) in THF (100 mL) was treated with sodium hydride (0.5 g, 21.2 mmol), stirred for 10 minute, treated with iodoethane (3.3 g, 21.2 mmol), stirred at 50° C. for 3 hours. then treated with HCl solution (10%) and partitioned between ethyl acetate and brine. The organic layer was dried, filtered and concentrated to provide 3.8 g (13.8 mmol, 98%) of title compound as white solid.

MS (DCI/NH$_3$) m/e 294 (M+NH$_4$).

EXAMPLE 68C

3-Ethyl-2,5-dioxo-4,4-dimethylimidazolidine

A solution of 3-ethyl-1-(4'-methoxybenzyl)-2,5-dioxo-4,4-dimethylimidazolidine (3.86 g, 14.0 mmol) in methoxy-benzene (100 mL) was treated with alumiun trichloride (5.5 g, 42 mmol), stirred at 75° C. for 30 minute, then poured the reaction into HCl solution (10%) and partitioned between ethyl acetate and brine. The organic layer was dried, filtered, and concentrated. Purification by recrystalization with ethyl acetate provided 2.1 g (13.5 mmol, 96%) of title compound as white solid.

MS (DCI/NH$_3$) m/e 174 (M+NH$_4$)$^+$.

EXAMPLE 68D

1-[(4'-cyano-[1,1'-biphenyl]-4-y)oxy]-3-(3-ethyl-5,5-dimethyl-2,4-dioxo-1-imidazolidinyl)-2-propanone A solution of 3-ethyl-2,5-dioxo-4,4-dimethylimidazolidine (0.7 g, 4.5 mmol) in DMF (100 mL) was treated with potassium carbonate (0.6 g, 4.5 mmol) and 1-[(4'-cyano-[1,1'-biphenyl]-4-y)oxy]-3-bromo-2-propynone (1.0 g, 3.0 mmol), stirred at 25° C. for 20 hours, then the reaction was poured into aqueous HCl solution (10%) and partitioned between ethyl acetate and brine. The organic layer was dried, filtered, and concentrated. Purification on silica gel with 50% ethyl acetate provided 0.8 g (1.97 mmol, 66%) of title compound as white solid.

MS (DCI/NH$_3$) m/e 424 (M+NH$_4$)$^+$.

EXAMPLE 68E (+)-N-[1-[[(4'-cyano-[1,1'-biphenyl]-4-yl)oxy]methyl]-2-(3-ethyl-4,4-dimethyl-2,5-dioxo-1-imidazolidinyl)ethyl]-N-hydroxyformamide Example 68B (0.72 g, 1.77 mmol) was processed sequentially according to the precedures in Example 2D, 2E, and 2F without purification of the intermediates. Purification on silica gel with 60% ethyl acetate/hexanes provided 158 mg (0.35 mmol) of the title compound.

$^1$H NMR (300 MHz, DMSO) δ 9.85 (s, 0.5H), 9.54 (s, 0.5H), 8.32 (s, 0.5H), 7.94 (s, 0.5H), d 7.86 (m, 4H), 7.72 (d, 2H J=9 Hz), 7.08 (d, 2H, J=9 Hz), 4.85 (m, 0.5H), 4.42 (m, 0.5H), 4.18 (m, 2H), 3.78 (m, 1H), 3.62 (m, 1H), 1.32 (s, 6H), 1.12 (m, 3H). MS (DCI/NH$_3$) m/e 468 (M+NH$_4$)$^+$.

EXAMPLE 69

(+)-N-[1-[[(4'-cyano-[1,1'-biphenyl]-4-yl)oxy]methyl]-2-(3-benzyl-4,4-dimethyl-2.5-dioxo-1-imidazolidinyl)ethyl]-N-hydroxyformamide

EXAMPLE 69A 3-benzyl-1-(4'-methoxybenzyl)-2,5-dioxo-4,4-dimethylimidazolidine The title compound was prepared as in Example 68B but using benzyl iodine (3.9 g, 18 mmol) in place of iodoethane. Purification on silica gel with 50% ethyl acetate provided 4.0 g of title compound.

MS (DCI/NH$_3$) m/e 356 (M+NH$_4$)$^+$.

EXAMPLE 69B 3-benzyl-2,5-dioxo-4,4-dimethylimidazolidine

A solution of 3-benzyl-1-(4'-methoxybenzyl)-2,5-dioxo-4,4-dimethylimidazolidine (3.9 g, 11.54 mmol) in acetonitrile (100 mL) was treated with a solution of ammonium cerium nitrate (31 g, 57.7 mmol) in 65 mL of water, stirred at 25° C. for 15 minute, then diluted the reaction with ethyl acetate and partitioned between ethyl acetate and brine. The organic layer was dried, filtered, and concentrated. Purification by recrystalization with ethyl acetate/hexane provided 1.58 g (7.25 mmol, 63%) of title compound as white solid. MS (DCI/NH$_3$) m/e 236 (M+NH$_4$)$^+$.

EXAMPLE 69C

1-[(4'-cyano-[1,1'-biphenyl]-4-y)oxy]-3-(3-ethyl-4,4-dimethyl-2,5-dioxo-1-imidazolidinyl)-2-propanone The title compound was prepared as in Example 68D but using 3-benzyl-2,5-dioxo-4,4-dimethylimidazolidine (0.5 g, 2.28 mmol) in place of using 3-ethyl-2,5-dioxo-4,4-dimethylimidazolidine. Purification on silica gel with 30% ethyl acetate/cloroform provided 634 mg of title compound.

MS (DCI/NH$_3$) m/e 485 (M+NH$_4$)$^+$.

EXAMPLE 69D (+)-N-[1-[[(4'-cyano-[1,1'-biphenyl]-4-yl)oxy]methyl]-2-(3-ethyl-4,4-dimethyl-2,5-dioxo-1-imidazolidinyl)ethyl]-N-hydroxyformamide Example 69C (0.62 g, 1.33 mmol) was processed sequentially according to the precedures in Example 2D, 2E, and 2F without purification of the intermediates. Purification on silica gel with 70% ethyl acetate/hexanes provided 230 mg (0.45 mmol) of the title compound.

$^1$H NMR (300 MHz, DMSO) δ 9.95 (s, 0.5H), 9.64 (s, 0.5H), 8.35 (s, 0.5H), 7.94 (s, 0.5H), d 7.86 (m, 4H), 7.75 (d, 2H, J=9 Hz), 7.30 (d, 2H, J=9 Hz), 7.25 (m, 3H), 7.06 (m, 2H), 4.90 (m, 0.5H), 4.52 (s, 2H), 4.50 (m, 0.5H), 4.18 (m, 2H), 3.82 (m, 1H), 3.62 (m, 1H), 1.22 (s, 6H); MS (DCI/NH$_3$) m/e 530 (M+NH$_4$)$^+$.

EXAMPLE 70

(+)-N-[1-[[(4'-cyano-[1,1'-biphenyl]-4-y)oxy]methyl]-2-(3,5,5-trimethyl-2,4-dioxo-1-imidazolidinyl)ethyl]-N-hydroxyformamide

EXAMPLE 70A

1-[(4'-cyano-[1,1'-biphenyl]-4-y)oxy]-3-(3,5,5-trimethyl-2,4-dioxo-1-imidazolidinyl)-2-propanol A solution of 5,5-dimethylhydantoin (2.0 g, 15.6 mmol) in DMF (20 mL) was treated with sodium tert-butoxide (1.5 g, 15.6 mmol), stirred for 10 minute, treated with iodomethane (2.2 g, 15.6 mmol), stirred at 40° C. for 3 hours. The resulting solution was treated with sodium tert-butoxide (1.5 g, 15.6 mmol) followed by 3-[(4'-cyano-[1,1'-biphenyl]-4-y)oxy]-(1,2) oxirane (1.15 g, 4.58 mmol), stirred at 100° C. for 20 minute, treated with HCl solution (10%) and partitioned between ethyl acetate and brine. The organic layer was dried and concentrated to provide 1.35 g (75%) of title compound as white solid.

MS (DCI/NH$_3$) m/e 411 (M+NH$_4$).

EXAMPLE 70B

1-[(4'-cyano-[1,1'-biphenyl]-4-y)oxy]-3-(3,5,5-trimethyl-2,4-dioxo-1-imidazolidinyl)-2-propanone Example 70A (1.35 g, 3.4 mmol) was processed according to the procedures in Example 2C. Purification on silica gel with 30% ethyl acetate provided 1.2 g (3.1 mmol, 90%) of the title compound.

MS (DCI/NH$_3$) m/e 409 (M+NH$_4$)$^+$.

EXAMPLE 70C (+)-N-[1-[[(4'-cyano-[1,1'-biphenyl]-4-yl)oxy]methyl]-2-(3,5,5-trimethyl-2,4-dioxo-1-imidazolidinyl)ethyl]-N-hydroxyformamide Example A-264890.0-B (1.2 g, 3.07 mmol) was processed sequentially according to the precedures in Example 2D, 2E, and 2F without purification of the intermediates. Purification on silica gel with 30% ethyl acetate/hexanes provided 380 mg (2.29 mmol) of the title compound.

$^1$H NMR (300 MHz, DMSO) δ 9.90 (s, 0.5H), 9.68 (s, 0.5H), 8.38 (s, 0.5H), 7.98 (s, 0.5H), d 7.88 (m, 4H), 7.72 (d, 2H, J=9 Hz), 7.08 (d, 2H, J=9 Hz), 4.92 (m, 0.5H), 4.42 (m, 0.5H), 4.20 (m, 2H), 3.50 (m, 2H), 2.88 (s, 3H), 1.32 (s, 6H); MS (DCI/NH$_3$) m/e 454 (M+NH$_4$)$^+$.

EXAMPLE 71

N-[1-[[(4'-methoxy[1,1'-biphenyl]-4-yl)sulfonyl]methyl]ethyl]-N-hydroxyformamide

EXAMPLE 71A

4'-methoxy-4-thiomethyl biphenyl

A solution of 4-bromothioanisole (6.15 g, 29.4 mmol) in DMF (60 mL) was treated sequentially with palladium (II) acetate (0.34 g, 1.5 mmol) and tri-o-tolylphosphine (0.94 g, 3.0 mmol) then 4-methoxyphenylboronic acid (5.06 g, 32.3 mmol) and cesium carbonate (19.2 g, 58.8 mmol). The mixture was stirred at 75° C. for 8 hours, then rt for 15 hours. The resulting suspension was partitioned between water and ether/hexane, 2:1. The organic layer was dried with Mg$_2$SO$_4$, filtered, and concentrated to provide crude product as a yellow solid. Recrystallization in ether at –20° C. afforded 2.61 g (39%) of the title compound.

MS (ESI+) m/e 231 (M+H).

EXAMPLE 71B 4-(4'-methoxyphenyl)-phenyl methyl sulfone

A solution of Example 71A (2.6 g, 11.3 mmol) in chloroform (100 mL) was treated with m-chloroperbenzoic acid (6.52 g, 22.7 mmol), stirred at 0° C. for 3 hours and then warmed to 10° C. over 1 hour. The mixture was partitioned between dilute sodium bicarbonate aqueous solution and chloroform, dried (Mg2SO4), filtered, and concentrated to provide crude product as a white solid. Recrystallized in dichloromethane and ether to afford 1.89 g (64%) of the title compound.

MS (ESI+) m/e 263 (M+H) and 280 (M+NH$_4$).

EXAMPLE 71C

N-[1-[[(4'-methoxy[1,1'-biphenyl]-4-yl)sulfonyl]methyl]ethyl]-N-benzyloxy amine

A suspension of Example 71B (0.26 g, 1.0 mmol) in THF (40 mL) cooled to –78° C. under argon atmosphere was treated with n-BuLi (0.40 mL of a 2.5 M solution in hexane, 1.0 mmol) and stirred for 3 hours. The resulting suspension was treated with BF$_3$.Et$_2$O (0.127 mL, 1.0 mmol) then the O-Benzyloxime of acetaldehyde (0.15 g, 1.0 mmol) (Stewart, et. al. *J. Med. Chem.* 1997, vol. 40, number 13, pages 1955–1968) in THF (10 mL), and stirred 1 hour at –78° C. and 1 hour at 25° C. The mixture was partitioned between ether and pH 7 phosphate buffer. The organic extracts were washed with brine, dried (Mg$_2$SO$_4$), filtered, and concentrated to afford crude product as a white powder which was purified on silica gel with dichloromethane/methanol to provide 0.15 g (36%) of the title to compound.

MS (ESI+) m/e 412 (M+H).

EXAMPLE 71D

N-[1-[[(4'-methoxy[1,1'-biphenyl]-4-yl)sulfonyl]methyl]ethyl]-N-nenzyloxyformamide A solution of Example 71c (0.11 g, 0.27 mmol) in THF (50 mL) cooled to 0° C. under argon atmosphere was treated with fornic acetic anhydride (0.24 g, 2.7 mmol), stirred for 5 minutes at 0° C. then rt for 16 hours. Partitioned between 1 N Hcl and ethyl acetate. Washed organic extracts with brine, dried (Mg$_2$SO$_4$), filtered, and concentrated to provide crude oil product which was purified on silica gel with dichloromethane/methanol to afford 114 mg (96%) of the title compound.

MS (ESI+) m/e 440 (M+H) and 457 (M+NH$_4$).

EXAMPLE 71E

N-[1-[[(4'-methoxy[1,1'-biphenyl]-4-yl)sulfonyl]methyl]ethyl]-N-hydroxyformamide A solution of Example 71D (114 mg, 0.26 mmol) in THF (20 mL) was treated with 10% palladium on carbon (35 mg, catalytic amount) and hydrogen gas at atmospheric pressure and stirred at rt for 18 hours. Filtered the suspension through Celite pad and concentrated to provide crude product as a white solid which was purified by trituration in ethyl acetate to afford 66 mg (73%) of the title compound.

mp 197–198° C.; 1H NMR (DMSO-d6) δ 1.16 (d, 1.5H, J=6.6 Hz), 1.22 (d, 1.5H, J=6.6 Hz), 3.43–3.70 (m, 2H), 3.82 (s, 3H), 4.28–4.41 (m, 0.5H), 4.62–4.76 (m, 0.5H), 7.08 (d, 2H, J=8.7 Hz), 7.74 (d, 2H, J=8.7 Hz), 7.87–7.96 (m, 4.5H), 8.08 (s, 0.5H), 9.47 (s, 0.5H), 9.89 (s, 0.5H); MS (ESI+) m/e 350 (M+H), 367 (M+NH$_4$); Anal. Calcd for: C$_{17}$H$_{19}$NO$_5$S.H2O C, 55.57; H, 5.76; N, 3.81. Found: C. 55.32; H, 5.20; N, 3.67.

EXAMPLE 72

N-[1-[[(4'-chloro[1,1'-biphenyl]-4-yl)sulfonyl]methyl]ethyl]-N-hydroxyformamide

The title compound was synthesized according to the procedures described in Example 71 except using 4-chlorophenylboronic acid in place of 4-methoxyphenylboronic acid in Example 71A. Purification of the crude final product by recrystallization in ethyl acetate afforded 36 mg of title compound.

mp 178–180° C.; 1H NMR (DMSO-d6) δ 1.16 (d, 1.5H, J=6.6 Hz), 1.22 (d, 1.5H, J=6.6 Hz), 3.50 (dd, 1H, J=4.8, 14.7 Hz), 3.57–3.73 (m, 1H), 4.28–4.41 (m, 0.5H), 4.61–4.77 (m, 0.5H), 7.59 (d, 2H, J=8.4 Hz), 7.81 (d, 2H, J=8.4 Hz), 7.91 (s, 0.5H), 7.92–8.00 (m, 4H), 8.07 (s, 0.5H), 9.45 (s, 0.5H), 9.86 (s, 0.5H); MS (ESI+) m/e 354 (M+H), 376 (M+Na); Anal. Calcd for: C$_{16}$H$_{16}$NO$_4$SCl C, 54.31; H, 4.55; N, 3.95. Found: C, 54.46; H, 4.43; N, 3.85.

EXAMPLE 73

N-[1-[[[4-(1,3-benzodioxol-5-yl)phenyl]sulfonyl]methyl]ethyl]-N-hydroxyformamide The title compound was synthesized according to the procedures described in Example 71 except using 3,4- methylenedioxybenzeneboronic acid in place of 4-methoxyphenylboronic acid in Example 71A. mp 200–201° C.; 1H NMR (DMSO-d6) δ 1.16 (d, 1.5H, J=6.6 Hz), 1.22 (d, 1.5H, J=6.6 Hz), 3.44–3.70 (m, 2H), 4.28–4.40 (m, 0.5H), 4.61–4.76 (m, 0.5H), 6.11 (s, 2H), 7.06 (d, 1H, J=7.8 Hz), 7.29 (d, 1H, J=8.4 Hz), 7.39 (s, 1H), 7.86–7.94 (m, 4.5H), 8.08 (s, 0.5H), 9.48 (s, 0.5H), 9.90 (s, 0.5H); MS (ESI+) 364 (M+H), 381 (M+NH$_4$); Anal. Calcd for: $C_{17}H_{17}NO_6S$ C, 56.19; H, 4.71; N, 3.85. Found: C, 55.97; H, 4.62; N, 3.81.

EXAMPLE 74

N-[1-[[[4-(4-chlorophenoxy)phenyl]sulfonyl]methyl] ethyl]-N-hydroxyformamide

EXAMPLE 74A 4-chlorophenoxyphenyl methyl sulfone

A solution of 4-chlorophenol (5.54 g, 43 mmol) in DMSO (75 mL) was treated sequentially with potassium t-butoxide (5.15 g, 46 mmol) then with a solution of 4-fluorophenyl methyl sulfone (5.00 g, 29 mmol) in DMSO (25 mL), heated at 120° C. for 2 hours, cooled to rt, then partitioned between dichloromethane and 1 N sodium hydroxide, dried (Mg$_2$SO$_4$), filtered, and concentrated to give crude product as a white solid. Recrystallization from ethyl acetate and hexane afforded 5.44 g (66%) of the title compound.

MS (ESI+) m/e 300 (M+NH$_4$).

EXAMPLE 74B

N-[1-[[[4-(4-chlorophenoxy)phenyl]sulfonyl]methyl] ethyl]-N-hydroxyformamide

The title compound was prepared from Example 74A according to the procedures described in Example 71C–71E. Purification of the crude final compound by recrystallization in ethyl acetate afforded 388 mg of the title compound.

mp 144–145° C.; 1H NMR (DMSO-d6) δ 1.15 (d, 1.5H, J=6.6 Hz), 1.21 (d, 1.5H, J=6.6 Hz), 3.39–3.68 (m, 2H), 4.25–4.37 (m, 0.5H), 4.60–4.70 (m, 0.5H), 7.16–7.23 (m, 4H), 7.53 (d, 2H, J=8.9 Hz), 7.83–7.92 (m, 2.5H), 8.06 (s, 0.5H), 9.45 (s, 0.5H), 9.87 (s, 0.5H); MS (ESI+) 370 (M+H), 387 (M+NH$_4$); Anal. Calcd for: $C_{16}H_{16}NO_5SCl$ C, 51.96; H, 4.36; N, 3.78. Found: C, 52.22; H, 4.37; N, 3.80.

EXAMPLE 75

N-[1-[[(4'-methoxy[1,1'-biphenyl]-4-yl)sulfonyl] methyl]propyl]-N-hydroxyformamide

EXAMPLE 75A 1-(4'-methoxy[1,1'-biphenyl]-4-yl)sulfonyl]-2-butanol

A solution of Example 71B (0.70 g, 2.67 mmol) in THF (200 mL) cooled to −78° C. under argon was treated with n-BuLi (1.17 mL of 2.5 M solution in hexane, 2.93 mmol), stirred 4 hours at −78° C., then treated with propionaldehyde (0.40 mL, 5.34 mmol) dropwise. Allowed reaction mixture to warm to rt over 1.5 hour, quenched with saturated aqueous NH$_4$Cl solution (50 mL), partitioned between ether and water, dried (Mg$_2$SO$_4$), filtered, and concentrated to afford 0.90 g of crude product which was purified on silica gel with dichloromethane/methanol to provide 0.78 g (91%) of the title compound.

MS (ESI+) m/e 321 (M+H), 338 (M+NH$_4$).

EXAMPLE 75B 1-(4'-methoxy[1,1'-biphenyl]-4-yl)sulfonyl]-1-butene

A solution of Example 75A (0.45 g, 1.40 mmol) in dichloromethane (40 mL) cooled to 0° C. was treated sequentially with triethylamine (0.29 mL, 2.11 mmol) and methanesulfonyl chloride (0.12 mL, 1.55 mmol) dropwise. Stirred at rt for 3 hours then treated with 1,8-diazabicyclo [5.4.0]undec-7-ene (0.21 mL, 1.40 mmol), refluxed for 2 hours, cooled to rt, and partitioned between dilute sodium bicarbonate solution and dichloromethane. The organic extract was washed with 1 N Hcl, then brine, dried (Mg$_2$SO$_4$), filtered, and concentrated to afford white solid crude product. Recrystallization in ether at −20° C. provided 0.34 g (80%) of title compound.

MS (ESI+) m/e 303 (M+H), 320 (M+NH$_4$).

EXAMPLE 75C

N-[1-[[(4'-methoxy[1,1'-biphenyl]-4-yl)sulfonyl] methyl]propyl]-N-hydroxy amine

A solution of Example 75B (0.34 g, 1.12 mmol) in THF (40 mL) was treated with hydroxylamine hydrochloride (0.39 g, 5.62 mmol) and potassium carbonate (0.78 g, 5.62 mmol), refluxed for 5 hours, cooled to rt, partitioned between ether and water, dried (Mg2SO4), and concentrated to give crude product as a clear, colorless oil. Recrystallization from ethyl acetate and ether provided 0.25 g (67%) of the title compound.

MS (ESI+) m/e 336 (M+H).

EXAMPLE 75D

N-[1-[[(4'-methoxy[1,1'-biphenyl]-4-yl)sulfonyl] methyl]propyl]-N-hydroxyformamide A solution of Example 75C (0.24 g, 0.72 mmol) in THF (30 mL) cooled to 0° C. was treated with formic acetic anhydride (64 mg, 0.72 mmol), stirred for 2 hours, partitioned between water and dichloromethane, dried (Mg$_2$SO$_4$), filtered, and concentrated to afford 0.25 g of crude product which was recrystallized in ethyl acetate to provide 106 mg (41%) of the title compound.

mp 199–200° C.; 1H NMR (DMSO-d6) δ 0.69–0.80 (m, 3H), 1.40–1.69 (m, 2H), 3.41–3.69 (m, 2H), 3.82 (s, 3H), 3.96–4.07 (m, 0.5H), 4.43–4.54 (m, 0.5H), 7.08 (d, 2H, J=9.0 Hz), 7.71–7.78 (m, 2H), 7.87–7.96 (m, 4.5H), 8.17 (s, 0.5H), 9.49 (s, 0.5H), 9.84 (s, 0.5H); MS (ESI+) 364 (M+H), 381 (M+NH$_4$); Anal. Calcd for: $C_{18}H_{21}NO_5S$ C, 59.48; H, 5.82; N, 3.85. Found: C, 59.67; H, 5.77; N, 3.80.

EXAMPLE 76

N-[1-[1,1-dimethyl-2-[(4'-(trifluoromethyl)[1,1'-biphenyl]-4-yl]sulfonyl]ethyl]-N-hydroxyformamide

EXAMPLE 76A 4-(4'-trifluoromethylphenyl)-phenyl methyl sulfone

The title compound was prepared according to the procedure given in Example 73A substituting 4-trifluoromethylphenylboronic acid for 3,4-methylenedioxybenzeneboronic acid. Purification by recrystallization in ethyl acetate and ether afforded 3.70 g (72%) of the title compound.

MS (ESI+) m/e 318 (M+NH$_4$).

EXAMPLE 76B 1-(4'-trifluoromethyl[1,1'-biphenyl]-4-yl)sulfonyl]-2-methyl-2-propanol The title compound was prepared according to the procedure described in Example 75A substituting Example 76A for Example 71B and substituting acetone for propionaldehyde. Purification of crude product by recrystallization in ethyl acetate, ether, and pentane provided 1.40 g (73%) of the title compound.

MS (ESI+) m/e 376 (M+NH$_4$).

EXAMPLE 76C

N-[1-[1,1-dimethyl-2-[(4'-(trifluoromethyl)[1,1'-biphenyl]-4-yl]sulfonyl]ethyl]-N-hydroxyformamide The title compound was prepared from Example 76B according to the procedures described in Examples 75B, 75C and 75D. Purification of the final product by recrystallization in ethyl acetate and ether provided 17 mg of the title compound.

mp 167–169° C.; 1H NMR (DMSO-d6) δ 1.52 (s, 6H), 3.71 (s, 2H), 7.83–8.03 (m, 8.5H), 8.17 (s, 0.5H), 9.43 (s, 0.5H), 10.0 (s, 0.5H); MS (ESI+) 402 (M+H), 419 (M+NH$_4$), 424 (M+Na); Anal. Calcd for: C$_{18}$H$_{18}$NO$_4$F$_3$SC, 53.86; H, 4.52; N, 3.48. Found: C, 53.58; H, 4.48; N, 3.19.

EXAMPLE 77

N-[1-[(phenylmethoxy)methyl]-2-[[4'-(trifluoromethyl)[1,1'-biphenyl]-4-yl]sulfonyl]ethyl]-N-hydroxyformamide The title compound was synthesized according to the procedures described in Examples 75A–75D except substituting Example 76A for Example 71B and substituting benzyloxyacetaldehyde for propionaldehyde in Example 75A. Purification of the crude final product by recrystallization in ethyl acetate afforded 0.53 g of title compound. mp 172° C.;

1H NMR (DMSO-d6) δ 3.37–3.61 (m, 3H), 3.61–3.72 (m, 1H), 4.28–4.50 (m, 2.5H), 4.81–4.93 (m, 0.5H), 7.20–7.35 (m, 5H), 7.85–8.06 (m, 8.5H), 8.18 (s, 0.5H), 9.57 (s, 0.5H); 9.96 (s, 0.5H); MS (ESI+) 494 (M+H), 511 (M+NH$_4$); Anal. Calcd for: C$_{24}$H$_{22}$NO$_5$F$_3$S C, 58.41; H, 4.49; N, 2.83. Found: C, 58.43; H, 4.54; N, 2.77.

EXAMPLE 78

N-[1-(hydroxymethyl)-2-[[(4'-(trifluoromethyl)[1,1'-biphenyl]-4-yl]sulfonyl]ethyl]-N-hydroxyformamide A solution of Example 78 (35 mg, 0.07 mmol) in THF (3 mL) and methanol (5 mL) was treated with palladium on carbon, 10% (30 mg, 0.03 mmol) and hydrogen gas at atmospheric pressure, stirred at rt for 16 hours, filtered through Celite, and concentrated to afford crude product. Purification by recrystallizations in ethyl acetate, ether, and hexane provided 20 mg (70%) of the title compound.

mp 159–161° C.; 1H NMR (DMSO-d6) δ 3.25–3.68 (m, 4H), 3.98–4.10 (m, 0.5H), 4.54–4.66 (m, 0.5H), 4.97–5.09 (m, 1H), 7.81–8.07 (m, 8.5H), 8.14 (s, 0.5H), 9.44 (s, 0.5H), 9.85 (s, 0.5H); MS (ESI+) 404 (M+H), 421 (M+NH$_4$), 426 (M+Na); Anal. Calcd for: C$_{17}$H$_{16}$NO$_5$F$_3$S C, 50.61; H, 3.99; N, 3.47. Found: C, 50.57; H, 3.93; N, 3.37.

EXAMPLE 79

N-[1-[(4,4-dimethy-2,5-dioxo-1-imidazolidinyl)methyl]-2-[[4'-(trifluoromethyl)[1,1'-biphenyl]-4-yl]thio]ethyl]-N-hydroxyformamide

EXAMPLE 79A

1-[(4'-trifluoromethyl[1,1'-biphenyl]-4-yl)thio]-3-(4,4-dimethyl-2,5-dioxoimidazolidin-1-yl)-2-propanone The mixture of example 46A (698 mg, 1.88 mmol), tetrakis(triphenyphosphine) palladium(0) (217 mg, 0.19 mmol), 4-triflorophenylboronic acid (714 mg, 3.76 mmol) and NaOH (1M, 3.76 mL, 3.76 mmol) in DME (20 mL) was refluxed under argon for 4 hour. The mixture was evaporated to a small volume, and partitioned between CH$_2$Cl$_2$/brine. The CH$_2$Cl$_2$ layer was collected, dried (Na$_2$SO$_2$), filtered and evaporated to dryness. Purification of the crude final product on silica gel with 20%–40% ethyl acetate/CH$_2$Cl$_2$ provided 0.820 g of the title compound. MS (DCI/NH$_3$) m/e 454 (M+NH$_4$)$^+$, 437 (M+H)+.

EXAMPLE 79B

N-[1-[(4,4-dimethy-2,5-dioxo-1-imidazolidinyl)methyl]-2-[[4'-(trifluoromethyl)[1,1'-biphenyl]-4-yl]thio]ethyl]-N-hydroxyformamide The title compound was obtained following the procedures in Examples 2D–F (inclusive) but substituting Example 79A (0.82 g, 1.88 mmol) for Example 2C. Purification of the crude final product on silica gel with 5% methanol/dichloromethane provided 434 mg of the title compound.

mp 172–174° C.; $^1$H NMR (300 MHz, d$_6$-DMSO) δ 9.75 and 9.52 (br s, 1H), 8.37 and 8.33 (s, 1H), 8.31 and 7.77 (s, 1H), 7.90 (d, 2H, J =8.4 Hz), 7.81 (d, 2H, J =8.4 Hz), 7.71 (m, 2H), 7.47 (m 2H), 4.60 and 4.09 (m, 1H), 3.52–3.77 (m, 2H), 3.08–3.46 (m, 2H), 1.28 and 1.25 and 1.23 (s, 6H); MS (DCI/NH$_3$) m/e499 (M+NH$_4$)$^+$, 482 (M+H)+; Anal. calcd for C$_{22}$H$_{22}$F$_3$N$_3$O$_4$S.0.5CH$_3$OH: C, 54.31; H, 4.86; N, 8.44. Found: C, 54.43; H, 4.82; N, 8.08.

EXAMPLE 80

N-[1-[(4,4-dimethy-2,5-dioxo-1-imidazolidinyl)methyl]-2-[[4'-(trifluoromethyl)[1,1'-biphenyl]-4-yl]sulfonyl]ethyl]-N-hydroxyformamide Example 79 was converted to example 80 following the procedure described in example 46D.

mp 180–182° C.; $^1$H NMR (300 MHz, d$_6$-DMSO) d 9.66 and 9.51 (br s, 1H), 8.39 and 8.35 (s, 1H), 8.10 and 7.73 (s, 1H), 7.79–8.02 (m, 6H), 7.89 (d, 2H, J =8.4 Hz), 4.91 and 4.55 (m, 1H), 3.45–3.80 (m, 4H), 1.24 and 1.23 and 1.21 (s, 6H). MS (DCI/NH$_3$) m/e531 (M+NH$_4$)$^+$, 514 (M+H)+; Anal. calcd for C$_{22}$H$_{22}$F$_3$N$_3$O$_6$S.0.75 H$_2$O: C, 50.14; H, 4.49; N, 7.97. Found: C, 50.27; H, 4.49; N, 7.97.

EXAMPLE 81

N-[1-[(2,5-dioxo-1-imidazolidinyl)methyl]-2-[[4'-(trifluoromethoxy)[1,1'-biphenyl]-4-yl]oxy]ethyl]-N-hydroxyformamide

EXAMPLE 81A 1-bromo-3-(2,5-dioxoimidazolidin-1-yl)propan-2-one

The title compound was prepared following the procedures in examples 16A and 16B, but substituting hydantoin for 1,5,5-trimethylhydantoin.

EXAMPLE 81B

N-[1-[(2,5-dioxo-1-imidazolidinyl)methyl]-2-[[4'-(trifluoromethoxy)[1,1'-biphenyl]-4-yl]oxy]ethyl]-N-hydroxyformamide The title compound was prepared following the sequence described in described in examples 16C and 16E, but substituting 81A for 16B and 4-(4'-trifluoromethoxyphenyl)-phenol for 4-bromophenol.

$^1$H NMR (DMSO-$\delta$6) $\delta$ 9.92 (s, 0.5H), 9.60 (bs, 0.5H), 8.31 (s, 0.5H), 8.16 (s, 0.5H), 8.14 (s, 0.5H), 7.92 (s, 0.5H), 7.76–7.72 (m, 4H), 7.64–7.62 (d, 4H, J=8.4 Hz), 7.42–7.40 (d, 4H, J=8.6 Hz), 7.02–6.98 (m, 4H), 4.84–4.82 (m, 0.5H), 4.38–4.35 (m, 0.5H), 4.19–4.04 (4H); Anal. Calcd for: $C_{20}H_{18}N_3O_6F_3$: C, 52.98; H, 4.00; N, 9.13. Found: C, 53.01; H, 4.03; N, 9.13.

EXAMPLE 82

N-[1-[[[4'-(trifluoromethyl)[1,1'-biphenyl]-4-yl]sulfonyl]methyl]-2-(3,4,4-trimethyl-2,5-dioxo-1-imidazolidinyl)ethyl]-N-hydroxyformamide The title compound was prepared following the procedures described in example 46A, 46B, 46C and 46D, except substituting example 16B for 23A in example 46A and 4-trifluoromethylbenzeneboronic acid for 4-butyloxybenzeneboronic acid in example 46B. $^1$H NMR (d6-DMSO) $\delta$ 9.70 (s, 0.5H), 9.54 (s, 0.5H), 8.10 (s, 0.5H), 8.05–7.97 (m, 6H), 7.89 (d, 2H, J=7.8 Hz), 7.75 (s, 0.5H), 4.97–4.86 (m, 0.5H), 4.60–4.48 (m, 0.5H), 3.80–3.44 (m, 4H), 2.75 (s, 3H), 1.24 (s, 3H), 1.22 (s, 3H); MS (ESI) 528 (M+H), 545 (M+NH$_4$), 526 (M−H); Anal. Calcd for: $C_{23}H_{24}N_3O_6SF_3$ C, 52.36; H, 4.58; N, 7.96. Found: C, 52.05; H, 4.70; N, 7.63.

EXAMPLE 83

N-[1-[[(4'-butyl[1,1'-biphenyl]-4-yl)oxy]methyl]-2-(3-methy-2,5-dioxo-1-imidazolidinyl)ethyl]-N-hydroxyformamide The title compound was prepared following the procedures described in example 16C and 16E. except substituting example 26A for 16B and 4-(4'-butylphenyl)phenol for 4-bromophenol.

$^1$H NMR (d6-DMSO) $\delta$ 10.00–9.94 (br, 0.5H), 9.64–9.58 (br, 0.5H), 8.34 (s, 0.5H), 7.98 (s, 0.5H), 7.58 (d, 2H, J=8.8 Hz), 7.52 (d, 2H, J=8.6 Hz), 7.24 (d, 2H, J=8.5 Hz), 7.00–6.92 (m, 2H), 4.92–4.79 (m, 0.5H), 4.41–4.30 (m, 0.5H), 4.20–4.03 (m, 2H), 3.95 (d, 2H, J=7.8 Hz), 3.75–3.57 (m, 2H), 2.86 (s, 1.5H), 2.85 (s, 1.5H), 2.60 (t, 2H, J=7.4 Hz), 1.63–1.51 (m, 2H), 1.39–1.25 (m, 2H), 0.91 (t, 3H, J=7.4 Hz); MS (ESI) 440 (M+H), 457 (M+NH$_4$), 438 (M−H); Anal. Calcd for: $C_{24}H_{29}N_3O_5 \cdot 0.25\ H_2O$ C, 64.92; H, 6.69; N, 9.46. Found: C, 64.76; H, 6.62; N, 9.29.

EXAMPLE 84

N-[1-[(3-methy-2,5-dioxo-1-imidazolidinyl)methyl]-2-[[4'-(trifluoromethoxy)[1,1'-biphenyl]-4-yl]oxy]ethyl]-N-hydroxyformamide The title compound was prepared following the procedures described in example 16C and 16E, except substituting example 26A for 16B and 4-(4'-trifluoromethoxy)phenol for 4-bromophenol.

$^1$H NMR (d6-DMSO) $\delta$ 10.02–9.92 (br, 0.5H), 9.64–9.58 (br, 0.5H), 8.35 (s, 0.5H), 7.98 (s, 0.5H), 7.74 (d, 2H, J=8.9 Hz), 7.64 (d, 2H, J=8.8 Hz), 7.41 (d, 2H, J=8.1 Hz), 7.03–6.97 (m, 2H), 4.91–4.82 (m, 0.5H), 4.41–4.31 (m, 0.5H), 4.21–4.07 (m, 2H), 3.96 (d, 2H, J=7.7 Hz), 3.72–3.57 (m, 2H), 2.86 (s, 1.5H), 2.85 (s, 1.5H); MS (ESI) 468 (M+H), 485 (M+NH$_4$), 466 (M−H); Anal. Calcd for: $C_{21}H_{20}N_3O_6F_3$ C, 53.96; H, 4.31; N, 8.99. Found: C, 53.85; H, 4.40; N, 8.85.

EXAMPLE 85

N-[4-[4-[(4'-chloro[1,1'-biphenyl]-4-yl)sulfonyl]methyl]tetrahydro-2H-pyran-4-yl]-N-hydroxyformamide

EXAMPLE 85A

N-[4-[4-[(4'-chloro[1,1'-biphenyl]-4-yl)sulfonyl]methyl]tetrahydro-2H-pyran-4-yl]-N-benzyloxy amine The title compound was prepared following the procedure described in example 54A, except using 4'-chloro-40methylsulfone-biphenyl in place of phenoxyphenyl-4-chloro-4'-methylsulfone.

EXAMPLE 85B

N-[4-[4-[(4'-chloro[1,1'-biphenyl]-4-yl)sulfonyl]methyl]tetrahydro-2H-pyran-4-yl]-N-hydroxy amine A solution of 85A (0.436 g, 0.92 mmol) was treated with $(CF_3CO_2)3B$ (4.6 mL, 1M solution in THF, 4.6 mmol), then stirred overnight at room temperature. The solution was concentrated, partitioned between ethyl acetate and aq. Na$_2$CO$_3$ and the organic layer was dried (Mg$_2$SO$_4$), filtered, concentrated and purified via column chromatography to give the title compound in 51% yield.

EXAMPLE 85C

N-[4-[4-[(4'-chloro[1,1'-biphenyl]-4-yl)sulfonyl]methyl]tetrahydro-2H-pyran-4-yl]-N-hydroxyformamide Example 85B was converted to the title compound using the formylation procedure of example 2F.

$^1$H NMR (d6-DMSO) $\delta$ 9.52–9.48 (br, 1H), 8.23 (s, 1H), 7.97 (s, 4H), 7.81 (d, 2H, J=8.4 Hz), 7.59 (d, 2H, J=8.5 Hz), 3.72 (s, 2H), 3.69–3.46 (m, 4H), 2.35–1.94 (m, 4H); MS (ESI) 410 (M+H), 427 (M+NH$_4$), 432 (M+Na), 408 (M−H).

EXAMPLE 86

N-[1-[[[4-(4-chlorophenoxy)phenyl]sulfonyl]methyl]-2-(4,4-dimethyl-2,5-dioxo-1-imidazolidinyl)ethyl]-N-hydroxyformamide The title compound was prepared following the procedures described in examples 46A, 46C and 46D, except using 4-(4'-chlorophenoxy)thiophenol instead of 4-bromothiophenol.

$^1$H NMR (d6-DMSO) $\delta$ 9.67 (s, 0.5H), 9.50 (s, 0.5H), 8.36 (d, 1H, J=13.2 Hz), 8.10 (s, 0.5H), 7.90 (dd, 2H, J=8.8, 3.0 Hz), 7.68 (s, 0.5H), 7.53 (d, 2H, J=8.8 Hz), 7.20 (d, 4H, J=8.8 Hz), 4.89–4.77 (m, 0.5H), 4.52–4.40 (m, 0.5H), 3.68–3.38 (m, 4H), 1.25–1.21 (m, 6H); MS (ESI) 496 (M+H), 513 (M+NH$_4$), 494 (M−H); Anal. Calcd for: $C_{21}H_{22}N_3O_7SCl$ C, 50.85; H, 4.47; N, 8.47. Found: C, 50.53; H, 4.58; N, 8.25.

EXAMPLE 87

N-[1-[[[4-(4-chlorophenoxy)phenyl]sulfonyl]methyl]-2-(3,4,4-trimethyl-2,5-dioxo-1-imidazolidinyl)ethyl]-N-hydroxyformamide The title compound was prepared following the procedures described in examples 46A, 46C and 46D, except using 16B in place of 23A and 4-(4'-chlorophenoxy) thiophenol instead of 4-bromothiophenol.
$^1$H NMR (d6-DMSO) δ 9.78–9.71 (m, 0.5H), 9.58–9.49 (m, 0.5H), 8.09 (s, 0.5H), 7.89 (dd, 2H, J=5.8, 2.9 Hz), 7.68 (s, 0.5H), 7.53 (d, 2H, J=9.2 Hz), 7.20 (d, 4H, J=8.8 Hz), 4.88–4.78 (m, 0.5H), 4.50–4.38 (m, 0.5H), 3.72–3.40 (m, 4H), 2.76 (s, 1.5H), 2.76 (s, 1.5H), 1.26–1.22 (m, 6H); MS (ESI) 510 (M+H), 527 (M+NH$_4$), 508 (M–H); Anal. Calcd for: $C_{22}H_{24}N_3O_7SCl$ C, 51.81; H, 4.74; N, 8.23. Found: C, 51.61; H, 4.90; N, 7.96.

EXAMPLE 88

N-[1-[[(4-butyl[1,1'-biphenyl]-4-yl)sulfonyl]methyl]-2-(3,4,4-trimethyl-2,5-dioxo-1-imidazolidinyl)ethyl]-N-hydroxyformamide The title compound was prepared following the procedures described in example 46A, 46B, 46C and 46D, except substituting example 16B for 23A in example 46A and 4-nbutylbenzeneboronic acid for 4-butyloxybenzeneboronic acid in example 46B. $^1$H NMR (d6-DMSO) δ 9.70 (s, 0.5H), 9.54 (s, 0.5H), 8.10 (s, 0.5H), 7.94 (d, 4H, J=1.0 Hz), 7.73 (s, 0.5H), 7.69 (dd, 2H, J=8.1, 2.0 Hz), 7.35 (d, 2H, J=8.4 Hz), 4.96–4.86 (m, 0.5H), 4.60–4.48 (m, 0.5H), 3.77–3.42 (m, 4H), 2.75 (s, 3H), 2.64 (t, 2H, J=7.4 Hz), 1.64–1.54 (m, 2H), 1.40–1.27 (m, 2H), 1.24 (s, 3H), 1.22 (s, 3H), 0.91 (t, 3H, J=7.5 Hz); MS (ESI) 516 (M+H), 533 (M+NH$_4$), 538 (M+Cl), 514 (M–H); Anal. Calcd for: $C_{26}H_{33}N_3O_6S$ C, 60.56; H, 6.45; N, 8.14. Found: C, 60.32; H, 6.44; N, 8.09.

EXAMPLE 89

N-[1-[[(4'-butyl[1,1'-biphenyl]-4-yl)oxy]methyl]-2-(4,4-dimethy-2,5-dioxo-1-imidazolidinyl)ethyl]-N-hydroxyformamide The title compound was prepared according to the procedures of example 23B, except substituting4-(4'-butylphenyl)-phenol in place of 4-(4'-ethoxyphenyl)-phenol. 1H NMR (DMSO-δ6) δ 0.93 (t, 3H, J=8 Hz), 1.28 (s, 6H), 1.30–1.39 (m, 2H), 1.50–1.65 (m, 2H), 2.60 (t, 2H, J=7 Hz), 3.51–3.64 (m, 1H), 3.67–3.80 (m, 1H), 4.03–4.24 (m, 2H), 4.35–4.48 (m, 0.5H), 4.78–4.92 (m, 0.5H), 6.99 (dd, 2H, J=3,9 Hz), 7.25 (d, 2H, J=9 Hz), 7.53 (d, 2H, J=9 Hz), 7.58 (d, 2H, J=9 Hz), 7.94 (s, 0.5H), 8.34 (d, 1H, J=6 Hz), 8.39 (s, 0.5H), 9.55 (s, 0.5H), 9.87 (s, 0.5H); MS (ESI–) 452 (M–H); Anal. Calcd for: $C_{25}H_{31}N_3O_5$ C, 66.20; H, 6.88; N, 9.26. Found: C, 65.99; H, 6.71; N, 9.19.

EXAMPLE 90

N-[1-[[[3'-(cyanomethyl)[1,1'-biphenyl]-4-yl]oxy]methyl]-2-(4,4-dimethy-2,5-dioxo-1-imidazolidinyl)ethyl]-N-hydroxyformamide The title compound was prepared according to the procedures of example 23B, except substituting4-(3'-cyanomethylphenyl)-phenol in place of 4-(4'-ethoxyphenyl)-phenol.
1H NMR (DMSO-δ6) δ 2.80 (s, 6H), 3.52–3.83 (m, 2H), 4.10 (s, 2H), 4.12–4.25 (m, 2H), 4.38 (4.46, mH, J=0.5 Hz), 4.80–4.90 (m, 0.5H), 7.03 (dd, 2H, J=3,9 Hz), 7.30 (d, 1H, J=10 Hz), 7.48 (t, 1H, J=10 Hz), 7.57–7.66 (m, 4H), 7.93 (s, 0.5H), 8.34 (d, 1H, J=6 Hz), 8.39 (s, 0.5H), 9.55 (s, 0.5H), 9.88 (s, 0.5H); MS (ESI–) 435 (M–H); Anal. Calcd for: $C_{23}H_{24}N_4O_5 \cdot 0.25CH_3CO_2C_2H_5$ C, 62.87; H, 5.71; N, 12.21. Found: C, 62.85; H, 5.80; N, 12.16.

EXAMPLE 91

N-[1-[4-(2-thienyl)phenoxy]methyl]-2-[1-(3,4,4-trimethyl-2,5-dioxo-1-imidazolidinyl)ethyl]-N-hydroxyformamide The title compound was preapred following the procedures of examples 16C and 16E, except substituting 4-(4'-(2-thienyl)phenyl)phenol for 4-bromophenol in example 16C.

1H NMR (DMSO-δ6) δ 1.29 (s, 6H), 2.80 (s, 3H), 3.54–3.66 (m, 1H), 3.69–3.84 (m, 1H), 4.04–4.22 (m, 2H), 4.33–4.47 (m, 0.5H), 4.77–4.90 (m, 0.5H), 6.96 (dd, 2H, J=3,9 Hz), 7.08–7.13 (m, 1H), 7.38 (d, 1H, J=3 Hz), 7.46 (d, 1H, J=4 Hz), 7.59 (d, 2H, J=9 Hz), 7.92 (s, 0.5H), 8.31 (s, 0.5H), 9.54 (s, 0.5H), 9.86 (s, 0.5H). MS (ESI–) 416 (M–H); Anal. Calcd for: $C_{20}H_{23}N_3O_5S \cdot 0.25H_2O$ C, 56.92; H, 5.61; N, 9.95. Found: C, 56.65; H, 5.48; N, 9.77.

EXAMPLE 92

N-[1-[[(3-nitro[1,1'-biphenyl]-4-yl)oxy]methyl]-2-(3,4,4-trimethyl-2,5-dioxo-1-imidazolidinyl)ethyl]-N-hydroxyformamide The title compound was preapred following the procedures of examples 16C and 16E, except substituting 4-phenyl-2-nitrophenol for 4-bromophenol in example 16C.
1H NMR (DMSO-δ6) δ 1.28 (s, 6H), 2.80 (s, 3H), 3.54–3.65 (m, 1H), 3.70–3.88 (m, 1H) 4.22–4.39 (m, 2H), 4.40–4.50 (m, 0.5H), 4.80–4.91 (m, 0.5H), 7.34–7.41 (m, 2H), 7.43–7.52 (m, 2H), 7.71 (d, 2H, J=8 Hz), 7.87 (s, 0.5H), 8.0 (d, 1H, J=9 Hz), 8.16 (dd, 1H, J=3,6 Hz), 8.29 (s, 0.5H), 9.55 (s, 0.5H), 9.80 (s, 0.5H); MS (ESI–) 455 (M–H); Anal. Calcd for: $C_{22}H_{24}N_4O_7$ C, 57.88; H, 5.29; N, 12.27. Found: C, 57.62; H, 5.44; N, 11.95.

EXAMPLE 93

N-[1-[[(4'-methyl[1,1'-biphenyl]-4-yl)oxy]methyl]-2-[[3-(methylsulfonyl)amino]phenyl]ethyl]-N-hydroxyformamide

EXAMPLE 93A 3-(methylsulfonyl)amino-1-bromo-benzene

The m-bromo aniline was dissolved in 40 mL of pyridine and cooled to 0° C. followed by addition of methansulfonyl chloride dropwise via syringe. After 10 min, the solution was warmed to room temperature and stirred for 4 h. Upon concentration in vacuo the residue was partitioned between 350 mL of $H_2O$ and 500 mL of $CH_2Cl_2$ in a separatory funnel. The organics were separated and washed with 100 mL of 3N HCl, 200 mL of sat'd $NaHCO_3$ and dried over $MgSO_4$. Upon filtration and concentration in vacuo an off-white solid was obtained. This product was recrystallized from $CH_2Cl_2$/Hexanes to afford 6.7 g (90%) of 93A as white needles.

EXAMPLE 93B 3-(methylsulfonyl)amino-1-(prop-2-enyl)-benzene

Using a glass sealed vessel the sulphonamide 93A (3.0 g, 12.1 mmol) was suspended in 10 mL of toluene followed by addition of the allyltributyl tin reagent and bubbled with argon for 5 min. To the above suspension was added 280 mg (2 mol %) of Pd(PPh$_3$)$_4$ and the vessel sealed and heated at 120° C. for 17 h. After 15 min a homogeneous solution was obtained which turned dark brown after 30 min. After cooling, the catalyst was filtered off washing with $CH_2Cl_2$/MeOH. Concentration of the filtrate followed by purification on silica gel eluting with 10% Ethyl Acetate/Hexanes then 20% Ethyl Acetate/Hexanes afforded 93B, 0.99g (38%) as a colorless oil which solidified upon standing.

EXAMPLE 93C

N-[1-[[(4'-methyl[1,1'-biphenyl]-4-yl)oxy]methyl]-2-[[3-(methylsulfonyl)amino]phenyl]ethyl]-N-hydroxyformamide The title compound was preapred from example 93B, first by epoxidizing as desribed in example 5C, then opening the epoxide with 4'-hydroxy-4-biphenylcarbonitrile as in example 5F, then following the sequence of reactions described in examples 2C through 2F.

1H NMR (DMSO-δ6) δ 2.32 (s, 3H), 2.88 (d, 2H, J=6 Hz), 2.96 (s, 1H), 2.98 (s, 3H), 4.03–4.11 (m, 1H), 4.15–4.27 (m, 1,5H), 4.72–4.82 (bs, 0.5H), 6.97–7.10 (m, 4H), 7.05 (s, 1H), 7.20–7.30 (m, 3H), 7.50 (d, 2H, J=9 Hz), 7.57 (d, 2H, J=9 Hz), 7.73 (s, 0.5H), 8.25 (s, 0.5H), 9.18 (s, 0.5H), 10.01 (s, 0.5H); MS (ESI–) 453 (M–H); Anal. Calcd for: $C_{24}H_{26}N_2O_5S$ C, 63.41; H, 5.76; N, 6.16. Found: C, 63.16; H, 6.12; N, 5.76.

EXAMPLE 94

N-[1-[[[3-(diethylamino)carbonyl]phenyl]methyl]-2-[(4'-methyl[1,1'-biphenyl]-4-yl)oxy]ethyl]-N-hydroxyformamide

EXAMPLE 94A 3-bromo-1-(N,N-diethylcarboxamide)-benzene

Diethylamine (10.0 ml, 97 mmol) was dissolved in 60 ml of dry ethyl ether and cooled to 0° C. Benzoyl chloride (3.67 ml, 28 mmol) was dissolved in 10 mL of dry ethyl ether and was slowly added dropwise via syringe to to the above solution. A white slurry developed upon addition and stirring was continued for 10 min at 0° C. then warmed to room temperature for 1 h. The mixture was poured into a separatory fuinnel containing 500 mL of ethyl ether and 75 mL of 10% NaOH. The organics were separated and washed a second time with 75 mL of 10% NaOH followed by 75 mL of 10% HCl then 200 mL of water. A final wash with 100 mL of brine followed by drying over MgSO4, filtering and then concentration in vacuo, afforded the 94A as a colorless liquid, 5.9 g (83%) which was used without further purification.

EXAMPLE 94B

N-[1-[[[3-(diethylamino)carbonyl]phenyl]methyl]-2-[(4'-methyl[1,1'-biphenyl]-4-yl)oxy]ethyl]-N-hydroxyformamide The title compound was prepared following the procedure described in examples 93B and 93C, except substituting 94A for 93A.

1H NMR (DMSO-δ6) δ 0.98–1.20 (bd, 6H), 2.32 (s, 3H), 2.93 (d, 2H, J=6 Hz), 3.11–3.48 (bd, 4H), 4.0–4.13 (m, 1H), 4.16–4.30 (m, 1.5H), 4.74–4.86 (bs, 0.5H), 6.98 (d, 2H, J=9 Hz), 7.13–7.40 (m, 6H), 7.50 (d, 2H, J=8 Hz), 7.56 (d, 2H, J=9 Hz), 7.73 (s, 0.5H), 8.23 (s, 0.5H), 9.63 (s, 0.5H), 10.02 (s, 0.5H). MS (ESI+) 461 (M+H). Anal. Calcd for: C28H32N2O4.1.5H2O C, 68.97; H, 7.23; N, 5.74. Found: C, 68.96; H, 7.09; N, 5.42

EXAMPLE 95

N-[1-[[(4'-cyano[1,1'-biphenyl]-4-yl)oxy]methyl]-2-[(4'-cyano[1,1'-biphenyl]-4-yl)oxy]ethyl]-N-hydroxyformamide The title compound was prepared using the procedures of examples 5F, 5G and 5H, except using example 3B in place of 5E.

1H NMR (DMSO-δ6) δ 4.18–4.36 (m, 4H), 4.43–4.57 (bs, 0.5H), 4.97–5.03 (bs, 0.5H), 7.10 (d, 4H, J=9 Hz), 7.77 (d, 4H, J=9 Hz), 7.81–7.95 (m, 8H), 8.13 (s, 0.5H), 8.42 (s, 0.5H), 9.75 (s, 0.5H), 10.15 (s, 0.5H); MS (DCI/NH3) M+H (490), M+18 (507); Anal. Calcd for: $C_{30}H_{23}N_3O_4.0.25H_2O$ C, 72.93; H, 4.79; N, 8.50. Found: C, 72.80; H, 4.74; N, 8.26.

EXAMPLE 96

N-[1-[[(4'-cyano[1,1'-biphenyl]-4-yl)oxy]methyl]-2-(4,4-dimethy-2,5-dioxo-1-imidazolidinyl)ethyl]-N-hydroxyformamide The title compound was prepared according to the procedures of example 23B, except substituting 4-(4'-cyanophenyl)-phenol in place of 4-(4'-ethoxyphenyl)-phenol.

1H NMR (DMSO-δ6) δ 1.27 (s, 6H), 3.50–3.66 (m, 1H), 3.67–3.82 (m, 1H), 4.08–4.28 (m, 2H), 4.38–4.50 (m, 0.5H), 4.80–4.93 (m, 0.5H), 7.06 (dd, 2H, J=3,9 Hz), 7.73 (d, 2H, J=9 Hz), 7.82–7.93 (m, 4H), 7.94 (s, 0.5H), 8.35 (d, 1H, J=6 Hz), 8.40 (s, 0.5H), 9.56 (s, 0.5H), 9.87 (s, 0.5H); MS (ESI–) 421 (M–H); Anal. Calcd for: $C_{22}H_{22}N_4O_5.0.25H_2O$ C, 61.89; H, 5.31; N, 13.12. Found: C, 61.82; H, 5.34; N, 12.82.

EXAMPLE 97

N-[1-[(4,4-dimethyl-2,5-dioxo-1-imidazolidinyl)methyl]-2-[[4'-(2-methoxyethoxy)[1,1'-biphenyl]-4-yl]oxy]ethyl]-N-hydroxyformamide The title compound was prepared according to the procedures of example 23B, except substituting 4-(4'-(2-methoxyethoxy)-phenyl)-phenol in place of 4-(4'-ethoxyphenyl)-phenol.

1H NMR (DMSO-δ6) δ 1.26 (s, 6H), 3.33 (s, 3H), 3.50–3.64 (m, 1H), 3.66–3.69 (m, 2H), 3.70–3.81 (m, 1H), 4.03–4.22 (m, 4H), 4.35–4.48 (m, 0.5H), 4.78–4.90 (m, 0.5H), 6.98 (dd, 4H, J=3,9 Hz), 7.55 (dd, 4H, J=3,6 Hz), 7.91 (s, 0.5H), 8.33 (d, 1H, J=7 Hz), 8.40 (s, 0.5H), 9.55 (s, 0.5H), 9.86 (s, 0.5H); MS (ESI–) 470 (M-1); Anal. Calcd for: $C_{24}H_{29}N_3O_7$ C, 61.13; H, 6.19; N, 8.91. Found: C, 60.86; H, 6.41; N, 8.65.

EXAMPLE 98

N-[1-[(4,4-dimethy-2,5-dioxo-1-imidazolidinyl)methyl]-2-[(4'-propoxy[1,1'-biphenyl]-4-yl)oxy]ethyl]-N-hydroxyformamide The title compound was prepared according to the procedures of example 23B, except substituting 4-(4'-propyloxyphenyl)-phenol in place of 4-(4'-ethoxyphenyl)-phenol. mp. 158–160° C.

Mass Spec. (ESI): +456 (m+H), +473 (m+18), –454 (m–H), –490 (m+35) $^1$H NMR (DMSO-d6): δ 0.90 (3H, t, J=6 Hz), 1.17 (2.4H, s), 1.20 (3.6H, s), 1.65 (2H, sextuplet, J=6 Hz), 3.46–3.55 (1H, m), 3.59–3.74 (1H, m), 3.86 (2H, t, J=6 Hz 3.96–4.06 (1H, m), 4.06–4.14 (1H, m), 4.28–4.38 (0.6H, m), 4.72–4.81 (0.4H, m), 6.88 (4H, d, J=4.8 Hz), 7.42, (2H, d, J=4.8 Hz), 7.44 (2H, d, J=4.8 Hz), 7.83 (0.4H, s), 8.24 (1H, s), 8.28 (0.6H, s), 9.43 (0.6H, s), 9.74 (0.4H, s); $^{13}$C NMR (DMSO-d6): δ 10.4, 22.0, 24.4, 24.5, 36.0, 36.4, 52.1, 56.1, 57.8, 57.9, 64.7, 65.0, 69.0, 114.8, 115.0, 127.2, 132.0, 132.8, 132.9, 155.0, 155.2, 157.0, 157.1, 157.9, 158.2, 163.1, 177.2, 177.3; Calc. for $C_{24}H_{29}N_3O_6$: C, 63.28; H, 6.42; N, 9.22. Found: C, 63.25; H, 6.48; N, 9.29.

EXAMPLE 99

N-[1-[(4,4-dimethy-2,5-dioxo-1-imidazolidinyl)methyl]-2-[(4'-pentyloxy[1,1'-biphenyl]-4-yl)oxy]ethyl]-N-hydroxyformamide The title compound was prepared according to the procedures of example 23B, except substituting 4-(4'-pentylyloxyphenyl)-phenol in place of 4-(4'-ethoxyphenyl)-phenol.

¹H NMR (300 MHz, DMSO-δ6) δ 0.90 (t, 3H, J=6.9 Hz), 1.27 (s, 6H), 1.3–1.5 (m, 4H), 1.7–1.8 (m, 2H), 3.5–3.8 (m, 2H), 3.98 (t, 2H, J=6.9 Hz), 4.0–4.2 (m, 2H), 4.35–4.45 (m, 0.5H), 4.8–4.9 (m, 0.5H), 6.9–7.0 (m, 4H), 7.5–7.6 (m, 4H), 7.92 (s, 0.5H), 8.3–8.4 (m, 1.5H), 9.53 (s, 0.5H), 9.84 (s, 0.5H); MS (ESI) 484 (M+H), 501 (M+NH$_4$); Anal. calcd for C$_{26}$H$_{33}$N$_3$O$_6$: C, 64.57; H, 6.87; N, 8.68. Found: C, 64.27; H, 6.85; N, 8.60.

EXAMPLE 100

N-[1-[[[3'-(cyanomethyl)[1,1'-biphenyl]-4-yl]sulfonyl]methyl]-3-(4,4-dimethy-2,5-dioxo-1-imidazolidinyl)propyl]-N-hydroxyformamide The title compound was made according to the procedures of example 61, but using example 23A in place of example 16B and 4'-thiol-3-cyanomethyl biphenyl in place of 4'-thiol-4-biphenylcarbonitrile in example 61A.

¹H NMR (300 MHz, d$_6$-DMSO) δ 9.98 (br, 0.5H), 9.63 (br, 0.5H), 8.31 (s, 0.5H), 8.23 (s, 0.5H), 8.12 (s, 0.5H), 7.99–7.92 (m, 4H), 7.82 (s, 0.5H), 7.74 (m, 2H), 7.57 (t, 1H), 7.46 (d, 1H), 4.52 (m, 0.5H), 4.14 (s, 2H), 4.00 (m, 0.5H), 3.69–3.57 (m, 2H), 3.42–3.28 (m, 2H), 2.02–1.88 (m, 1H), 1.78–1.64 (m, 1H), 1.21 (s, 6H); MS (ESI) m/e 499 (M+H)$^+$; Anal. calcd for C$_{24}$H$_{26}$N$_4$O$_6$S: C, 57.82; H, 5.26; N, 11.24. Found: C, 57.56; H, 5.41; N, 10.89.

EXAMPLE 101

N-[1-[[[4'-(trifluoromethoxy)[1,1'-biphenyl]-4-yl]sulfonyl]methyl]-2-(3,4,4-trimethy-2,5-dioxo-1-imidazolidinyl)ethyl]-N-hydroxyformamide The title compound was prepared following the procedures of example 46, except substituting example 16B for 23A in example 46A and 4-trifluoromethoxybenzeneboronic acid for 4-butoxybenzeneboronic acid in example 46B.

¹H NMR (300 MHz, d$_6$-DMSO) δ 9.72 (br, 0.5H), 9.56 (br, 0.5H), 8.10 (s, 0.5H), 7.99 (m, 4H), 7.94–7.88 (m, 2H), 7.74 (s, 0.5H), 7.53 (d, 2H), 4.91 (m, 0.5H), 4.54 (m, 0.5H), 3.75–3.44 (m, 4H), 2.75 (s, 3H), 1.24–1.22 (m, 6H); MS (ESI) m/e 544 (M+H)$^+$; Anal. calcd for C$_{23}$H$_{24}$F$_3$N$_3$O$_7$S: C, 50.83; H, 4.45; N, 7.73. Found: C, 51.17; H, 4.77; N, 7.29.

EXAMPLE 102

N-[1-[[(4'-cyano[1,1'-biphenyl]-4-yl)sulfonyl]methyl]-2-(3-methy-2,5-dioxo-1-imidazolidinyl)ethyl]-N-hydroxyformamide The title compound was made according to the procedures of example 61, but using example 26A in place of example 16B in example 61A.

¹H NMR (300 MHz, d$_6$-DMSO) δ 9.83 (s, 0.5H), 9.58 (s, 0.5H), 8.09 (s, 0.5H), 8.04–8.00 (m, 8H), 7.80 (s, 0.5H), 4.94–4.85 (m, 0.5H), 4.52–4.43 (m, 0.5H), 3.91–3.88 (m, 2H), 3.78–3.44 (m, 4H), 2.80 (s, 1.5H), 2.79 (s, 1.5H); MS (ESI) m/e 457 (M+H)$^+$; Anal. calcd for C$_{21}$H$_{20}$N$_4$O$_6$S: C, 55.26; H, 4.42; N, 12.27. Found: C, 54.99; H, 4.38; N, 12.07.

EXAMPLE 103

N-[1-[[[3'-(cyanomethyl)[1,1'-biphenyl]-4-yl]sulfonyl]methyl]-2-(3,4,4-trimethyl-2,5-dioxo-1-imidazolidinyl)ethyl]-N-hydroxyformamide The title compound was prepared following the procedures of example 46, except substituting example 16B for 23A in example 46A and 3-cyanomethylbenzeneboronic acid for 4-butoxybenzeneboronic acid in example 46B. The title compound was made in the usual way from the o-bromo ketone and 4-bromothiophenol.

¹H NMR (300 MHz, d$_6$-DMSO) δ 9.71 (s, 0.5H), 9.56 (s, 0.5H), 8.10 (s, 0.5H), 8.03–7.94 (m, 4H), 7.75 (m, 2.5H), 7.57 (t, 2H), 7.46 (d, 2H), 4.96–4.88 (m, 0.5H), 4.59–4.49 (m, 0.5H), 4.14 (s, 2H), 3.69–3.48 (m, 4H), 2.75 (s, 3H), 1.24 (s, 3H), 1.22 (s, 3H); MS (ESI) m/e 499 (M+H)$^+$; Anal. calcd for C$_{24}$H$_{26}$N$_4$O$_6$S: C, 57.82; H, 5.26; N, 11.24. Found: C, 57.73; H, 5.36; N, 10.95.

EXAMPLE 104

N-[1-[[(4'-cyano[1,1'-biphenyl]-4-yl)oxy]methyl]-2-(1,6-dihydro-3-methyl-6-oxo-1-pyridazinyl)ethyl]-N-hydroxyformamide The title compound was prepared following the procedures of example 3C and 3D, except substituting the potassium salt 6-methyl-3(2H)-pyridazinone (generated in situ with potassium carbonate) for potassium phthalimide in example 3C.

¹H NMR (300 MHz, CD$_3$OD) δ 8.31 (s, 0.5H), 7.91 (s, 0.5H), 7.76 (s, 4H), 7.67.64 (d, 2H), 7.38 (dd, 1H), 7.08 (d, 2H), 6.94 (dd, 1H), 5.20–5.11 (m, 0.5H), 4.64–4.52 (m, 2H), 4.42–4.32 (m, 2H), 4.27–4.19 (m 0.5H), 2.35 (s, 1.5H), 2.34 (s, 1.5H); MS (ESI) m/e 405 (M+H)$^+$; Anal. calcd for C$_{22}$H$_{20}$N$_4$O$_4$: C, 65.34; H, 4.98; N, 13.85. Found: C, 64.85 H, 5.36; N, 13.44.

EXAMPLE 105

(±)-N-[1-[[(4'-cyano[1,1'-biphenyl]-4-yl)sulfonyl]methyl]-2-(4,4-dimethyl-2,5-dioxo-1-imidazolidinyl)ethyl]-N-hydroxyformamide;

The title compound was made according to the procedures of example 61, but using example 47A in place of example 16B in example 61A.

¹H NMR (300 MHz, d$_6$-DMSO) δ 9.98 (s, 0.5H0, 9.62 (s, 0.5H), 8.31 (s, 0.5H), 8.22 (s, 0.5H), 8.12 (s, 0.5H), 8.05–7.96 (m, 8H), 7.82 (s, 0.5H), 4.55–4.46 (m, 0.5H), 4.07–3.97 (m, 0.5H), 3.70–3.56 (m, 2H), 3.32–3.24 (m, 2H), 2.02–1.88 (m, 0.5H), 1.76–1,64 (m, 0.5H), 1.21–1.18 (m, 6H); MS (ESI) m/e 485 (M+H)$^+$.

EXAMPLE 106

(±)-N-[1-[[[4-(4-fluorophenoxy)phenyl]sulfonyl]methyl]-2-(4,4-dimethyl-2,5-dioxo-1-imidazolidinyl)ethyl]-N-hydroxyformamide The title compound was made according to the procedures of example 61, but using example 26A in place of example 16B and 4-(4'-fluoroohenoxy)-benzene thiol in place of 4'thiol-4-biphenyl carbonitrile in example 61A.

¹H NMR (300 MHz, d$_6$-DMSO) δ 9.66 (s, 0.5H), 9.50 (s, 0.5H), 8.39 (s, 0.5H), 8.35 (s, 0.5H), 8.10 (s, 0.5H), 7.88 (dd, 2H), 7.68 (s, 0.5H), 7.36–7.30 (m, 2H), 7.26–7.20 (m, 2H), 7.15 (d, 2H), 4.88–4.80 (m, 0.5H), 4.51–4.41 (m, 0.5H), 3.70–3.39 (m, 4H), 1.24–1.22 (m, 6H); MS (ESI) m/e 480 (M+H)$^+$; Anal. calcd for C$_{21}$H$_{22}$FN$_3$O$_7$S: C, 52.60; H, 4.62; N, 8.76. Found: C, 52.79; H, 4.57; N, 8.68.

EXAMPLE 107

N-[1-[[4-(4-pyridinyl)phenoxy]methyl]-2-(3,4,4-trimethy-2,5-dioxo-1-imidazolidinyl)ethyl]-N-hydroxyformamide The title compound was prepared following the procedures of examples 16C and 16E, except substituting 4-(4-pyridinyl)-phenol in place of 4-bromophenol in example 16C.

mp: 217–218° C.

1H NMR (DMSO-d6): δ 9.53–9.97 (c, 1H), 8.55–8.60 (c, 2H), 8.32 (s, ½H), 7.92 (s, ½H), 7.77 (s, 1H), 7.75 (s, 1H), 7.65 (s, 1H), 7.64 (s, 1H), 7.01–7.08 (c, 2H), 4.82–4.89 (c, ½H), 4.39–4.46 (c, ½H), 4.18–4.25 (c, 1H), 4.08–4.17 (c, 1H), 3.71–3.83 (c, 1H), 3.57–3.66(c, 1H), 2.78(s, 1.5H), 2.77(s, 1.5H), 1.27(s, 3H), 1.26(s, 3H); MS (ESI(+)) 413 (M+H), 435 (M+Na), 847 (2M+Na); Anal. Calcd for: $C_{21}H_{24}N_4O_5 \cdot 0.5H_2O$ C, 59.84; H, 5.98; N, 13.29. Found: C, 60.18; H, 6.05; N, 13.10.

EXAMPLE 108

(S)-N-[1-[(4,4-dimethy-2,5-dioxo-1-imidazolidinyl) methyl]-2-[[4'-(trifluoromethoxy)[1,1'-biphenyl]-4-yl]oxy]ethyl]-N-hydroxyformamide

EXAMPLE 108A (R)1-(4-(4'-(trifluoromethoxyphenyl)phenoxy)-3-benzyloxy-2-propanol A solution of 4-(4'-trifluoromethoxyphenyl)-phenol (1.854 g, 7.3 mmol) and (S)-2-(benzyloxymethyl)-oxirane (1.0 g, 6.1 mmol) in DMF (15 mL) was treated with potassium carbonate (1.007 g, 7.3 mmol), then stirred at 80° C. overnight. The reaction mixture was allowed to cool to 25° C., poured into water (100 mL) and extracted twice with ethyl acetate (200 mL×2). The combined organics were washed with sat. aq. $NH_4Cl$, water, brine, dried ($Na_2SO_4$), filtered, and concentrated. Purification via flash silica chromatography eluting with 20 to 25% ethyl acetate: hexane afforded 2.03 g (80% yield) of 108A as a white solid.

EXAMPLE 108B

A solution of example 108A (1.505 g, 3.6 mmol), di-Boc hydroxylamine (1.007 g, 4.3 mmol), triphenyl phosphine (1.23 g, 4.7 mmol) in THF (15 mL) was treated with diethylazodicarboxylate (0.735 mL, 4.7 mmol) at room temperature, stirred for 1 h, then concentrated. The crude was purified by column chromatography eluting with 10% ethyl acetate: hexane to give 1.16 g (50%) of 108B.

EXAMPLE 108C

A solution of example 108B (248 mg, 0.4 mmol) in THF (3 mL) was hydrogenated (H2 balloon) overnight in the presence of 23 mg of 10% pd on carbon. The reaction mixture was filtered, concentrated and purified via silca gel column chromatography eluting with 25% ethyl acetate: hexane to afford 180 mg (85%) of the title compound.

EXAMPLE 108D

A solution of example 108C (228 mg, 0.42 mmol), 5,5-dimethyl hydantoin (94 mg, 0.73 mmol) and triphenyl phospine (165 mg, 0.63 mmol) in THF (4 mL) was treated with diethylazodicarboxylate (0.1 mL, 0.63 mmol) added drowise via syringe. The resulting light yellow solution was stirred at 25° C. for 45 mn, concentarted and purigies via silca gel column chromatography eluting with 25% ethyl acetate: hexane to afford 193 mg (71%) of 108D.

EXAMPLE 108E (S)-N-[1-[(4,4-dimethy-2,5-dioxo-1-imidazolidinyl) methyl]-2-[[4'-(trifluoromethoxy)[1,1'-biphenyl]-4-yl]oxy]ethyl]-N-hydroxy amine A solution of example 108D (191 mg, 0.29 mmol) in methylene chloride (3 mL) was treated with TFA (1.5 mL), added dropwise via syringe. The reaction was stirred at rt for 40 min then concentrated and the residue was partitioned between ethyl acetate and aq. $NaHCO_3$. the organic extract was washed with brine, dried ($Na_2SO_4$), filtered, and concentrated to afford 113 mg (86%) of 108E as a white solid.

EXAMPLE 108F (S)-N-[1-[(4,4-dimethy-2,5-dioxo-1-imidazolidinyl) methyl]-2-[[4'-(trifluoromethoxy)[1,1'-biphenyl]-4-yl]oxy]ethyl]-N-hydroxyformamide The title compound was prepared from 108E following the procedure of example 2F.

MS (ESI) m/e 482 (M+H)⁺.

EXAMPLE 109

(R)-N-[1-[(4,4-dimethy-2,5-dioxo-1-imidazolidinyl) methyl]-2-[[4'-(trifluoromethoxy)[1,1'-biphenyl]-4-yl]oxy]ethyl]-N-hydroxyformamide The title compound was prepared following the procedures of example 108, except using (R)-2-(benzyloxymethyl)-oxirane in place of (S)-2-(benzyloxymethyl)-oxirane.

$^1$H NMR (300 MHz, $d_6$-DMSO) δ 9.86 (s, 0.5H), 9.55 (s, 0.5H), 8.39 (s, 0.5H), 8.35 (s, 0.5H), 8.33 (s, 0.5H), 7.93 (s, 0.5H), 7.76–7.73 (m, 2H), 7.64 (d, 2H), 7.42 (d, 2H), 7.02 (dd, 2H), 4.91–4.80 (m, 0.5H), 4.47–4.38 (m, 0.5H), 4.23–4.06 (m, 2H), 3.79–3.50 (m, 2H), 1.27 (s, 1.5H), 1.26 (s, 1.5H); MS (ESI) m/e 482 (M+H)⁺.

EXAMPLE 110

N-[1-[[[4'-(trifluoromethoxy))[1,1'-biphenyl]-4-yl]oxy]methyl]-3-(4,4-dimethyl-2,5-dioxo-1-imidazolidinyl)propyl]-N-hydroxyformamide The title compound was prepared according to the procedures of example 5, except avoiding the methylation step in example 5B and substituting 4-(4'-trifluoromethoxyphenyl)phenol for 4'-hydroxy-4-biphenylcarbonitrile in example 5F .

mp: 197.1–197.9° C.;

$^1$H NMR (300 MHz, DMSO-δ6) δ; 1.27 (s, 6H), 1.70–2.00 (m, 2H), 3.35–3.46 (2H), 3.97–4.16 (m, 2.75H), 4.51 (br s, 0.25H), 7.00–7.03 (d, 2H, J=9 Hz), 7.39–7.42 (d, 2H, J=9 Hz), 7.60–7.63 (d, 2H, J=9 Hz), 7.72–7.75 (d, 2H, J=9 Hz), 8.25–8.35 (2H), 9.55 (s, 0.75H), 9.95 (br s, 0.25H); MS (ESI) m/e 496 (M+H)⁺, 518 (m+Na)+, 494 (m−H)−, 530 (m+Cl)−; Anal. calcd for $C_{23}H_{24}F_3N_3O_6$: C, 55.75; H, 4.88; N, 8.48. Found: C, 55.72; H, 5.07; N, 8.59.

EXAMPLE 111

N-[1-[4-[(4-pyridinylthio)phenoxy]methyl]-2-(4,4-dimethyl-2,5-dioxo-1-imidazolidinyl)ethyl]-N-hydroxyformamide The title compound was prepared following the procedures of example 23B, except substituting (prepared by the addition of 4-hydroxythiophenol to 4-chloropyridine) for 4-(4'-butyloxyphenyl)-phenol.

$^1$H NMR (300 MHz, DMSO-δ6) δ; 1.258–1.272 (6H), 3.492–3.793 (m, 2H), 4.082–4.248 (m, 2H), 4.437 (m, 0.5H), 3.861 (m, 0.5H), 5.759 (s, 1H), 6.927–6.948 (dd, 2H, J=1.5, 4.8 Hz), 7.063–7.102 (dd, 2H, J=3, 8.7 Hz), 7.529–7.557 (d, 2H, J=8.4 Hz), 7.939 (s, 0.5H), 8.323–8.343

(dd, 2H, J=1.2, 4.8 Hz), 8.391 (s, 0.5H), 9.555 (s, 0.5H), 9.866 (s, 0.5H); MS (ESI) m/e 431 (M+H)+, 453 (m+Na)+, 429 (m–H)–, 465 (m+Cl)–.

EXAMPLE 112

N-[1-[[[(4-chlorophenoxy)phenyl]sulfonyl]methyl]-3-(4,4-dimethyl-2,5-dioxo-1-imidazolidinyl)propyl]-N-hydroxyformamide The title compound was prepared according to the procedures of example 61, except substituting 4-(4'-chlorophenoxy)benzene thiol for 4'-thiol-4-biphenylcarbonitrile and example 47A for example16B in example 61A.

$^1$H NMR (d6-DMSO) δ 9.94 (s, 0.5H), 9.58 (s, 0.5H), 8.23 (d, 0.5H, J=9.5 Hz), 8.11 (s, 0.5H), 8.05 (d, 0.5H, J=9.2 Hz), 7.89–7.83 (m, 2H), 7.76 (s, 0.5H), 7.54–7.50 (m, 2H), 7.22–7.16 (m, 4H), 4.52–4.41 (m, 0.5H), 4.10–3.92 (m, 0.5H), 3.66–3.37 (m, 2H), 3.31–3.24 (m, 3H), 1.96–1.84 (m, 1H), 1.74–1.62 (m, 1H), 1.28–1.21 (m, 6H); MS (ESI) 508 (M–H), 510 (M+H), 532 (M+Na).

EXAMPLE 113

N-[1-[[(4'-cyano[1,1"-biphenyl]-4-yl)oxy]methyl]-2-(1,6-dihydro-6-oxo-1-pyridazinyl)ethyl]-N-hydroxyformamide The title compound was prepared following the procedures of example 104, except using pyridazinone in place of 6-methyl-3(2H)-pyridazinone.

$^1$H NMR (d6-DMSO) δ 9.99 (s, 0.5H), 9.64 (s, 0.5H), 8.28 (s, 0.5H), 7.96–7.83 (m, 5.5H), 7.75–7.71 (m, 2.0H), 7.47–7.41 (m, 1H), 7.07–6.95 (m, 3H), 5.11–5.00 (m, 0.5H), 4.62–4.12 (m, 4.5H); MS (ESI) 391 (M+H), 413 (M+Na), 389 (M–H); Anal. Calcd for: C21H$_{18}$N$_4$O$_4$.0.5H$_2$O C, 63.15; H, 4.79; N, 14.02. Found: C, 63.33; H, 4.66; N, 13.68.

EXAMPLE 114

N-[1-[[[4'-(aminosulfonyl)[1,1'-biphenyl]-4-yl]oxy]methyl]-2-(3,4,4-trimethyl-2,5-dioxo-1-imidazolidinyl)ethyl]-N-hydroxyformamide The title compound was prepared following the procedures of examples 16C and 16E, except substituting 4-(4'-sulfonamidephenyl)-phenol for 4-bromophenol.

mp 203–205° C.; 1H NMR (DMSO-d6): d 9.88 (bs, ½H), 9.54 (bs, ½H), 8.32 (s, ½H), 7.56–8.01 (c, 5½H), 7.34 (s, 1H), 7.00–7.14 (c, 4H), 4.78–4.97 (c, ½H), 4.34–4.50 (c, ½H), 4.06–4.27 (c, 2H), 3.69–3.85 (c, 1H), 3.57–3.68 (c, 1H), 2.78 (s, 3H), 1.17–1.28 (c, 6H); 13C NMR (DMSO-d6): δ 176.5, 176.2, 163.1, 158.1, 154.2, 154.1, 128.3, 128.2, 128.0, 127.0, 126.8, 126.2, 115.2, 64.8, 60.7, 36.7, 36.4, 24.2, 21.4; MS (ESI(+)) 491 (M+H), 508 (M+NH$_4$), 513 (M+Na).

EXAMPLE 115

N-[1-[[[4'-(trifluoromethoxy)[1,1'-biphenyl]-4-yl]sulfonyl]methyl]-2-(4,4-dimethyl-2,5-dioxo-1-imidazolidinyl)ethyl]-N-hydroxyformamide The title compound was prepared following the procedures of example 46, except substituting 4-trifluoromethoxybenzeneboronic acid for 4-butyloxybenzeneboronic in example 46B.

mp 195–197° C.; 1H NMR, (DMSO-d6): δ 9.62 (bs, 1H), 8.29–8.43 (c, 1H), 8.10 (s, ½H), 7.95–8.05 (c, 4H), 7.92 (d, 1H, J=3 Hz), 7.88 (d, 1H, J=3 Hz), 7.74 (s, ½H), 7.54 (s, 1H), 7.49 (s, 1H), 4.87–4.99 (c, ½H), 4.50–4.63 (c, ½H), 3.43–3.80 (c, 4H), 1.22 (s, 6H); 13C NMR(DMSO-d6): δ 177.2, 177.1, 162.3, 157.1, 155.0, 154.8, 148.7, 144.0, 143.9, 138.0, 137.8, 137.5, 129.2, 128.6, 128.4, 127.9, 127.7, 121.5, 118.4, 57.8, 53.3, 53.0, 51.3, 47.5, 38.8, 38.1, 24.31, 24.30; MS (ESI(+)) 530 (M+H), 547 (M+NH$_4$), 552 (M+Na), 1076 (2M+NH$_4$), 1081 (2M+Na); HRMS: Calcd: 530.120. Found: 530.1193; Anal. Calcd for: C$_{22}$H$_{22}$F$_3$N$_3$O$_7$S C, 49.90; H, 4.19; N, 7.94; F, 10.76; S,6.06. Found: C, 49.58; H, 4.10; N, 7.75; F, 11.04; S, 5.96.

EXAMPLE 116

N-[1-[4-[(4-pyridinyloxy)phenyl]sulfonyl]]ethyl]-N-hydroxyformamide

EXAMPLE 116A

4-[4-(methylsulfonyl)phenoxy]pyridine

A mixture of 4-methylsulfonylphenol (2.93g, 17 mmol) and 4-chloropyridine hydrochloride (2.93 g, 19.5 mmol) was heated at 150° C., resulting in a gradual melt, which was stirred at 150° C. for 4 h, then partitioned between ethyl acetate and 1N NaOH. The organic extract was dried over MgSO$_4$, filtered, and concentrated to 1.3 g of a yellow solid. The solid was recrystallized from ethyl acetate-ether to give 0.81 g of the title compound as a white solid.

EXAMPLE 116B

N-[1-[4-[(4-pyridinyloxy)phenyl]sulfonyl]]ethyl]-N-hydroxyformamide

The tiltle compound was prepared following the procedures of examples 75, except substituting example 11 6A for 71 B and acetaldehyde for propionaldehyde.

mp 180–181° C.;

1H NMR, 400 MHz (DMSO-d6): δ 9.71 (bs, 1H), 8.54 (d, 2H, J=3 Hz), 8.05 (s, ½H), 7.97 (d, 2H, J=6 Hz), 7.84 (s, ½H), 7.49 (d, 2H, J=6 Hz), 7.03–7.13 (c, 2H), 4.63–4.73 (c, ½H), 4.28–4.39 (c, ½H), 3.59–3.78 (c, 1H), 3.48 (dd, 1H, J=3,10.5 Hz), 1.20 (dd, 3H, J=4.5, 10.5 Hz); 13C NMR (DMSO-d6): δ 162.62, 162.61, 161.33, 158.33, 158.31, 156.74, 151.77, 135.40, 135.13, 130.74, 130.45, 120.56, 120.34, 113.27, 56.50, 49.69, 45.02, 19.05, 17.71; MS (ESI(+)) 337 (M+H), 359 (M+Na), 391 (M+Na+MeOH), 695 (2M+Na); Anal. Calcd for: C$_{15}$H$_{16}$N$_2$O$_5$S.0.5H$_2$O: C, 52.16; H, 4.96; N, 8.11; S, 9.28. Found: C, 52.32; H, 4.78; N, 7.98; S, 9.45.

EXAMPLE 117

N-[1-[[[(4-cyanophenoxy)phenyl]sulfonyl]methyl]-2-(4,4-dimethyl-2,5-dioxo-1-imidazolidinyl)ethyl]-N-hydroxyformamide The title compound was prepared according to the procedures of example 61, except substituting 4-(4'-cyanophenoxy)benzene thiol for 4-thiol-4-biphenylcarbonitrile and example 23A for example 16B, in example 61A.

$^1$H NMR (300 MHz, d$_6$-DMSO) δ 9.70 (s, 0.5H), 9.50 (s, 0.5H), 8.39 (s, 0.5H), 8.34 (s, 0.5H), 8.10 (s, 0.5H), 7.98–7.91 (m, 4H), 7.68 (s, 0.5H), 7.37–7.27 (m, 4H), 4.88–4.77 (m, 0.5H), 4.52–4.41 (m, 0.5H), 3.78–3.39 (m, 4H), 1.24–1.22 (m, 6H); MS (ESI) m/e 487 (M+H)+; Anal. calcd for C$_{22}$H$_{22}$N$_4$O$_7$S: C, 54.31; H, 4.56. Found: C, 54.17; H, 4.79.

EXAMPLE 118

N-[1-[[4-[[4-(trifluoromethoxy)phenoxy]phenyl]
sulfonyl]methyl]-3-(4,4-dimethyl-2,5-dioxo-1-
imidazolidinyl)propyl]-N-hydroxyformamide The title compound was prepared according to the procedures of example 61, except substituting 4-(4'-trifluoromethoxyphenoxy)benzene thiol for 4'-thiol-4-biphenylcarbonitrile and example 47A for example 16B, in example 61A.

1H NMR (d6-DMSO) δ 9.96 (s, 0.5H), 9.60 (s, 0.5H), 8.32 (s, 0.5H), 8.23 (s, 0.5H), 8.11 (s, 0.5H), 7.93–7.86 (m, 2H), 7.75 (s, 0.5H), 7.48 (d, 0.5H, J=8.8 Hz), 7.25 (dd 4H, J=22.8, 8.8 Hz), 4.53–4.42 (m, 0.5H), 4.04–3.93 (m, 0.5H), 3.65–3.46 (m, 2H), 3.34–3.22 (m, 2H), 2.02–1.62 (m, 2H), 1.26 (s, 3H), 1.23 (s, 3H); MS (ESI) 560 (M+H), 577 (M+NH$_4$), 582 (M+Na), 558 (M–H); Anal. Calcd for: C$_{23}$H$_{24}$N$_3$O$_8$SF$_3$: C, 49.37; H, 4.32; N, 7.51. Found: C, 49.46; H, 4.23; N, 7.47.

EXAMPLE 119

N-[1-[[4-[[4-(trifluoromethoxy)phenoxy]phenyl]
sulfonyl]methyl]-2-(4,4-dimethyl-2,5-dioxo-1-
imidazolidinyl)ethyl]-N-hydroxyformamide The title compound was prepared according to the procedures of example 61, except substituting 4-(4'-trifluoromethoxyphenoxy)benzene thiol for 4'-thiol-4-biphenylcarbonitrile in example 61A.

1H NMR (d$_6$-DMSO) δ 9.51 (s, 0.5H), 9.70 (s, 0.5H), 8.09 (s, 0.5H), 7.91 (dd, 2H, J=8.9, 3.1 Hz), 7.68 (s, 0.5H), 7.47 (d, 2H, J=9.2 Hz), 7.31–7.21 (m, 4H), 4.90–4.78 (m, 0.5H), 4.51–4.40 (m, 0.5H), 3.74–3.40 (m, 4H), 2.76 (d, 3H, J=1.7 Hz), 1.27–1.22 (m, 6H); MS (ESI) 558 (M–H), 560 (M+H), 577 (M+NH$_4$), 582 (M+Na); Anal. Calcd for: C$_{23}$H$_{24}$N$_3$O$_8$SF$_3$: C, 49.37; H, 4.32; N, 7.51. Found: C, 49.41; H, 4.29; N, 7.36.

EXAMPLE 120

(±)-N-hydroxy-N-[1-(3-pyridinyl)-2-[[4'-
(trifluoromethyl)[1,1'-biphenyl]-4-yl]sulfonyl]ethyl]
formamide The title compound was prepared according to the procedures of Example 75, except substituting 3-pyridine carboxaldehyde for propionaldehyde and 4-(4'-trifluoromethylphenyl)phenyl methyl sulfone (ex. 76A) for 4-(4'-methoxylphenyl)phenyl methyl sulfone in Example 75A.

mp 186.5–188.8° C.; MS (ESI) m/z 451 (M+H)$^+$, 473 (M+Na)$^+$, 449 (M–H)$^-$; $^1$H NMR (300 MHz, DMSO-d$_6$) δ 4.16–4.34 (m, 2H), 5.58 (brs, 0.5H), 5.79 (brs, 0.5H), 7.27–7.32 (dd, 1H, J=4.8, 7.8 Hz), 7.78–7.98 (9H), 8.14 (brs, 0.5H), 8.27 (brs, 0.5H), 8.46–8.47 (d+brs 1.5H, J=4.5 Hz), 8.60 (brs, 0.5H), 9.70 (brs, 0.5H), 10.14 (brs, 0.5H); Anal. calcd for C$_{21}$H$_{17}$N$_2$F$_3$O$_4$S: C, 55.99; H, 3.80; N, 6.21. Found: C, 55.79; H, 3,76; N, 6.18.

EXAMPLE 121

(±)-N-hydroxy-N-[1-(hydroxymethyl)-2-[[4-[(4-
chlorophenoxy)phenyl]sulfonyl]ethyl]formamide The title compound was prepared according to the procedures described in Examples 77 and 78, except substituting Example 74A for Example 76A.

mp 108.3–110.5° C.; MS (ESI) m/z 403 (M+NH$_4$)$^+$, 420 (M+Cl)$^-$, 384 (M–H)$^-$; $^1$H NMR (300 MHz, DMSO-d$_6$) δ 3.29–3.59 (m, 4H), 3.94–4.06 (m, 0.7H), 4.50–4.60 (m, 0.3H), 4.94–5.01 (m, 1H), 7.17–7.21 (dd, 4H, J=3, 8.7 Hz), 7.51–7.54 (d, 2H, J=8.7 Hz), 7.76 (s, 0.7H), 7.86–7.90 (2H), 8.12 (s, 0.3H), 9.39 (s, 0.7H), 9.80 (s, 0.3H); Anal. calcd for C$_{16}$H$_{16}$NClO$_6$S: C, 49.80; H, 4.18; N, 3.63. Found: C, 49.51; H, 4.31; N, 3.46.

EXAMPLE 122

(±)-N-hydroxy-N-[1-methyl-2-[[4'-(trifluoromethyl)
[1,1'-biphenyl]-4-yl]sulfonyl]ethyl]formamide The title compound was prepared according to the procedures described in Examples 71C–71E, except substituting Example 76A for Example 71A.

mp 174.6–175.2° C.; MS (ESI) m/z 388 (M+H)$^+$, 410 (M+Na)$^+$, 386 (M–H)$^-$, 422 (M+Cl)$^-$; $^1$H NMR (300 MHz, DMSO-d$_6$) δ 1.16–1.24 (dd, 3H, J=6.3, 17.7 Hz), 3.49–3.56 (dd, 1H, J=4.2, 14.4 Hz), 3.61–3.74 (m, 1H), 4.30–4.43 (m, 0.5H), 4.64–4.78 (m, 0.5H), 7.87–8.07 (9H), 9.48 (brs, 0.5H); Anal. calcd for C$_{17}$H$_{16}$NF$_3$O$_4$S: C, 52.71; H, 4.16; N, 3.61. Found: C, 52.74; H, 4.23; N, 3.57.

EXAMPLE 123

(±)-N-hydroxy-N-[1-(2-pyridinyl)-2-[[4'-
(trifluoromethyl)[1,1'-biphenyl]-4-yl]sulfonyl]ethyl]
formamide The title compound was prepared according to the procedures of Example 75, except substituting 2-pyridine carboxaldehyde for propionaldehyde and 4-(4'-trifluoromethylphenyl)phenyl methyl sulfone (ex. 76A) for 4-(4'-methoxylphenyl)phenyl methyl sulfone in Example 75A.

mp 168.5–168.9° C.; MS (ESI) m/z 451 (M+H)$^+$, 473 (M+Na)$^+$, 449 (M–H)$^-$, 485 (M+Cl)$^-$; $^1$H NMR (300 MHz, DMSO-d$_6$) δ 3.98–4.12 (m, 1H), 4.36–4.42 (d, 1H, J=15.3 Hz), 5.57 (br, 0.5H), 5.89 (br, 0.5H), 7.28–7.33 (m, 1.5H), 7.41–7.44 (d, 0.5H, J=6.9 Hz), 7.73–7.83 (m, 1H), 7.87–7.90 (2H), 7.97–7.80 (m, 6H), 8.25 (s, 1H), 8.45 (br, 1H), 9.69 (s, 0.5H), 10.07 (s, 0.5H); Anal. calcd for C$_{21}$H$_{17}$N$_2$F$_3$O$_4$S: C, 55.99; H, 3.80; N, 6.21. Found: C, 55.88; H, 3.61; N, 6.17.

EXAMPLE 124

(±)-N-[1-[(4,4-dimethyl-2,6-dioxo-1-piperidinyl)
methyl]-2-[[4'-(trifluoromethyl)[1,1'-biphenyl]-4-yl]
sulfonyl]ethyl]-N-hydroxyformamide The title compound was prepared using the following sequence of reactions (i) alkylation of epibromohydrin with 3,3-dimethylglutarimide in the presence of potassium carbonate in methanol (ii) opening the resulting epoxide with 4-bromothiophenol as in Example 2B in the presence of potassium carbonate (iii) alcohol oxidation to the ketone as in Example 2C (iv) coupling the resulting ketone with 4-trifluorobenzene boronic acid, as in Example 46B and (v) converting the resulting ketone to the title compound following the procedures of Examples 46C–D.

mp 185.6–187.3° C.; MS (APCI) m/z 527 (M+H)$^+$, 544 (M+NH$_4$)$^+$, 561 (M+Cl)$^-$; $^1$H NMR (300 MHz, DMSO-d$_6$) δ 0.927–0.935 (s+s, 6H), 3.443–3.538 (m, 1H), 3.652–3.784 (m, 2H), 3.884–3.993 (m, 1H), 4.390–4.416 (m, 0.5H), 4.916–4.945 (m, 0.5H), 7.765 (s, 0.5H), 7.882–7.910 (2H), 7.987–8.065 (m, 6.5H), 9.523 (s, 0.5H), 9.660 (s, 0.5H); Anal. calcd for C$_{24}$H$_{25}$N$_2$F$_3$O$_6$S.0.25 hexanes: C, 55.88; H, 5.24; N, 5.11. Found: C, 55.65; H, 5.15; N, 5.02.

EXAMPLE 125

(±)-N-hydroxy-N-[3-hydroxy-1-[[[4'-(trifluoromethyl)[1,1'-biphenyl]-4-yl]sulfonyl]methyl]propyl]formamide

EXAMPLE 125A (±)-N-[3-[[(1,1-dimethylethyl)dimethylsilyl]oxy]-1-[[[4'-(trifluoromethyl)[1,1'-biphenyl]-4-yl]sulfonyl]methyl]propyl]-N-hydroxyformamide The title compound was prepared according to the procedures of Example 75, except substituting 3-tert-butuldimethylsilyloxy-propionaldehyde for propionaldehyde and 4-(4'-trifluoromethylphenyl)phenyl methyl sulfone (Example 76A) for 4-(4'-methoxylphenyl)phenyl methyl sulfone in Example 75A.

EXAMPLE 125B (±)-N-hydroxy-N-[3-hydroxy-1-[[[4'-(trifluoromethyl)[1,1'-biphenyl]-4-yl]sulfonyl]methyl]propyl]formamide A solution of 125A (488 mg, 0.92 mmol) in THF (20 mL) at 0° C. was treated with TBAF (1.0M/THF, 1.84 mL, 1.84 mmol), stirred at 0° C. for one hour, treated with water, extracted with ethyl acetate, dried ($Na_2SO_4$), concentrated and triturated sequentially with ethyl ether and dichloromethane to provide 257 mg (67%) of the title compound as an off-white solid.

mp 186.5–188.8° C.; MS (APCI) m/z 418 (M+H)$^+$, 435 (M+NH$_4$)$^{+b, 452}$ (M+Cl)$^-$; $^1$H NMR (300 MHz, DMSO-d$_6$) δ 1.56–1.82 (m, 2H), 3.51–3.57 (dd, 1H, J=3, 15 Hz), 3.63–3.76 (m, 1H), 4.26–4.38 (m, 0.5H), 4.50–4.51 (br, 0.7H), 4.52–4.53 (m, 0.3H), 7.81–8.09 (9H), 9.48 (br, 0.5H); Anal. calcd for $C_{18}H_{18}NF_3O_5S$: C, 51.79; H, 4.34; N, 3.35. Found: C, 51.77; H, 4.50; N, 3.28.

EXAMPLE 126

(±)-N-hydroxy-N-[1-(methoxymethyl)-2-[[4'-(trifluoromethyl)[1,1'-biphenyl]-4-yl]sulfonyl]ethyl]formamide

EXAMPLE 126A 1-methoxy-3-[[4'-(trifluoromethyl)[1,1'-biphenyl]-4-yl]sulfonyl]-2-propanone A solution of 4-(4'-trifluoromethylphenyl)phenyl methyl sulfone (1.0 g, 3.33 mmol) in THF (50 mL) at −78° C. was treated with n-butyllithium (2.5M/hexanes, 1.4 mL, 3.50 mmol), stirred at −78° C. for 1.5 hours and then treated with ethyl methoxyacetate (0.78 mL, 6.66 mmol), stirred at −78° C. for three hours, treated with saturated NH$_4$Cl solution, and extracted with ethyl acetate. The combined organic extracts were washed with brine, dried ($Na_2SO_4$), concentrated and purified on silica gel with 30–50% ethyl acetate/hexanes to provide 902 mg (73%) of the title compound as a white solid. MS (APCI) m/z 390 (M+NH$_4$)$^+$, 371 (M−H)$^-$, 470 (M+Cl)$^-$.

EXAMPLE 126B (±)-1-methoxy-3-[[4'-(trifluoromethyl)[1,1'-biphenyl]-4-yl]sulfonyl]-2-propanol A suspension of Example 126A (850 mg, 2.28 mmol) in ethanol (100 mL) at ambient temperature was treated with sodium borohydride (103 mg, 2.74 mmol), stirred for 30 minutes, treated with water, extracted with ethyl acetate, dried ($Na_2SO_4$) and concentrated to provide 820 mg (96%) of the title compound as a white solid.

(APCI) m/z 392 (M+NH$_4$)$^+$, 409 (M+Cl)$^-$.

EXAMPLE 126C (±)-N-hydroxy-N-[1-(methoxymethyl)-2-[[4'-(trifluoromethyl)[1,1'-biphenyl]-4-yl]sulfonyl]ethyl]formamide Example 126B was converted to the title compound following the procedures of Examples 75B, 75C and 75D.

mp 175.3–176.3° C.; MS (ESI) m/z 418 (M+H)$^+$, 435 (M+NH$_4$)$^+$, 440 (M+Na)$^+$, 416 (M−H)$^-$; $^1$H NMR (300 MHz, DMSO-d$_6$) δ 3.17 (s, 1.5H), 3.21 (s, 1.5H), 3.41–3.51 (m, 2H), 3.63–3.68 (m, 1H), 4.28 (m, 0.5H), 4.80 (m, 0.5H), 7.87–7.90 (2.5H), 7.98–8.03 (6H), 8.14 (s, 0.5H), 9.54 (br s, 0.5H), 9.94 (0.5H); Anal. calcd for $C_{18}H_{18}NF_3O_5S$: C, 51.79; H, 4.34; N, 3.35. Found: C, 51.57; H, 4.50; N, 3.31.

EXAMPLE 127

(±)-N-[1-(1,3-benzodioxol-5-yl)-2-[[4'-(trifluoromethyl)[1,1'-biphenyl]-4-yl]sulfonyl]ethyl]-N-hydroxyformamide The title compound was prepared according to the procedures of Example 75, except substituting piperonal for propionaldehyde and 4-(4'-trifluoromethylphenyl)-phenyl methyl sulfone (ex. 76A) for 4-(4'-methoxylphenyl)phenyl methyl sulfone in Example 75A.

mp 159.5–160.5° C.; MS (ESI) m/z 516 (M+Na)$^+$, 492 (M−H)$^-$, 528 (M+Cl)$^-$; 1H NMR (300 MHz, DMSO-d$_6$) δ 4.02–4.18 (br, 2H), 5.30–5.40 (br, 0.5H), 5.60–5.70 (br, 0.5H), 5.85 (s, 0.5H), 5.92 (s, 0.5H), 6.77–6.93 (3H), 7.88–7.98 (m, 8H), 8.09–8.10 (br, 0.5H), 8.19–8.22 (br, 0.5H), 9.52–9.64 (br, 0.5H), 9.94–10.10 (br, 0.5H); Anal. calcd for $C_{23}H_{18}N_2F_3O_6S$: C, 55.98; H, 3.67; N, 2.83. Found: C, 55.86; H, 3.65; N, 2.79.

EXAMPLE 128

(±)-N-hydroxy-N-[4-hydroxy-1-[[[4'-(trifluoromethyl)[1,1'-biphenyl]-4-yl]sulfonyl]methyl]butyl]formamide The title compound was prepared according to the procedures of Example 125, except substituting 4-tert-butyldimethylsilyloxybutanaldehyde for 3-tert-butyldimethylsilyloxypropionaldehyde.

mp 138.9–140.3° C.; MS (ESI) m/z 432 (M+H)$^+$, 454 (M+Na)$^+$, 466 (M+Cl)$^-$; $^1$H NMR (300 MHz, DMSO-d$_6$) δ 1.22–1.36 (m, 2H), 1.44–1.66 (m, 2H), 3.47–3.54 (1H), 3.62–3.71 (m, 1H), 4.10–4.20 (m, 0.6H), 4.39–4.44 (m, 1H), 4.52–4.62 (m, 0.4H), 7.88–8.13 (10H), 9.47 (s, 0.6H), 9.85 (s, 0.4H); Anal. calcd for $C_9H_{20}N_2F_3O_5S$: C, 52.89; H. 4.67; N, 3.24. Found: C, 53.26; H, 5.00; N, 3.25.

EXAMPLE 129

(±)-N-hydroxy-N-[1-[4-(methoxymethoxy)phenyl]-2-[[4'-(trifluoromethyl)[1,1'-biphenyl]-4-yl]sulfonyl]ethyl]formamide The title compound was prepared according to the procedures of Example 75, except substituting 4-(methoxymethoxy)benzaldehyde for propionaidehyde and 4-(4'-trifluoromethylphenyl)-phenyl methyl sulfone (ex. 76A) for 4-(4'-methoxylphenyl)-phenyl methyl sulfone in Example 75A.

mp 137.1–138.5° C.; MS (ESI) m/z 527 (M+NH$_4$)$^+$, 508 (M−H)$^−$, 544 (M+Cl)$^−$; $^1$H NMR (300 MHz, DMSO-d$_6$) δ 3.28 (s, 3H), 4.00–4.20 (2H), 5.12 (s, 2H), 5.40 (br, 0.5H), 5.60 (br, 0.5H), 6.88–6.91 (d, 2H, J=8.7 Hz), 7.18–7.32 (m, 2H), 7.87–7.99 (m, 8H), 8.09 (br, 0.5H), 8.22 (br, 0.5H), 9.58 (s, 0.5H), 10.02 (s, 0.5H); Anal. calcd for C$_{24}$H$_{22}$NF$_3$O$_6$S: C, 56.57; H, 4.35; N, 2.74. Found: C, 56.59; H, 4.50; N, 2.70.

EXAMPLE 130

(±)-N-hydroxy-N-[1-(1-methyl-1H-pyrrol-2-yl)-2-[[4-[4-(trifluoromethoxy)phenoxy]phenyl]sulfonyl]ethyl]formamide The title compound was prepared according to the procedures of Example 75, except substituting 2-N-Methylpyrrole carboxaldehyde for propionaldehyde and 4-(4'-trifluoromethoxyphenoxy)phenyl methyl sulfone for 4-(4'-methoxylphenyl)phenyl methyl sulfone in Example 75A.

MS (ESI) M−H (483); $^1$H NMR (300 MHz, DMSO-d$_6$) δ 9.90 (s, 1H), 9.51 (s, 1H), 8.07 (s, 1H), 7.87–7.83 (d, 2H, J=8.9 Hz), 7.49–7.46 (d, 2H, J=8.4 Hz), 7.27–7.24 (d, 2H, J=8.8 Hz), 7.17–7.14 (d, 2H, J=8.8 Hz), 6.65 (s, 1H), 6.02 (s, 1H), 5.85–5.79 (m, 1H), 4.04–3.87 (mm, 2H), 3.53–3.44 (m, 3H); Anal. calcd for C$_{21}$H$_{19}$N$_2$O$_6$SF$_3$: C, 52.06; H, 3.95; N, 5.78. Found: C, 52.42; H, 4.12; N, 5.48.

EXAMPLE 131

(±)-N-hydroxy-N-[1-phenyl-2-[[4-[4-(trifluoromethoxy)phenoxy]phenyl]sulfonyl]ethyl]formamide The title compound was prepared according to the procedures of Example 75, except substituting benzaldehyde for propionaldehyde and 4-(4'-trifluoromethoxy-phenoxy) phenyl methyl sulfone for 4-(4'-methoxylphenyl)phenyl methyl sulfone in Example 75A.

MS (ESI) M−H (480); $^1$H NMR (300 MHz, DMSO-d$_6$) δ 10.06 (s, 0.5H), 9.96 (s, 0.5H), 8.18–8.11 (m, 1H), 7.87–7.85 (m, 2H), 7.50–7.47 (d, 2H, J=8.8 Hz), 7.30–7.24 (m, 5H), 7.15–7.13 (d, 2H, J=8.5 Hz), 5.78 (s, 0.5H), 5.41 (s, 0.5H), 4.24–4.04 (mm, 3H); Anal. calcd for C$_{22}$H$_{18}$NO$_6$SF$_3$: C, 54.88; H, 3.76; N, 2.90. Found: C, 54.58; H, 3.89; N, 2.96.

EXAMPLE 132

(±)-N-hydroxy-N-[1-(2-thienyl)-2-[[4-[4-(trifluoromethoxy)phenoxy]phenyl]sulfonyl]ethyl]formamide The title compound was prepared according to the procedures of Example 75, except substituting 2-thiophene carboxaldehyde for propionaldehyde and 4-(4'-trifluoromethoxyphenoxy)phenyl methyl sulfone for 4-(4'-methoxylphenyl)phenyl methyl sulfone in Example 75A.

MS (ESI) M−H (486); $^1$H NMR (300 MHz, DMSO-d$_6$) δ 10.15 (s, 0.5H), 9.75 (s, 0.5H), 8.16–8.12 (m, 1H), 7.88–7.85 (d, 2H, J=8.1 Hz), 7.50–7.47 (m, 2H), 7.29–7.25 (d, 2H, J=8.2 Hz), 7.17–7.14 (d, 2H, J=8.8 Hz), 7.08–7.04 (m, 1H), 6.95–6.92 (m, 1H), 5.92 (s, 0.5H), 5.76 (m, 0.5H), 4.05–4.00 (m, 3H); Anal. calcd for C$_{20}$H$_{16}$NO$_6$S$_2$F$_3$: C, 49.27; H, 3.30; N, 2.87. Found: C, 49.01; H, 3.24; N, 2.75.

EXAMPLE 133

(±)-N-[1-(2-furanyl)-2-[[4-[4-(trifluoromethoxy)phenoxy]phenyl]sulfonyl]ethyl]-N-hydroxyformamide The title compound was prepared according to the procedures of Example 75, except substituting 2-furyl carboxaldehyde for propionaldehyde and 4-(4'-trifluoromethoxyphenoxy)phenyl methyl sulfone for 4-(4'-methoxylphenyl)phenyl methyl sulfone in Example 75A.

MS (ESI) M−H (470); $^1$H NMR (300 MHz, DMSO-d$_6$) δ 10.03 (s, 0.5H), 9.60 (s, 0.5H), 8.14 (s, 1H), 7.90–7.89 (m, 2H), 7.57 (s, 1H), 7.49–7.46 (d, 2H, J=8.5 Hz), 7.29–7.25 (d, 2H, J=8.5 Hz), 7.19–7.16 (d, 8.5H), 6.41 (s, 1H), 6.39 (s, 1H), 4.04–4.00 (m, 3H); Anal. calcd for C$_{20}$H$_{16}$NO$_7$SF$_3$: C, 50.95; H, 3.42; N, 2.97. Found: C, 51.25; H, 3.70; N, 2.99.

EXAMPLE 134

(±)-N-[1-(5,5-dimethyl-2,4-dioxo-3-oxazolidinyl)-2-[[4'-(trifluoromethoxy)[1,1'-biphenyl]-4-yl]sulfonyl]ethyl]-N-hydroxyformamide

EXAMPLE 134A 1-bromo-3-[[4'-(trifluoromethoxy)1,1'-biphenyl]-4-yl]oxy]-2-propanone The title compound was prepared from 3-(4-(4'-trifluoromethoxyphenyl)-phenoxy)propan[1,2]oxirane using the procedure described in Example 47A.

EXAMPLE 134B (±)-N-[1-(5,5-dimethyl-2,4-dioxo-3-oxazolidinyl)-2-[[4'-(trifluoromethoxy) [1,1'-biphenyl]-4-yl]sulfonyl]ethyl]-N-hydroxyformamide Example 134B was converted to the tile compound by first reacting with 5,5-dimethyloxazolidinine-2,4-dione as in Example 3C, then applying the sequence of reactions described in Examples 2D, 2E and 2F.

$^1$H NMR (300 MHz, DMSO-d$_6$) δ 10.09 (s, 0.5H), 9.71 (s, 0.5H), 8.34 (s, 0.5H), 7.98 (s, 0.5H), 7.76–7.73 (d, 2H, J=8.8 Hz), 7.65–7.63 (d, 2H, J=8.5 Hz), 7.43–7.40 (d, 2H, J=8.8 Hz), 7.05–7.02 (d, 2H, J=8.8 Hz), 4.90–4.88 (m, 0.5H), 4.44–4.40 (m, 0.5H), 4.22–4.15 (m, 2H), 3.86–3.68 (m, 1H), 3.66–3.59 (m, 1H), 1.49 (s, 6H); Anal. calcd for C$_{22}$H$_{21}$N$_2$O$_7$F$_3$.0.25 ethyl acetate; C, 54.76; H, 4.59; N, 5.55. Found: C, 54.91; H, 4.49; N, 5.44.

EXAMPLE 135

(±)-N-hydroxy-N-[1-(methoxymethyl)-2[[4-[4-(trifluoromethoxy)phenoxy]phenyl]sulfonyl]ethyl]formamide The title compound was prepared according to the procedures of Example 126, except substituting 4-(4'-trifluoromethoxyphenoxy)phenyl methyl sulfone for 4-(4'-trifluoromethylphenyl)phenyl methyl sulfone.

MS (ESI−) 448 (M−H); $^1$H NMR (300 MHz, DMSO-d$_6$) δ 3.20 (s, 3H), 3.23–3.45 (m, 3H), 3.52–3.65 (m, 1H), 4.16–4.27 (m, 0.5H), 4.70–5.02 (m, 0.5H), 7.21 (dd, 2H, J=3,9 Hz), 7.28 (dd, 2H, J=6,9 Hz), 7.47 (d, 2H, J=9 Hz), 7.81 (s, 0.5H), 7.90 (dd, 2H, J=3,9 Hz), 8.12 (s, 0.5H), 9.56 (bs, 0.5H), 9.91 (bs, 0.5H); Anal. calcd for C$_{18}$H$_{18}$NO$_7$SF$_3$.0.25 ethyl acetate: C, 48.40; H, 4.27; N, 2.97. Found: C, 48.61; H, 4.33; N, 3.06.

EXAMPLE 136

(S)-N-hydroxy-N-[1-[(phenylmethoxy)methyl-]2-[[4'-(trifluoromethoxy)[1,1'-biphenyl]-4-yl]oxy]ethyl]formamide The title compound was prepared from Example 108B following the procedures of Examples 108E and 108F.

MS (ESI−) 460 (M−H); $^1$H NMR (300 MHz, DMSO-$d_6$) δ 3.58–3.73 (m, 2H), 4.0–4.2 (m, 2H), 4.28–4.35 (m, 0.5H), 4.55 (s, 2H), 4.8–4.9 (m, 0.5H), 7.03 (d, 2H, J=9 Hz), 7.25–7.38 (m, 5H), 7.43 (d, 2H, J=9 Hz), 7.63 (d, 2H, J=9 Hz), 7.75 (d, 2H, J=9 Hz), 8.06 (s, 0.5H), 8.42 (s, 0.5H), 9.62 (s, 0.5H), 10.03 (s, 0.5H); Anal. calcd for $C_{24}H_{22}F_3NO_5$: C, 62.47; H, 4.80; N, 3.03. Found: C, 62.29; H, 5.03; N, 2.92.

EXAMPLE 137

(S)-N-hydroxy-N-[1-(hydroxymethyl)-2-[[4'-(trifluoromethoxy)[1,1'-biphenyl]-4-yl]oxy]ethyl]formamide The title compound was prepared from Example 108B following the procedures of Examples 108C, 108E and 108F.

MS (ESI−) 370 (M−H); $^1$H NMR (300 MHz, DMSO-$d_6$) δ 3.45–3.53 (m, 2H), 3.95–4.20 (m, 2.5H), 4.55–4.68 (m, 0.5H), 4.90–4.98 (m, 1H), 7.05 (d, 2H, J=9 Hz), 7.42 (d, 9H), 7.64 (d, 2H, J=9 Hz), 7.75 (d, 2H, J=9 Hz), 7.98 (s, 0.5H), 8.39 (s, 0.5H), 9.47 (s, 0.5H), 9.89 (s, 0.5H); Anal. calcd for $C_{17}H_{16}F_3NO_5$: C, 54.99; H, 4.34; N, 3.77. Found: C, 54.77; H, 4.57; N, 3.54.

EXAMPLE 138

(±)-N-hydroxy-N-[1-(hydroxymethyl)-2-[[4-[4-(trifluoromethoxy)phenoxy]phenyl]sulfonyl]ethyl]formamide The title compound was prepared according to the procedures of Example 125, except substituting t-butyldimethylsilyloxy-acetaldehyde for 3-tert-butyldimethylsilyloxy-propionaldehyde and 4-(4'-trifluoromethoxyphenoxy)phenyl methyl sulfone for 4-(4'-trifluoromethylphenyl)phenyl methyl sulfone.

mp 115–117° C.; MS (ESI+) 436 (M+H), 453 (M+NH$_4$), 458 (M+Na); $^1$H NMR (300 MHz, DMSO-$d_6$) δ 3.30–3.62 (m, 4H), 3.93–4.03 (m, 0.5H), 4.51–4.61 (m, 0.5H), 4.95–5.06 (m, 1H), 7.22 (d, 2H, J=9.0 Hz), 7.25–7.32 (m, 2H), 7.48 (d, 2H, J=9.0 Hz), 7.76 (s, 0.5H), 7.86–7.94 (m, 2H), 8.13 (s, 0.5H), 9.41 (bs, 0.5H), 9.82 (bs, 0.5H); Anal. calcd for $C_{17}H_{16}NO_7SF_3$: C, 46.89; H, 3.70; N, 3.21. Found: C, 46.65; H, 3.71; N, 3.14.

EXAMPLE 139

[S-(R*,S*)]-N-[-(2,2-dimethyl-1,3-dioxol-4-yl)-2-[[4-[4-(trifluoromethoxy)phenoxy]phenyl]sulfonyl]ethyl]-N-hydroxyformamide

EXAMPLE 139A and 139B

[S-(R*,S*)]-N-[1-(2,2-dimethyl-1,3-dioxol-4-yl)-2-[[4-[4-(trifluoromethoxy)phenoxy]phenyl]sulfonyl]ethyl]hydroxylamine

139B

[S-(R*,R*)]-N-[1-(2,2-dimethyl-1,3-dioxol-4-yl)-2-[[4-[4-(trifluoromethoxy)phenoxy]phenyl]sulfonyl]ethyl]hydroxylamnine The title compounds were prepared as a diastereomeric mixture according to the procedures of Examples 75A, 75B and 75C, except substituting (R)-2,2-dimethyl-1,3-dioxolane-4-carboxaldehyde for propionaldehyde and 4-(4'-trifluoromethoxyphenoxy)phenyl methyl sulfone for 4-(4'-methoxylphenyl)phenyl methyl sulfone in Example 75A. The two distereomers were separated via silica gel choromatography to give Example 139A and Example 139B.

EXAMPLE 139C

[S-(R*,S*)]-N-[1-(2,2-dimethyl-1,3-dioxol-4-yl)-2-[[4-[4-(trifluoromethoxy)phenoxy]phenyl]sulfonyl]ethyl]-N-hydroxyformamide Example 139A was converted to the title compound following the formylation procedure described in Example 1E.

mp 149–150° C.; MS (ESI+) 506 (M+H), 523 (M+NH$_4$), 528 (M+Na); $^1$H NMR (300 MHz, DMSO-$d_6$) δ 1.04 (s, 1.5H), 1.13 (s, 1.5H), 1.20 (s, 1.5H), 1.23 (s, 1.5H), 3.57–4.11 (m, 5.5H), 4.39 (t, 0.5H, J==9.80 Hz), 7.19–7.30 (m, 4H), 7.49 (d, 2H, J=8.70 Hz), 7.86–7.97 (m, 2.5H), 8.15 (s, 0.5H), 9.71 (bs, 0.5H), 10.20 (s, 0.5H); Anal. calcd for $C_{21}H_{22}NO_8SF_3$: C, 49.90; H, 4.38; N, 2.77. Found: C, 49.90; H, 4.35; N, 2.52.

EXAMPLE 140

[S-(R*,R*)]-N-[1-(2,2-dimethyl-1,3-dioxol-4-yl)-2-[[4-[4-(trifluoromethoxy)phenoxy]phenyl]sulfonyl]ethyl]-N-hydroxyformamide Example 139B was converted to the title compound following the formylation procedure described in Example 1E.

mp 127–128° C.; MS (ESI+) 506 (M+H), 523 (M+NH$_4$), 528 (M+Na); $^1$H NMR (300 MHz, DMSO-$d_6$) δ 1.21 (s, 1.5H), 1.23 (s, 1.5H), 1.26 (s, 1.5H), 1.30 (s, 1.5H), 3.28–3.40 (m, 1H), 3.61–3.73 (m, 2H), 3.92–4.14 (m, 2.5H), 4.56 (t, 0.5H, J=8.25 Hz), 7.20–7.31 (m, 4H), 7.48 (d, 2H, J=8.70 Hz), 7.81 (s, 0.5H), 7.92 (t, 2H, J=9.0 Hz), 8.13 (s, 0.5H), 9.63 (bs, 0.5H), 10.01 (bs, 0.5H); Anal. calcd for $C_{21}H_{22}NO_8SF_3$: C, 49.90; H, 4.38; N, 2.77. Found: C, 49.96; H, 4.46; N, 2.76.

EXAMPLE 141

[S-(R*,R*)]-N-[(2,3-dihydroxy)-1-[[[4-[4-(trifluoromethoxy)phenoxy]phenyl]-sulfonyl]methyl]propyl]-N-hydroxyformamide

EXAMPLE 141A

[S-(R*,R*)]-3-(hydroxyamino-4-[[[4-(trifluoromethoxy)phenoxy]phenyl]sulfonyl]-1,2-butanediol Example 139B (9.6 gm, 20 mmol) was dissolved in THF (300 mL) and treated with 3N HCl (40 mL) dropwise, and the clear solution was stirred at 45° C. for 1 hr. The reaction mixture was neutralized with a slow addition of NaHCO$_3$ solution and extracted with ether. The organic layer was dried with MgSO4 and concentrated to white solid. Recrystallization from CH$_2$Cl$_2$ afforded pure title compound as a white powder (6.94 gm, 79%).

MS (ESI+) 439 (M+H).

EXAMPLE 141B[S-(R*,R*)]-N-[(2,3-dihydroxy)-1-[[[4-[4-(trifluoromethoxy)phenoxy]phenyl]-sulfonyl]methyl]propyl]-N-hydroxyformamide Example 141A was converted to the title compound following the formylation procedure described in Example 1E.

mp 137–138° C.; MS (ESI+) 466 (M+H), 483 (M+NH$_4$), 488 (M+Na); $^1$H NMR (300 MHz, DMSO-d$_6$) δ 3.30–3.60 (m, 3H), 3.65–3.78 (m, 1H), 3.90–3.99 (m, 0.5H), 4.53–4.62 (m, 0.5H), 4.78 (bs, 1H), 4.94 (bs, 1H), 7.21 (d, 2H, J=9.0 Hz), 7.25–7.32 (m, 2H), 7.47 (d, 2H, J=8.60 Hz), 7.70 (s, 0.5H), 7.84–7.92 (m, 2H), 8.09 (s, 0.5H), 9.30 (bs, 0.5H), 9.65 (bs, 0.5H); Anal. calcd for C$_{18}$H$_{18}$NO$_8$SF$_3$: C, 46.45; H, 3.89; N, 3.00. Found: C, 46.29; H, 3.88; N, 2.91; [α]$_D$=+4.2° (MeOH).

EXAMPLE 142

(±)-N-[1-[(dimethylamino)methyl]-2-[[4-[4-(trifluoromethoxy)phenoxy]phenyl]-sulfonyl]ethyl]-N-hydroxyformamide The title compound was prepared according to the procedures of Example 126, except substituting 4-(4'-trifluoromethoxyphenoxy)phenyl methyl sulfone for 4-(4'-trifluoromethylphenyl)phenyl methyl sulfone and N,N-dimethylglycine ethyl ester for ethyl methoxyacetate.

MS (ESI+) 463 (M+H), 485 (M+Na); $^1$H NMR (300 MHz, DMSO-d$_6$) δ 2.04 (s, 3H), 2.10 (s, 3H), 2.21–2.39 (m, 2H), 3.40–3.48 (m, 1H), 3.53–3.63 (m, 1H), 4.05–4.17 (m, 0.5H), 4.62–4.72 (m, 0.5H), 7.19–7.30 (m, 4H), 7.47 (d, 2H, J=9.0 Hz), 7.86 (s, 0.5H), 7.87–7.94 (m, 2H), 8.10 (s, 0.5H), 9.45 (bs, 0.5H), 9.85 (bs, 0.5H); Anal. calcd for C$_{19}$H$_{21}$N$_2$O$_6$F$_3$S: C, 49.34; H, 4.57; N, 6.05. Found: C, 49.12; H, 4.72; N, 6.04.

EXAMPLE 143

[S-(R*,R*)]-N-[2-[(4'-chloro[1,1'-biphenyl]-4-yl)sulfonyl]-1-(2,2-dimethyl-1,3-dioxol-4-yl)ethyl]-N-hydroxyformamide The title compound was prepared according to the procedures described for Examples 139 and 140, starting with 4-(4'-chlorophenyl)phenyl methyl sulfone and (R)-2,2-dimethyl-1,3-dioxolane-4-carboxaldehyde.

MS (ESI+) 440 (M+H), 457 (M+NH$_4$); $^1$H NMR (300 MHz, DMSO-d$_6$) δ 1.20 (s, 1.5H), 1.22 (s, 1.5H), 1.26 (s, 1.5H), 2.30 (s, 1.5H), 3.32–3.40 (m, 1H), 3.62–3.78 (m, 2H), 3.93–4.15 (m, 2.5H), 4.64 (t, 0.5H, J=8.4 Hz), 7.58 (d, 2H, J=8.4 Hz), 7.77–7.83 (m, 2H), 7.89 (s, 0.5H), 7.93–8.02 (m, 4H), 8.13 (s, 0.5H), 9.62 (bs, 0.5H), 9.97 (bs, 0.5H); Anal. calcd for C$_{20}$H$_{22}$NO$_6$SCl: C, 54.60; H, 5.04; N, 3.18. Found: C, 54.48; H, 5.30; N, 3.13.

EXAMPLE 144

(±)-N-[1-[(1,1-dioxido-3-oxo-1,2-benzisothiazol-2(3H)-yl)methyl]-2-[[4'-(trifluoromethoxy)[1,1'-biphenyl]-4-yl]oxy]ethyl]-N-hydroxyformamide The title compound was prepared according to the procedures described in Example 134, except substituting saccharin for 5,5-dimethyloxazolidinine-2,4-dione.

MS (ESI–) 535 (M–1); $^1$H NMR (300 MHz, DMSO-d$_6$) δ 3.9–4.2 (m, 2H), 4.2–4.3 (m, 2H), 4.45–4.55 (m, 0.5H), 5.0–5.1 (m, 0.5H), 7.0–7.1 (m, 2H), 7.42 (d, 2H, J=8.4 Hz), 7.64 (d, 2H, J=8.4 Hz), 7.74 (d, 2H, J=9.0 Hz), 8.0–8.2 (m, 3.5H), 8.3–8.4 (m, 1.5H), 9.78 (s, 0.5H), 10.14 (s, 0.5H); Anal. calcd for C$_{24}$H$_{19}$F$_3$N$_2$O$_7$S: C, 53.73; H, 3.56; N, 5.22. Found: C, 53.81; H, 3.78; N, 5.07.

EXAMPLE 145

[R-(R*,R*)]-N-[1-(2,2-dimethyl-1,3-dioxol-4-yl)-2-[[4-[4-(trifluoromethoxy)phenoxy]phenyl]sulfonyl]ethyl]-N-hydroxyformamide

EXAMPLE 145A and 145B

[R-(R*,R*)]-N-[1-(2,2-dimethyl-1,3-dioxol-4-yl)-2-[[4-[4-(trifluoromethoxy)phenoxy]phenyl]sulfonyl]ethyl]hydroxylamine

145B

[R-(S*,R*)]-N-[1-(2,2-dimethyl-1,3-dioxol-4-yl)-2-[[4-[4-(trifluoromethoxy)phenoxy]phenyl]sulfonyl]ethyl]hydroxylamine The title compounds were prepared as a diastereomeric mixture according to the procedures of Examples 126A, 126B, 75A and 75B and 75C, starting with 4-(4'-trifluoromethoxyphenoxy)phenyl methyl sulfone and methyl (S)-2,2-dimethyl-1,3-dioxolane-4-carboxylate. The two distereomers were separated via silica gel chromatography to give Example 145A and Example 145B.

EXAMPLE 145C

[R-(R*,R*)]-N-[1-(2,2-dimethyl-1,3-dioxol-4-yl)-2-[[4-[4-(trifluoromethoxy)phenoxy]phenyl]sulfonyl]ethyl]-N-hydroxyformamide Example 145A was converted to the title compound following the formylation procedure described in Example 1E.

MS (ESI+) 506 (M+1), 523 (M+18); $^1$H NMR (300 MHz, DMSO-d$_6$) δ 1.21 (s, 1.5H), 1.23 (s, 1.5H), 1.26 (s, 1.5H), 1.30 (s, 1.5H), 3.3–3.4 (m, 1H), 3.60–3.75 (m, 2H), 3.9–4.1 (m, 2.5H), 4.5–4.6 (m, 0.5H), 7.2–7.3 (m, 4H), 7.48 (d, 2H, J=8.7 Hz), 7.81 (s, 0.5H), 7.85–7.95 (m, 2H), 8.13 (s, 0.5H), 9.63 (br s, 0.5H), 10.0 (br s, 0.5H); Anal. calcd for C$_{21}$H$_{22}$F$_3$NO$_8$S: C, 49.90; H, 4.38; N, 2.77. Found: C, 49.90; H, 4.51; N, 2.66.

EXAMPLE 146

[R-(S*,R*)]-N-[[1-(2,2-dimethyl-1,3-dioxol-4-yl)-2-[[4-[4-(trifluoromethoxy)phenoxy]phenyl]sulfonyl]ethyl]-N-hydroxyformamide Example 145B was converted to the title compound following the formylation procedure described in Example 1E.

MS (ESI+) 506 (M+H), 523 (M+18); $^1$H NMR (300 MHz, DMSO-d$_6$) δ 1.05 (s, 1.5H), 1.14 (s, 1.5H), 1.20 (s, 1.5H), 1.23 (s, 1.5H), 3.3–3.4 (m, 1H), 3.5–4.1 (m, 4.5H), 4.3–4.4 (m, 0.5H), 7.2–7.3 (m, 4H), 7.48 (d, 2H), 7.8–8.0 (m, 2.5H), 8.15 (s, 0.5H), 9.68 (br s, 0.5H), 10.10 (br s, 0.5H).

EXAMPLE 147

[S-(R*,R*)]-N-[1-(2,2-diethyl-1,3-dioxol-4-yl)-2-[[4-[4-(trifluoromethoxy)phenoxy]phenyl]sulfonyl]ethyl]-N-hydroxyformamide The title compound was prepared according to the procedures described for Examples 139 and 140, except substituting (R)-2,2-diethyl-1,3-dioxolane-4-carboxaldehyde for (R)-2,2-dimethyl-1,3-dioxolane-4-carboxaldehyde.

MS (ESI+) 534 (M+1H), 551 (M+18); $^1$H NMR (300 MHz, DMSO-d$_6$) δ 0.7–0.8 (m, 6H), 1.4–1.6 (m, 4H), 3.2–3.3 (m, 1H), 3.45–3.55 (m, 1H), 3.69 (dd, 1H, J=8.7, 15.6 Hz), 3.95–4.15 (m, 2.5H), 4.5–4.6 (m, 0.5H), 7.2–7.3 (m, 4H), 7.47 (d, 2H, J=8.4 Hz), 7.81 (s, 0.5H), 7.85–7.95 (m, 2H), 8.14 (s, 0.5H), 9.66 (br s, 0.5H), 10.11 (br s, 0.5H); Anal. calcd for $C_{23}H_{26}NO_8SF_3$: C, 51.77; H, 4.91; N, 2.62. Found: C, 51.98; H, 5.12; N, 2.63.

EXAMPLE 148

(±)-N-hydroxy-N-[1-(hydroxymethyl)-2-[[4'-(methylsulfonyl)[1,1'-biphenyl]-4-yl]sulfonyl]ethyl]formamide The title compound was prepared according to the procedures of Example 125, except substituting tert-butyldimethylsilyloxy-acetaldehyde for 3-tert-butyldimethylsilyloxy-propionaldehyde and 4-(4'-methylsulfonylphenyl)phenyl methyl sulfone for 4-(4'-trifluoromethylphenyl)phenyl methyl sulfone.

mp 165–167° C.; MS (ESI(−)) 412 (M−H), 825 (2M−H), 847 (2M+Na−2H); $^1$H NMR (300 MHz, DMSO-$d_6$): δ 8.23 (s, ½H), 7.97–8.13 (m, 9H), 7.93 (s, ½H), 4.75–4.84 (m, 1H), 4.17–4.35 (m, 1H), 3.57–3.84 (m, 3H), 3.41–3.53 (m, 1H), 3.18 (s, 3H); HRMS: calc: 414.0681, Found: 414.0668; Anal. calcd for $C_{17}H_{19}NO_7S_2$: C, 49.38; H, 4.63; N, 3.38; S, 15.50. Found: C, 34.24; H, 3.47; N, 2.32; S, 14.61.

EXAMPLE 149

(±)-N-[1-[[4-[(1,3-benzodioxol-5-yl)phenyl]sulfonyl]methyl]-2-hydroxyethyl]-N-hydroxyformamide The title compound was prepared according to the procedures of Example 125, except substituting tert-butyldimethylsilyloxyacetaldehyde for 3-tert-butyldimethylsilyloxypropionaldehyde and 4-(3',4'-methylenedioxyphenyl)phenyl methyl sulfone for 4-(4'-trifluoromethylphenyl)phenyl methyl sulfone.

mp 160–161° C.; MS (APCI) 380 (M+H), 397 (M+NH$_4$); $^1$H NMR (300 MHz, DMSO-$d_6$): δ 9.42–9.83 (m, 1·1H), 8.19 (s, ½H), 7.85–8.00 (m, 4.5H), 7.49 (s, 1H), 7.41 (d, 1H, J=8 Hz), 7.08 (d, 1H, J=8 Hz), 6.13 (s, 2H), 4.96–5.27 (m, 1H), 4.52–4.62 (m, ½H), 4.04–4.14 (m, ½H), 3.60–3.70 (m, 2H), 3.38–3.46 (m, 2H); Anal. calcd for $C_{17}H_{17}NO_7S$: C, 53.82; H, 4.51; N, 3.69; S, 8.45. Found: C, 53.49; H, 4.54; N, 3.58; S, 8.32.

EXAMPLE 150

(±)-N-hydroxy-N-[1-(hydroxymethyl)-2-[[4'-(methylthio)[,11'-biphenyl]-4-yl]sulfonyl]ethyl]formamide The title compound was prepared according to the procedures of Example 125, except substituting tert-butyldimethylsilyloxyacetaldehyde for 3-tert-butyldimethylsilyloxypropionaldehyde and 4-(4'-thiomethylphenyl)phenyl methyl sulfone for 4-(4'-trifluoromethylphenyl)phenyl methyl sulfone.

mp 161–162° C.; MS (DCI): 382 (M+H), 399 (M+NH$_4$); $^1$H NMR (300 MHz, DMSO-$d_6$) δ 9.77–10.05 (m, ½H), 9.27–9.68 (m, ½H), 8.15 (s, ½H), 7.89–7.99 (m, 4H), 7.84 (s, ½H), 7.72 (s, 1H), 7.70 (s, 1H), 7.58 (s, 1H), 7.56 (s, 1H), 4.98–5.12 (m, 1H), 4.58–4.70 (m, ½H), 4.01–4.10 (m, ½H), 3.57–3.67 (m, 1.5H), 3.35–3.44 (m, 2H), 3.09–3.19 (m, ½H); HRMS: calc:382.0783. Found:382.0784; Anal. calcd for $C_{17}H_{19}NO_5S_2.0.25$ $C_4H_8O_2$: C, 53.58; H, 5.25; N, 3.47; S, 15.90. Found: C, 53.77; H, 5.50; N, 3.63; S, 16.02.

EXAMPLE 151

(±)-N-hydroxy-N-[1-(hydroxymethyl)-2-[[4'-(trifluoromethoxy)[1,1'-biphenyl]-4-yl]sulfonyl]ethyl]formamide The title compound was prepared according to the procedures of Example 125, except substituting tert-butyldimethylsilyloxyacetaldehyde for 3-tert-butyldimethyl-silyloxypropionaldehyde and 4-(4'-trifluoromethoxyphenyl)phenyl methyl sulfone for 4-(4'-trifluoromethylphenyl)phenyl methyl sulfone.

mp 167–168° C.; MS (APCI) 420 (M+H), 437 (M+NH$_4$); $^1$H NMR (300 MHz, DMSO-$d_6$): δ 9.85–9.98 (m, ½H), 9.41–9.58 (m, ½H), 8.18 (s, ½H), 7.98–8.07 (m, 3.5H), 7.86–7.97 (m, 3H), 7.56 (s, 1H), 7.53 (s, 1H), 5.03–5.14 (m, 1H), 4.62–4.73 (m, 1H), 4.06–4.17 (m, 1H), 3.64–3.74 (m, 1H), 3.40–3.47 (m, 2H); HRMS: calc: 420.0729. Found:420.0722; Anal. calcd for $C_{17}H_{16}F_3NO_6S$: C, 48.68; H, 3.84; F, 13.59; N, 3.33; S, 7.64. Found: C, 48.54; H, 4.00; F, 13.67; N, 3.20; S, 7.95.

EXAMPLE 152

(±)-N-hydroxy-N-[1-(hydroxymethyl)-2-[(4'chloro[1,1'-biphenyl]-4-yl)sulfonyl]ethyl]formamide The title compound was prepared according to the procedures of Example 125, except substituting tert-butyldimethylsilyloxyacetaldehyde for 3-tert-butyldimethyl-silyloxypropionaldehyde and 4-(4'-chlorophenyl)phenyl methyl sulfone for 4-(4'-trifluoromethylphenyl)phenyl methyl sulfone.

mp 153–154° C.; MS (ESI(+)) 370 (M+H), 387 (M+NH$_4$), 392 (M+Na); $^1$H NMR (300 MHz, DMSO-$d_6$): δ 9.34–9.92 (m, 1H), 8.19 (s, ½H), 7.95–8.09 (m, 4H), 7.78–7.93 (m, 2.5H), 7.56–7.68 (m, 2H), 4.94–5.21 (m, 1H), 4.62–4.73 (m, 1H), 4.05–4.16 (m, 1H), 3.62–3.74 (m, 2H), 3.52–3.56 (m, 1H); HRMS: calc: 370.0516. Found: 370.0526; Anal. calcd for $C_{16}H_{16}ClNO_5S.0.25$ $H_2O$: C, 51.33; H, 4.44; Cl, 9.47; N, 3.74; S, 8.56; Found: C, 51.30; H, 4.37; Cl, 9.33; N, 3.72; S, 8.43.

EXAMPLE 153

(±)-N-[1-(2,5-dioxo-3,4,4-trimethl-1-imidazolidinyl)methyl]-2-[[4-[4-(trifluoromethyl)phenoxy]phenyl]sulfonyl]ethyl]-N-hydroxyfomamide The title compound was prepared according to the procedures of Example 61, except substituting 4-(4'-trifluoromethylphenoxy)benzenethiol in place of 4'-thiol-4-biphenylcarbonitrile in Example 61A.

mp 141–143° C.; MS (ESI(+)) 544 (M+H), 561 (M+NH$_4$), 566 (M+Na), 1104 (2M+N H$_4$), 1109 (2M+Na); $^1$H NMR (300 MHz, DMSO-$d_6$): δ 9.78 (bs, ½H), 9.58 (bs, ½H), 8.15 (s, ½H), 7.96–8.03 (m, 2H), 7.84–7.90 (m, 2H), 7.74 (s, ½H), 7.34–7.41 (m, 4H), 4.86–4.95 (m, ½H), 4.49–4.58 (m, ½H), 4.10 (s, ½H), 3.50–3.82 (m, 3.5H), 2.82 (s, 3H), 1.36–1.44 (m, 6H); Anal. calcd for $C_{23}H_{24}F_3N_3O_7S.0.25$ $C_4H_8O_2$: C, 50.97; H, 4.63; N, 7.43; S, 5.66; Found: C, 50.75; H, 4.73; N, 7.27; S, 5.60.;

EXAMPLE 154

(±)-N-hydroxy-N-[1-(hydroxymethYl)-2-[[[4-(methylsulfonyl)phenoxy]phenyl]sulfonyl]ethyl]formamide

EXAMPLE 154A (±)-1-[[[(1,1-dimethylethyl)dimethylsilyl]oxy]-3-[4-[4-(methylthio)phenoxy]phenyl]thio]-2-propanone Reaction of 4-(4'methylsulfonephenoxy)benzenethiol with 3-(tert-butyldimethylsilyloxy)propan-[1,2]oxirane followed by Dess Martin oxidation as described in Examples 2B and 2C afforded the title compound.

EXAMPLE 154B (±)-N-hydroxy-N-[1-(hydroxymethyl)-2-[[[4-(methylsulfonyl)phenoxy]phenyl]sulfonyl]ethyl]formamide The title compound was prepared from Example 154A, following the procedures described in Examples 61B and 61C.

MS (ESI) 430 (M+H), 447 (M+NH$_4$), 452 (M+Na), 428 (M−H); $^1$H NMR (300 MHz, DMSO-d$_6$) δ 9.84 (br, 0.5H), 9.40 (br, 0.5H), 8.12 (s, 0.5H), 8.02–7.91 (m, 4H), 7.75 (s, 0.5H), 7.38–7.29 (m, 4H), 5.09–4.94 (m, 1H), 4.61–4.52 (m, 0.5H), 4.06–3.95 (m, 0.5H), 3.67–3.34 (m, 4H), 3.24 (s, 3H).

EXAMPLE 155

(±)-N-[1-methyl-3-(4'-chloro[1,1'-biphenyl]-4-yl)-3-oxopropyl]-N-hydroxyformamide

EXAMPLE 155A (E)-1-(4'-chloro[1,1'-biphenyl]-4-yl)but-2-en-1-one

A solution of 4-chlorodiphenyl (3.94 g, 0.02 mol) and crotonyl chloride (2 mL, 0.02 mol) in CH$_2$Cl$_2$ (50 mL) was treated with AlCl$_3$ (2.78 g, 0.02 mol) at rt, stirred overnight, quenched with H$_2$O, extracted with CH$_2$Cl$_2$, washed with brine, dried over MgSO4, filtered, and concentrated. Purification on silica gel with 5% CH$_2$Cl$_2$/hexanes provided 2.6 g (51%) of the desired compound.

EXAMPLE 155B (±)-3-(hydroxyamino)-1-(4'-chloro[1,1'-biphenyl]-4-yl)-1-butanone A solution of Example 155A (0.1 g, 0.39 mmol), N H$_2$OH.HCl (0.13 g, 1.95 mmol), and K$_2$CO$_3$ (0.27 g, 1.95 mmol) in THF (50 mL) was refluxed for 5 h, quenched with H$_2$O, extracted with ethyl acetate, dried over MgSO$_4$, filtered, and concentrated. Purification on silica gel with 1% methanol/CH$_2$Cl$_2$ provided 0.009 g (8%) of the desired compound.

EXAMPLE 155C (±)-N-[1-methyl-3-(4'-chloro[1,1'-biphenyl]-4-yl)-3-oxopropyl]-N-hydroxyformamide Example 155C was formylated according to the procedure of Example 1E to give the title compound.

MS (ESI) 318 (M+H), 335 (M+NH$_4$), 340 (M+Cl), 316 (M−H); $^1$H NMR (300MHz, DMSO-d$_6$-) δ 9.80 (s, 0.5H), 9.32 (s, 0.5H), 8.20 (s, 0.5H), 8.04 (d, 2H, J=8.2 Hz), 7.82 (dd, 4H, J=14.9, 8.4 Hz), 7.57 (d, 2H, J=8.5 Hz), 4.91–4.79 (m, 0.5H), 4.50–4.36 (m, 0.5H), 3.54 (dd, 1H, J=17.6, 8.1 Hz), 3.10 (dd, 1H, J=17.0, 4.1 Hz), 1.26 (d, 1.5H, J=6.7 Hz), 1.18 (d, 1.5H, J=6.5 Hz); Anal. calcd for C$_{17}$H$_{16}$NO$_3$Cl.0.25 H$_2$O: C, 63.35; H, 5.16; N, 4.34. Found: C, 63.01; H, 5.42; N, 4.08.

EXAMPLE 156

(±)-N-[1-[(2,5-dioxo-3,4,4-trimethyl-1-imidazolidinyl)methyl]-2-[[4-(4-butylphenoxy)phenyl]sulfonyl]ethyl]-N-hydroxyformamide The title compound was prepared according to the procedures of Example 61, except substituting 4-(4'-n-butylphenoxy)benzenethiol in place of 4'-thiol-4-biphenylcarbonitrile in Example 61A.

MS (ESI) 532 (M+H), 549 (M+NH$_4$), 554 (M+Na), 530 (M−H);

$^1$H NMR (300MHz, DMSO-d$_6$) δ 9.69 (s, 0.5H), 9.52 (s, 0.5H), 8.09 (s, 0.5H), 7.87 (dd, 2H, J=8.8, 3.0 Hz), 7.68 (s, 0.5H), 7.28 (d, 2H, J=8.5 Hz), 7.14–7.04 (m, 4H), 4.90–4.78 (m, 0.5H), 4.51–4.40 (m, 0.5H), 3.74–3.40 (m, 4H), 2.76 (s, 0.5H), 2.76 (s, 1.5H), 2.61 (t, 2H, J=7.5 Hz), 1.63–1.52 (m, 2H), 1.39–1.26 (m, 2H), 1.26–1.22 (m, 6H), 0.91 (t, 3H, J=7.2 Hz); Anal. calcd for C$_{26}$H$_{33}$N$_3$O$_7$S: C, 58.74; H, 6.25; N, 7.90. Found: C, 58.50; H, 6.43; N, 7.76.

EXAMPLE 157

(±)-N-[3-[(2,5-dioxo-3,4,4-trimethyl-1-imidazolidinyl)-1-[[4-[4-(trifluoromethyl)phenoxy]phenyl]sulfonyl]methyl]propyl]-N-hydroxyfomamide The title compound was prepared according to the procedures of Example 61, except substituting 4-(4'-trifluoromethylphenoxy)-benzenethiol in place of 4'-thiol-4-biphenylcarbonitrile and Example 47A in place of Example 16B.

MS (ESI) 544 (M+H), 566 (M+Na), 542 (M−H); $^1$H NMR (300MHz, DMSO-d$_6$) δ 9.97 (s, 0.5H), 9.60 (s, 0.5H), 8.32 (s, 0.5H), 8.23 (s, 0.5H), 8.11 (s, 0.5H), 7.95–7.89 (m, 2H), 7.82 (d, 2H, J=8.8 Hz), 7.76 (s, 0.5H), 7.35–7.28 (m, 4H), 4.54–4.42 (m, 0.5H), 4.06–3.95 (m, 0.5H), 3.68–3.22 (m, 4H), 2.04–1.62 (m, 2H), 1.26 (s, 3H), 1.23 (s, 3H).

EXAMPLE 158

(±)-N-[1-[(2,5-dioxo-3,4 4-trimethyl-1-imidazolidinyl)methyl]-2-[[4-[4-(trifluoromethoxy)phenoxy]phenyl]sulfonyl]ethyl]-N-hydroxyformamide The title compound was prepared according to the procedures of Example 61, except substituting 4-(4'-trifluoromethoxyphenoxy)-benzenethiol in place of 4'-thiol-4-biphenylcarbonitrile and Example 26A in place of Example 16b.

MS (ESI) 546 (M+H), 568 (M+Na), 544 (M−H); 1H NMR (300MHz, DMSO-d$_6$) δ 9.64 (s, 0.5H), 9.45 (s, 0.5H), 8.35 (d, 1H, J=12.2 Hz), 8.10 (s, 0.5H), 7.91 (dd, 2H, J=8.9, 2.8 Hz), 7.68 (s, 0.5H), 7.47 (d, 2H, J=9.2 Hz), 7.30–7.21 (m, 4H), 4.88–4.77 (m, 0.5H), 4.51–4.40 (m, 0.5H), 3.73–3.38 (m, 4H), 1.24 (s, 3H), 1.22 (s, 3H); Anal. calcd for C$_{22}$H$_{22}$N$_3$O$_8$SF$_3$: C, 48.44; H, 4.06; N, 7.70. Found: C, 48.34; H, 4.29; N, 7.54.

EXAMPLE 159

(±)-N-[1-[[4-[(4-chlorophenoxy)phenyl]sulfonyl]methyl]-3-[(2,5-dioxo-3,4,4-trimethy-1-imidazolidinyl)methyl]propyl]-N-hydroxyformamide The title compound was prepared according to the procedures of Example 61, except substituting 4-(4'-chlorophenoxy)-benzenethiol in place of 4'-thiol-4-biphenylcarbonitrile and 1-bromo-4-(3,4,4-trimethyl-2,5-dioxoimidazolidin-1-yl)butan-2-one in place of Example 16b.

MS (ESI) 524 (M+H), 541 (M+NH$_4$), 546 (M+Na), 522 (M−H); $^1$H NMR (300MHz, DMSO-d$_6$) δ 9.97 (s, 0.5H), 9.60 (s, 0.5H), 8.10 (s, 0.5H), 7.89–7.84 (m, 2H), 7.76 (s, 0.5H), 7.53 (d, 2H, J=8.9 Hz), 7.25–7.16 (m, 4H), 4.50–4.38 (m, 0.5H), 4.04–3.92 (m, 0.5H), 3.64–3.24 (m, 4H), 2.79 (s, 1.5H), 2.75 (s, 1.5H), 2.02–1.86 (m, 1H), 1.74–1.61 (m, 1H), 1.27 (s, 3H), 1.24 (s, 3H); Anal. calcd for $C_{23}H_{26}N_3O_7SCl \cdot 0.5\ H_2O$: C, 51.83; H, 5.10; N, 7.88. Found: C, 51.84; H, 4.95; N, 7.92.

EXAMPLE 160

(±)-N-[2-[4-(4'-cyano[1,1'-biphenyl]-4-yl)oxy]cyclohexyl]-N-hydroxyformamide

The title compound was prepared from 2-chlorocyclohexanone first by alkylating with 4'hydroxy-4-biphenylcarbonitrile as descibed in Example 16C, then converting the resulting ketone to the title compound through the oxime formation, reduction and formylation procedures described in examples 2D, 2E and 2F.

MS(ESI): 337(M+H), 354(M+18), 359(M+23), 673(2M+H), 695(2M+23); $^1$H NMR (300MHz, DMSO-$d_6$): δ 9.90(s, 0.2 H), 9.69(s, 0.3H), 9.48 (s, 0.5H), 8.27(s, 0.2H), 8.05 (s, 0.3H), 8.01(s, 0.5H), 7.93–7.78(m, 4H), 7.67(m, 2H), 7.06 (m, 2H), 4.55–4.17(m, 1H), 3.80–3.68(m, 1H), 2.30–2.00 (m, 1H), 1.88–1.22(m, 7H).

EXAMPLE 161

(±)-N-L2-[4-[4'-(trifluoromethoxy)[1,1'-biphenyl]-4-yl)oxylcyclohexyl]-N-hydroxyformamide

EXAMPLE 161A

To a solution of 100 mg (0.434 mmol) of (1S*,2S*)-2-((tert-butyldimethyl)silyl)oxy)-cyclohexanol, 132 mg (0.521 mmol) of 4-(p-trifluoromethoxyphenyl)phenol and 342 mg (1.302 mmol) of triphenylphosphine in 5 ml THF under nitrogen at room temperature was added 171 ml (1.085 mmol) diethyl azodicarboxylate (DEAD). The resulting mixture was stirred at room temperature for 18 h and then under reflux for 2 days. The solvent was removed under reduced pressure and the residue was chromatographed on silica gel with hexanes/ethyl acetate (24:1) to give 55 mg (27%) of the title compound as colorless oil.

MS(ESI): 467(M+H), 484 (M+NH$_4$).

EXAMPLE 161B (±)-N-[2-[4-[4'-(trifluoromethoxy)[1,1'-biphenyl]-4-yl)oxy]cyclohexyl]-N-hydroxyformamide The title compound was prepared from Example 161A, by first deprotecting the silyl ether as in Example 4D, then applying the sequence of reactions described in Examples 1C, 1D and 1E.

MS(ESI): 396 (M+H), 413 (M+18), 418 (M+23), 813 (2M+23); $^1$H NMR (CD$_3$OD): δ 8.29 (s, 0.3H), 8.05 (s, 0.7H), 7.63 (d, J=7.5 Hz, 2H), 7.52 (d, J=7.5 Hz, 2H), 7.29 (d, J=7.5 Hz, 2H), 7.02 (d, J=7.5 Hz, 2H), 4.55–4.30 (m, 1.3H), 3.72 (m, 0.7H), 2.38–2.28 (m, 1H), 2.00–1.72 (m, 3H), 1.52–1.20 (m, 4H).

EXAMPLE 162

(±)-1-[[[[4-(4-chlorophenoxy)phenyl]sulfonyl]methyl]-2-(3-methyl-6-oxo-1(6H)-pyridazinyl)ethyl]-N-hydroxyformamide

EXAMPLE 162A (±)-1-[3-[4-(4-chlorophenoxy)phenyl]thiol-2-hydroxypropyl]-3-methyl-1H-pyridazin-6-one The title compound was prepared following the procedures of Example 1A and 1B, except substituting 6-methyl-3-[2H]-pyridazinone for phenol in Example 1A and 4-(4'-chlorophenoxy)benzene thiol for 4'-hydroxy-4-biphenylcarbonitrile in Example 1B.

EXAMPLE 162B (±)-1-[[[[4-(4-chlorophenoxy)phenyl]sulfonyl]methyl]-2-(3-methyl-6-oxo-1(6H)-pyridazinyl)ethyl]-N-hydroxyformamide Example 162A was converted to the title compound follwing the procedures described in Examples 2C–2F (inclusive) and 46D.

MS (ESI) m/z 478 (M+H)$^+$; $^1$H NMR (300 MHz, DMSO-$d_6$) δ 9.79 (br, 0.5H), 9.52 (br, 0.5H); 8.04 (s, 0.5H), 7.89–7.84 (m, 2H), 7.66 (s, 0.5H), 7.55–7.52 (m, 2H), 7.32 (d, 1H), 7.23–7.16 (m, 4H), 6.86 (d, 1H), 5.04–4.95 (m, 0.5H), 4.58–4.49 (m, 0.5H), 4.26–4.18 (m, 1H), 4.12–4.05 (m, 1H), 3.79–3.66 (m, 1H), 3.56–3.51 (m, 1H), 2.22–2.20 (m, 3H); Anal. calcd for $C_{21}H_{20}ClN_3O_6S$: C, 52.78; H, 4.22; N, 8.79. Found: C, 52.71; H, 4.45; N, 8.49.

EXAMPLE 163

(±)-N-hydroxy-[1-[[(6-oxo-1(6H)-pyridazinyl)methyl]-2-[[4'-(trifluoromethoxy)[1,1'-biphenyl]-4-yl]oxy]ethy]formamide The title compound was prepared following the procedures of Example 134 except substituting 3-[2H]-pyridazinone for 5,5-dimethyloxazolidin-2,4-dione.

MS (ESI) m/z 450 (M+H)$^+$; $^1$H NMR (300 MHz, DMSO-$d_6$) δ 9.97 (br, 0.5H), 9.61 (br, 0.5 H), 8.28 (s, 0.5H), 7.96–7.92 (m, 1H), 7.87 (s, 0.5H), 7.76–7.72 (m, 2H), 7.65–7.61 (m, 2H), 7.46–7.40 (m, 3H), 7.04–6.94 (m, 3H), 5.09–5.00 (m, 0.5H), 4.59–4.50 (m, 0.5H), 4.46–4.11 (m, 4H); Anal. calcd for $C_{21}H_{18}F_3N_3O_6$: C, 56.13; H, 4.04; N, 9.35. Found: C, 56.23; H, 3.79; N, 9.36.

EXAMPLE 164

(±)-N-[1-[(1,6-dihydro-3-methyl-2,6-dioxo-1(6H)-pyrimidinyl)methyl]-2-[[4-[4-(trifluoromethoxy)phenoxy]phenyl]sulfonyl]ethyl]-N-hydroxyformamide The title compound was prepared following the procedures of Example 162 except substituting 1-methyluracil for 6-methyl-3-[2H]-pyridazinone and 4-(4'-trifluoromethoxyphenoxy)benzene thiol for 4-(4'-chlorophenoxy)benzene thiol.

MS (ESI) m/z 544 (M+H)$^+$; $^1$H NMR (300 MHz, DMSO-$d_6$) δ 9.52 (br, 0.5H), 9.42 (br, 0.5H), 8.04 (s, 0.5H), 7.89–7.85 (m, 2H), 7.73 (s, 0.5H), 7.70–7.66 (m, 1H), 7.49–7.46 (m, 2H), 7.31–7.26 (m, 2H), 7.22–7.18 (m, 2H), 5.64 (d, 1H), 4.99–4.90 (m, 0.5H), 4.43–4.34 (m, 0.5H), 4.03–3.87 (m, 2H), 3.75–3.63 (m, 1H), 3.52–3.41 (m, 1H), 3.17 (s, 3H); Anal. calcd for $C_{22}H_{20}F_3N_3O_8S$: C, 48.62; H, 3.71; N, 7.73. Found: C, 48.84; H, 3.99; N, 7.55.

EXAMPLE 165

(±)-N-[1-[(2,5-dioxo-3,4,4-trimethyl-1-imidazolidinyl)methyl]-2-[[4-(4-bromophenoxy)phenyl]sulfonyl]ethyl]-N-hydroxyformamide The title compound was prepared following the procedures of Example 61, except substituting 4-(4'-bromophenoxy)benzene thiol in place of 4'-thiol-4-biphenylcarbonitrile.

MS (ESI) m/z 573 (M+H)$^+$; $^1$H NMR (300 MHz, DMSO-d$_6$) δ 9.70 (br, 0.5H), 9.51 (br, 0.5H), 8.09 (s, 0.5H), 7.91–7.88 (m, 2H), 7.68 (s, 0.5H), 7.66–7.62 (m, 2H), 7.22–7.19 (m, 2H), 7.16–7.12 (m, 2H), 4.88 (m, 0.5H), 4.49–4.42 (m, 0.5H), 3.71–3.42 (m, 4H), 2.77 (s, 1.5H), 2.76 (s, 1.5H), 1.25–1.23 (m, 6H); Anal. calcd for C$_{22}$H$_{24}$brN$_3$O$_7$S: C, 47.66; H, 4.36; N, 7.58. Found: C, 48.21; H, 4.79; N, 7.23.

EXAMPLE 166

(±)-N-[1-[(2,5-dioxo-4,4-dimethyl-1-imidazolidinyl)methyl]-2-methyl-2-[[4'-(trifluoromethoxy)[1,1'-biphenyl]-4-yl]oxy]propyl]-N-hydroxyformamide

EXAMPLE 166A 3-bromo-3-methyl-2-butanone

A solution of 3-methyl-2-butanone (5 mL, 4.67 mol) in 70 mL of THF at 0° C. was treated with phenyltirmethylammonium tribromide, stirred 30 min at 0° C., quenched with NaHCO$_3$, filtered, and concentrated to provide 7.5 g (97%) of the title compound.

$^1$H NMR (300 MHz, CDCl$_3$) δ 2.45 (s, 3H), 1.87 (s, 6H).

EXAMPLE 166B 3-methyl-3-[[4'-(trifluoromethoxy)[1,1'-biphenyl]-4-yl]oxy]-2-butanone A soln of 4-(4-trifluoromethoxyphenyl)phenol (6 g, 23.6 mmol) in 23 mL of DMF was treated with potassium carbonate (4 g) and Example 166A (5 g), stirred at rt for 16 h, filtered, and concentrated to provide 4.4 g (55%) of the title compound.

MS (ESI) m/z 356 (M+18)$^+$.

EXAMPLE 166C 1-bromo-3-methyl-3-[[4'-(trifluoromethoxy)[1,1'-biphenyl]-4-yl]oxy]-2-butanone A soln of Example 166B (4.4 g, 13.2 mmol) in 40 mL of CHCl$_3$ at 0° C. was treated with bromine (1 mL), stirred at rt for 30 min, quenched with 2:1 satd NaHCO$_3$/10% NaHSO$_3$, extracted with ethyl acetate (2×50 mL), washed with brine, dried over Na$_2$SO$_4$, filtered, and concentrated to provide 5.5 g (100%) of the title compound.

MS (ESI) m/z (M+18)$^+$.

EXAMPLE 166D (±)1-[(2,5-dioxo-4,4-dimethyl-1-imidazolidinyl)-3-methyl-3-[4'-(trifluoromethoxy)[1,1-biphenyl]-4-yl]oxy]-2-butanone A soln of Example 166C (55 g, 13.2 mmol) in 26 mL of DMF was treated with 5,5-dimethylhydantoin (1.69 g) and potassium carbonate (1.82 g), stirred at rt for 16 h, diluted wtih 150 mL of CHCl$_3$, filtered, and concentrated. Purification on silica gel with 1:1 hexanes/ethyl acetate provided 4.05 g (66%) of the title compound.

MS (ESI) m/z 463 (M-1)$^-$.

EXAMPLE 166E (±)-N-[1-[(2,5-dioxo-4,4-dimethyl-1-imidazolidinyl)-2-methyl-2-[4'-(trifluoromethoxy)[1,1'-biphenyl]-4-yl]oxylhydroxylamine A soln of Example 166D (550 mg, 1.18 mmol) in 6 mL of 1:1 THF/ethanol was treated with hydroxylamine.HCl (99 mg) and pyridine (115 μL), heated at 75–80° C. for 8 h, cooled to 0° C., treated with borane.pyridine (359 μL) and HCl (1.78 mL, 4N in dioxane), stirred 16 h at rt, quenched with satd NaHCO$_3$, extracted with ethyl acetate (3×20 mL), washed with brine, dried over Na$_2$SO$_4$, filtered, and concentrated. Purification on silica gel with 1:2 hexanes/ethyl acetate provided 230 mg (40%) of the title compound.

MS (ESI) m/z 482 (M+H)$^+$.

EXAMPLE 166F (±)-N-[1-[(2,5-dioxo-4,4-dimethyl-1-imidazolidinyl)methyl]-2-methyl-2-[[4'-(trifluoromethoxy)[1,1'-biphenyl]-4-yl]oxy]propyl]-N-hydroxyformamide Example 166E was converted to the title compound following the formylation procedure described in Example 1E.

MS (ESI) m/z 510 (M+1)$^+$; $^1$H NMR (300 MHz, DMSO-d$_6$) δ 9.56 (br, 0.5H), 9.39 (br, 0.5H), 8.40 (br, 0.5H), 8.38 (br, 1H), 8.32 (s, 0.5H), 7.94 (s, 0.5H), 7.80–7.76 (m, 2H), 7.65–7.60 (m, 2H), 7.45–7.42 (m, 2H), 7.24–7.16 (m, 2H), 4.70 (dd, 0.5H), 4.26 (dd, 0.5H), 4.12–3.98 (m, 1H), 3.91–3.79 (m, 1H), 1.38–1.25 (m, 12H).

EXAMPLE 167

(±)-N-[1-[[4-[(4-chlorophenoxy)phenyl]sulfonyl]methyl]-2-(1,6-dihydro-3-methyl-2,6-dioxo-1(6H)-pyrimidinyl)ethyl]-N-hydroxyformamide The title compound was prepared following the procedures of Example 162 except substituting 1-methyluracil for 6-methyl-3-[2H]-pyridazinone.

MS (ESI)m/z 511 (M+18)$^+$; $^1$H NMR (300 MHz, DMSO-d$_6$) δ 9.52 (br, 0.5H), 9.43 (br, 0.5H), 8.04 (s, 0.5H), 7.87–7.83 (m, 2H), 7.73 (s, 0.5H), 7.70 (d, 0.5H), 7.66 (d, 0.5H), 7.55–7.50 (m, 2H), 7.22–7.15 (m, 4H), 5.64 (d, 1H), 4.99–4.90 (m, 0.5H), 4.42–4.34 (m, 0.5H), 4.04–3.86 (m, 2H), 3.74–3.62 (m, 1H), 3.52–3.40 (m, 1H), 3.26 (s, 3H); Anal. calcd for C$_{21}$H$_{20}$ClN$_3$O$_7$S: C, 51.07; H, 4.08; N, 8.51. Found: C, 51.35; H, 4.29; N, 8.40.

EXAMPLE 168

(±)-N-hydroxy-N-[1-[(3-methyl-6-oxo-1(6H)-pyridazinyl)meth]2-[[4-[4-(trifluoromethoxy)phenoxy]phenyl]sulfonyl]ethyl]formamide The title compound was prepared following the procedures of Example 162 except subtituting 4-(4'-trifluoromethoxyphenoxy)benzene thiol for 4-(4'-chlorophenoxy)benzene thiol.

MS (ESI) m/z 528 (M+H)$^+$; $^1$H NMR (300 MHz, DMSO-d$_6$) δ 9.78 (br, 0.5H), 9.50 (br, 0.5H), 8.03 (s, 0.5H), 7.91–7.86 (m, 2H), 7.65 (s, 0.5H), 7.49 (d, 2H), 7.34–7.26 (m, 3H), 7.22–7.18 (m, 2H), 6.86(d, 1H), 5.06 (m, 0.5H), 4.60–4.48 (m, 0.5H), 4.27–4.18 (m, 1H), 4.13–4.06 (m, 1H), 3.80–3.66 (m, 1H), 3.59–3.49 (m, 1H), 2.22 (d, 3H); Anal. calcd for C$_{22}$H$_{20}$F$_3$N$_3$O$_7$S: C, 50.10; H, 3.82; N, 7.97. Found: C, 50.21; H, 3.97; N, 7.96.

EXAMPLE 169

(±)-N-hydroxy-N-[1-(1-methyl-1H-indol-4-yl)-[2-[[4-(trifluoromethoxy)phenoxy]phenyl]sulfonyl]]ethy]formamide The title compound was prepared according to the procedures of Example 126, except substituting methyl 1-methyl-4-indolecarboxylate for ethyl methoxyacetate and 4-(4'-trifluoromethoxyphenyl)-phenyl methyl sulfone for 4-(4'-trifluoromethylphenyl)-phenyl methyl sulfone.

MS (ESI) 533 (M−H); $^1$H NMR (300 MHz, DMSO-d$_6$) δ 9.95 (s, 0.5H), 9.56 (s, 0.5H), 8.13 (s, 0.5H), 7.90–7.85 (d, 2H, J=8.9 Hz), 7.50–7.40 (m, 4H), 7.2–7.0 (m, 6H), 6.53 (s, 1H), 6.1 (s, 0.5H), 5.70 (s, 0.5H), 4.15 (m, 2H), 3.7–3.65 (m, 4H); Anal. calcd for C$_{25}$H$_{21}$N$_2$O$_6$SF$_3$: C, 56.17; H, 3.96; N, 5.24. Found: C, 56.33; H, 4.38; N, 4.78.

EXAMPLE 170

(±)-N-hydroxy-N-[1-(1-methyl-1H-indol-2-yl)-2-[[4-[4-(trifluoromethoxy)phenoxy]phenyl]sulfonyl]] ethyl]formamide The title compound was prepared according to the procedures of Example 126, except substituting methyl 1-methyl-2-indolecarboxylate for ethyl methoxyacetate and 4-(4'-trifluoromethoxyphenyl)phenyl methyl sulfone for 4-(4'-trifluoromethylphenyl)-phenyl methyl sulfone.

MS (ESI) 533 (M−H); $^1$H NMR (300 MHz, DMSO-d$_6$) δ 9.9 (s, 0.5H), 9.6 (s, 0.5H), 7.9–7.85 (d, 2H, J=8.8 Hz), 7.52–7.48 (d, 2H, J=8.8 Hz), 7.4–7.35 (m, 2H), 7.25–7.20 (d, 2H, J=8.67 Hz), 7.15–7.00 (m, 4H), 6.40 (s, 0.5H), 6.1 (s, 0.5H), 4.2 (s, 1H), 4.05–3.90 (m, 2H), 3.75 (s, 3H); Anal. calcd for C$_{25}$H$_{21}$N$_2$O$_6$SF$_3$.0.25 ethyl acetate: C, 56.11; H, 4.16; N, 5.03. Found: C, 56.62; H, 4.49; N, 4.80.

EXAMPLE 171

(±)-N-[1-(4-chlorophenyl)-2-[[[4-(trifluoromethoxy)phenoxy]phenyl]sulfonyl]ethyl]-N-hydroxyformamide The title compound was prepared according to the procedures of Example 75, except substituting 4-chlorobenzaldehyde for propionaldehyde and 4-(4'-trifluoromethoxyphenyl)phenyl methyl sulfone for 4-(4'-methoxyphenyl)phenyl methyl sulfone in Example 75A.

MS (ESI) 548 (M−H); $^1$H NMR (300 MHz, DMSO-d$_6$) δ 10.25 (s, 0.5H), 9.70 (s, 0.5H), 8.25–8.1 (m, 1H), 7.90–7.85 (d, 2H, J=8.6 Hz), 7.77–7.7.70 (d, 2H, J=8.8 Hz), 7.65 (s, 1H), 7.52–7.46 (d, 2H, J=8.7 Hz), 7 23–7.10 (d, 2H, J=8 Hz), 5.87 (s, 0,5H), 5.55 (s, 0.5H), 4.20–4.00 (m, 3H); Anal. calcd for C$_{23}$H$_{17}$NO$_6$SF$_6$.1.25 ethyl acetate: C, 48.29; H, 3.43; N, 2.44. Found: C, 48.01; H, 3.00; N, 2.00.

EXAMPLE 172

(±)-N-hydroxy-N-[2-[[[4-(trifluoromethoxy)phenoxy]phenyl]sulfonyl]-1-[4-(trifluoromethyl)phenyl]ethyl]formamide The title compound was prepared according to the procedures of Example 75, except substituting 4-trifluoromethylbenzaldehyde for propionaldehyde and 4-(4'-trifluoromethoxyphenyl)phenyl methyl sulfone for 4-(4'-methoxyphenyl)phenyl methyl sulfone in Example 75A.

MS (ESI) 514 (M−H), 516 (M+H); $^1$H NMR (300 MHz, DMSO-d$_6$) δ 10.01 (s, 0.5H), 9.65 (s, 0.5H), 8.25–8.15 (m, 1H), 7.90–7.80 (d, 2H, J=8.9 Hz), 7.55–7.49 (d, 8.7H), 7.4 (m, 3H), 7.34–7.25 (m, 3H), 7.20–7.15 (d, 2H, J=8.9 Hz), 5.7 (s, 0.5H), 5/48 (s, 0.5H), 4.25–4.0 (m, 3H); Anal. calcd for C$_{22}$H$_{17}$NO$_6$SF$_3$Cl: C, 51.22; H, 3.32; N, 2.71. Found: C, 51.30; H, 3.35; N, 2.53.

EXAMPLE 173

(±)-N-[1-[(2,5-dioxo-3,4,4-trimethyl-1-imidazolidinyl)methyl]-2-[[4-[4-(trifluoromethoxy)phenoxy]phenyl]sulfonyl]ethyl]-N-hydroxyformamide The title compound was prepared following the procedures of Example 162, except using hydantoin on place of 6-methyl-3-[2H]-pyridazinone and 4-(4'-trifluoromethoxyphenyl)benzenethiol in place of 4-(4'-chlorophenyl)benzenethiol.

MS (ESI) 518 (M+H), 535 (M+NH$_4$), 540 (M+Na), 516 (M−H); $^1$H NMR (300 MHz, DMSO-d$_6$) δ 9.79 (s, 0.5H), 9.53 (s, 0.5H), 8.15 (d, 1H, J=6.6 Hz), 8.10 (s, 0.5H), 7.93–7.88 (m, 2H), 7.73 (s, 0.5H), 7.48 (d, 2H, J=9.2 Hz), 7.32–7.20 (m, 4H), 4.88–4.77 (m, 0.5H), 4.48–4.34 (m, 0.5H), 3.94–3.40 (m, 6H).

EXAMPLE 174

(±)-N-hydroxy-N-[1-[[(2-thienylthio)methyl]-2-[[4-(trifluoromethoxy)phenoxy]phenyl]sulfonyl]ethyl] formamide

EXAMPLE 174A methyl 2-(2-thienylthio)acetate

To a solution of thiophene-2-thiol (1.2 g, 10.3 mmol) in anhydrous DMF (30 mL) was added cesium carbonate (3.9 g, 12 mmol) and the resulting suspension was stirred for 15 min at ambient temperature, then treated with methyl bromoacetate (1.53 g, 10 mmol). The purple suspension was stirred for 1 h, then poured into water (30 mL) and extracted twice with 300 mL EtOAc. The combined organic extracts were washed with brine, dried, filtered, concentrated and the residue was purified via column chromatography eluting with 10% EtOAc/Hexanes to give 1.48 g (79%) of the title compound.

EXAMPLE 174B (±)-N-hydroxy-N-[1-[[(2-thienylthio)methyl]-2-[[4-(trifluoromethoxy)phenoxy]phenyl]sulfonyl]ethyl] formamide The title compound was prepared according to the procedures of Example 126, except substituting Example 174A for ethyl methoxyacetate and 4-(4'-trifluoromethoxyphenoxy)phenyl methyl sulfone for 4-(4'-rifluoromethylphenyl)phenyl methyl sulfone.

mp 120–122° C.; MS (ESI(+)) 533 (M+NH$_4$—H$_2$O), 550 (M+NH$_4$), 555 (M+Na); $^1$H NMR (300 MHz, DMSO-d$_6$): δ 10.12 (bs, ½H), 9.80 (bs, ½H), 8.35 (s, ½H), 7.89–7.98 (m, 2.5H), 7.73–7.79 (m, 1H), 7.55–7.63 (m, 2H), 7.34–7.42 (m, 2H), 7.23–7.32 (m, 3H), 7.11–7.20 (m, 1H), 4.72–4.82 (m, ½H), 4.04–4.13 (m, ½H), 3.63–3.88 (m, 2H), 2.99–3.19 (m, 2H); Anal. calcd for C$_{21}$H$_{18}$F$_3$NO$_6$S$_3$: C, 47.27; H, 3.40; N, 2.62; S, 18.02, F, 10.68. Found: C, 47.05; H, 3.43; N, 2.82; S, 17.83, F, 10.37.

EXAMPLE 175

(±)-N-hydroxy-N-[1-[[[(4-methylphenyl)sulfonyl] methylamino]methyl[2-[[[4-(trifluoromethoxy)phenoxy]phenyl]sulfonyl]ethyl]formamide

EXAMPLE 175A ethyl 2-[methyl[(4-methylphenyl)sulfonyl]amino] acetate

An ice cold suspension of sarcosine ethyl ester hydrochloride salt (3.1 g, 20 mmol) in CH$_2$Cl$_2$ (150 mL) was sequentially treated with triethyl amine (4.45 g, 44 mmol) and tosyl chloride (4.19 g, 22 mmol) and stirred for 1 h, after which time the ice bath was removed, and the reaction was allowed to stir for an additional 1 h. The reaction mixture was then partitioned between water and $CH_2Cl_2$ and the organic extract was washed with brine, dried, filtered, and concentrated to give 5.7 g of the title compound as a white solid.

EXAMPLE 175B (±)-N-hydroxy-N-[1-[[[(4-methylphenyl)sulfonyl] methylamino]methyl]2-[[[4-(trifluoromethoxy) phenoxy]phenyl]sulfonyl]ethyl]formamide

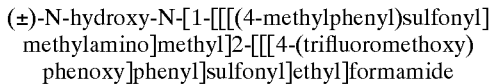

The title compound was prepared according to the procedures of Example 126, except substituting Example 175A for ethyl methoxyacetate and 4-(4'-trifluoromethoxyphenoxy)phenyl methyl sulfone for 4-(4'-trifluoromethylphenyl)phenyl methyl sulfone.

mp 160.7–162.5° C.; $^1$H NMR (300 MHz, DMSO-d$_6$): δ 9.97 (bs, ½H), 9.72 (bs, ½H), 8.18 (s, ½H), 7.88–7.98 (m, 2H), 7.82 (s, ½H), 7.59–7.68 (m, 2H), 7.37–7.50 (m, 4H), 7.20–7.32 (m, 4H), 4.76–4.85 (m, ½H), 4.25–4.36 (m, ½H), 3.62 (dd, 1H, J=14, 8 Hz), 3.44–3.56 (m, 1H), 3.25 (dd, ½H, J=8, 14 Hz), 3.07 (d, ½H, J=8 Hz), 2.90 (dd, ½H, J=14, 8 Hz), 2.59–2.66 (m, 1.5H), 2.54–2.59 (m, 1H), 2.48–2.54 (m; 1H), 2.40 (s, 3H); MS (ESI(−)) 600.8 (M−H), 636.9 (M+Cl), 1203.4 (2M−H); Anal. calcd for $C_{25}H_{25}F_3N_2O_8S_2$: C, 49.82; H, 4.18; N, 4.65; S, 10.64; F, 9.46. Found: C,49.67; H, 4.19; N, 4.50; S, 10.59; F, 9.38.

EXAMPLE 176

(±)-N-hydroxy-N-[[[2-(methoxyethoxy)methyl]-1-[[4-(trifluoromethoxy)phenoxy]phenyl]sulfonyl] ethyl]formamide

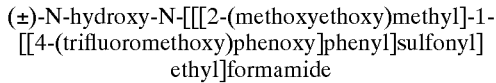

The title compound was prepared according to the procedures of Example 126, except substituting ethyl (2'-methoxy)ethoxyacetate for methyl methoxyacetate and 4-(4'-trifluoromethoxyphenyl)phenyl methyl sulfone for 4-(4'-trifluoromethylphenyl)phenyl methyl sulfone. MS (ESI−) 492 (M−H); $^1$H NMR (DMSO-d$_6$) δ 3.22 (s, 3H), 3.42–3.66 (m, 8H), 4.14–4.25 (m, 0.5H), 4.68–4.79 (m, 0.5H), 7.23 (d, 2H, J=9 Hz), 7.28 (d, 2H, J=9 Hz), 7.48 (d, 2H, J=9 Hz), 7.83 (s, 0.5H), 7.93 (d, 2H, J=9 Hz), 8.14 (s, 0.5H), 9.55 (bs, 0.5H), 9.96 (bs, 0.5H); Anal. calcd for $C_{20}H_{22}NO_8SF_3$: C, 48.68; H, 4.49; N, 2.83. Found: C, 48.61; H, 4.60; N, 2.80.

EXAMPLE 177

(±)-N-[1-[(1,6-dihydro-3-methyl-2,6-dioxo-1(6H)-pyrimidinyl)methyl]2-[[(4-phenoxyphenyl)sulfonyl] ethyl]-N-hydroxyformamide

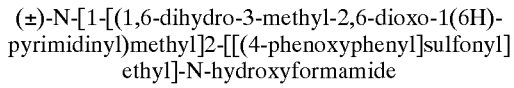

The title compound was prepared following the procedures of Example 162, except using 4-(phenoxy)-benzenethiol in place of 4-(4'-chlorophenoxy)-benzenethiol.

MS (ESI) m/z 460 (M+H)$^+$; $^1$H NMR (300 MHz, DMSO-d$_6$) δ 9.55 (br, 0.5H), 9.47 (br, 0.5H), 8.05 (s, 0.5H), 7.86–7.83 (m, 2H), 7.74 (s, 0.5H), 7.71–7.67 (m, 2H), 7.52–7.47 (m, 2H), 7.30–7.25 (m, 2H), 7.19–7.11 (m, 4H), 5.64 (d, 1H), 4.99–4.91 (m, 0.5H), 4.42–4.34 (m, 0.5H), 4.05–3.85 (m, 2H), 3.73–3.62 (m, 1H), 3.51–3.39 (m, 1H), 3.27 (s, 3H); Anal. calcd for $C_{21}H_{21}N_3O_7S$: C, 54.90; H, 4.61; N, 9.15. Found: C, 55.01; H, 4.91; N, 8.90.

EXAMPLE 178

(±)-N-hydroxy-N-[1-(4-hydroxyphenyl)-2-[[4'-(trifluoromethyl)[1,1'-biphenyl]-4-yl]sulfonyl]ethyl] formamide

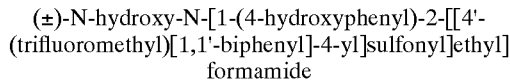

A suspension of Example 129 (186 mg, 0.366 mmol) in dichloromethane (20 mL) at −78° C. was treated with boranetrifluoride diethyl etherate (55.6 mL, 0.439 mmol), stirred at 0° C. for 3 hours and left at room temperature overnight, treated with water, extracted with ethyl acetate, dried ($Na_2SO_4$), filtered, concentrated and purified on silica gel with 80% ethyl acetate/hexanes to provide 45 mg (26%) of the title compound as an orange solid.

mp 225° C. decomposed; MS (ESI) m/z 466 (M+H)$^+$, 483 (M+NH$_4$), 464 (M−H)$^-$, 488 (M+Na)$^+$; $^1$H NMR (300 MHz, DMSO-d$_6$) d 3.90–4.22 (br, 2H), 5.32 (br, 0.5H), 5.66 (br, 0.5H), 6.61–6.64 (d, 2H, J=9 Hz), 7.00–7.20 (2H), 7.84–8.23 (m, 10H), 9.50 (s, 1H); Anal. calcd for $C_{22}H_{18}NF_3O_5S$ 0.25 $H_2O$: C, 56.22; H, 3.96; N, 2.98. Found: C, 56.09; H, 4.00; N, 2.83.

EXAMPLE 179

(±)-N-hydroxy-N-[1-(2,2-dimethyl-1,3-dioxan-5-yl)-2-[[4-(trifluoromethoxy)phenoxy]phenyl]sulfonyl] ethyl]formamide

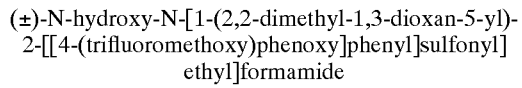

EXAMPLE 179A (±)-N-[1-(2,2-dimethyl-1,3-dioxan-5-yl)-2-[[[4-(trifluoromethoxy)phenoxy]phenyl]sulfonyl]ethyl] hydroxylamine

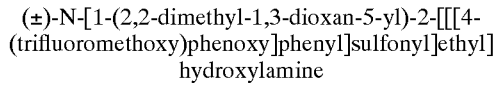

The title compound was prepared according to the procedures of Example 126A, 126B, 75C except substituting 2,2-dimethyl-5-ethylcarboxylate-1,3-dioxane (*Tetrahedron* 1991, 47, 1001) for methyl methoxyacetate and 4-(4'-trifluoromethoxyphenyl)-phenyl methyl sulfone for 4-(4'-trifluoromethylphenyl)-phenyl methyl sulfone.

EXAMPLE 179B (±)-N-hydroxy-N-[1-(2,2-dimethyl-1,3-dioxan-5-yl)-2-[[4-(trifluoromethoxy)phenoxy]phenyl]sulfonyl] ethyl]formamide

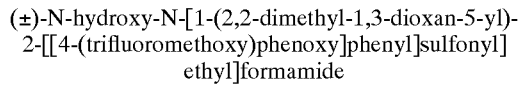

Example 179A was converted to the title compound following the fomylation procedure of Example 75D.

mp 139.5–140.7° C.; MS (ESI) mlz 520 (M+H)$^+$, 542 (M+Na)$^+$, 518 (M−H)$^-$, 554 (M+Cl)$^-$; $^1$H NMR (300 MHz, DMSO-d$_6$) δ 1.17–1.30 (6H), 3.36–3.77 (m, 5H), 3.79–3.92 (0.75H), 4.03 (0.25H), 4.15–4.24 (m, 0.75H), 6.57–4.68 (0.25H), 7.19–7.28 (m, 4H), 7.42–7.50 (d, 2H, J=9 Hz), 7.76 (s, 0.75H), 7.88–7.96 (m, 2H), 8.12 (s, 0.25H), 9.71 (br, 0.75H); Anal. calcd for $C_{22}H_{24}NF_3O_8S$: C, 50.86; H, 4.65; N, 2.69. Found: C, 50.99; H, 4.97; N, 2.73.

EXAMPLE 180

(±)-N-hydroxy-N-[3-hydroxy-2-(hydroxymethyl)-1-[[[[4-(trifluoromethoxy)phenoxy]phenyl]sulfonyl] methyl]propyl]formamide

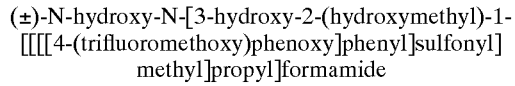

Example 179A was converted to the title compound following the procedures of Example 141A and B.

mp 129.2–131.3° C.; MS (ESI) m/z 480 (M+H)$^+$, 502 (M+Na)$^+$, 478 (M−H)$^-$; $^1$H NMR (300 MHz, DMSO-d$_6$) δ 1.69–1.79 (m, 1H), 3.57–3.80 (m, 2H), 3.24–3.51 (m, overlapped w/solventH), 4.13–4.19 (dt, 1H, J=1.5, 8.4 Hz), 4.64–4.70 (1H), 7.19–7.30 (m, 4H), 7.45–7.48 (d, 2H, J=9 Hz), 7.678 (s, 0.7H), 7.86–7.90 (m, 2H), 8.04 (s, 0.38H); Anal. calcd for $C_{19}H_{20}NF_3O_8S \cdot 0.25 H_2O$: C, 47.15; H, 4.26; N, 2.89. Found: C, 47.29; H, 4.44; N, 2.56.

EXAMPLE 181

(±)-N-hydroxy-N-[1-(hydroxymethyl)-2-[[[(4-chlorophenyl)thio]phenyl]sulfonyl]ethyl]formamide

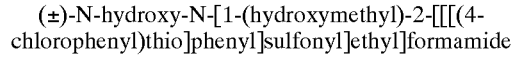

The title compound was prepared according to the procedures of Example 125, except substituting tertbutyldimethylsilyloxy-acetaldehyde for 3-tert-butyldimethylsilyloxypropionaldehyde and 4-(4'-chlorophenylthio)phenyl methyl sulfone for 4-(4'-trifluoromethylphenyl)phenyl methyl sulfone.

mp 148.5–150.0° C.; MS (ESI) m/z 402 (M+H)$^+$, 424 (M+Na)$^+$, 400 (M–H)$^-$; $^1$H NMR (300 MHz, DMSO-d$_6$) δ 3.30–3.62 (m, overlaped w/solventH), 3.90–4.01 (m, 0.5H), 4.47–4.60 (m, 0.3H, J=1.5), 5.01 (br, 0.7H), 7.36–7.39 (d, 2H, J=9 Hz), 7.73–7.85 (m, 2.7H), 8.11 (s, 0.3H), 9.41 (brs, 0.7H), 9.83 (brs, 0.3H); Anal. calcd for C$_{16}$H$_{16}$NClO$_5$S$_2$: C, 47.81; H, 4.01; N, 3.48. Found: C, 47.55; H, 4.14; N, 3.28.

EXAMPLE 182

(±)-N-hydroxy-N-[1-(4-morpholinylmethyl)-2-[ [[4-(trifluoromethoxy)phenoxy]phenyl]sulfonyl]ethyl] formamide The title compound was prepared according to the procedures of Example 126, except substituting methyl morpholinoacetate for ethyl methoxyacetate and 4-(4'-trifluoromethoxyphenyl)phenyl methyl sulfone for 4-(4'-trifluoromethylphenyl)phenyl methyl sulfone.

mp 160.9–162.7° C.; MS (ESI) m/z 505 (M+H)$^+$, 527 (M+Na)$^+$, 503 (M–H)$^-$, 539(M+Cl)$^+$; $^1$H NMR (300 MHz, DMSO-d$_6$) δ 2.10–2.42 (m, 6H), 3.48–3.65 (m, 6H), 4.13 (br, 0.6H), 4.68 (br, 0.4H), 7.18–7.32 (m, 4H), 7.46–7.49 (d, 2H, J=9 Hz), 7.84–7.95 (2.6H), 8.14 (s, 0.4H), 9.46 (s, 0.6H), 9.88 (s, 0.4H); Anal. calcd for C$_{21}$H$_{23}$N$_2$F$_3$O$_7$S: C, 49.99; H, 4.59; N, 5.55. Found: C, 49.77; H, 4.62: N, 5.39.

EXAMPLE 183

(±)-N-hydroxy-N-[4-hydroxy-[1-[[[4-(trifluoromethoxy)phenoxy]phenyl]sulfonyl]methyl] butyl]formamide The title compound was prepared according to the procedures of Example 125, except substituting 4-tert-butyldimethylsilyloxy-butanaldehyde for 3-tert-butyldimethylsilyloxy-propionaldehyde and 4-(4'-trifluoromethoxyphenyl)phenyl methyl sulfone for 4-(4'-trifluoromethylphenyl)phenyl methyl sulfone.

mp 92.0–93.9° C.; MS (ESI) m/z 464 (M+H)$^+$, 486 (M+Na)$^+$, 462 (M–H)$^-$; $^1$H NMR (300 MHz, DMSO-d$_6$) δ 1.13–1.40 (m, 2H), 1.40–1.68 (m, 2H), 3.22–3.47 (m, overlaped w/solventH), 3.53–3.68 (m, 1H), 4.02–4.13 (m, 0.5H), 4.37–4.49 (m, 1H), 4.49–4.58 (m, 0.45H), 7.20–7.23 (d, 2H, J=9 Hz), 7.25–7.32 (dd, 2H, J=3, 9 Hz), 7.46–7.49 (d, 2H, J=9 Hz), 7.81 (s, 0.6H), 7.88–7.91 (d, 2H, J=9 Hz), 8.12 (s, 0.4H), 9.46 (s, 0,6H), 9.83 (s, 0.4H); Anal. calcd for C$_{19}$H$_{20}$NF$_3$O$_7$S: C, 49.24; H, 4.35; N, 3.02. Found: C, 49.22; H, 4.49; N, 2.95.

EXAMPLE 184

(±)-N-[1-[(1H-isoindole-1,3(2H)-dione)methyl]-2-[[4-(4-chlorophenoxy)phenyl]sulfonyl]ethyl]-N-hydroxyformamide

EXAMPLE 184A 2-(3-bromo-2-oxopropyl)-1H-isoindole-1,3(2H)-dione

The title compound was prepared following the procedures of examples 16A and 16B, except substituting phthalimide for 1,5,5-trimethylhydantoin in example 16A.

EXAMPLE 184B (±)-N-[1-f(1H-isoindole-1,3(2H)-dione)methyl]-2-[[4-(4-chlorophenoxy)phenyl]sulfonyl]ethyl]-N-hydroxyformamide Alkylation of example 184A with 4-(4'-chlrophenoxy) benzene thiol as described in example 61A followed by the synthetic transformations described in example 61B and 61C gave the title compound. $^1$H NMR (300 MHz, d$_6$-DMSO) δ 9.96 (br, 0.5H), 9.67 (br, 0.5H), 8.06 (s, 0.5H), 7.91–7.84 (m, 6H), 7.75 (s, o=0.5H), 7.55–7.51 (m, 2H), 7.22–7.13 (m, 4H), 5.01–4.91 (m, 0.5H), 4.56–4.46 (m, 0.5H), 3.89–3.62 (m, 4H); MS (ESI) m/e 532 (M+1 8)$^+$; Anal. calcd for C$_{24}$H$_{19}$ClN$_2$O$_7$S: C, 55.98; H, 3.72; N, 5.44. Found: C, 56.09; H, 3.71; N, 5.31.

EXAMPLE 185

(±)-N-[1-[(2,5-dioxo-3,4,4-trimethyl-1-imidazolidinyl)methyl]-2-[[4-(4-cyanophenoxy) phenyl]sulfonyl]ethyl]-N-hydroxyformamide The title compound was prepared according to the procedures of example 61, except substituting 4-(4'-cyanophenoxy)-benzene thiol for 4-thiol-4-biphenylcarbonitrile.

$^1$H NMR (300 MHz, d$_6$-DMSO) δ 9.74 (br, 0.5H), 9.52 (br, 0.5H), 8.10 (s, 0.5H), 7.97–7.90 (m, 4H), 7.68 (s, 0.5H), 7.36–7.28 (m, 4H), 4.89–4.79 (m, 0.5H), 4.52–4.42 (m, 0.5H), 3.76–3.37 (m, 4H), 2.76 (s, 1.5H), 2.76 (s, 1.5H), 1.26–1.23 (m, 6H); MS (ESI) m/e 501 (M+H)$^+$; Anal. calcd for C$_{23}$H$_{24}$N$_4$O$_7$S: C, 55.19; H, 4.83; N, 11.19. Found: C, 55.39; H, 5.19; N, 10.96.

EXAMPLE 186

(±)-N-hydroxy-N-[1-(2-pyridinyl)-2-[[4'-(trifluoromethoxy)[1,1'-biphenyl]-4-yl]sulfonyl] ethyl]formamide The title compound was prepared according to the procedures of example 75, except substituting 2-pyridine carboxaldehyde for propionaldehyde and 4-(4'-trifluoromethoxyphenoxy)phenyl methyl sulfone for 4-(4'-methoxylphenyl)phenyl methyl sulfone in example 75A.

m.p. 116.4–117.6° C.; $^1$H NMR (300 MHz, DMSO-d$_6$) δ 3.88–4.04 (m, 1H), 4.28–4.36 (dd, 1H, J=4.5, 15 Hz), 5.50 (br, 0.5H), 5.84 (br, 0.5H), 7.12–7.44 (m, 6H), 7.44–7.50 (d, 2H, J=9 Hz), 7.74–7.95 (2H), 8.18 (s, 0.5H), 8.25 (s, 0.5H), 8.47 (1H), 9.66 (s, 0.5H); MS (ESI) m/e 483 (M+H)$^+$, 505 (M+Na)$^+$, 481 (M–H)$^-$. 517 (M+Cl); Anal. calcd for C$_{21}$H$_{17}$N$_2$F$_3$O$_6$S: C, 52.28; H, 3.55; N, 5.80. Found: C, 51.95; H, 3.24; N, 5.63.

EXAMPLE 187

(±)-N-[1-[[[(4-chlorophenoxy)phenyl]sulfonyl] methly]-4-hydroxybutyl]-N-hydroxyformamide The title compound was prepared according to the procedures of example 125, except substituting 4-tert-butuldimethylsilyloxy-butanaldehyde for 3-tert-butuldimethylsilyloxypropionaldehyde and 4-(4'-chlorophenoxy)phenyl methyl sulfone for 4-(4'-trifluoromethylphenyl)phenyl methyl sulfone m.p.126.9–128.8° C.; $^1$H NMR (300 MHz, DMSO-d$_6$) δ 1.20–1.38 (m, 2H), 1.41–1.65 (m, 2H), 3.35–3.44 (dd, 1H, J=3, 12 Hz), 3.52–3.67 (m, 1H), 4.01–4.13 (br, 0.4H), 4.33–4.58 (0.6H), 7.15–7.23 (dd, 4H, J=3, 9 Hz), 7.48–7.56 (d, 2H, J=9 Hz), 7.81 (s, 0.6H), 7.85–7.92 (d, 2H, 9 Hz), 8.12 (s, 0.4H), 9.44 (br, 0.6H), 9.82 (br, 0.4H); MS (ESI) m/e 414 (M+H)$^+$, 431 (M+NH$_4$)$^+$, 436 (M+Na)$^+$, 412 (M–H); Anal. calcd for C$_{18}$H$_{20}$NClO$_6$S: C, 52.23; H, 4.87; N, 3.38. Found: C, 52.21; H, 4.93; N, 3.21

EXAMPLE 188

(±)-N-[1-[[[(4-trifluoromethonphenoxy)phenyl] sulfonyl]methyl]-3-hydroxypropyl]-N-hydroxyformamide The title compound was prepared according to the procedures of example 125, except substituting 4-(4'- trifluoromethoxyphenoxy)phenyl methyl sulfone for 4-(4'-trifluoromethylphenyl)phenyl methyl sulfone.

m.p. 119.5–122.6° C.; $^1$H NMR (300 MHz, DMSO-d$_6$) δ 1.52–1.80 (m, 2H), 3.18–3.31 (m, 1H), 3.47–3.50 (1H), 3.54–3.72 (m, 1H), 4.20–4.32 (m, 0.7H), 4.43–4.49 (t, 0.3H, J=6 Hz), 4.55–4.61 (t, 0.7H, J=6 Hz), 4.64–4.76 (m, 0.3H), 7.17–7.26 (d, 2H, J=9 Hz), 7.26–7.32 (2H), 7.43–7.51 (d, 2H, J=9 Hz), 7.74 (s, 0.7H), 7.86–7.93 (d, 2H, J=9 Hz), 8.09 (s, 0.3H), 9.46 (s, 0.7H), 9.81 (s, 0.3H);

MS (ESI) m/e 450 (M+H)$^+$, 467 (M+NH$_4$)$^+$, 472 (M+Na)$^+$, 448 (M−H)$^−$; Anal. calcd for C$_{18}$H$_{18}$NF$_3$O$_7$S: C, 48.10; H, 4.03; N, 3.11. Found: C, 48.47; H, 4.10; N, 2.97.

EXAMPLE 189

(±)-N-hydroxy-N-[1-[(4-trifluoromethoxyphenoxy)methyl]-2-[[4-[4-(trifluoromethoxy)phenoxy]phenyl]sulfonyl]ethyl]formamide The title compound was prepared according to the procedures of example 126, except substituting ethyl 4-trifluomethoxyphenoxy-acetate (prepared from ethyl bromoacetate and 4-trifluoromethoxy phenol as in example 174A) for ethyl methoxyacetate and 4-(4'-trifluoromethoxyphenoxy)phenyl methyl sulfone for 4-(4'-trifluoromethylphenyl)phenyl methyl sulfone.

1H NMR (DMSO-d$_6$) δ 3.55–3.79 (m, 2H), 3.96–4.15 (m, 2H), 4.38–4.50 (m, 0.5H), 4.97 (m, 0.5H), 6.95 (dd, 2H, J=3,9 Hz), 7.23 (d, 2H, J=9 Hz), 7.24–7.35 (m, 4H), 7.47 (d, 2H, J=9 Hz), 7.93 (d, 2H, J=6 Hz), 7.96 (s, 0.5H), 8.18 (s, 0.5H), 9.68 (bs, 0.5H), 10.08 (bs, 0.5H); MS (ESI−) 594 (M−H); Anal. Calcd for: C$_{24}$H$_{19}$NO$_8$SF$_6$ C, 48.40; H, 3.21; N, 2.35. Found: C, 48.35; H, 3.42; N, 2.35.

EXAMPLE 190

[S-(R*,R*)]-N-hydroxy-N-[1-(2,2-dimethyl-1,3-dioxol-4-yl)-2-[4-[(4-phenyl-1-piperidinyl)phenyl]sulfonyl]ethyl]formamide The title compound was prepared following the procedures described in example 145 starting with [4-(4-phenylpiperidine)phenyl]methyl sulfone (prepared by addition of 4-phenylpiperidine to (4-fluorophenyl)methyl sulfone) and commercially available methyl (R)-2,2-dimethyl-1,3-dioxolane-4-carboxylate.

$^1$H NMR (300 MHz, DMSO-d$_6$) δ 1.15–1.35 (m, 6H), 1.6–1.9 (m, 4H), 2.7–3.3 (m, 4H), 3.5–3.6 (m, 2H), 3.9–4.2 (m, 4.5H), 4.5–4.6 (t, 0.5H, J=5.6 Hz), 7.12 (d, J=9.3 Hz), 7.15–7.35 (m, 5H), 7.6–7.7 (m, 2H), 7.82 (s, 0.5H), 8.18 (s, 0.5H), 9.65 (s, 0.5H), 10.00 (br s, 0.5H); MS (ESI+) 489 (M+H); Anal Calcd for C$_{25}$H$_{32}$N$_2$O$_6$S: C, 61.45; H, 6.60; N, 5.73. Found: C, 61.54; H, 6.53; N, 5.57.

EXAMPLE 191

(±)-N-hydroxy-N-[1-(4-trifluoromethoxyphenyl)-2-[[4-[4-(trifluoromethoxy)phenoxy]phenyl]sulfonyl]ethyl]formamide The title compound was prepared according to the procedures of example 75, except substituting 4-trifluoromethoxy)benzaldehyde for propionaldehyde and 4-(4'-trifluoromethoxyphenoxy)phenyl methyl sulfone for 4-(4'-methoxylphenyl)phenyl methyl sulfone in example 75A.

$^1$H NMR (300 MHz, DMSO-d$_6$) δ 4.0–4.2 (m, 4H), 5.45–5.55 (br m, 0.5H), 5.7–5.8 (br m, 0.5H), 7.14 (d, 2H, J=8.1 Hz), 7.20–7.35 (m, 4H), 7.35–7.60 (m, 4H), 7.84 (d, 2H, J=7.5 Hz), 8.1–8.3 (m, 1H), 9.66 (br s, 0.5H), 10.10 (br s, 0.5H); MS (ESI+) 566 (M+H), 588 (M+23); Anal. Calcd for C$_{23}$H$_{17}$NO$_7$SF$_6$: C, 48.85; H, 3.03; N, 2.47. Found: C, 48.96; H, 3.17; N, 2.45.

EXAMPLE 192

[S-(R*,R*,R*)]-N-[1-(2,2,5-trimethyl-1,3-dioxol-4-yl)-2-[[4-[4-(trifluoromethoxy)phenoxy]phenyl]sulfonyl]ethyl]-N-hydroxyformamide The title compound was prepared following the procedures described in example 145 except substituting commercially available methyl 3,4-isopropylidene-L-threonate for methyl (S)-2,2-dimethyl-1,3-dioxolane-4-carboxylate.

$^1$H NMR (300 MHz, DMSO-d$_6$) δ 1.2–1.3 (m, 9H), 3.3–3.5 (m, 2H), 3.6–3.9 (m, 3H), 4.1–4.2 (apparent t, 0.5H, J=5.0 Hz), 4.6–4.7 (apparent t, 0.5H, J=5.0 Hz), 7.2–7.3 (m, 4H), 7.48 (d, 2H, J=9.0 Hz), 7.85–8.00 (m, 2.5H), 8.15 (s, 0.5H), 9.69 (s, 0.5H), 9.95 (s, 0.5H); MS (ESI+) 520 (M+H), 537 (M+18); Anal. Calcd for C$_{22}$H$_{24}$NO$_8$SF$_3$: C, 50.86; H, 4.65; N, 2.69. Found: C, 51.01; H, 4.38; N, 2.47.

EXAMPLE 193

(±)-N-hydroxy-N-[1-(2-trifluoromethylphenyl)-2-[[4-[4-(trifluoromethoxy)phenoxy]phenyl]sulfonyl]ethyl]formamide The title compound was prepared according to the procedures of example 75, except substituting 2-trifluoromethylbenzaldehyde for propionaldehyde and 4-(4'-trifluoromethoxyphenoxy)phenyl methyl sulfone for 4-(4'-methoxylphenyl)phenyl methyl sulfone in example 75A.

$^1$H NMR (DMSO-d$_6$) δ 9.8 (bs, 0.5H), 8.17 (s, 0.5H), 8.10 (s, 0.5H), 7.5–7.98 (mm, 8H), 7.15–7.35 (mm, 4H), 6.05–6.15 (m, 0.5H), 5.48–5.50 (m, 0.5H), 4.39–4.44 (m, 1.0H), 3.90–4.15 (m, 2H); MS (ESI) 550 (M+H), 567 (M+NH$_4$), 548 (M−H); Anal. Calcd for: C$_{23}$H$_{17}$NO$_6$SF$_6$.0.25EtOAc; C, 50.44; H, 3.35; N, 2.454. Found: C, 50.50; H, 3.48; N, 2.32.

EXAMPLE 194

(±)-N-hydroxy-N-[1-(4-fluorophenyl)-2-[[4-[4-(trifluoromethoxy)phenoxy]phenyl]sulfonyl]ethyl]formamide The title compound was prepared according to the procedures of example 75, except substituting 4-fluorobenzaldehyde for propionaldehyde and 4-(4'-trifluoromethoxyphenoxy)phenyl methyl sulfone for 4-(4'-methoxylphenyl)phenyl methyl sulfone in example 75A.

$^1$H NMR (DMSO-d$_6$) δ 9.65 (s, 0.5H), 8.11–8.20 (m, 1H), 7.81–7.89 (d, 2H, 7.9 Hz), 7.46–7.51 (d, 8.0H), 7.40–7.50 (m, 1H), 7.24–7.30 (d, 2H, 7.8 Hz), 7.11–7.19 (d, 4H, J=8.0 Hz), 5.70–5.73 (bs, 0.5H), 5.48–5.51 (bs, 0.5H), 3.98–4.10 (m, 2H); MS (ESI) 498 (M−H), 500 (M+H), 517 (M+NH$_4$); Anal. Calcd for: C$_{22}$H$_{17}$NO$_6$SF$_4$; C, 52.90; H, 3.43; N, 2.80. Found: C, 52.63; H, 3.60; N, 2.59.

EXAMPLE 195

(±)-N-hydroxy-N-[1-(cyclohexyl)-2-[[4-[4-(trifluoromethoxy)phenoxy]phenyl]sulfonyl]ethyl]formamide The title compound was prepared according to the procedures of example 75, except substituting cyclohexane carboxaldehyde for propionaldehyde and 4-(4'-trifluoromethoxyphenoxy)phenyl methyl sulfone for 4-(4'-methoxylphenyl)phenyl methyl sulfone in example 75A.

$^1$H NMR (DMSO-d$_6$) δ 9.86 (s, 0.5H), 9.50 (s, 0.5H), 8.13 (s, 0.5H), 7.89–7.97 (m, 2H), 7.75 (s, 0.5H), 7.47–7.51 (d, 2H, J=7.8 Hz), 7.26–7.48 (m, 4H), 4.21–4.26 (m, 0.5H), 4.01–3.97 (m, 0.5H), 3.56–3.41 (m, 4H), 0.56–1.7(m, 11H); MS (ESI) 486 (M–H), 488 (M+H), 505 (M+NH$_4$); Anal. Calcd for: C$_{22}$H$_{24}$NO$_6$SF$_3$.0.25H$_2$O: C, 53.70; H, 5.01; N, 2.84. Found: C, 54.67; H, 5.35; N, 2.69.

EXAMPLE 196

(–)-(S) N-[1-[[[4-(4-chlorophenoxy)phenyl]sulfonyl]methyl]-2-(3,4,4-trimethyl-2,5-dioxo-1-imidazolidinyl)ethyl]-N-hydroxyformamide

EXAMPLE 196A (S)-4-[[4-[(4-chlorophenoxy)phenyl]thio]methyl]-2-oxazolidinone A 0° C. solution of 4-(4'-chlorophenoxy)-benzenethiol (25.5 g, 108 mmol) in DMF (250 mL) was treated with K$_2$CO$_3$ (14.9 g, 108 mmol) followed by (S)-(+)-4-(4'-toluenesulfonyloxymethyl)-2-oxazolidinone (22.09 g, 83 mmol) [*J. Chem. Soc. Perkin Trans.* 1, 1994, 13, 1675]. The reaction was allowed to stir overnight at ambient temperature, then partitioned between ethyl acetate and brine. The organics were washed with brine twice, dried, filtered, concentrated and purified via silica gel chromatography eluting with 5 to 20% ethyl acetate/hexane to give 22.08 g (81% yield) of the title compound.

MS (ESI) m/e 353 (M+NH$_4$)$^+$.

EXAMPLE 196B (S)-4-[[4-[(4-chlorophenoxy)phenyl]sulfonyl]methyl]-2-oxazolidinone A 0° C. mixture of 196A (3.6 g, 10 mmol) and NaHCO$_3$ (2.26 g, 26 mmol) in 200 mL of methanol and 50 mL of water was treated with oxone (9.6 g, 27 mol), then stirred at room temperature for 3 h, after which time the reaction was quenched with water and extracted with ethyl acetate. The organics were dried, filtered, and concentrated to give 3.53 g (96%) of the title compound.

MS (ESI) m/e 368 (M+H)$^+$, 385 (M+NH$_4$)$^+$, 390 (M+Na)$^+$.

EXAMPLE 196C (S)-2-amino3-[4-[(4-chlorophenoxy)phenyl]sulfonyl]-1-propanol

A mixture of 196B (3.53 g, 9.6 mmol) and NaOH (0.62 g, 15 mmol) in ethanol (20 mL) was stirred at reflux for 30 h, then concentrated and partinioned between brine and CH$_2$Cl$_2$. The aqueous layer was back extracted with CH$_2$Cl$_2$ twice and the combined organics were washed with brine, dried, filtered, and concentrated to give 3.0 g (92%) of the title compound.

MS (ESI) m/e 342 (M+H)$^+$, 364 (M+Na)$^+$.

EXAMPLE 196D (–) (S)-N-[1-[[[4-(4-chlorophenoxy)phenyl]sulfonyl]methyl]-2-(3 4,4-trimethyl-2,5-dioxo-1-imidazolidinyl)ethyl]hydroxylamine A solution of 196C (9.89 g, 29 mmol) and 4-methoxybenzaldehyde (3.53 g, 29 mmol) in toluene (300 mL) was refluxed for 18 h in a Dean-Stark apparatus. The reaction was then concentrated and the crude product was dissolved in THF (200 mL), sequentially treated with triphenyl phosphine (9.1 g, 35 mmol), 1,5,5-trimethyl hydantoin (4.9 g, 35 mmol) and diethyl azodicarboxylate (5.5 g, 35 mmol). The reaction was concentrated and the residue was dissolved in chloroform (100 mL), cooled to 0° C., treated with 69 mL of sat. aq. NaHCO$_3$, and benzyltriethylammonium chloride (0.726 g, 3.18 mmol) followed by dropwise addition of a solution of m-chloroperbenzoic acid (11 g, 32 mmol, 50%-Aldrich) in 100 mL CH$_2$Cl$_2$. The reaction was stirred at 0° C. for 7 h then partitioned between water and CH$_2$Cl$_2$. The organics were washed with aq. NaHSO$_3$, water, brine, dried, filtered, and concentrated. The crude product was dissolved in 200 mL of methanol, treated with hydroxylamine hydrochloride (4 g, 58 mmol) and stirred at room temperature for 3 days. The reaction was then concentrated and the residue was partitioned between sat. aq. NaHCO$_3$ and ethyl acetate. The organics were dried, filtered, concentrated and purified via silica gel chromatography eluting with 1 to 5% methanol/methylene chloride to give 1.29 g (9%) of the title compound.

MS (ESI) m/e 482 (M+H)$^+$, 504 (M+Na)$^+$.

EXAMPLE 196E (–) N-[1-[[[4-(4-chlorophenoxy)phenyl]sulfonyl]methyl]-2-(3,4,4-trimethyl-2,5-dioxo-1-imidazolidinyl)ethyl]-N-hydroxyformamide Example 196E was converted to the title compound following the procedure of example 2F.

mp 111° C; [α$_D$]=–6.4° (c=0.25).

EXAMPLE 197

(+)-N-hydroxy-N-[1-[[[4-[4-(trifluorophenoxy)phenyl]sulfonyl]methyl]-2-(3,4,5-trimethoxyphenyl)ethyl]formamide The title compound was prepared according to the procedures of example 126, except substituting ethyl 3,4,5-trimethoxyphenoxyacetate (prepared from ethyl bromoacetate and 3,4,5-trimethoxyphenol as in example 174A) for ethyl methoxyacetate and 4-(4'-trifluoromethoxyphenoxy) phenyl methyl sulfone for 4-(4'-trifluoromethylphenyl) phenyl methyl sulfone.

1H NMR (DMSO-d6) δ 3.53–3.62 (m, 4H), 3.65–3.77 (m, 7H), 3.92–4.0 (m, 1H), 4.02–4.15 (m, 1H), 4.35–4.46 (bs, 0.5H), 4.85–4.97 (bs, 0.5H), 6.16 (d, 2H, J=4 Hz), 7.16–7.30 (m, 4H), 7.47 (d, 2H, J=9 Hz), 7.91 (d, 2H, J=12 Hz), 7.96 (s, 0.5H), 8.21 (s, 0.5H), 9.68 (s, 0.5H), 10.08 (s, 0.5H); MS (ESI–) 600 (M–H)–; Anal. Calcd for: C$_{26}$H$_{26}$NO$_{10}$SF3 C, 51.91; H, 4.35; N, 2.32. Found: C, 51.90; H, 4.41; N, 2.26.

EXAMPLE 198

3-(cyanomethyl)-4'-({3-(4,4-dimethyl-2,5-dioxo-1-imidazolidinyl)-2-[formyl(hydroxy)amino]propyl}sulfonyl)-1,1'-biphenyl The title compound was prepared following the procedures of Examples 56B–D, substituting 3-cyanomethylbenzene boronic acid for 4-n-butyloxybenzene boronic acid.

m.p.186.5–188.8° C. $^1$H NMR (300 MHz, DMSO-d6) δ 1.21–1.23 (m, 6H), 3.35–3.78 (m, 5H), 4.47–4.60 (m, 0.5H), 4.86–4.96 (m, 0.5H), 7.45–7.47 (d, 1H, J=7.5 Hz), 7.54–7.59 (t, 1H, J=8.4 Hz), 7.74–7.77 (m, 2.5H), 7.94–8.02 (m, 4H), 8.09 (s, 0.5H), 8.33–8.36 (d, 1H, J=9.6 Hz), 9.48 (s, 0.5H), 9.63 (s, 0.5H). MS (ESI) m/e 485 (M+H)$^+$, 502 (M+NH4)$^+$, 507 (M+Na)+$^+$, 483 (M–H)$^-$, Anal. calcd for $C_{23}H_{24}N_4O_6S.0.4\ H_2O.0.4\ Et_2O$: C, 56.77; H, 5.66; N, 10.74. Found: C, 56.92; H, 5.51; N,10.63.

EXAMPLE 199 hydroxy {3-(4-morpholinyl)-1-[({4-[4-(trifluoromethoxy)phenoxy]phenyl}sulfonyl)methyl]propyl}formamide Methyl 4-morpholinepropionate was converted to the title compound following the procedures of Examples 126A–B and Examples 75B–D, substituting 4-(4'-trifluoromethoxyphenyloxy)-phenyl methyl sulfone for 4-(4'-trifluoromethylphenyl)-phenyl methyl sulfone.

m.p.139.1–140.5° C. $^1$H NMR (300 MHz, DMSO-d$_6$) δ 1.58–2.40 (m, 4H), 2.90–3.20 (bs, 2H), 3.40–3.75 (m, 4H), 3.85–4.08 (bs, 0.6H), 4.60–4.70 (bs, 0.4H), 7.21–7.29 (m, 4H), 7.46–7.49 (d, 2H, J=8.4 Hz), 7.80 (s, 0.6H), 7.89–7.92 (d, 2H, J=8.7 Hz), 8.10 (s, 0.4H), 9.63 (s, 0.6H), 10.1 (bs, 0.4H). MS (ESI) m/e 519 (M+H)$^+$, 541 (M+Na)$^+$, 517 (M–H)$^-$, 553 (M+Cl)$^-$. Anal. calcd for $C_{22}H_{25}N_2F_3O_7S.H_2O$: C, 49.29; H, 5.07; N, 5.26. Found: C, 49.07; H, 4.76; N, 5.11.

EXAMPLE 200

4-({3-(4,4-dimethyl-2,5-dioxo-1-imidazolidinyl)-2-[formyl(hydroxy)amino]propyl}sulfonyl)-4'-fluoro-1,1'-biphenyl

EXAMPLE 200A ethyl (4,4-dimethyl-2,5-dioxo-1-imidazolidinyl) acetate

A solution of 5,5-dimethylhydantoin (10 g, 78 mmol) in DMF (400 mL) was treated with cesium carbonate (25 g, 78 mmol) stirred at r.t. for 30 min then treated with ethyl bromoacetate (11.3 mL, 102 mmol) and allowed to stir overnight. The reaction mixture was partitioned between ethyl acetate and a 1 to 1 mixture of brine and water. The organics were washed with brine, dried ($Na_2SO_4$), filtered, concentrated and purified via silica gel column chromatography eluting with 30 to 50% ethyl acetate/hexane to give 5.47 g of the title compound as a white solid.

MS (APCI) 215 (M+H)$^+$.]

EXAMPLE 200B 4-({3-(4,4-dimethyl-2,5-dioxo-1-imidazolidinyl)-2-[formyl(hydroxy)amino]propyl}sulfonyl)-4'-fluoro-1,1'-biphenyl Example 200A was converted to the title compound following the procedures of Examples 126A–B and Examples 75B–D, substituting 4-(4'-fluorophenyl)-phenyl methyl sulfone for 4-(4'-trifluoromethylphenyl)-phenyl methyl sulfone.

$^1$H NMR (300 MHz, DMSO-d$_6$) δ 1.20–1.23 (m, 6H), 3.40–3.76 (m, 6H), 4.48–4.60 (m, 0.5H), 4.85–4.97 (m, 0.5H), 7.34–7.40 (t, 2H, J=9 Hz), 7.73 (s, 0.5H), 7.81–7.86 (m, 2H), 7.96 (s, 4H), 8.10 (s, 0.5H), 8.34–8.38 (d, 1H, J=10.2 Hz), 9.51 (s, 0.5H), 9.66 (s, 0.5H). MS (ESI) m/e 464 (M+H)$^+$, 481 (M+NH4)$^+$, 486 (M+Na)$^+$, 462 (M–H)$^-$, High resolution MS (FAB) Calc.m/z for M$^+$464.1692, observed m/z 464.1300.

EXAMPLE 201

4-({3-(4,4-dimethyl-2,5-dioxo-1-imidazolidinyl)-2-[formyl(hydroxy)amino]propyl}sulfonyl)-4'-(methylsulfanyl)-1,1'-biphenyl Example 200A was converted to the title compound following the procedures of Examples 126-A,B and Examples 75-D, substituting 4-(4'-thiomethylphenyl)-phenyl methyl sulfone for 4-(4'-trifluoromethylphenyl)-phenyl methyl sulfone.

m.p.215.3–217.7° C. $^1$H NMR (300 MHz, DMSO-d$_6$) δ 1.20–1.23 (m, 6H), 2.53 (s, 3H), 3.34–3.76 (m, 4H), 4.47–4.60 (m, 0.47H), 4.84–4.95 (m, 0.53H), 7.38–7.41 (d, 2H, J=8.4 Hz), 7.71–7.75 (dd+s, 2.47H, J=2.7, 8.7 Hz), 7.94–7.95 (d, 4H, J=1.8 Hz), 8.10 (s, 0.53H), 8.26–8.32 (d, 1H, J=9.6 Hz), 9.50 (s, 0.47H), 9.65 (s, 0.53H). MS (ESI) m/e 492 (M+H)$^+$, 509 (M+NH4)$^+$, 514 (M+Na)$^+$, 490 (M–H)$^-$, Anal. calcd for $C_{23}H_{24}N_4O_6S$: C, 53.75; H, 5.12; N, 8.54. Found: C, 53.66; H, 5.37; N 8.27.

EXAMPLE 202

4-({3-(4,4-dimethyl-2,5-dioxo-1-imidazolidinyl)-2-[formyl(hydroxy)amino]propyl}sulfonyl)-4'-methoxy-1,1'-biphenyl Example 200A was converted to the title compound following the procedures of Examples 126-A–B and Examples 75-B–D, substituting 4-(4'-methoxyphenyl)-phenyl methyl sulfone for 4-(4'-trifluoromethylphenyl)-phenyl methyl sulfone. $^1$H NMR (300 MHz, DMSO-d$_6$) δ 1.20–1.23 (6H), 3.41–3.75 (m, 4H), 3.82 (s, 3H), 4.48–4.60 (m, 0.5H), 4.83–4.95 (m, 0.5H), 7.06–7.09 (d, 2H, J=8.7 Hz), 7.72–7.75 (dd+s, 2.5H, J=2.7, 8.7 Hz), 7.89–7.92 (4H), 8.10 (s, 0.5H), 8.32–8.36 (d, 1H, J=10.2 Hz), 9.50 (s, 0.5H), 9.64 (s, 0.5H). MS (ESI) m/e 476 (M+H)$^+$, 493 (M+NH4)$^+$, 474 (M–H)$^-$, Anal. calcd for $C_{22}H_{25}N_5O_7S.0.5H_2O$: C, 54.53; H, 5.72; N, 7.56. Found: C, 54.50; H, 5.64; N, 7.82.

EXAMPLE 203

4-fluoro-4'-({2-[formyl(hydroxy)amino]-4-hydroxybutyl}sulfonyl)-1,1'-biphenyl

The title compound was prepared following the procedures of Example 125 substituting 4-(4'-fluorophenyl)-phenyl methyl sulfone for 4-(4'-trifluoromethylphenyl)-phenyl methyl sulfone.

m.p.159.9–162.0° C. $^1$H NMR (300 MHz, DMSO-d$_6$) δ 1.56–1.79 (m, 2H), 3.21–3.31 (m, 1H), 3.47-3.76 (m, 2H), 4.25–4.37 (m, 0.6H), 4.69–4.80 (m, 0.4H), 7.34–7.40 (t, 2H, J=9 Hz), 7.80–7.86 (m, 2.6H), 7.92–7.98 (4H), 8.10 (s, 0.4H), 9.50 (brs, 0.6H). MS (ESI) m/e 368 (M+H)$^+$, 385 (M+NH4)$^+$, 390 (M+Na)$^+$366 (M–H)$^-$, 402 (M+Cl)$^-$. Anal. calcd for $C_{17}H_{18}NFO_5S$: C, 55.57; H, 4.93; N, 3.81. Found: C, 55.63; H, 5.08; N, 3.72.

EXAMPLE 204

4-chloro-4'-({2-[formyl(hydroxy)amino]-4-hydroxybutyl}sulfonyl)-1,1'-biphenyl

The title compound was prepared following the procedures of Example 125 substituting 4-(4'-chlorophenyl)-phenyl methyl sulfone for 4-(4'-trifluoromethylphenyl) phenyl methyl sulfone.

m.p.158.2–158.7° C. $^1$H NMR (300 MHz, DMSO-d$_6$) δ 1.53–1.83 (m, 2H), 3.48–3.54 (dd, 1H, J=1.8, 15 Hz), 3.59–3.74 (m, 1H), 4.24–4.38 (m, 0.6H), 4.67–4.82 (m, 0.4H), 7.57–7.60 (d, 2H, J=8.4 Hz), 7.79–7.83 (m, 2.6H), 7.96 (s, 4H), 8.09 (s, 0.4H). MS (ESI) m/e 384 (M+H)$^+$, 401 (M+NH4)$^+$, 406 (M+Na)$^+$, 382 (M–H)$^-$. Anal. calcd for $C_{17}H_{18}NClO_5S$.: C, 53.19; H, 4.72; N, 3.64. Found: C, 53.09; H, 4.78; N, 3.39.

EXAMPLE 205

4-fluoro-4'-({2-[formyl(hydroxy)amino]-5-hydroxypentyl}sulfonyl)-1,1'-biphenyl

The title compound was prepared according to the procedures of Example 125, substituting 4-tbutyldimethylsilyloxy-butanaldehyde for 3-tbutyldimethylsilyloxy-propionaldehyde and 4-(4'-fluorophenyl)-phenyl methyl sulfone for 4-(4'-trifluoromethylphenyl)-phenyl methyl sulfone.

m.p. 143.1–143.8° C. $^1$H NMR (300 MHz, DMSO-d$_6$) δ 1.25–1.61 (m, 4H), 3.44–3.76 (m, 2H), 4.07–4.22 (m, 0.6H), 4.32–4.51 (1H), 4.51–4.63 (m, 0.4H), 7.33–7.39 (t, 2H, J=8.4 Hz), 7.80–8.13 (m, 7H), 9.47 (s, 0.6H), 9.84 (s, 0.4H). MS (ESI) m/e 382 (M+H)$^+$, 399 (M+NH4)$^+$, 404 (M+Na)$^+$, 380 (M–H)$^-$, 416 (M+Cl)$^-$. Anal. calcd for $C_{18}H_{20}FNO_5S$: C, 56.68; H, 5.28; N, 3.67. Found: C, 56.54; H, 5.19; N, 3.44.

EXAMPLE 206

4-chloro-4'-({2-[formyl(hydroxy)amino]-5-hydroxypentyl}sulfonyl)-1,1'-biphenyl

The title compound was prepared according to the procedures of Example 125, substituting 4-tert-butyldimethylsilyloxy-butanaldehyde for 3-tert-butyldimethylsilyloxy-propionaldehyde and 4-(4'-chlorophenyl)-phenyl methyl sulfone for 4-(4'-trifluoromethylphenyl)-phenyl methyl sulfone.

m.p.159.5–160.4° C. $^1$H NMR (300 MHz, DMSO-d$_6$) δ 1.23–1.61 (m, 4H), 3.45–3.51 (dd, 1H, J=3, 15 Hz), 3.60–3.70 (m, 1H), 4.08–4.20 (m, 0.6H), 4.33–4.50 (1H), 4.50–4.63 (m, 0.4H), 7.58–7.60 (d, 2H, J=8.4 Hz), 7.79–7.83 (dd, 2H, J=3.9, 8.4 Hz), 7.88 (s, 0.6H), 7.96 (s, 4H), 8.13 (s, 0.4H), 9.48 (s, 0.6H), 9.86 (s, 0.4H). MS (ESI) m/e 398 (M+H)$^+$, 415 (M+NH4)$^+$, 420 (M+Na)$^+$396 (M–H)$^-$, Anal. calcd for $C_{18}H_{20}NClO_5S$: C, 54.33; H, 5.06; N, 3.52. Found: C, 54.36; H, 5.16; N,3.42.

EXAMPLE 207

4-chloro-4'-({3-(4,4-dimethyl-2,6-dioxo-1-piperidinyl)-2-[formyl(hydroxy)amino]propyl}sulfonyl)-1,1'-biphenyl Ethyl 3,3-dimethylglutarimideacetate (prepared from 3,3-Dimethylglutarimide and ethyl bromoacetate (as in Example 200A) was converted to the title compound following the procedures of Examples 126A–B and Examples 75B–D, substituting 4-(4'-chlorophenyl)-phenyl methyl sulfone for 4-(4'-trifluoromethylphenyl)-phenyl methyl sulfone.

$^1$H NMR (300 MHz, DMSO-d$_6$) δ 0.93 (6H), 2.46 (4H), 3.43–3.50 (m, 1H), 3.63–3.76 (m, 2H), 3.88–4.02 (m, 1H), 4.33–4.45 (m, 0.5H), 4.85–4.99 (m, 0.5H), 7.58–7.61 (d, 2H, J=8.4 Hz), 7.76 (s, 0.5H), 7.79–7.83 (dd, 2H, J=3.6, 8.7 Hz), 7.97 (s, 4H), 8.06 (s, 0.5H), 9.52 (s, 0.5H), 9.66 (s, 0.5H). MS (E SI) m/e 493 (M+H)$^+$, 510 (M+NH4)$^+$, 491 (M–H)$^-$, Anal. calcd for $C_{23}H_{25}N_2ClO_6S$: C, 56.03; H, 5.11; N, 5.68. Found: C, 56.11; H, 5.40; N,5.39.

EXAMPLE 208 ethyl 5-({3-[(4'-fluoro[1,1'-biphenyl]-4-yl)sulfonyl]-2-[formyl(hydroxy)amino]propyl}amino)-3,3-dimethyl-5-oxopentanoate

EXAMPLE 208A and 208B ethyl 5-({3-[(4'-fluoro[1,1'-biphenyl]-4-yl)sulfonyl]-2-hydroxypropyl}amino)-3,3-dimethyl-5-oxopentanoate and 1-{3-[(4'-fluoro[1,1'-biphenyl]-4-yl)sulfonyl]-2-hydroxypropyl}-4,4-dimethyl-2,6-piperidinedione Reaction of 4-(4'-fluorophenyl)-phenyl methyl sulfone with ethyl 3,3-dimethylglutarimideacetate (prepared from 3,3-Dimethylglutarimide and ethyl bromoacetate (as in Example 120A) following the procedures of Example 126A, followed by reduction as described in Example 126B afforded the two title products which were chromatographically separated to give the desired products.

Example 208A: MS (APCI) 480 (M+H)$^+$; Example 208B: MS (APCI) 451 (M+H)$^+$.

EXAMPLE 208C ethyl 5-({3-[(4'-fluoro[1,1'-biphenyl]-4-yl)sulfonyl]-2-[formyl(hydroxy)amino]proyl} amino)-3,3-dimethyl-5-oxopentanoate Example 208A was converted to the title compound following the procedure of Example 126C.

m.p. 150.6–150.9° C. $^1$H NMR (300 MHz, DMSO-d$_6$) δ 0.94–0.96 (d, 6H, J=4.8 Hz), 1.13–1.18 (t, 3H, J=7.2 Hz), 2.07 (2H), 2.26–2.28 (d, 2H, J=6.3 Hz), 3.10–3.25 (m, 2H), 3.43–3.72 (m, 2H), 3.98–4.05 (q, 2H, J=6.6 Hz), 4.13–4.28 (m, 0.5H), 4.57–4.72 (m, 0.5H), 7.33–7.39 (t, 2H, J=8.1 Hz), 7 (s, 0.5H), 7.78–7.87 (m, 2H), 7.93–7.94 (d, 4H, J=2.7 Hz), 8.09 (s, 0.5H), 9.43 (s, 0.5H), 9.75 (s, 0.5H). MS (ESI) m/e 523 (M+H)$^+$, 540 (M+NH4)$^+$, 545 (M+Na)$^+$, 521 (M–H)$^-$; Anal. calcd for $C_{25}H_{31}N_2FO_7S$: C, 57.45; H, 5.97; N, 5.36. Found: C, 57.18; H, 5.95; N,5.24.

EXAMPLE 209

4-({3-(4,4-dimethyl-2,6-dioxo-1-piperidinyl)-2-[formyl(hydroxy)amino]propyl}sulfonyl)-4'-fluoro-1,1'-biphenyl Example 208B was converted to the title compound following the procedures of Example 126C.

m.p.105.4–108.7° C. $^1$H NMR (300 MHz, DMSO-d$_6$) δ 0.92 (s, 6H), 2.46–2.47 (4H), 3.43–3.48 (m, 1H), 3.62–3.75 (m, 2H), 3.87–3.98 (m, 1H), 4.32–4.45 (m, 0.5H), 4.85–5.00 (m, 0.5H), 7.34–7.40 (t, 2H, J=8.7 Hz), 7.75 (s, 0.5H), 7.81–7.87 (m, 2H), 7.95 (s, 4H), 8.06 (s, 0.5H), 9.52 (s, 0.5H), 9.67 (s, 0.5H), MS (ESI) m/e 477 (M+H)$^+$, 494 (M+NH4)$^+$, 475 (M–H)$^-$; Anal. calcd for $C_{23}H_{25}N_2FO_6S$: C, 57.97; H, 5.28; N, 5.87. Found: C, 58.20; H, 5.42; N,5.54.

EXAMPLE 210 hydroxy[3-(4-morpholinyl)-1-({[4'-(trifluoromethyl)[1,1'-biphenyl]-4-yl]sulfonyl}methyl)propyl]formamide Methyl 4-morpholinepropionate was converted to the title compound following the procedures of Examples 126A–B and Examples 75B–D.

m.p.115.5–1° C. $^1$H NMR (300 MHz, DMSO-$d_6$) δ 1.16–1.17 (m, 2H), 2.09–2.27 (m, 6H), 3.45–3.46 (m, 4H), 3.55–3.75 (m, 2H), 4.18–4.21 (m, 0.67H), 4.66–4.77 (m, 0.33H), 7.82–8.14 (9H). MS (ESI) m/e 487 (M+H)$^+$, 509 (M+Na)$^+$, 971 (2M−H)$^-$, Anal. calcd for $C_{22}H_{25}N_2F_3O_5S \cdot H_2O$: C, 52.37; H, 5.39; N, 5.19. Found: C, 52.05; H, 5.14; N,5.19.

EXAMPLE 211

4-chloro-4'-{[2-[formyl(hydroxy)amino]-4-(4-morpholinyl)butyl]sulfonyl}-1,1'-biphenyl Methyl 4-morpholinepropionate was converted to the title compound following the procedures of Examples 126A–B and Examples 75B–D, substituting 4-(4'-chlorophenyl)-phenyl methyl sulfone for 4-(4'-trifluoromethylphenyl)-phenyl methyl sulfone.

m.p. 246.1–246.7° C. $^1$H NMR (300 MHz, DMSO-$d_6$) δ 1.87–2.16 (broad, 2H), 2.88–3.20 (broad, 4H), 3.54–3.80 (m, 5H), 3.92–3.96 (2H), 4.34–4.50 (m, 0.5H), 4.60–4.73 (m, 0.5H), 7.58–7.61 (d, 2H, J=8.4 Hz), 7.79–7.83 (dd, 2H, J=2.7, 8.4 Hz), 7.93 (s, 0.5H), 7.97–7.98 (d, 4H, J=1.8 Hz), 8.12 (s, 0.5H), 10.20 (s, 0.5H), 10.46 (s, 0.5H); MS (ESI) m/e 453 (M+H)$^+$, 475 (M+Na)$^+$, 451 (M−H)$^-$; High resolution MS (FAB) Calc.m/z for (M+H)$^+$453.1251, observed m/z 453.1245.

EXAMPLE 212

4-chloro-4'-{[2-[formyl(hydroxy)amino]-4-(1-piperidinyl)butyl]sulfonyl}-1,1'-biphenyl Ethyl 1-piperidinepropionate was converted to the title compound following the procedures of Examples 126-A,B and 75-B,C,D, substituting 4-(4'-chlorophenyl)-phenyl methyl sulfone for 4-(4'-trifluoromethylphenyl)-phenyl methyl sulfone.

m.p.131.2–132.2° C. $^1$H NMR (300 MHz, DMSO-$_6$) δ 1.22–1.50 (bs, 6H), 1.62–1.85 (m, 2H), 2.03–2.40 (m, 6H), 3.50–3.80 (m, 2H), 4.13–4.24 (m, 0.6H), 4.68–4.79 (m, 0.4H), 7.58–7.61 (dd, 2H, J=1.5, 8.4 Hz), 7.79–7.83 (m, 2.6H), 7.96–7.97 (d, 4H, J=3.6 Hz), 8.03 (s, 0.4H), 10.04 (bs, 0.6H), 11.37 (bs, 0.4H). MS (ESI) m/e 451 (M+H)$^+$, 473 (M+Na)$^+$, 449 (M−H)$^-$; Anal. calcd for $C_{22}H_{27}N_2ClO_4S$: C, 58.59; H, 6.03; N, 6.21. Found: C, 58.54; H, 6.03; N,5.99.

EXAMPLE 213 hydroxy{3-(1-piperidinyl)-1-[({4-[4-(trifluoromethoxy)phenoxy]phenyl}sulfonyl)methyl]propyl}formamide

Example 213A

N-{3-(1-piperidinyl)-1-[({4[-4-(trifluoromethoxy)phenoxy]phenyl}sulfonyl)methyl]propyl}hydroxylamine Ethyl 1-piperidinepropionate was reacted with (4'-trifluoromethoxyphenyloxy)-phenyl methyl sulfone as described in Example 126A and the product was converted to the title compound following the procedures of Examples 126B, 75B and 75C.

EXAMPLE 213B hydroxy{3-(1-piperidinyl)-1-[({4-[4-(trifluoromethoxy)phenoxy]phenyl}sulfonyl)methyl]propyl}formamide A solution of Example 213A (900 mg, 1.84 mmol) in THF (10 mL) was treated with 2,2,2-trifluoroethyl formate (2.45 mL)-see below, heated to reflux for 5 h, then cooled to rt, diluted with CH2Cl2, washed with aq. NaHCO3, brine, dried, concentrated and purified via silica gel chromatography eluting with 10% MeOH/CH2Cl2 to give 208 mg of the title compound.

$^1$H NMR (300 MHz, DMSO-$d_6$) δ 1.26–1.50 (m, 6H), 1.60–1.73 (2H), 2.03–2.48 (m, 6H), 3.45–3.53 (td, 1H, J=3.3, 15 Hz), 3.63–3.74 (td, 1H, J=8.4, 15 Hz), 4.10–4.22 (m, 0.6H), 4.63–4.75 (m, 0.4H), 7.19–7.29 (m, 4H), 7.46–7.49 (d, 2H, J=9.3 Hz), 7.73 (s, 0.6H), 7.87–7.91 (dd, 2H, J=3.6, 9 Hz), 8.01 (s, 0.4H), 10.02 (bs, 0.6H), 11.35 (bs, 0.4H). MS (ESI) m/e 517 (M+H)$^+$, 539 (M+Na)$^+$, 515 (M−H)$^-$, 551 (M+Cl)$^-$. Anal. calcd for $C_{23}H_{27}N_2F_3O_6S$: C, 53.48; H, 5.27; N, 5.42. Found: C, 53.47; H, 5.38; N,5.38.

Preparation of the TFE-F Reagent:

In a 2L 3-necked flask (mechanical stirrer, thermometer and a 20 cm Vigreux column with stillhead) were placed 500 mL 2,2,2-trifluoroethanol, and 1140 mL 95–97 % formic acid. After heating at 73° C. (just short of reflux) overnight the temperature was raised to slowly distill (br 63–66° C.) 633 g of the reagent which was assayed by $^1$H-NMR in CDCl$_3$. This batch was 88.6% TFE-F (4.55, q, 2H; 8.12, s, 1 H), 6.4% TFE (3.96, q, 2H), 5.0% formic acid (8.0 s, 1H) by weight. With a density of 1.345 g/mL this calculates to 9.3 M TFE-F

EXAMPLE 214

4-chloro-4'-{[2-[formyl(hydroxy)amino]-3-(1-piperidinyl)propyl]sulfonyl}-1,1'-biphenyl Ethyl 1-piperidineacetate was converted to the title compound following the procedures of Examples 126A–B and Examples 75B–D, substituting 4-(4'-chlorophenyl)-phenyl methyl sulfone for 4-(4'-trifluoromethylphenyl)-phenyl methyl sulfone.

m.p.153.5–156.7° C. $^1$H NMR (300 MHz, DMSO-$d_6$) δ 1.20–1.40 (brs, 6H), 2.05–2.40 (m, 6H), 3.49–3.67 (m, 2H), 4.07–4.22 (m, 0.5H), 4.64–4.78 (m, 0.5H), 7.57–7.60 (d, 2H, J=8.4 Hz), 7.77–7.81 (dd, 2H, J=2.7, 8.7 Hz), 7.94–8.01 (4.5H), 8.13–8.14 (0.5H); MS (ESI) m/e 437 (M+H)$^+$, 435 (M−H)$^-$; High resolution MS (FAB) Calc.m/z for (M+H)$^+$ 437.1302, observed m/z 437.1319.

EXAMPLE 215 hydroxyy{2-(1-piperidinyl)-1-[({4-[4-(trifluoromethoxy)phenoxy]phenyl}sulfonyl)methyl]ethyl}formamide Ethyl 1-piperidineacetate was converted to the title compound following the procedures of Example 213.

$^1$H NMR (300 MHz, DMSO-$d_6$) δ 1.33 (bs, 6H), 2.22–2.31 (m, 6H), 3.44–3.61 (2H), 4.07–4.99 (m, 0.6H), 4.63–4.66 (m, 0.4H), 7.20–7.29 (m, 4H), 7.47–7.50 (d, 2H, J=8.7 Hz), 7.86–7.93 (2.6H), 8.14 (s, 0.4H), 9.45 (s, 0.6H), 9.88 (s, 0.4H); MS (ESI) m/e 503 (M+H)$^+$, 525 (M+Na)$^+$, 501 (M−H)$^-$; Anal. calcd for $C_{22}H_{25}N_2F_3O_6S$: C, 52.58; H, 5.01; N, 5.57. Found: C, 52.83; H, 5.21; N,5.43.

EXAMPLE 216

3-(4-acetyl-1-piperazinyl)-1-[({4-[4-(trifluoromethoxy)phenoxy]phenyl}sulfonyl)methyl]propyl(hydroxy)formamide

EXAMPLE 216A

Ethyl 3-(4-acetyl-1-piperazinyl)propionate

A solution of 1-acetylpiperazine (5 g, 39 mmol) in THF (100 mL) was treated with ethyl acrylate (4.2 mL, 39 mmol)

then stirred overnight at r.t. after which an additional 4.2 mL of ethyl acrylate was added. The reaction heated at reflux for 5 h, cooled to r.t. and partitioned between dichloromethane and 1N HCl. The acid wash was basified with NaHCO3 to pH 9–10 and extracted 3 times with dichloromethane. Combined organics were dried, filtered and concentrated to give 4.49 g of the title compound as a yellow oil.

MS (APCI): 229 (M+H)$^+$.

EXAMPLE 216B 3-(4-acetyl-1-piperazinyl)-1-[({4-[4-(trifluoromethoxy)phenoxy]phenyl}sulfonyl)methyl]propyl(hydroxy)formamide Example 216A was converted to the title compound following the procedures of Example 213.

$^1$H NMR (300 MHz, DMSO-d$_6$) δ 1.62–1.75 (m, 2H), 1.97 (s, 3H), 2.04–2.37 (m, 6H), 3.59–3.69 (1H), 4.10–4.22 (m, 0.7H), 4.62–4.74 (m, 0.3H), 7.20–7.30 (m, 4H), 7.46–7.49 (d, 2H, J=9 Hz), 7.77 (s, 0.7H), 7.89–7.93 (dd, 2H, J=9, 2.4 Hz), 8.10 (s, 0.3H), 9.60 (s, 0.7H), 10.24 (s, 0.3H).;+H)$^+$, 582 (M+Na)$^+$, 558 (M–H)$^-$; Anal. calcd for C$_{24}$H$_{28}$N$_3$F$_3$O$_7$S: C, 51.52; H, 5.04; N, 7.51. Found: C, 51.60; H, 5.42; N,7.33.

EXAMPLE 217 hydroxy{3-(4-thiomorpholinyl)-1-[({4-[4-(trifluoromethoxy)phenoxy]phenyl}sulfonyl)methyl]propyl}formamide Ethyl 3-(4-thiomorpholinyl)propionate (prepared from thiomorpholine and ethylacrylate as described in Example 216A) was converted to the title compound following the procedures of Examples 126A–B and Examples 75B–D, substituting 4-(4'-trifluoromethoxyphenyloxy)-phenyl methyl sulfone for 4-(4'-trifluoromethylphenyl)-phenyl methyl sulfone.

$^1$H NMR (300 MHz, DMSO-d$_6$) δ 1.60–1.71 (m, 2H), 2.14–2.24 (m 2H), 3.44–3.68 (2H), 4.06–4.20 (m, 0.6H), 4.60–4.72 (m, 0.4H), 7.20–7.30 (m, 4H), 7.46–7.49 (d, 2H, J=9 Hz), 7.75 (s, 0.6H), 7.89–7.92 (2H), 8.09 (s, 0.4H), 9.60 (s, 0.6H), 10.25 (s, 0.4H); MS (ESI) m/e 535 (M+H)$^+$, 557 (M+Na)$^+$, 533 (M–H)$^-$; Anal. calcd for C$_{22}$H$_{25}$N$_2$F$_3$O$_6$S$_2$: C, 49.43; H, 4.71; N, 5.24. Found: C, 49.36; H, 4.62; N,4.97.

EXAMPLE 218 hydroxy{3-(4-methyl-1-piperazinyl)-1-[({4-[4-(trifluoromethoxy)phenoxy]phenyl}sulfonyl)methyl]propyl}formamide Ethyl 3-(4-methyl-1-piperazinyl)propionate (prepared from 1-Methylpiperazine and ethylacrylate as described in Example 216A) was converted to the title compound following the procedures of Examples 126A–B and Examples 75B–D, substituting 4-(4'-trifluoromethoxyphenyloxy)-phenyl methyl sulfone for 4-(4'-trifluoromethylphenyl)-phenyl methyl sulfone.

$^1$ H NMR (300 MHz, DMSO-d$_6$) δ 1.63–1.78 (m, 2H), 2.08–2.30 (m+s, 13H), 3.46–3.51 (1H), 3.63–3.69 (dd, 1H, J=1 5, 5.1 Hz), 4.12–4.17 (m, 0.6H), 4.65–4.70 (m, 0.4H), 7.19–7.23 (m, 2H), 7.26–7.29 (m, 2H), 7.46–7.48 (d, 2H, J=5.1 Hz), 7.72 (s, 0.6H), 7.88–7.91 (m, 2H), 8.05(s,0.4H); MS (ESI) m/e 532 (M+H)$^+$, 566 (M+Cl)$^-$, 530 (M–H)$^-$; Anal. calcd for C$_{23}$H$_{28}$N$_3$F$_3$O$_6$S.0.75H$_2$O: C, 50.68; H, 5.45; N, 7.70. Found: C, 50.60; H, 5.41; N,7.47.

EXAMPLE 219 hydroxy{2-tetrahydro-2H-pyran-4-yl-1-[({4-[4-(trifluoromethoxy)phenoxy]phenyl}sulfonyl)methyl}ethyl}formamide

EXAMPLE 219A ethyl tetrahydro-4H-pyran-4-ylideneacetate

A solution of tetrahydo-4H-pyran-4-one (5 g, 50 mmol) in CH2Cl2 (500 mL) was treated with (carbethoxymethylene)triphenylphosphorane (19.29 g, 55 mmol) stirred at reflux for 24 h, concentrated and purified via silica gel column chromatography eluting with 10% ethyl acetate/hexane to give 4.8 g of the title compound. MS (APCI): m/z 188 (M+NH$_4$)$^+$.

EXAMPLE 219B ethyl tetrahydro-2H-pyran-4-ylacetate

A mixture of Example 219A (1 g) and 10% Pd/carbon (100 mg) in methanol(30 mL) was stiffed under hydrogen for 3.5 h, then filtered through a pad of celite and concentrated to give 0.97 g of the title compound.

EXAMPLE 219C hydroxy{2-tetrahydro-2H-pyran-4-yl-1-[({4-[4-(trifluoromethoxy)phenoxy]phenyl}sulfonyl)methyl]ethyl}formamide Example 219B was converted to the title compound following the procedures of Examples 126A–B and Examples 75B–D, substituting 4-(4'-trifluoromethoxyphenyloxy)-phenyl methyl sulfone for 4-(4'-trifluoromethylphenyl)-phenyl methyl sulfone.

$^1$H NMR (300 MHz, DMSO-d$_6$) δ 0.95–1.20 (m, 2H), 1.22–1.40 (m, 3H), 1.53–1.67 (m, 2H), 3.08–3.25 (m, 2H), 3.37–3.43 (dd, 1H, J=14.7, 3 Hz), 3.55–3.66 (m, 1H), 3.75–3.79 (2H), 4.05–4.17 (m, 0.5H), 4.6–4.72 (m, 0.5H), 7.20–7.30 (m, 4H), 7.46–7.49 (d, 2H, J=9.3 Hz), 7.88–7.93 (2.5H), 8. 10 (s, 0.5H), 9.50 (s, 0.5H), 9.87 (s, 0.5H); MS (ESI) m/e 504 (M+H)$^+$, 521 (M+NH4)$^+$, 502 (M–H)$^-$; Anal. calcd for C$_{22}$H$_{24}$NF$_3$O$_7$S: C, 52.48; H, 4.80; N, 2.78. Found: C, 52.20; H, 4.79; N, 2.61.

EXAMPLE 220 AND 221 hydroxy[(1R)-1-[(2R)-1-(methylsulfonyl)pyrrolidinyl]-2-({4-[4-(trifluoromethoxy)phenoxy]phenyl}sulfonyl)ethyl]formamide and hydroxy[(1S)-1-[(2R)-1-(methylsulfonyl)pyrrolidinyl]-2-({4-[4-(trifluoromethoxy)phenoxy]phenyl}sulfonyl)ethyl]formamide

EXAMPLE 220A methyl 1-(methylsulfonyl)-2-pyrrolidinecarboxylate

D-proline methyl ester (Synthesis, 195, 772) was converted to the title compound follwing the mesylation conditions described in Example 223A.

EXAMPLE 220B hydroxy[(1R)-1-[(2R)-1-(methylsulfonyl)pyrrolidinyl]-2-({4-[4-(trifluoromethoxy)phenoxy]phenyl}sulfonyl)ethyl]formamide, The title compound was prepared following the procedures of Examples 145 and 146 substituting Example 220A for methyl (S)-2,2-dimethyl-1,3-dioxolane-4-carboxylate. m.p.89.6–93° C.

EXAMPLE 220

$^1$H NMR (300 MHz, DMSO-d$_6$) δ 1.63–1.89 (m, 4H), 288–3.01 (m+s+s, 4H), 3.63–3.83 (3H), 3.96–4.00 (t, 0.67H, J=8.5 Hz), 4.36–4.39 (t, 0.33H, J=9 Hz), 7.22–7.30 (m, 4H), 7.45–7.47 (dd, 2H, J=9 Hz), 7.83–7.91 (2.67H), 8.17 (s, 0.33H), 9.76 (s, 0.67H), 10.16 (s, 0.33H). MS (ESI) m/e 553 (M+H)$^+$, 570 (M+NH4)$^+$, 551 (M–H)$^-$; Anal. calcd for C$_{21}$H$_{23}$N$_2$F$_3$O$_8$S$_2$: C, 45.65; H, 4.20; N, 5.07. Found: C, 45.57; 4.17; N,4.75; [α]$_D$:–13.33°, (CHCl$_3$, c 0.3).

EXAMPLE 221 hydroxy[(1S)-1-[(2R)-1-(methylsulfonyl) pyrrolidinyl]-2-({4-[4-(trifluoromethoxy)phenoxy] phenyl}sulfonyl)ethyl]formamide The title compound was prepared following the procedures of Examples 145 and 146 substituting Example 220A for methyl (S)-2,2-dimethyl-1,3-dioxolane-4-carboxylate. $^1$H NMR (300 MHz, DMSO-d$_6$) δ 1.65–1.78 (m, 3H), 1.93–2.08 (m, 1H), 2.85 (s, 0.4H), 2.88 (s, 0.6H), 3.12–3.45 (m, 3H), 3.71–3.79 (m, 0.6H), 4.23–4.28 (m, 0.4H), 7.19–7.29 (m, 4H), 7.43–7.46 (d, 2H, J=8.7 Hz), 7.80 (s, 0.6H), 7.86–7.92 (m, 2H), 8.17 (s, 0.4H), 9.48 (s, 0.6H), 9.71 (s, 0.4H). MS (ESI) m/e 553 (M+H)$^+$, 570 (M+NH4)$^+$, 551 (M–H)$^-$; High resolution MS (FAB) Calc.m/z for (m+H)$^+$553.0926, observed m/z 553.0930. [α]$_D$:–12.33°, (CHCl$_3$, c 0.3).

EXAMPLE 222

2-(1,1-dioxidotetrahydro-2H-thiopyran-4-yl)-1-[({4-[4-(trifluoromethoxy)phenoxy]phenyl}sulfonyl) methyl]ethyl(hydroxy)formamide

EXAMPLE 222A methyl (1,1-dioxidotetrahydro-2H-thiopyran-4-yl) acetate

Tetrahydrothiopyran-4-one was converted to the title compound following the procedures described in Examples 219A (Wittig), 46D (oxone oxidation) and 219B (reduction).

EXAMPLE 222B 2-(1,1-dioxidotetrahydro-2H-thiopyran-4-yl)-1-[({4-[4-(trifluoromethoxy)phenoxy]phenyl}sulfonyl) methyl]ethyl(hydroxy)formamide Example 222A was converted to the title compound following the procedures of Example 213.

m.p.142.7–144.1° C. $^1$H NMR (300 MHz, DMSO-d$_6$) δ 1.28–2.14 (m, 7H), 2.99 (bs, 4H), 3.38–3.68 (m, 2H), 4.06–4.16 (m, 0.5H), 4.57–4.68 (m, 0.5H), 7.21–7.31 (m, 4H), 7.46–7.49 (d, 2H, J=8.4 Hz), 7.87–7.92 (dd, 2H, J=12, 3 Hz), 7.90 (s, 0.5H), 8.12 (s, 0.5H), 9.52 (brs, 0.5H), 9.91 (brs, 0.5H); MS (ESI) m/e 552 (M+H)$^+$, 569 (M+NH4)$^+$, 574 (M+Na)+, 550 (M–H)$^-$; Anal. calcd for C$_{22}$H$_{24}$NF$_3$O$_8$S$_2$: C, 47.91; H, 4.39; N, 2.54. Found: C, 47.88; H, 4.30; N,2.31.

EXAMPLE 223 hydroxy{2-[4-(methylsulfonyl)-1-piperazinyl]-1-[({4-[4-(trifluoromethoxy)phenoxy]phenyl}sulfonyl) methy]ethyl}formamide

EXAMPLE 223A

Ethyl 4-methylsulfonyl-1-piperazine acetate

An ice cold solution of 1-ethoxycarbonylmethylpiperazine (5 g, 29 mmol), mesyl chloride (3.37 mL, 43.5 mmol) and triethyl amine (6.05 mL, 43.5 mmol) in CH2Cl2 (150 mL) was stirred at 0° C. for 5 min then at rt for 30 min, then partitioned between CH2Cl2 and aq. sat. NH4Cl. The organics were washed with aq. NaHCO3, brine, dried (Na2SO4), filtered and concentrated to give 6.88 g of the title compound. MS (APCI) m/z 251 (M+H)$^+$.

EXAMPLE 223B hydroxy{2-[4-(methylsulfonyl)-1-piperazinyl]-1-[({4-[4-(trifluoromethoxy)phenoxy]phenyl}sulfonyl) methyl]ethyl}formamide Example 223A was converted to the title compound following the procedures of Examples 126-A,B and 75-B, C,D, substituting 4-(4'-trifluoromethoxyphenyloxy)-phenyl methyl sulfone for 4-(4'-trifluoromethylphenyl)-phenyl methyl sulfone.

m.p.143.1–144.2° C. $^1$H NMR (300 MHz, DMSO-d$_6$) δ 2.25–2.47 (m, 4H), 2.85–2.86 (s, 3H), 2.90–3.06 (bs, 4H), 3.41–3.64 (m, 2H), 4.13–4.17 (m, 0.57H), 4.65–4.68 (m, 0.43H), 7.21–7.29 (m, 4H), 7.46–7.49 (d, 2H, J=8.4 Hz), 7.87–7.93 (2.57H), 8.14 (s, 0.43H), 9.50 (bs, 0.57H), 9.90 (bs, 0.43H); MS (ESI) m/e 582 (M+H)$^+$, 604 (M+Na)$^+$, 580 (M–H)$^-$, 616 (M+Cl)$^-$; Anal. calcd for C$_{22}$H$_{26}$N$_3$F$_3$O$_8$S$_2$: C, 45.43; H, 4.51; N, 7.22. Found: C, 45.44; H, 4.38; N,7.15.

EXAMPLE 224 hydroxy{3-[4-(methylsulfonyl)-1-piperazinyl]-1-[({4-[4-(trifluoromethoxy)phenoxy]phenyl}sulfonyl) methyl]propyl}formamide tert-Butyl 1-piperazinecarboxylate was reacted with ethyl acrylate as in Example 216A, then coupled with 4-(4'-trifluoromethoxyphenyloxy)-phenyl methyl sulfone as in Example 126A and reduced as in Example 126B. The N-tert-butylcarboxylate group was then removed under acidic conditions(HCl in dioxane). Treatment with mesyl chloride,followed by hydroxylamine addition and formylation as in Example 75B,C and D gave the title compound.

m.p.165.9–167.2° C. $^1$H NMR (300 MHz, DMSO-d$_6$) δ 1.61–1.74 (m, 2H), 2.10–2.46 (m, 6H), 2.87 (s, 3H), 2.94–3.13 (m, 4H), 3.44–3.72 (2H), 4.10–4.22 (m, 0.7H), 4.63–4.73 (m, 0.3H), 7.21–7.30 (m, 4H), 7.46–7.49 (d, 2H, J=8.4 Hz), 7.78 (s, 0.7H), 7.89–7.92 (2H), 8.10 (s, 0.7H), 10.09 (s, 0.3H); MS (ESI) m/e 596 (M+H)$^+$, 618 (M+Na)$^+$, 594 (M–H)$^-$; Anal. calcd for C$_{23}$H$_{28}$N$_3$F$_3$O$_8$S$_2$: C, 46.55; H, 4.81; N, 6.97. Found: C, 46.38; H, 4.74; N,7.05.

EXAMPLE 225

2-[4-(2,2-dimethylpropanoyl)-1-piperazinyl]-1-[({4-[4-(trifluoromethoxy)phenoxy]phenyl}sulfonyl) methyl]ethyl(hydroxy)formamide Ethyl 4-(2,2-dimethylpropanoyl)-1-piperazinylacetate (prepared from 1-ethoxycarbonylmethylpiperazine and tri-methylacetyl chloride) was converted to the title compound following the procedures of Examples 126A–B and Examples 75B–D, substituting 4-(4'-trifluoromethoxyphenyloxy)-phenyl methyl sulfone for 4-(4'-trifluoromethylphenyl)-phenyl methyl sulfone.

$^1$H NMR (300 MHz, DMSO-d$_6$) δ 1.16 (s, 9H), 2.12–3.43 (m, 6H), 3.32–3.48 (m, 4H), 3.53–3.64 (m, 2H), 4.11–4.15 (m, 0.6H), 4.66–4.69 (m, 0.4H), 7.22–7.29 (4H), 7.47–7.49 (d, 2H, J=8.4 Hz), 7.89–7.92 (d, 2H, J=7.8 Hz), 7.94 (s, 0.6H), 8.16 (s, 0.4H), 9.51 (s, 0.6H), 9.91 (s, 0.4H); MS (ESI) m/e 588 (M+H)⁺, 610 (M+Na)⁺, 586 (M−H)⁻, 622 (M+Cl)⁻; Anal. calcd for $C_{26}H_{32}N_3F_3O_7S$: C, 53.14; H, 5.49; N, 7.15. Found: C, 53.11; H, 5.60; N, 6.88.

EXAMPLE 226

2,2-dimethyl-1-[({4-[4-(trifluoromethoxy)phenoxy]phenyl}sulfonyl)methyl]propyl(hydroxy)formamide Methyl trimethylacetate was converted to the title compound following the procedures of Example 213.

m.p.159.5–160.1° C. ¹H NMR (300 MHz, DMSO-d₆) δ 0.79 (s, 3.6H), .83 (s, 5.4H), 3.47–3.72 (m, 2.6H), 4.18–4.21 (d, 0.4H, J=8.7 Hz), 7.20–7.30 (m, 4H), 7.45–7.49 (2H), 7.80 (s, 0.6H), 7.89–7.95 (m, 2H), 8.12 (s, 0.4H), 9.55 (s, 0.6H), 9.94 (s, 0.4H); MS (ESI) m/e 462 (M+H)⁺, 479 (M+NH₄)⁺, 460 (M−H)⁻; Anal. calcd for $C_{20}H_{22}NF_3O_6S$: C, 52.06; H, 4.81; N, 3.04. Found: C, 51.97; H, 4.78; N,2.98.

EXAMPLE 227

1-cyclopropyl-2-({4-[4-(trifluoromethoxy)phenoxy]phenyl}sulfonyl)ethyl(hydroxy)formamide Cyclopropane carboxaldehyde converted to the title compound following the procedures of Example 125, substituting 4-(4'-trifluoromethoxyphenyloxy)-phenyl methyl sulfone for 4-(4'-trifluoromethylphenyl)-phenyl methyl sulfone m.p.136.2–136.9° C. ¹H NMR (300 MHz, DMSO-d₆) δ 0.11–0.24(m, 1 H), 0.33–0.46 (m, 2H), 0.49–0.55 (m, 1H), 1.10–1.19 (m, 1H), 3.45–3.51 (dd, 1H, J=2.4, 15.3 Hz), 2.76–3.88 (m, 1H), 7.19–7.29 (m, 4H), 7.46–7.49 (d, 2H, J=9.3 Hz), 7.79 (s, 0.66H), 7.87–7.91 (dd, 2H, J=2.1, 8.7 Hz), 8.08 (s, 0.34H), 9.59 (s, 0.66H), 10.02 (s, 0.34H); MS (ESI) m/e 446 (M+H)⁺, 468 (M+Na)⁺, 444 (M−H)⁻. 480 (M+Cl)⁻; Anal. calcd for $C_{19}H_{18}NF_3O_6S$: C, 51.23; H, 4.07; N, 3.14. Found: C, 51.15; H, 4.11; N,3.00.

EXAMPLE 228

2-(1,4-dioxaspiro[4.5]dec-8-yl)-1-[({4-[4-(trifluoromethoxy)phenoxy]phenyl}sulfonyl)methyl]ethyl(hydroxy)formamide Ethyl 1-cyclohexane 4-ethylene ketal-acetate (prepared from 1,4-dioxaspiro[4,5]decan-8-one following the procedures of Examples 219A—except substituting triethylphosphonoacetate for (carbethoxymethylene)triphenylphosphorane—and 219B) was converted to the title compound following the procedures of Example 213.

m.p.139.5–141.2° C. ¹H NMR (300 MHz, DMSO-d₆) δ 0.93–1.70 (m, 11H), 3.51–3.65 (m, 1H), 3.81–3.82 (s+s, 4H), 4.02–4.10 (m, 0.5H), 4.57–4.67 (m, 0.5H), 7.19–7.31 (m, 4H), 7.46–7.49 (d, 2H, J=9.3 Hz), 7.88–7.93 (m, 2.5H), 8.11 (s, 0.5H), 9.50 (s, 0.5H), 9.85 (s, 0.5H); MS (ESI) m/e 560 (M+H)⁺, 577 (M+NH₄)⁺, 582 (M+Na)⁺, 558 (M−H)⁻. 594 (M+Cl)⁻; Anal. calcd for $C_{25}H_{28}NF_3O_8S$: C, 53.66; H, 5.04; N, 2.50. Found: C, 53.65; H, 5.19; N, 2.29.

EXAMPLE 229 hydroxy[1-[(4S)-2-oxo-1,3-oxazolidin-4-yl]-2-({4-[4-(trifluoromethoxy)phenoxy]phenyl}sulfonyl)ethy]formamide The title compound was prepared as a mixture of diastereomers following the procedures of Examples 145 substituting methyl (4R)-2-oxo-1,3-oxazolidine-4-carboxylate (Tet. Lett. 1994, 2397) for methyl (S)-2,2-dimethyl-1,3-dioxolane-4-carboxylate and using the formylation conditions decribed in Example 213B. ¹H NMR (400MHz, DMSO-d6): δ 3.42–3.60 (m, 1H), 3.68–4.00 (m, 3H), 4.05–4.60 (m, 2H), 7.20–7.32 (m, 4H), 7.47 (d, 2H, J=6.6 Hz), 7.80–7.96 (m, 3.5H), 8.15 (s, 0.5H), 9.53 (s, 0.25H), 9.71 (s, 0.25H), 9.97 (s, 0.25H), 10.12 (s, 0.25H). MS (ESI, +Q1MS) 508 (M+NH4). Anal. Calcd for: $C_{19}H_{17}F_3N_2O_8S$: C, 46.53; H, 3.49; N, 5.71. Found: C, 46.26; H, 3.43; N, 5.57.

EXAMPLES 230 hydroxy[(1S)-1-[(2R)-tetrahydro-2-furanyl]-2-({4-[4-(trifluoromethoxy)phenoxy]phenyl}sulfonyl)ethyl]formamide and

EXAMPLE 231 hydroxy[(1R)-1-[(2R)-tetrahydro-2-furanyl]-2-({4-[4-(trifluoromethoxy)phenoxy]phenyl}sulfonyl)ethyl]formamide Examples 230 and 231 were prepared following the procedures of Examples 145 and 146 substituting methyl (R)-tetrahydro-2-furoate for methyl (S)-2,2-dimethyl-1,3-dioxolane-4-carboxylate and using the formylation conditions described in Example 213B.

EXAMPLE 230 mp 121–122° C.; [α]$_D$=2.50°(c 1.08, MeOH). ¹H NMR (500MHz, DMSO-d6): δ 1.37–1.45 (m, 1H), 1.71–1.82 (m, 2H), 1.88–1.99 (m, 1H), 3.28 (m, 0.6H), 3.56–3.73 (m, 4H), 3.81–3.91 (m, 2H), 4.46 (t, 0.4H, J=10.0 Hz), 7.22 (d, 2H, J=9.0 Hz), 7.25–7.29 (m, 2H), 7.46 (d, 2H, J=8.5 Hz), 7.77 (s, 0.6H), 7.90 (d, 2H, J=9.0 Hz), 7.93 (d, 2H, J=8.5 Hz), 8.12 (s, 0.4H), 9.45 (s, bs, 0.6H), 9.82 (s, bs, 0.4H) MS (ESI, +Q1MS) m/z 476 (M+H)⁺, 493 (M+NH₄)⁺; Anal. Calcd for: $C_{20}H_{20}F_3NO_7S$: C, 50.52; H, 4.24; N, 2.95. Found: C, 50.69; H, 4.47; N, 2.89.

EXAMPLE 231 mp 142.5–143.5° C.; [α]$_D$=−23.8°(c=0.98, MeOH);
¹H NMR (400MHz, DMSO-d6): δ 1.47–3.93 (m, 4H), 3.38–3.93 (m, 5.5H), 4.36 (t, 0.5H, J=8.8 Hz), 7.20–7.30 (m, 4H), 7.46 (d, 2H, J=8.88 Hz), 7.87–7.92 (m, 2.5H), 8.11 (s, 0.5H), 9.63 (s, 0.5H), 10.05 (s, 0.5H); MS (ESI, +Q1MS) m/z 476 (M+H)⁺, 493 (M+NH₄)⁺; Anal. Calcd for: $C_{20}H_{20}F_3NO_7S$: C, 50.52; H, 4.24; N, 2.95. Found: C, 50.76; H, 4.34; N, 2.77.

EXAMPLE 232 hydroxy[1-[(4S)-3-methyl-2-oxo-1,3-oxazolidin-4-yl]-2-({4-[4-(trifluoromethoxy)phenoxy]phenyl}sulfonyl)ethyl]formamide The title compound was prepared as a mixture of diastereomers following the procedures of Examples 145 substituting methyl (4R)-3-methyl-2-oxo-1,3-oxazolidine-4-carboxylate for methyl (S)-2,2-dimethyl-1,3-dioxolane-4-carboxylate and using the formylation conditions described in Example 213B.

¹H NMR (400MHz, DMSO-d6): δ 2.69 (s, 1.5H)),2.76 (s, 1.5H), 3.54–3.65 (m, 1H), 3.79–3.94 (m, 2H), 4.21 (t, 2H, J=8.8 Hz), 4.27–4.35 (m, 2H), 4.49 (m, 0.5H), 4.89 (m, 0.5H), 7.22–7.32 (m, 4H), 7.47 (d, 2H), 7.90–7.98 (m, 2.5H), 8.17 (s, 0.5H), 9.88 (s, bs, 0.5H), 10.20 (s, bs, 0.5H). MS (ESI, Q+1MS) 505 (M+H), 522 (M+NH4). Anal. Calcd for: C20H19F3N2O8S: C, 47.62; H, 3.80; N, 5.55. Found: C, 47.95; H, 4.03; N, 5.34.

EXAMPLE 233 hydroxy[1-[(2R)-5-oxotetrahydro-2-furanyl-2-({4-[4-(trifluoromethoxy)phenoxy]phenyl}sulfonyl) ethyl]formamide The title compound was prepared as a mixture of diastereomers following the procedures of Examples 145 substituting methyl (2R)-5-oxotetrahydro-2-furan carboxylate for methyl (S)-2,2-dimethyl-1,3-dioxolane-4-carboxylate and using the formylation conditions decribed in Example 213B.

$^1$H NMR (300MHz, DMSO-d6): δ 1.67–1.83 (m, 1H), 2.20–2.6 0 (m, 3H), 3.45–3.80 (m, 2H), 4.25–4.70 (m, 2H), 7.20–7.32 (m, 4H), 7.48 (d, 2H, J=9.0 Hz), 7.80 (s, 0.6H), 7.88–7.96 (m, 2H), 8.17 (s, 0.4H), 9.70 (s, bs, 0.6H), 10.10 (s, bs, 0.4H). MS (ESI, +Q1MS) 490 (M+H), 507 (M+NH4). Anal. Calcd for: C20H18F3NO8SC: 49.08; H, 3.71; N, 2.86. Found: C, 49.20; H, 3.74; N, 2.76.

EXAMPLE 234 hydroxy[1-[1-(methylsulfonyl)-4-piperidinyl]-2-({4-[4-(trifluoromethoxy)phenoxy]phenyl}sulfonyl) ethyl]formamide Methyl 1-methylsulfonyl-4 piperidinylcarboxylate (prepared form 4-piperidine carboxylic acid methyl ester and mesyl chloride as in Example 223A) was converted to the title compound following the procedures of Example 213.

mp178–179° C. $^1$H NMR (300MHz, DMSO-d6): δ 0.92–1.28 (m, 2H), 1.52–1.70 (m, 2H), 1.77 (d, 1H, J=12 Hz), 2.58 (m, 2H), 3.45–3.72 (m, 4H), 3.86 (t, 0.7H, J=9.0 Hz), 4.32 (t, 0.3H, J=9.0 Hz), 7.21–7.30 (m, 4H), 7.47 (d, 2H, J=9.3 Hz), 7.81 (s, 0.7H), 7.88–7.95 (m, 2H), 8.14 (s, 0.3H), 9.62 (s, bs, 0.7H), 9.97 (s, bs, 0.3H) MS (ESI, +Q1MS) 567 (M+H), 584 (M+NH4) Anal. Calcd for: C22H25F3N2O8S2: C, 46.64; H, 4.45; N, 4.94. Found: C, 46.77; H, 4.38; N, 4.90.

EXAMPLE 235 hydroxy[1-(1-isobutyryl-4-piperidinyl)-2-({4-[4-(trifluoromethoxy)phenoxy]phenyl}sulfonyl)ethyl] formamide Methyl 1-isobutyryl -4 piperidinylcarboxylate (prepared form 4-piperidine carboxylic acid methyl ester and isobutyryl chloride) was converted to the title compound following the procedures of Example 213.

mp 139–140° C. $^1$H NMR (300MHz, DMSO-d6): δ 0.62–1.20 (m, 8H), 1.43–1.58 (m, 3H), 2.38 (m, 1H), 2.78–2.95 (m, 2H), 3.50–4.00 (m, 4H), 4.20–4.42 (m, 1H), 7.25 (m, 4H), 7.48 (d, 2H, J=8.7 Hz), 7.72–8.18 (m, 3H), 9.60 (s, bs, 0.7H), 9.97 (s, bs, 0.3H). MS (ESI, +Q1MS) 559 (M+H). Anal. Calcd for: C25H29F3N2O7S: C, 53.76; H, 5.23; N, 5.02. Found: C, 53.80; H, 5.26; N, 4.91.

EXAMPLE 236 hydroxy{2-(4-morpholinylsulfonyl)-1-[({4-[4-(trifluoromethoxy)phenoxy]phenyl}sulfonyl)methyl] ethyl}formamide

EXAMPLE 236A

O-ethyl S-(4-(4-(trifluoromethoxy)phenoxy)phenyl) dithiocarbonate

Reaction of 4-fluoro-nitrobenzene with 4-trifluoromethoxyphenol in the presence of KOtBu as described in Example 74A, followed by reduction of the nitro group (hydrogen, 10% Pd/C) gave 4-(4-trifluoromethoxyphenoxy)-aniline. The aniline (4.58 g, 17 mmol) was dissolved in conc. HCl (3.1 mL) and ice (4.5 g) cooled to –5 C., then treated with a solution of NaNO2 (1.17 g, 17 mmol) in water (7mL) which was added dropwise. The cold soltion was added to an aqueous (7 mL) solution of potassium xanthate (5.46 g, 34 mmol) and the resulting mixture was heated at 70 C for 2 h, then allowed to cool to rt and partitioned between EtOAc and water. The organic extract was dried (MgSO4), filt ered and concentrated to give the title compound

EXAMPLE 236B methyl ({4-[4-(trifluoromethoxy)phenoxy] phenyl}sulfanyl)acetate A mixture of Example 236 A (5.0 g, 13.95 mmol) and powdered KOH (2 g, 35 mmol) in EtOH (50 mL) was heated to 80 C fro 2 h, then cooled to rt and treated with powder KOH (1 g) and bromoacetic acid (1.94 g, 13.9 mmol). Stirred overnight at rt then at 80 C for 3 h, cooled in an ice bath and quenched with 1N HCl. Diluted with water, extracted 3 times with EtOAc. Combined organics were washed with water, brine, dried and concentrated. The oily residue was dissolved in MeOH (50 mL), cooled to 0 C, then treated with SO12 (1.5 mL) and stirred overnight at rt. Quenceh with water, extracted 3× with EtOAc. Combined organics were washed with water, brine, dried, concentrated and purified via silica gel chromatography eluting with 8 to 1 hexane/EtOAc to give 2.93 g (59%) of the title compound. Rf=0.37 (Hexane: EtOAc 8 : 1).

EXAMPLE 236C 1-(4-morpholinylsulfonyl)-3-({4-[4-(trifluoromethoxy)phenoxy]phenyl}sulfanyl)acetone Deprotonation of N-Methylsulfonyl morpholine with n-BuLi followed by reaction with Example 236B, as described in Example 126A gave the title compound in 55% yield.

EXAMPLE 236D hydroxy{2-(4-morpholinylsulfonyl)-1-[({4-[4-(trifluoromethoxy)phenoxy]phenyl}sulfonyl)methyl] ethyl}formamide Example 236C was converted to the title compound following the sequence of reaction described in Example 126B, 46D, 75B, 75C, 75D and 213B._ mp 123–125° C. $^1$H NMR (300MHz, DMSO-d6): δ 3.03–3.15 (m, 4H), 3.37–3.41 (m, 1H), 3.43–3.82 (m, 7H), 4.51 (m, 0.5H), 5.04 (m, 0.5H), 7.21–7.30 (m, 4H), 7.48 (d, 2H, J=9.0 Hz), 7.86 (s, 0.5H), 7.90 (dd, 2H, J=9.0 Hz, 3.0 Hz), 8.12 (s, 0.5H), 9.82 (s, bs, 0.5H), 10.12 (s, bs, 0.5H); MS (ESI, +Q1MS) 569 (M+H), 586 (M+NH4), 591 (M+Na) Anal. Calcd for: C21H23F3N2O9S2: C, 44.36; H, 4.08; N, 4.93. Found: C, 44.52; H, 4.09; N, 4.86.

EXAMPLE 237 hydroxy{2-methyl-2-(4-morpholinylsulfonyl)-1-[({4-[4-(trifluoromethoxy)phenoxy]phenyl}sulfonyl) methyl]propyl}formamide The title compound was prepared following the procedures of Example 236 substituting N-isopropylsulfone morpholine in place of N-Methylsulfonyl morpholine.

¹H NMR (300 MHz, DMSO-d6): δ 1.18–1.35 (m, 6H), 3.15–3.32 (m, 3H), 3.50–3.65 (m, 5H), 3.76–3.96 (m, 2H), 4.33 (d, 0.5H, J=6.0 Hz), 5.06 (d, 0.5H, J=6.0 Hz), 7.22–7.30 (m, 4H), 7.45–7.50 (m, 2H), 7.82–7.90 (m, 2H), 7.96 (s, 0.5H), 8.17 (s, 0.5H), 9.95 (s, bs, 0.5H), 10.28 (s, bs, 0.5H). MS (ESI, +Q1MS) 597 (M+H), 614 (M+NH4)

EXAMPLE 238 hydroxy{8-[({4-[4-(trifluoromethoxy)phenoxy] phenyl}sulfonyl)methyl]-1,4-dioxaspiro[4.5]dec-8-yl}formamide The title compound was prepared following the procedures of Example 75 substituting 1,4-cyclohexanedione-mono-ethylene ketal for propionaldehyde and 4-(4'-trifluoromethoxyphenyloxy)-phenyl methyl sulfone for 4-(4'-methoxyphenyl)-phenyl methyl sulfone.

mp 133–134° C. ¹H NMR (300 MHz, DMSO-d6): δ 160 (m, bs, 4H), 1.86–2.02 (m, bs, 2H), 2.20–2.31 (m, bs, 2H), 3.60 (s, bs, 2H), 3.86 (m, 4H), 7.18–7.32 (m, 4H), 7.46 (d, 2H, J=9.3 Hz), 7.90 (m, 2H), 8.21 (s, 1H), 9.45 (s, bs, 1H). MS (ESI, +Q1MS) 532 (M+H), 549 (M+NH4), 554 (M+Na). Anal. Calcd for: C23H24F3NO8S: C, 51.97; H, 4.55; N, 2.64. Found: C, 51.90; H, 4.41; N, 2.60.

EXAMPLE 239

1,1-dimethyl-2-({4-[4-(trifluoromethoxy)phenoxy] phenyl}sulfonyl)ethyl(hydroxy)formamide The title compound was prepared following the procedures of Example 75 substituting acetone for propionaldehyde and 4-(4'-trifluoromethoxyphenyloxy)-phenyl methyl sulfone for 4-(4'-methoxyphenyl)-phenyl methyl sulfone, and using the formylation conditions of Example 213B.

mp=128.5–129.0° C. ¹H NMR (300 MHz, DMSO) δ 1.50 (s, 6H), 3.64 (s, 2H), 7.17–7.32 (m, 4H), 7.46 (d, 2H, J=9.0 Hz), 7.85–7.92 (m, 2H), 8.11 (s, 1H), 9.40 (s, 1 H). MS (ESI+) 434 (M+H), 451 (M+NH4), 456 (M+Na). Anal. Calcd for: C18H18NO6SF3 C, 49.88; H, 4.19; N, 3.23. Found: C, 50.15; H, 4.38; N, 2.95. TFE-F formylation.

EXAMPLE 240 hydroxy{2-(2-thienyl)-1-[({4-[4-(trifluoromethoxy) phenoxy]phenyl}sulfonyl)methyl]ethyl}formamide Ethyl 2-thiopheneacetate was converted to the title compound following the procedures of Examples 126-A,B and 75-B,C,D, substituting 4-(4'-trifluoromethoxyphenyloxy)-phenyl methyl sulfone for 4-(4'-trifluoromethylphenyl)-phenyl methyl sulfone.

1H NMR (300 MHz, DMSO-d6) δ 2.98–3.17 (m, 2H), 3.41–3.53 (m, 1H), 3.63–3.80 (m 1H), 4.15–4.25 (m, 0.5H), 4.68–4.79 (m, 0.5H), 6.81–6.96 (m, 2H), 7.16–7.38 (m, 5H), 7.48 (d, 2H, J=9.0 Hz), 7.62 (s, 0.5H), 7.83–7.91 (m, 2H), 8.07 (s, 0.5H), 9.67 (s, 0.5H), 10.10 (s, 0.5H). MS (ESI+) 502 (M+H), 519 (M+NH4). Anal. Calcd for: C21H18NO6S2F3 C, 50.29; H, 3.61; N, 2.79. Found: C, 49.99; H, 3.53; N, 2.69.

EXAMPLE 241

(1S)-1-[(4S)-2,2-dimethyl-1,3-dioxolan-4-yll -2-{[4-(4-methoxyphenoxy)phenyl]sulfonyl}ethyl(hydroxy) formamide The title compound was prepared following the procedures of Examples 139 and 140, starting with 4-(4'-methoxyphenyloxy)-phenyl methyl sulfone, but using the formylation conditions described in Example 213B.

mp: 167.8–169° C. [α]$_D$=+4.4°(c=0.4, MeOH). 1H NMR (300 MHz, DMSO-d6) δ 1.20–1.32 (m, 6H), 3.24–3.35 (m, 1H), 3.58–3.70 (m, 2H), 3.78 (s, 3H), 3.92–4.13 (m, 2.5H), 4.57 (t, 0.5H, J=8.1 Hz), 7.00–7.14 (m, 6H), 7.84 (dd, 2H, J=12.3,2.1 Hz), 7.89 (s, 0.5H), 8.13 (s, 0.5H), 9.64 (s, 0.5H), 10.02 (s, 0.5H). MS (ESI+) 452 (M+H), 469 (M+NH4). Anal. Calcd for: C21H25NO8S C, 55.87; H, 5.58; N, 3.10. Found: C, 55.72; H, 5.59; N, 2.96.

EXAMPLE 242

1,2,3-trideoxy-2-[formyl(hydroxy)amino]-4,5-O-(1-methylethylidene)-1-({4-[4-(trifluoromethoxy) phenoxy]phenyl}sulfonyl)-D-threo-pentitol The title compound was prepared following the procedures of Example145, starting with 4-(4'-methoxyphenyloxy)-phenyl methyl sulfone and methyl [(4S)-2,2-dimethyl-1,3-dioxolan-4-yl]acetate.

1H NMR (300 MHz, DMSO-d6) δ 1.18–1.27 (m, 6H), 1.56–1.74 (m, 1H), 1.74–1.93 (m, 1H), 3.26–3.71 (m, 3H), 3.81–3.94 (m, 2H), 4.12–4.23 (m, 0.5H), 4.66–4.76 (m, 0.5H), 7.19–7.31 (m, 4H), 7.48 (d, 2H, J=9.0 Hz), 7.76 (s, 0.5H), 7.87–7.94 (m, 2H), 8.12 (s, 0.5H), 9.59 (s, 0.5H), 9.88 (s, 0.5H). MS (ESI+) 520 (M+H), 537 (M+NH4). Anal. Calcd for: C22H24NO8SF3C, 50.86; H, 4.65; N, 2.69. Found: C, 50.94; H, 4.89; N, 2.42.

EXAMPLE 243

(1S)-2-{[4-(4-chlorophenoxy)phenyl]sulfonyl}-1-[(4S)-2,2-dimethyl-1,3-dioxolan-4-yl]ethyl(hydroxy) formamide The title compound was prepared following the procedures of Examples 139 and 140, starting with 4-(4'-chlorophenyloxy)-phenyl methyl sulfone.

mp: 157–158° C. [α]$_D$=+2.2°(c=0.4, MeOH). 1H NMR (DMSO) δ 1.19–1.33 (m, 6H), 3.28–3.36 (m, 1H), 3.50–3.72 (m, 2H), 3.92–4.13 (m, 2.5H), 4.55 (t, 0.5H, J=8.1 Hz), 7.15–7.24 (m, 4H), 7.49–7.56 (m, 2H), 7.81 (s, 0.5H), 7.90 (t, 2H, J=9.3 Hz), 8.12 (s, 0.5H), 9.62 (s, 0.5H), 10.03 (s, 0.5H). MS (ESI+) 456 (M+H), 473 (M+NH4), 478 (M+Na). Anal. Calcd for: C20H22NO7SCl C, 52.69; H, 4.86; N, 3.07. Found: C, 52.67; H, 4.79; N, 2.87.

EXAMPLE 244

2-[formyl(hydroxy)amino]-N,N-dimethyl-3-({4-[4-(trifluoromethoxy)phenoxy]phenyl}sulfonyl) propanamide

EXAMPLE 244A ethyl (2E)-3-({4-[4-(trifluoromethoxy)phenoxy] phenyl}sulfonyl)-2-propenoate The title compound was prepared from ethyl glyoxalate and 4-(4'-trifluoromethoxyphenyloxy)-phenyl methyl sulfone following the procedures of Examples 126A, 126B and 75B.

EXAMPLE 244B (2E)-N,N-dimethyl-3-({4-[4-(trifluoromethoxy) phenoxy]phenyl}sulfonyl)-2-propenamide A solution of Example 244A (3 g, 7.2 mmol) in THF (180 mL) and isopropanol (70 mL) was treated with LiOH (1M, 28 mL), stirred for 2 h, then acidified with 1N HCl and extracted twice with ether. The combined organices were washed with brine, dried and concentrated. The crude residue was recrystallized from hexane-ether-ethyl acetate to give 1.5 g of the acid. A 0 C solution of the acid (1.24 g) in THF (80 mL) was sequentially treated with Me2NH (2M in THF, 1.9 mL) BOP-Cl (1 g, 3.9 mmol) and Et3N (1.78 mL, 12.7 mmol), then stirred at rt for 16 h. The reaction was partitioned between 1N HCl and ether (twice). The combined ethereal extracts were washed with aq. NaHCO3, brine, dried (MgSO4), filtered and concentrated to afford 0.95 g of the title compound.

EXAMPLE 244C

2-[formyl(hydroxy)amino]-N,N-dimethyl-3-({4-[4-(trifluoromethoxy)phenoxy]phenyl}sulfonyl)propanamide Example 245B was converted to the title compound following the procedures of Examples 75C and 75D.

mp: 138–140° C. 1H NMR (300 MHz, DMSO-d6) δ 2.76–3.00 (m, 6H), 3.60–3.89 (m, 2H), 5.27–5.34 (m, 0.5H), 5.43–5.51 (m, 0.5H), 7.22 (d, 2H, J=8.7 Hz), 7.26–7.33 (m, 2H), 7.48 (d, 2H, J=9.0 Hz), 7.86–7.94 (m, 2H), 8.10–8.15 (m, 1H), 9.70 (s, 1H). MS (ESI+) 477 (M+H), 494 (M+NH4), 499 (M+Na). Anal. Calcd for: C19H19N2O7SF3 C, 47.90; H, 4.01; N, 5.87. Found: C, 47.72; H, 3.97; N, 5.64.

EXAMPLE 245 hydroxy{2-(4-morpholinyl)-2-oxo-1-[({4-[4-(trifluoromethoxy)phenoxy]phenyl}sulfonyl)methyl]ethyl}fornamide The title compound was prepared from Example 244A substituting morpholine in place of dimethylamine.

mp =163.8–164.5° C. 1H NMR (300 MHz, DMSO-d6) δ 3.25–3.43 (m, 4H), 3.44–3.64 (m, 4H), 3.66–3.79 (m, 1H), 3.80–3.89 (m, 1H), 5.35–5.42 (m, 0.5H), 5.46 (t, 0.5H, J=4.2 Hz), 7.22 (d, 2H, J=6.6 Hz), 7.27 (d, 2H, J=6.6 Hz), 7.47 (d, 2H, J=6.6 Hz), 7.90 (d, 2H, J=6.6 Hz), 8.10–8.15 (m, 1H), 9.73 (s, 0.5H), 10.26 (s, 0.5H). MS (ESI+) 519 (M+H), 536 (M+NH4), 541 (M+Na). Anal. Calcd for: C21H21N2O8SF3 C, 48.56; H, 4.06; N, 5.23. Found: C, 48.64; H, 4.08; N, 5.40

EXAMPLE 246

N-[2-[formyl(hydroxy)amino]-3-({4-[4-(trifluoromethoxy)phenoxy]phenyl}sulfonyl)propyl]-N-methylmethanesulfonamide Ethyl [methyl(methylsulfonyl)amino]acetate (prepared from sarcosine ethyl ester and mesyl chloride as in Example 223a) was converted to the title compound following the procedures of Examples 126-A,B and 75-B,C,D, substituting 4-(4'-trifluoromethoxyphenyl)-phenyl methyl sulfone for 4-(4'-trifluoromethylphenyl)-phenyl methyl sulfone.

mp135–138° C. 1H NMR (CDCl3) δ 8.28 (s, ½H), 7.95 (s, ½H), 7.82–7.90 (m, 2H), 7.23–7.31 (m, 2H), 7.05–7.14 (m, 2H), 5.02–5.12 (m, ½H), 4.45 (bs, ½H), 3.42–3.75 (m, 2H), 3.23–3.40 (m, 2H), 2.80–2.95 (m, 6H) MS (ESI(–)) 525 (M–H). Anal. Calcd for: C19H21F3N2O8S2 C. 43.34; H, 4.02; N, 5.32; F,]0.82; S,12.17. Found: C,43.06; H, 4.18; N, 5.23; F, 11.11; S,12.45.

EXAMPLE 247

(1S)-1-[(4S)-2,2-dimethyl-1,3-dioxolan-4-yl]-2-({4-[4-(trifluoromethyl)phenoxy]phenyl}sulfonyl)ethyl(hydroxy)formamide The title compound was prepared following the procedures of Examples 139 and 140, starting with 4-(4'-trifluoromethylphenyloxy)-phenyl methyl sulfone, but using the formylation conditions described in Example 213B.

mp.141–143° C. [α]$_D$=+2.0°(c=0.1, MeOH). 1H NMR (DMSO-d6) δ 9.50–9.85 (m, 1H), 8.13 (s, ½H), 7.91–7.99 (m, 2H), 7.77–7.85 (m, 2½H), 7.27–7.35 (m, 4H), 4.57 (t, ½H, J=8 Hz), 3.95–4.15 (C, 2½H), 3.62–3.77 (m, 2H), 3.35–3.41 (m, 1H), 1.20–1.33 (m, 6H). MS (APCI(+)) 490 (M+H), 507 (M+NH4). Anal. Calcd for: C21H22F3NO7S C, 51.53; H, 4.53; N, 2.86 Found: C,51.60; H, 4.61; N, 2.88.

EXAMPLE 248

(1S)-1-[(4S)-2,2-dimethyl-1,3-dioxolan-4-yl]-2-{[4-(4-methylphenoxy)phenyl]sulfonyl}ethyl(hydroxy)formamide The title compound was prepared following the procedures of Examples 139 and 140, starting with 4-(4'-methylphenyloxy)-phenyl methyl sulfone, but using the formylation conditions described in Example 213B.

mp. 156–158° C. [α]$_D$=+5.0°(c=0.2, MeOH). 1H NMR (DMSO-d6) δ 9.41–10.12 (bs, 1H), 8.13 (s, ½H), 7.78–7.93 (m, 2½H), 7.26 (d, 2H, J=9 Hz), 7.10 (d, 2H, J=9 Hz), 6.97–7.06 (m, 2H), 4.57–4.64 (m, ½H), 3.91–4.16 (m, 2½H), 3.58–3.73 (m, 2H), 3.34 (s, 3H), 3.21–3.31 (m, 1H), 1.17–1.36 (m, 6H). MS (APCI(+)) 436 (M+H), 453 (M+NH4). Anal. Calcd for: C21H25NO7S C, 57.92; H, 5.79; N, 3.22; S,7.36. Found: C,57.63; H, 5.81; N, 3.1 1; S,7.21.

EXAMPLE 249

4-({(2S)-2-[(4S)-2,2-dimethyl-1,3-dioxolan-4-yl]-2-[formyl(hydroxy)amino]ethyl}sulfonyl)-4'-(trifluoromethyl)-1,1'-biphenyl The title compound was prepared following the procedures of Examples 139 and 140, starting with 4-(4'-trifluoromethylphenyl)-phenyl methyl sulfone, but using the formylation conditions described in Example 213B.

mp 204–205° C. [α]$_D$=+6.0°(c=0.1, MeOH). 1H NMR (DMSO-d6) δ 9.79–10.20 (m, 1H), 7.79–8.27 (m, 9H), 4.61–4.76 (m, ½H) 3.93–4.24 (m, 2½H), 3.62–3.85 (m, 2H), 3.35–3.48 (m, 1H), 1.13–1.42 (m, 6H) MS (ESI(+)) 474 (M+H), 491 (M+NH4), 496 (M+Na), 532 (M+CH3CN+NH4) Anal. Calcd for: C21H22F3NO6S C, 53.27; H, 4.68; N, 2.96; S,6.77; F,12.04. Found: C,53.09; H, 4.74; N, 2.89; S,6.79; F,12.21.

EXAMPLE 250 methyl 4-[3-[formyl(hydroxy)amino]-4-({4-[4-(trifluoromethoxy)phenoxy]phenyl}sulfonyl)butyl]benzoate Methyl 4-(3-methoxy-3-oxopropyl)benzoate was converted to the title compound following the procedures of Example 213.

mp 153–154° C. 1H NMR (DMSO-d6) δ 9.84–10.09 (m, ½H), 9.55–9.73 (m, ½H), 8.21 (s, ½H), 7.83–7.94 (m, 4H), 7.80 (s, ½H), 7.42–7.52 (m, 2H), 7.23–7.34 (m, 4H), 7.13–7.23 (m, 2H), 4.52–4.61 (m, ½H), 4.04–4.15 (m, ½H), 3.83 (s, 3H), 3.57–3.74 (m, 1H), 3.44–3.55 (m, 1H), 2.43–2.68 (m, 2H), 1.86–2.01 (m, 1H), 1.71–1.83 (m, 1H). MS (APCI(+)) 568 (M+H), 585 (M+NH4) Anal. Calcd for: C26H24F3NO8S C, 55.02; H, 4.26; N, 2.47; S,5.65; F,10.04. Found: C,54.99; H, 4.23; N, 2.44; S,5.68; F,10.29.

EXAMPLE 251

4-[3-[formyl(hydroxy)amino]-4-({4-[4-(trifluoromethoxy)phenoxy]phenyl}sulfonyl)butyl]benzoic acid A solution of Example 251 (609 mg, 1.07 mmol) in THF (2.5 mL) and methanol (2.5 mL) was treated with a solution of KOH (73 mg, 1.3 mmol) in watre (1.2 mL) and stritted overnight. Partitioned between water and EtOAc. The aq. layer was acidified to pH 3 and extracted with EtOAc. The organics were dried, concentrated and then recrystallized from EtOAc-hexane to give 430 mg of the title compound.

mp 189–191° C. 1H NMR (DMSO-d6) δ 9.50–9.85 (m, ½H), 8.21 (s, ½H), 7.82–7.94 (m, 4H), 7.79 (s, ½H), 7.44–7.52 (m, 2H), 7.23–7.32 (m, 4H), 7.15–7.23 (m, 2H), 4.52–4.62 (m, ½H), 4.04–4.14 (m, ½H), 3.58–3.74 (m, 1H), 3.46–3.55 (m, 1H), 2.42–2.66 (m, 2H), 1.85–2.01 (m,1H0, 1.72–1.83 (m, 1H) MS (APCI(+)) 554 (M+H), 571 (M+NH4) Anal. Calcd for: C25H22F3NO8S C, 54.25; H, 4.01; N, 2.53; S,5.79; F,10.30. Found: C,54.14; H, 4.00; N, 2.38; S,5.70; F,10.79.

EXAMPLE 252 hydroxy{3-[4-(hydroxymethyl)phenyl[-1-[({4-[4-(trifluoromethoxy)phenoxy]phenyl}sulfonyl)methyl] propyl}formamide A –5° C. solution of Example 251 (570 mg, 1.03 mmol) in THF (8 mL) was treated with BH3.THF (1M in THF, 0.56 mL), stirred at –5 C for 2 h, then treated with an additional 2.5 mL of BH3.THF and stirred at rt for 48 h. Quenched with 0.7 mL of 1N HCl, stirred for 15 min, then partitioned between aq. NaHCO3 and EtOAc (3×). Combined organics, dried, concentrated and purified first by silica gel chromatography eluting with 3% MeOH—CH2Cl2 followed by 100% isopropanol and then reverse phase chromatography eluting with 60% CH3CN-water to give 45 mg of the title compound.

mp.128–130° C. 1H NMR (DMSO-d6) δ 9.88–10.11 (m, ½H), 8.30 (s, ½H), 7.81–7.91 (m, 2H), 7.75 (s, ½H), 7.41–7.51 (m, 2H), 7.24–7.32 (m, 2H), 7.12–7.24 (m, 4H), 7.03–7.12 (m, 2H), 5.08 (s, 1H), 4.53–4.65 (m, ½H), 4.45 (s, 2H), 4.00–4.11 (m, ½H), 3.55–3.72 (m, 1H), 3.47 (dd, J=4,12 Hz, 1H), 2.32–2.69 (m, 2H), 1.82–1.97 (m, 1H), 1.65–1.79 (m, 1H). MS (APCI(–)) 574 (M+Cl) Anal. Calcd for: C25H24F3NO7S C, 55.65; H, 4.48; N, 2.60; S,5.94; F,10.56. Found: C,55.49; H, 4.69; N, 2.47; S,5.80; F,10.84.

EXAMPLE 253

2-{[4-(4-chlorophenoxy)phenyl]sulfonyl}-1-[(4-chlorophenyl)sulfonyl]methyl}ethyl(hydroxy) formnamide Epibromohydrin was sequentially reacted 4-chlorothiophenol and 4-(4'-chlorophenoxy-thiophenol (as in Examples 1A and 1B). The resulting alcohol was then converted to the final product following the reactions described in Examples 2C, 2D, 2E,2F and 46D.

mp 116–118° C. $^1$H NMR (300 MHz, d$_6$-DMSO) δ 10.13 (s, 0.5H), 9.73 (s, 0.5H), 7.97 (s, 0.5H), 7.87–7.71 (m, 6.5H), 7.56–7.52 (m, 2H), 7.22–7.15 (m, 4H), 3.87–3.48 (m, 4H); MS (ESI) m/e 544 (M+l)$^+$. Anal. calcd for C$_{22}$H$_{19}$Cl$_2$NO$_7$S$_2$: C, 48.54; H, 3.52; N, 2.57. Found: C, 48.74; H, 3.55; N, 2.32.

EXAMPLE 254 hydroxy{(1S)-4-hydroxy-1-[({4-[4-(trifluoromethoxy)phenoxy]phenyl}sulfonyl)methyl] butyl}formamide

EXAMPLE 254A methyl (4S)-4-{[(benzyloxy)carbonyl]amino}-5-hydroxypentanoate

A solution of methyl (4S)-4-{[(benzyloxy)carbonyl] amino}-5-[(2,5-dioxo-1-pyrrolidinyl)oxy]-5-oxopentanoate (BACHEM, 17.2 g, 43.9 mmol) in 150 mL of THF at 0° C. was treated with NaBH$_4$ (1.7 g, 45 mmol) and ethanol (50 mL), stirred for 15 min, quenched with 1N HCl, extracted with ethyl acetate, washed with brine, dried over MgSO$_4$, filtered, and concentrated. The crude product was purified by silica gel chromatography (2% methanol/dichloromethane) to give 7.23 g (59%) of the alcohol 254A.

MS (ESI) m/e 282 (M+l)$^+$.

EXAMPLE 254B methyl(4S)-4-{[(benzyloxy)carbonyl]amino}-5-{[(4-methylphenyl)sulfonyl]oxy}pentanoate A solution of the alcohol 254A (4 g, 14.2 mmol) in 30 mL of pyridine at 0° C. was treated with a solution of p-toluenesulfonyl chloride (6.8 g, 36 mmol) in 30 mL of pyridine, stirred 5 h, quenched with water, extracted with ethyl ether, washed with brine, dried over MgSO$_4$, filtered, and concentrated to give 6.18 g (99%) of the tosylate 254B.

MS (ESI) m/e 436 (M+l)$^+$.

EXAMPLE 254C methyl(4S)-4-{[(benzyloxy)carbonyl]amino}-5-({4-[4-(trifluoromethoxy)phenoxy]phenyl}sulfanyl) pentanoate A solution of the tosylate 254B (5.45 g, 13 mmol) in 100 mL of DMF at 0° C. was treated with K$_2$CO$_3$ (2.25 g, 16 mmol) and 4-(4'-trifluoromethoxyphenoxy)benzene thiol (4.65 g, 16 mmol), stirred at rt on, quenched with H$_2$O, extracted with ethyl acetate, washed with H$_2$O and brine, dried over MgSO$_4$, filtered, and concentrated. The crude material was purified by silica gel chromatography (20% ethyl acetate/CH$_2$Cl$_2$) to give 6.76 g (94%) of the sulfide 254C.MS (ESI): 582 (M+H)+.

EXAMPLE 254D methyl(4S)-4-{[(benzyloxy)carbonyl]amino}-5-({4-[4-(trifluoromethoxy)phenoxy]phenyl}sulfonyl) pentanoate A solution of the sulfide 254C (6.76 g, 12 mmol) in 4:1 MeOH/H20 (250 mL) at 0° C. was treated with NaHCO$_3$ (2.6 g, 30 mmol) and OXONE (11 g, 30 mmol), stirred at rt 5 h, filtered, concentrated, extracted with ethyl acetate, washed with brine, dried over MgSO$_4$, filtered, and concentrated to give 4.51 g (65 %) of the sulfone 254D. MS (ESI) m/e 582 (M+l)$^+$.

EXAMPLE 254E (4S)-4-{[(benzyloxy)carbonyl]amino}-5-({4-[4-(trifluoromethoxy)phenoxy]pheny}sulfonyl) pentanoic acid A solution of Example 254D (4.29 g, 7.38 mmol) in 2:1 THF/H$_2$O (30 mL) at 0° C. was treated with LiOH.H$_2$O (1.86 g, 44.26 mmol), stirred Ih at rt, concentrated, quenched with 1N HCl, extracted with ethyl acetate, washed with brine, dried over MgSO$_4$, filtered, and concentrated to give 3.3 g (76%) of the carboxylic acid 254E. MS (ESI) m/e 568 (M+l)$^+$.

EXAMPLE 254F benzyl(1S)-4-hydroxy-1-[({4-[4-(trifluoromethoxy) phenoxy]phenyl}sulfonyl)methyl]butylcarbamate A solution of the acid 254E (3.3 g, 5.8 mmol) in 30 mL of THF at 0° C. was treated with triethylamine (810 mL, 5.8 mmol) and ethyl chloroformate (500 mL, 6.4 mmol), stirred 1 h, filtered, concentrated, cooled to 0° C., treated with NaBH$_4$ (484 mg, 12.8 mmol) in 3 mL of H$_2$O, stirred 3 h, quenched with 1N HCl, extracted with ethyl acetate, washed with satd NaHCO$_3$ and brine, dried over MgSO$_4$, filtered, and concentrated. The crude material was purified by silica gel chromatography (2% methanol/CH$_2$Cl$_2$) to give 2.7 g (84%) of the alcohol 254F.

MS (ESI) m/e 554 (M+l)$^+$.

EXAMPLE 254G (4S)-4-(hydroxyamino)-5-({4-[4-(trifluoromethoxy) phenoxy]phenyl}sulfonyl)-1-pentanol A solution of Example 254F (2.69 g, 4.86 mmol) in 35 mL of methanol was treated with 20% Pd(OH)$_2$/C (270 mg) under 4 atm of H$_2$ at 50° C. for 18 h, cooled to rt, flushed with N$_2$, filtered, and concentrated to give the amine (2 g, 98%). Oxidation of the amine as in Example 196D gave the title compound.

MS (ESI) m/e 436 (M+1)$^+$.

EXAMPLE 254H hydroxy{(1S)-4-hydroxy-1-[({4-[4-(trifluoromethoxy)phenoxy]phenyl}sulfonyl)methyl] butyl}formamide A solution of Example 254G (1.7 g, 3.9 mmol) in 20 mL of THF at 0° C. was treated with trifluoroethylformate (3.8 mL, 71.9 wt %, 39 mmol), heated at reflux on, cooled to rt, quenched with satd NaHCO$_3$, extracted with ethyl acetate, washed with brine, dried over Na$_2$SO$_4$, filtered, and concentrated.

The crude mixture was dissolved in 20 mL of 2:2:1 THF/methanol/H$_2$O, cooled to 0° C., treated with LiOH.H$_2$O (491 mg, 11.7 mmol), stirred 20 min, quenched with 1N HCl, concentrated, extracted with ethyl acetate, washed with brine, dried over Na$_2$SO$_4$, filtered, and concentrated. The crude material was purified by silica gel chromatography (5% methanol/CH$_2$Cl$_2$) then recrystallized from ethyl ether/pentane to give 990 mg (55%) of the title compound.

mp 85–86° C. $[\alpha]_D^{25}$ −1.9°(c 0.52, CHCl$_3$) $^1$H NMR (300 MHz, d$_6$-DMSO) δ 9.84 (s, 0.5H), 9.46 (s, 0.5H), 8.12 (s, 0.5H), 7.90 (d, 2H), 7.81 (s, 0.5H), 7.48 (d, 2H), 7.30–7.26 (m, 2H), 7.22 (d, 2H), 4.52 (m, 0.5H), 4.44 (m, 1H), 4.08 (m, 0.5H), 3.67–3.55 (m, 2H), 3.44–3.26 (m, 2H), 1.64–1.44 (m, 2H), 1.36–1.23 (m, 2H); MS (ESI) m/e 464 (M+1)$^+$. Anal. calcd for C$_{19}$H$_{20}$F$_3$NO$_7$S: C, 49.24; H, 4.25; N, 3.02. Found: C, 49.41; H, 4.35; N, 3.01.

EXAMPLE 255 hydroxyl{(1S)-2-({4-[4-(trifluoromethoxy)phenoxy] phenyl}sulfonyl)-1-[(4S)-3,5,5-trimethyl-2-oxo-1,3-thiazolidin-4-yl]ethyl}formamide N-methyl D-penicillamine methyl ester was converted to the title compound following the procedures of Example 145.

mp84–86° C. $^1$H NMR (300 MHz, d$_6$-DMSO) δ 10.34 (s, 0.5H), 9.90 (s, 0.5H), 8.12 (s, 0.5H), 8.04 (s, 0.5H), 7.96–7.91 (m, 2H), 7.48 (d, 2H), 7.30–7.21 (m, 4H), 5.12 (dd, 0.5H), 4.58 (dd, 0.5H), 3.99–3.86 (m, 1H), 3.54–3.42 (m, 2H), 3.25–3.12 (m, 1H), 2.90 (s, 3H), 1.50 (s, 1.5H), 1.47 (s, 1.5H), 1.41 (s, 1.5H), 1.29 (s, 1.5H); MS (ESI) m/e 549 (M+1)$^+$. Anal. calcd for C$_{22}$H$_{23}$F$_3$N$_2$O$_7$S$_2$: C, 48.17; H, 4.23; N, 5.11. Found: C, 47.96; H, 4.37; N, 5.02.

EXAMPLE 256 hydroxy{1-o(4-[4-(trifluoromethoxy)phenoxy] phenyl}sulfonyl)methyl]cyclopentyl}formamide The title compound was prepared following the procedures of Example 261 substituting cyclopentanone for tetrahydro-4H-pyran-4-one.

mp 150–152° C. $^1$H NMR (300 MHz, d$_6$-DMSO) δ 9.42 (s, 1H), 8.02 (s, 1H), 7.90–7.87 (m, 2H), 7.48–7.45 (m, 2H), 7.30–7.27 (m, 2H), 7.21–7.19 (m, 2H), 3.68 (s, 2H), 2.20–2.12 (m, 2H), 1.89–1.80 (m, 2H), 1.70–1.54 (m, 4H); MS (ESI) m/e 460 (M+1)$^+$. Anal. calcd for C$_{20}$H$_{20}$F$_3$NO$_6$S: C, 52.29; H, 4.39; N, 3.05. Found: C, 52.26; H, 4.32; N, 2.94.

EXAMPLE 257

(1S)-1-[(4S)-5,5-dimethyl-2-oxo-1,3-thiazolidin4-yl]-2-({4-[4-(trifluoromethoxy)phenoxy] phenyl}sulfonyl)ethyl(hydroxy)formamide N-methyl D-penicillamine methyl ester was converted to the title compound following the procedures of Example 145.

$^1$H NMR (300 MHz, d$_6$-DMSO) δ 9.90 (s, 0.5H), 9.52 (s, 0.5H), 8.10 (s, 0.5H), 7.94–7.89 (m, 2.5H), 7.84 (s, 0.5H), 7.69 (s, 0.5H), 7.50–7.47 (m, 2H), 7.31–7.22 (m, 4H), 4.90–4.85 (m, 0.5H), 4.42–4.37 (m, 0.5H), 3.88–3.79 (m, 1H), 3.54–3.44 (m, 2H), 1.57 (s, 1.5H), 1.51 (s, 1.5H), 1.40 (s, 1.5H), 1.31 (s, 1.5H); MS (ESI) m/e 535 (M+1)$^+$.

EXAMPLE 258

1,1-dioxido-4-[({4-[4-(trifluoromethoxy)phenoxyl] pheny}sulfonyl)methyl]tetrahydro-2H-thiopyran-4-yl(hydroxy)formamide

EXAMPLE 258A

4-[({4-[4-(trifluoromethoxy)phenoxy] phenyl}sulfonyl)methylene]tetrahydro-2H-thiopyran A −20 C solution of for 4-(4'-trifluoromethoxyphenyl)-phenyl methyl sulfone (2.86 g) in THF (40 mL) was treated with n-BuLi (2.5M in hexanes, 7 mL), stirred for 1 h, treated with diethylchlorophosphate (1.05 mL), stirred for 1 h, then treated with tetrahydrothiopyran-4-one (1 g) and stirred overnight allowing the reaction to warm up to rt. The reaction was quenched with 1N HCl, extracted with EtOAc (3×). the combined organics were washed with brine, dried (Na2SO4), filtered, concentrated and purified via silica gel chromatography eluting with 4 to 1 hexane-EtOAc to give the title compound. MS (ESI) 448 (M+NH4)+.

EXAMPLE 258B 1.1-dioxido-4-[({4-[4-(trifluoromethoxy)phenoxy] phenyl}sulfonyl)methyl]tetrahydro-2H-thiopyran-4-yl(hydroxy)formamide Example 258A was converted to the title compound following the procedures of Examples 261C and 213B.

mp 118–119° C. 1H NMR (300 MHz, d6-DMSO) δ 9.68 (s, 1IH), 8.32 (s, 11H), 7.92–7.89 (m, 2H), 7.4 (m, 2H), 7.30–7.22 (m, 4H), 3.77 (s, 2H), 3.19–3.04 (m, 4H), 2.72 (s,

2H), 2.44 (s, 2H); MS (ESI) m/e 524 (M+1)⁺. Anal. calcd for C$_{20}$H$_{20}$F$_3$NO$_8$S$_2$: C, 45.89; H, 3.85; N, 2.68. Found: C, 45.59; H, 3.86; N, 2.65.

EXAMPLE 259

(1S)-2-{[4-(4-chlorophenoxy)pheny]sulfonyl}-1-[(4,4-dimethyl-2,5-dioxo-1-imidazolidinyl)methyl]ethyl (hydroxy)fornamide The title compound was prepared following the procedures of Example 196, substituting 5,5 dimethyl hydantoin for 1,5,5 trimethyl hydantoin in step 196D.

mp 178° C. [α]$_D^{25}$=−5.7°(c=0.7, MeOH). $^1$H NMR (d6-DMSO) δ 9.66 (bs, 0.5H), 9.48 (bs, 0.5H), 8.37 (bs, 0.5H), 8.33 (bs, 0.5H), 8.09 (s, 0.5H), 7.89 (dd, 2H, J=8.8, 2.7 Hz), 7.67 (s, 0.5H), 7.52 (d, 2H, J=8.8 Hz), 7.20 (d, 4H, J=8.8 Hz), 4.88–4.78 (m, 0.5H), 4.52–4.40 (m, 0.5H), 3.74–3.36 (m, 4H), 1.24 (s, 3H), 1.22 (s, 3H). MS (ESI) 496 (M+H), 513 (M+NH$_4$), 494 (M−H). Anal. Calcd for: C$_{21}$H$_{22}$N$_3$O$_7$SCl.1.00H$_2$O C, 49.07; H, 4.70; N, 8.17. Found: C, 49.33; H, 4.41; N, 7.83.

EXAMPLE 260

(1S)-2-(4,4-dimethyl-2,5-dioxo-1-imidazolidinyl)-1-({[4-(trifluoromethyl)[1,1'-biphenyl]-4-yl]sulfonyl}methyl)ethyl(hydroxy)formamide The title compound was prepared following the procedures of Example 196, substituting 4-(4'-trifluoromethylphenyl)-benzene thiol for 4-(4'-chlorophenoxyl)-benzene thiol in step 196A and 5,5 dimethyl hydantoin for 1,5,5 trimethyl hydantoin in step 196D. mp 206° C. [α]$_D^{25}$=−5.2° in (c=0.5, MeOH) $^1$H NMR (d6-DMSO) δ 9.66 (s, 0.5H), 9.50 (s, 0.5H), 8.37 (s, 0.5H), 8.33 (s, 0.5H), 8.10 (s, 0.5H), 8.06–7.96 (m, 6H), 7.89 (d, 2H, J=8.1 Hz), 7.74 (s, 0.5H), 4.96–4.85 (m, 0.5H), 4.62–4.48 (m, 0.5H), 3.80–3.40 (m, 4H), 1.25–1.18 (m, 6H). MS (ESI) 514 (M+H), 531 (M+NH$_4$), 512 (M−H). Anal. Calcd for: C$_{22}$H$_{22}$N$_3$O$_6$SF$_3$. 0.50H$_2$O C, 50.57; H, 4.43; N, 8.04. Found: C, 50.62; H, 4.37; N, 7.96.

EXAMPLE 261 hydroxy{4-[({4-[4-(trifluoromethoxy)phenoxy]phenyl}sulfonyl)methyl]tetrahydro-2H-pyran-4-yl}formamide

EXAMPLE 261A 4-(((4-(4-(trifluoromethoxy)phenoxy)phenyl)sulfonyl)methyl)tetrahydro-2l-pyran-4-ol In a 2 L 3-necked flask (mechanical stirrer, nitrogen inlet, septum with thermometer probe) were placed 90.1 g (0.27 mole) 4-(4'-trifluoromethoxyphenoxy)phenyl methyl sulfone(prepared from 4-trifluoromethoxyphenol as in Example 74A) and 1 L dry THF.

The solution was cooled to −78° C. and 108 mL 2.5 M n-butyllithium in hexane was added. After 30 min. stirring, 25 mL (27.1 g, 0.271 mole) tetrahydro-4H-pyran-4-one was added over 20 min. After 2 h stirring at −78° C., the reaction was quenched with 50 mL saturated ammonium chloride and allowed to warm to 0° C. The supernatant was decanted and concentrated and the residue recombined with the aqueous layer. The mixture was extracted with 500 and 200 mL MTBE washing with water and brine. The organic layers were dried over Na$_2$SO$_4$ and concentrated by distillation to about 250 mL; 300 mL hexane was added with stirring resulting in crystal formation. After cooling the solid was collected and washed with 1:3 MTBE-hexane and dried to give 110.49 g (95 %) of 261A, mp 91–92° C.

EXAMPLE 261B 4-(((4-(4-(trifluoromethoxy)phenoxy)phenyl)sulfonyl)methylene)tetrahydro-2H-pyran and 4-(((4-(4-(trifluoromethoxy)phenoxy)phenyl)sulfonyl)methyl-3,6-dihydro-2H-pyran In a 1 L 3-necked flask (Nitrogen inlet, dropping funnel, thermometer, stirrer) were placed 110.49 g (0.256 mole) of Example 261A and 350 mL dry pyridine. The solution was cooled to −25° C. 23.8 mL (39.15 g, 0.255 mole) phosphorous oxychloride was added over 10 min. The bath was permitted to warm slowly over 68 h to 18° C. After cooling again to −30° C., 500 mL water was added (very slowly until the exotherm subsided) over 2 h. The bath was removed and while stirring at room temperatures for 2 h the gummy material became a nice solid. The mixture was chilled, filtered, and the solid washed well with water and dried to give 104.2 g (98 %) of a ca 1 to 1 mixture of olefins, mp 62–72° C. This mixture was used directly.

EXAMPLE 261C 4-(hydroxyamino)-4-(((4-(4-(trifluoromethoxy)phenoxy)phenyl)sulfonyl)methyl)tetrahydro-2H-pyran To a 1 L flask, containing a solution of 104.2 g (0.251 mole) of the mixture of olefins from Example 261B in 500 mL THF, was added 36 mL (0.587 mole) 50 % aqueous hydroxylamine. After stirring 2 h at room temperatures, the solution was concentrated to a small volume and the residue was partitioned between MTBE (700 and 300 mL) and water (2×200 mL) The organic layers were washed with brine and dried over sodium sulfate. The solution was concentrated to dryness and the residue in toluene was concentrated again. To the residue in 400 mL toluene was added a hot solution prepared from 23.6 g (0.124 mole) p-toluenesulfonic acid hydrate and 500 mL toluene refluxed under a Dean-Stark trap to remove the water. Fine crystals formed quickly. After chilling in an ice bath the solid was collected and rinsed with toluene. Upon drying in a 40° C. vacuum oven, 71.58 g of tosylate salt, mp 168–173° C. (dec.) was obtained. This material was suspended in 500 mL water and 150 mL 1 M sodium bicarbonate was added slowly. After gas evolution had subsided the mixture was digested at 60° C. until the foamy surface broke up (30 min.) The mixture was chilled and the solid was collected washed well with water and dried to give 51.4 g of crude product. Crystallization from MTBE-hexane yielded 48.07 g (43%) of Example 261 C, mp 100–101° C.

EXAMPLE 261D hydroxy{4-[({4-[4-(trifluoromethoxy)phenoxy]phenyl}sulfonyl)methyl]tetrahydro-2H-pyran-4-yl}formamide A solution of 216.03 g (0.483 mole) of A-320370 in 400 mL of 2,2,2-trifluoroethyl formate reagent (see 213B) in a 1L 3-necked flask (condenser with nitrogen inlet, thermometer, and stirrer) was refluxed (65° C.) for 4 days and then some of the excess reagent (350 g, bp 61–63° C.) was distilled out through a 10 cm Vigreux column (pot rising to 69° C.). After cooling and concentration with a rotary evaporator, the residue in 1 L MTBE was washed with 200 mL portions of water, 1 M NaHCO$_3$ (to pH 8, 2X), water, and brine. back extracting with 500 mL more MTBE. After drying over MgSO$_4$, the solution was concentrated to about 900 mL when crystals were noted. After dilution with 300 mL hexane and brief digestion the mixture was chilled and the solid collected and rinsed with 1:1 MTBE-hexane and dried to yield 163.8 g (71%) of 261 D.

mp 115–116° C. $^1$H-NMR (DMSO-d$_6$): 1.94–2.26 (m, 4H), 3.48–3.58 (m, 2H), 3.61–3.77 (m, 6H), 7.23 (d, 2H, J=9.6 Hz), 7.29 (d, 2H, J=9.2 Hz), 7.47 (d, 2H, J=9.2 Hz), 7.92 (d, 2H, J=9.6 Hz), 8.23 (s, 1H), 9.49 (s, 1H). MS (APCI): +476 (M+1), +493 (M+18), −510 (M+35). Anal. Calcd. For C$_{20}$H$_{20}$NO$_7$SF$_3$: C, 50.53; H, 4.24; N, 2.95; S, 6.74; F, 11.99. Found: C, 50.55; H, 4.15; N, 2.67; S, 6.95; F, 11.83.

EXAMPLE 262

(1S)-2-(2,5-dioxo-1-imidazolidinyl)-1-[({4-[4-(trifluoromethoxy)phenoxy]phenyl}sulfonyl)methyl] ethyl(hydroxy)formamide The title compound was prepared following the procedures of Example 196, substituting 4-(4'-trifluoromethoxyphenoxy)-benzene thiol for 4-(4'-chlorophenoxy)-benzene thiol in step 196A and 5,5 dimethyl hydantoin for 1,5,5 trimethyl hydantoin in step 196D and using the formylation conditions described in Example 213B.

mp 154° C. [α]$_D^{25}$−6.0° (c=0.3, MeOH) $^1$H NMR (d6-DMSO) δ 9.79 (s, 0.5H), 9.52 (s, 0.5H), 8.14 (d, 1H, J=7.0 Hz), 8.10 (s, 0.5H), 7.92–7.88 (m, 2H), 7.73 (s, 0.5H), 7.48 (d, 2H, J=9.2 Hz), 7.29 (dd, 2H, J=9.2, 3.7 Hz), 7.22 (d, 2H, J=8.8 Hz), 4.88–4.77 (m, 0.5H), 4.46–4.36 (m, 0.5H), 3.95–3.40 (m, 6H). MS (ESI) 518 (M+H), 535 (M+NH$_4$), 516 (M−H). Anal. Calcd for: C$_{20}$H$_{18}$N$_3$O$_8$SF$_3$C, 46.42; H, 3.51; N, 8.12. Found: C, 46.59; H, 3.57; N, 7.95.

EXAMPLE 263

1-acetyl-4-[({4-[4-(trifluoromethoxy)phenoxy] phenyl}sulfonyl)methyl]-4-piperidinyl(hydroxy) formamide The title compound was prepared following the procedures of Example 75 substituting N-acetyl-4-piperidone for propionaldehyde and 4-(4'-trifluoromethoxyphenyloxy)-phenyl methyl sulfone for 4-(4'-methoxyphenyl)-phenyl methyl sulfone and using the formylation conditions described in Example 213B.

$^1$H NMR (d6-DMSO) δ 9.59 (s, 1H), 7.97 (s, 1H), 7.87 (d, 2H, J=9.2 Hz). 7.51–7.45 (m, 2H), 7.24 (dd, 4H, J=9.1, 16.9 Hz), 3.88–3.77 (m, 3H), 3.56–3.45 (m, 1H), 3.02–2.91 (m, 1H), 2.58–2.38 (m, 3H), 1.87 (s, 3H), 1.84–1.62 (m, 2H). MS (ESI) 517 (M+H), 539 (M+Na), 515 (M−H).

EXAMPLE 264 hydroxyl{1-(methylsulfonyl)-4-[({4-[4-(trifluoromethoxy)phenoxy]phenyl}sulfonyl) methyl]-4-piperidinyl}formamide The title compound was prepared following the procedures of Example 75 substituting N-mesyl-4-piperidone (prepared from 4-piperidone ethylene ketal via mesylation as in Example 223A and ketal deprotection) for propionaldehyde and 4-(4'-trifluoromethoxyphenyloxy)-phenyl methyl sulfone for 4-(4'-methoxyphenyl)-phenyl methyl sulfone and using the formylation conditions described in Example 213B.

$^1$H NMR (d6-DMSO) δ 9.54 (s, 1H), 8.21 (s, 1H), 7.90 (d, 2H, J=9.2 Hz), 7.47 (d, 2H, J=9.2 Hz), 7.29 (d, 2H, J=9.2 Hz), 7.23 (d, 2H, J=8.8 Hz), 3.70 (s, 2H), 2.97–2.87 (m, 4H), 2.44–2.25 (m, 2H), 2.10–1.96 (m, 2H). MS (ESI) 553 (M+H), 570 (M+NH$_4$), 575 (M+Na), 551 (M−H), 587 (M+Cl).

EXAMPLE 265

2,2-dimethyl-5-[({4-[4-(trifluoromethoxy)phenoxy [phenyl}sulfonyl)methyl]-1,3-dioxan-5-yl(hydroxy) formamide The title compound was prepared following the procedures of Example 75 substituting 2,2-dimethyl-1,3-dioxan-5-one for propionaldehyde and 4-(4'-trifluoromethoxyphenyloxy)-phenyl methyl sulfone for 4-(4'-methoxyphenyl)-phenyl methyl sulfone and using the formylation conditions described in Example 213B.

mp 160° C. $^1$H NMR (d6-DMSO) δ 9.49 (s, 1H), 8.14 (s, 1H), 7.88 (d, 2H, J=8.8 Hz), 7.46 (d, 2H, J=8.2 Hz), 7.28 (d, 2H, J=9.1 Hz), 7.20 (d, 2H, J=8.8 Hz), 4.17–4.02 (m, 4H), 3.69 (s, 2H), 1.44 (s, 3H), 1.27 (s, 3H). MS (ESI) 506 (M+H), 528 (M+Na), 504 (M−H), 540 (M+Cl). Anal. Calcd for: C$_{21}$H$_{22}$F$_3$NO$_8$S C, 49.90; H, 4.39; N, 2.77. Found: C, 50.03; H, 4.27; N 2.69.

EXAMPLE 266

(1S)-1-[(4S)-1,3-dioxolan-4-yl]-2-({4-[4-(trifluoromethoxy)phenoxy]phenyl}sulfonyl)ethyl (hydroxy)formamide

EXAMPLE 266A (2R,3E)-4-({4-[4-(trifluoromethoxy)phenoxy] phenyl}sulfonyl)-3-butene-1,2-diol A solution of (4S)-2,2-dimethyl-4-((E)-2-((4-(4-(trifluoromethoxy)phenoxy)phenyl)sulfonyl)ethenyl)-1,3-dioxolane(see Example 139) (760 mg, 0.95 mmol) in THF (15 mL) was treated with 3 ml of a 3N aq. HCl solution and stirred at 45 C for 1.5 h. Let cool to rt poured into water and extracted twice with ether. Combined extracts were washed with brine, dried (Na2SO4), filtered and concentrated to give 0.62 g of 265A as a white solid. MS(DCI): 422 (M+NH4)+.

EXAMPLE 266B (4S)-4-[(E)-2-({4-[4-(trifluoromethoxy)phenoxy] phenyl}sulfonyl)ethenyl]-1,3-dioxolane POC13 (0.8 mL) was added dropwise to a warm (65 C) solution of the diol 266A (970 mg) in DMSO (12 mL) and the resulting mixture was stirredat 65 C for 2.5 h, after which it was partitioned between water and ether. The extract was washed with with brine, dried (Na2SO4), filtered and concentrated to give a residue which was purified via silica gel chromatography to give 195 mg of the title compound. MS(DCI): 434 (M+NH4)+.

EXAMPLE 266C (1S)-1-[(4S)-1,3-dioxolan-4-yl]-2-({4-[4-(trifluoromethoxy)phenoxy]phenyl}sulfonyl)ethyl (hydroxy)formamide Example 266B was converted to the title compound following the procedures of Examples 75C and 213B.

¹H NMR (DMSO-d6) δ 3.53–4.16 (m, 5.5H), 4.51–4.63 (m, 0.5H), 4.74 (d, 1H, J=12 Hz), 4.84 (s, 0.5H), 4.95 (s, 0.5H), 7.23 (d, 2H, J=9 Hz), 7.28 (d, 2H, J=9 Hz), 7.48 (d, 2H, J=9 Hz), 7.83 (s, 0.5H), 7.94 (dd, 2H, J=9,8.8 Hz), 8.17 (s, 0.5H), 9.15 (s, 0.5H), 10.03 (s, 0.5H). MS (ESI−) 476 (M−1). Anal. Calcd for: $C_{19}H_{18}NO_8SF_3$ C, 47.80; H, 3.80; N, 2.93. Found: C, 47.55; H, 3.76; N 2.82.

EXAMPLE 267

4-({(2S)-2-[(4S)-2,2-dimethyl-1,3-dioxolan-4-yl]-2-[formyl(hydroxy)amino]ethyl}sulfonyl)-4'-(2-methoxyethoxy)-1,1'-biphenyl The title compound was prepared following the procedures of Examples 139 and 140, starting with 4-(4'-methoxyethoxyphenyl)-phenyl methyl sulfone.

¹H NMR (DMSO-d6) δ 1.21 (d, 3H, J=9 Hz), 1.25–1.35 (m, 3H), 3.28–3.42 (m, 4H), 3.46–3.57 (m, 1H), 3.10–3.26 (m, 3H), 3.86–4.20 (m, 4H), 4.29–4.45 (m, 0.5H), 4.57–4.68 (m, 0.5H), 7.08 (d, 2H, J=9 Hz), 7.68–7.77 (m, 2H), 7.83–7.97 (m, 4.5H), 8.14 (s, 0.5H), 9.62 (s, 0.5H), 9.98 (s, 0.5H). MS (ESI−) 478 (M−1). Anal. Calcd for: $C_{23}H_{29}NO_8S$ C, 57.60; H, 6.09; N, 2.92. Found: C, 57.61; H, 6.10; N, 2.92.

EXAMPLE 268

(1S)-1-[(4S)-2,2-dimethyl-1,3-dioxolan-4-yl]-2-({4-[4-(2-methoxyethoxy)phenoxy]phenyl}sulfonyl)ethyl(hydroxy)formamide The title compound was prepared following the procedures of Examples 139 and 140, starting with 4-(4'-methoxyethoxyphenyloxy)-phenyl methyl sulfone.

1H NMR (DMSO-d6) δ 1.22 (d, 3H, J=9 Hz), 1.28 (d, 3H, J=12 Hz), 3.22–3.35 (m, 3H), 3.57–3.60 (m, 4H), 3.93–4.15 (m, 5.5H), 4.52–4.63 (m, 0.5H), 7.0–7.13 (m, 6H), 7.38 (d, 0.5H, J=3 Hz), 7.87 (d, 2H, J=10 Hz), 8.12 (s, 0.5H), 9.63 (s, 0.5H), 9.98 (s, 0.5H). Anal. Calcd for: $C_{23}H_{29}O_9SN$ C, 55.74; H, 5.89; N, 2.82. Found: C, 55.65; H, 5.82; N, 2.79.

EXAMPLE 269 hydroxy{4-(4-morpholinyl)-4-oxo-1-[({4-[4-(trifluoromethoxy)phenoxy]phenyl}sulfonyl)methyl]butyl}formamide Methyl 4-morpholino-4-oxobutyrate (prepared from methyl-4-chloro-4-oxobutyrate and morpholine) was converted to the title compound following the procedures of Examples 126-A,B and 75-B,C,D, substituting 4-(4'-trifluoromethoxyphenyloxy)-phenyl methyl sulfone for 4-(4'-trifluoromethylphenyl)-phenyl methyl sulfone.

1H NMR (DMSO-d6) δ 1.64–1.86 (m, 2H), 2.17–2.31 (m, 2H), 3.40–3.71 (m, 10H), 4.10–4.23 (m, 0.5H), 4.52–4.63 (m, 0.5H), 7.22 (d, 2H, J=9 Hz), 7.28 (d, 2H, J=8.9 Hz), 7.47 (d, 2H, J=9.1 Hz), 7.74 (s, 0.5hH), 7.85 (d, 2H, J=9 Hz), 8.11 (s, 0.5H), 9.48 (s, 0.5H), 9.82 (s, 0.5H). MS (ESI−) 545 (M−1). Anal. Calcd for: $C_{23}H_{25}N_2OSF_3$ C, 50.54; H, 4.61; N, 5.12. Found: C, 50.25; H, 4.71; N, 4.95.

EXAMPLE 270

1,2,4-trideoxy-2-[formyl(hydroxy)amino]-4,4-dimethyl-3,5-O-(1-methylethylidene)-1-({4-[4-(trifluoromethoxy)phenoxy]phenyl}sulfonyl)-D-threo-pentitol

EXAMPLE 270A (3R)-3,5-dihydroxy-1-({4-[4-(trifluoromethoxy)phenoxy]phenyl}sulfonyl)-2-pentanone Reaction of (R)-dihydro-3-tertbutyldimethylsilyloxy-4,4-dimethyl-2(3H)-furanone with 4-(4'-trifluoromethoxyphenyloxy)-phenyl methyl sulfone as in Example 126A followed by silyl ether deprotection as in Example 125B gave the title compound.

EXAMPLE 270B

1-[(4R)-2,2-dimethyl-1,3-dioxan-4-yl]-2-({4-[4-(trifluoromethoxy)phenoxy]phenyl}sulfonyl)ethanone A solution of Example 270A (1.1 g, 2.4 mmol) and dimethyl acetal (350 mL) in DMF (10 mL) was treated with a catalytic amount of camphorsulfonic acid, stirred at rt for 15 h than partitioned between water ant ethyl acetate. The organics were washed with brine, dried (MgSO4), filtered, concentrated and purified via silca gel column chromatography eluting with 25% hexanes-ethyl acetate to give 693 mg of the title compound as a viscous oil.

EXAMPLE 270C 1,2,4-trideoxy-2-[formyl(hydroxy)amino]-4,4-dimethyl-3,5-O-(1-methylethylidene)-1-({4-[4-(trifluoromethoxy)phenoxy]phenyl}sulfonyl)-D-threo-pentitol Example 270B was converted to the title compound following the procedures of Examples 126B and 126C.

¹H NMR (DMSO-d6) δ 0.64–0.83 (m, 3H), 0.90 (s, 3H), 1.25–1.33 (m, 6H), 3.03–3.14 (m, 1H), 3.33–3.54 (m, 2H), 3.62–3.72 (m, 1H), 3.73–3.85 (m, 1H), 3.92–4.05 (m, 0.5H), 4.69–4.78 (m, 0.5H), 7.19–7.20 (m, 4H), 7.48 (d, 2H, J=9 Hz), 7.76 (s, 0.5H), 7.88–7.97 (m, 2H), 8.05 (s, 0.5H), 9.28 (s, 1H). MS (ESI−) 546 (M−1). Anal. Calcd for: $C_{24}H_{28}NO_8SF_3$ C, 52.64; H, 5.15; N, 2.55. Found: C, 52.83; H, 5.30; N, 2.30.

EXAMPLE 271 hydroxy{(2R)-2-phenyl-1-[({4-[4-(trifluoromethoxy)phenoxy]phenyl}sulfonyl)methyl]propyl}formamide The title compound was prepared a 3 to 1 mixture of diastereomers starting with methyl (R)-2-phenylpropioniate and 4-(4'-trifluoromethoxyphenyloxy)-phenyl methyl sulfone following the procedures of Examples 126-A,B and 75-B,C,D.

MS (ESI+) 510 (M+1). Anal. Calcd for: $C_{24}H_{22}NO_6SF_3$ C, 56.57; H, 4.35; N, 2.74. Found: C, 56.44; H, 4.38; N, 2.71.

EXAMPLE 272

2-(2-{[tert-butyl(dimethyl)silyl]oxy}ethoxy)-1-[({4-[4-(trifluoromethoxy)phenoxy]phenyl}sulfonyl)methyl]ethyl(hydroxy)formamide The title compound was prepared from 2-{[tert-butyl(dimethyl)silyl]oxy}ethoxy)acetaldehyde and 4-(4'-trifluoromethoxyphenyloxy)-phenyl methyl sulfone following the procedures of Example 75

¹H NMR (DMSO-d6) δ 0.05 (s, 6H), 0.83 (s, 9H), 3.35–3.50 (m, 4H), 3.52–3.64 (m, 4H), 4.1–4.23 (m, 0.5H), 4.65–4.77 (m, 0.5H), 7.2 (d, 2H, J=9 Hz), 7.27 (d, 2H, J=9 Hz), 7.46 (d, 2H, J=9 Hz), 7.78 (s, 0.5H), 7.84–7.93 (m, 2H), 8.12 (s, 0.5H), 9.55 (s, 0.5H), 9.92 (s, 0.5H). MS (ESI−) 592 (M−1). Anal. Calcd for: $C_{25}H_{34}NO_8SF_3Si$ C, 50.57; H, 5.77; N, 2.35. Found: C, 50.55; H, 5.70; N, 2.18.

EXAMPLE 273 hydroxy{2-(2-hydroxyethoxy)-1-[({4-[4-(trifluoromethoxy)phenoxy]phenyl}sulfonyl)methyl]ethyl}formamide Example 272 was converted to the title compound following the procedure of Example 125B.

$^1$H NMR (DMSO-d6) δ 3.4–3.63 (m, 6H), 4.13–4.26 (m, 0.5H), 4.63 (s, 1 H), 4.69–4.8 (m, 0.5H), 7.23 (d, 2H, J=9 Hz), 7.29 (d, 2H, J=9 Hz), 7.48 (d, 2H, J=9 Hz), 7.8 (s, 0.5H), 7.91 (dd, 2H, J=9.1,8.8 Hz), 8.14 (s, 0.5H), 9.54 (s, 0.5H), 9.92 (s, 0.5H). MS (ESI–) 478 (M–H). Anal. Calcd for: $C_{19}H_{20}NO_8SF_3$ C, 47.60; H, 4.20; N, 2.92. Found: C, 47.36; H, 4.25; N 2.69.

EXAMPLE 274

(1S)-2-(4,4-dimethyl-2,5-dioxo-1-imidazolidinyl)-1-{[(4'-methoxy[1,1'-biphenyl]-4-yl)oxy]methyl}ethyl(hydroxy)formamide

EXAMPLE 274A

3-[(2S)-3-(4-bromophenoxy)-2-(hydroxyamino)propyl]-5,5-dimethyl-2,4-imidazolidinedione p-toluenesulfonic acid The title compound was prepared following the procedures described in Examples 196A, 196C and 196D, substituting 4-bromophenol for 4-(4'-chlorophenoxy)-benzenethiol and 5,5-dimethylhydantoin in place of 2,5,5-trimethylhydantoin. The hydroxylamine was treated with p-toluenesulfonic acid to give the title salt.

EXAMPLE 274B

3-{(2S)-2-(hydroxyamino)-3-[(4'-methoxy[1,1'-biphenyl]-4-yl)oxy]propyl}-5,5-dimethyl-2,4-imidazolidinedione A mixture of Example 274A (1.265 g, 2.32 mmol), 4-methoxyphenylboronic acid (530 mg, 3.5 mmol), K3PO4 (2.46 g, 11.6 mmol) in toluene (10 mL) and water (10 mL) was degassed, then treated with PdCl2(dppf)-2.CH2Cl2 (20 mg), and stirred at 65 C overnight. Diluted with water, extracted with ethyll acetate. Extracts were filtere through a pad of silica, then concentrated. The residue was recrystallized from ethyl acetate-hexane to give 432 mg of 274B as a white solid. ESI (–): 398 (M–H)+.

EXAMPLE 274C (1S)-2-(4,4-dimethyl-2,5-dioxo-1-imidazolidinyl)-1-{[(4'-methoxy[1,1'-biphenyl]-4-yl)oxy]methyl}ethyl(hydroxy)formamide A suspension of Example 274B (432 mg, 1.08 mmol) in ethyl formate (30 mL) was stirred overnight at reflux resulting in a clear solution then allowed to cool to rt. The resulting suspension was filtered to afford 141 mg of the title compound.

Mp. 205–207 C $^1$H NMR (DMSO-d6) δ 9.87 (s, 0.5H), 9.55 (s, 0.5H), 8.40 (s, 0.5H), 8.35 (s, 0.5H), 8.32 (s, 0.5H), 7.91 (s, 0.5H), 7.60–7.50 (m, 4H), 7.0–6.92 (m, 4H), 4.92–4.80 (s, 0.5H), 4.45–4.38 (s, 0.5H), 4.20–4.0 (m, 2H), 3.79 (s, 3H), 3.75–3.65 (m, 1H), 3.62–3.50 (m, 1H), 1.28 (s, 3H), 1.26 (s, 3H). MS ESI (–); 426 (M–H)+. Anal. Calcd. For C22H25N3O6: C: 61.82; H: 5.89; N;9.83. Found: C: 61.98; H:5.90; N: 9.88.

EXAMPLE 275

(1S)-2-(4,4-dimethyl-2,5-dioxo-1-imidazolidinyl)-1-{[(4'-methyl[1,1'-biphenyl]-4-yl)oxy]methyl}ethyl(hydroxy)formamide The title compound was prepared following the procedures of Example 274 substituting 4-methylphenylboronic acid for 4-methoxyphenylboronic acid.

mp. 174–175.5 C $^1$H NMR (DMSO-d6) δ 9.88 (s, 0.5H), 9.55 (s, 0.5H), 8.40 (s, 0.5H), 8.34 (s, 0.5H), 8.32 (s, 0.5H), 7.92 (s, 0.5H), 7.58 (d, J=8 Hz, 2H), 7.51 (d, J=8 Hz, 2H), 7.24 (d, J=8 Hz, 2H), 6.98 (dd, J=2, 8 Hz, 2H), 4.88–4.80 (s, 0.5H), 4.46–4.36 (s. 0.5H), 4.22–4.0 (m, 2H), 3.80–3.66 (m, 1H), 3.62–3.50 (m, 1H), 2.33 (s, 3H), 1.28 (s, 3H), 1.25 (s, 3H). MS ESI (+): 412 (M+H)+. Anal. Calcd. For C22H25N3O5: C: 64.22; H: 6.12; N: 10.21. Found: C: 64.23; H:6.19; N: 10.15.

EXAMPLE 276

4-{[(2S)-2-[formyl(hydroxy)amino]-3-(3,4,4-trimethyl-2,5-dioxo-1-imidazolidinyl)propyl]oxy}-4'-(trifluoromethoxy)-1,1'-biphenyl Example 108C was converted to the title compound following the procedures of Example 108D, 108E and 108F substituting 2,5,5-trimethylhydantoin for 5,5-dimethylhydantoin. Mp. 114–118° C.

EXAMPLE 277 hydroxy{(1S,2S)-2-(4-isobutylphenyl)-1-[({4-[4-(trifluoromethoxy)phenoxy]phenyl}sulfonyl)methyl]propyl}formamide The title compound was prepared as a mixture of diastereomers starting with (S) Methyl 4-isobutyl-a-methyl phenylacetate and 4-(4'-trifluoromethoxyphenyloxy)-phenyl methyl sulfone following the procedures of Examples 126-A,B and 75-B,C,D.

MS (ESI): 566 (M+H)+. Anal. Calcd. for C28H30N6SF3: C: 59.45; H: 5.34; N: 2.47. Found: C: 59.83; H: 5.51; N: 2.30.

EXAMPLE 278 hydroxy{3-hydroxy-2,2-dimethyl-1-[({4-[4-(trifluoromethoxy)phenoxy]phenyl}sulfonyl)methyl]propyl}formamide Methyl 3-tertButyldimethylsilyloxy-2,2-dimethyl-propionate was converted to the title compound following the procedures of Examples 126A, substituting 4-(4'-trifluoromethoxyphenyloxy)-phenyl methyl sulfone for 4-(4'-trifluoromethylphenyl)-phenyl methyl sulfone, 126B, 75B, 75C, 213B and 125B.

mp 112.5–113.5° C. $^1$HNMR (300 MHz, DMSO-d6) δ 0.76 (s, 6H), 3.03–3.16 (m, 2H), 3.50–3.75 (m, 2H), 3.88 (d, 0.7H, J=9.0 Hz), 4.45 (d, 0.3H, J=9.0 Hz), 7.20–7.32 (m, 4H), 7.47 (d, 2H, J=9.0 Hz), 7.68 (s, 0.7H), 7.80 (m, 2H), 8.09 (s, 0.3H) MS (ESI, +Q1MS) 478 (M+H), 495 (M+NH4) Anal. Calcd for C20H22F3NO7S: C, 50.31; H, 4.64; N, 2.93. Found: C, 50.29; H, 4.68; N, 2.76.

EXAMPLE 279

1,2,3-trideoxy-2-[formyl(hydroxy)amino]-4,5-O-(1-methylethylidene)-1-({4-[4-(trifluoromethoxy)phenoxy]phenyl}sulfonyl)-D-erythro-pentitol The diastereomer of Example 242 was prepared following the procedures of Example 145, starting with 4-(4'- methoxyphenyloxy)-phenyl methyl sulfone and methyl [(4S)-2,2-dimethyl-1,3-dioxolan-4-yl]acetate and separating the diasteromeric hydroxylamine intermediates.

$^1$H NMR (300 MHz, DMSO-d6) δ 1.20 (s, 3H), 1.26 (d, 3H, J=4.5 Hz), 1.60–1.80 (m, 1H), 1.80–1.97 (m, 1H), 3.35–3.70 (m, 3H), 3.85–4.02 (m, 2H), 4.06–4.20 (m, 0.5H), 4.50–4.62 (m, 0.5H), 7.18–7.32 (m, 4H), 7.48 (d, 2H, J=8.7 Hz), 7.86–7.94 (m, 2.5H), 8.07 (s, 0.5H), 9.59 (s, 0.5H), 9.97 (s, 0.5H). MS (ESI+) 520 (M+H), 537 (M+NH4). Anal. Calcd for: C22H24NO8SF3 C, 50.86; H, 4.65; N, 2.69. Found: C, 50.94; H, 4.66; N, 2.15.

EXAMPLE 280 hydroxy(3-(((4-(4-(trifluoromethoxy)phenoxy) phenyl)sulfonyl)methyl)-3,4-dihydro-2H-1,5-benzodioxepin-3-yl)formamide

EXAMPLE 280A 3-methylene-3,4-dihydro-2H-1,5-benzodioxepine

A solution of catechol (4.4 g, 40 mmol), Cs2CO3 (27.7 g, 85 mmol) and 3-chloro-2 chloromethyl-prop-1-ene(5 g, 40 mmol) in DMF (80 mL) was striired overnight at rt. The reaction was partitioned between ether and water and the organic extract was washed with brine, dried (MgSO4), filtered and concentrated to 5.46 g (84%) of a yellow oil. MS 163 (M+H)+.

EXAMPLE 280B 3-(hydroxymethyl)-3,4-dihydro-2H-1,5-benzodioxepin-3-ol

A cloudy solution of Example 280A (0.81 g, 5 mmol), 4-methylmorpholine N-oxide (644 mg, 5.5 mmol) in t-butanol (0.4 mL), water (2.5 mL) and acetone (1.5 mL) was treated with OsO4 (0.1 mL, 4% aq. solution) then stirred overnight. The reaction mixture was treated with 2 g NaHCO3, concentrated and partitioned between water and EtOAc. The organics were dried (MgSO4), filtered and concentrated to a white solid (740 mg, 75%). MS (ESI): 219 (M+Na)+.

EXAMPLE 280C 2H-1,5-benzodioxepin-3(4H)-one

A solution of Example 280B (5.29 g, 27 mmol) in THF (50 mL) was treated with a suspension of NaIO4 (6.33 g, 30 mmol) in water (10 ml) and THF (50 mL), then stirred at rt for 1.5 h. Diluted with water, extracted twice with ether. The combined organics were washed with brine, dried (MgSO4), filtered and concentrated. The residue was suspended in ether, filtered and the filtrate was concentrated to give 2.75 g (55%) of the title compound as a yellow oil.

EXAMPLE 280D hydroxy(3-(((4-(4-(trifluoromethoxy)phenoxy) phenyl)sulfonyl)methyl)-3,4-dihydro-2H-1,5-benzodioxepin-3-yl)formamide Example 208D was reacted with 4-(4'-trifluoromethoxyphenyloxy)-phenyl methyl sulfone following the procedures of Example 75A, then converted to the title compound following the procedures of Examples 75B, 75C and 213B.

mp 178–180° C. 1H NMR (DMSO-d6): δ 9.81 (bs, ½H), 8.38 (s, ½H), 8.05 (bs, ½H), 7.89–7.97 (m, 2½H), 7.47 (s, 1H), 7.45 (s, 1H), 7.30 (s, 1H), 7.23 (s, 1H), 7.20 (s, 1H), 7.00 (bs, 4H), 4.72 (d, 2H, J=12 Hz), 4.31–4.59 (m, 2H), 3.79–3.99 (m, 2H). MS (ESI(+)) 540 (M+H), 557 (M+NH4), 562 (M+Na), 598 (M+CH3CN+NH4) Anal. Calcd for: C24H20F3NO8S C, 53.43; H, 3.74; N, 2.60; S, 5.94; F, 10.57. Found: C, 53.41; H, 3.80; N, 2.32; S, 5.94; F, 10.72.

EXAMPLE 281 ethyl 4-(formyl(hydroxy)amino)-4-(((4-(4-(trifluoromethoxy)phenoxy)phenyl)sulfonyl)methyl) cyclohexanecarboxylate Ethyl 4-oxocyclohexanecarboxylate was converted to the title compound following the procedures of Example 258.

mp 150–151° C. 1H NMR (d6-DMSO) δ 9.41 (s, 0.5H), 8.19 (s, 0.5H), 7.88 (d, 2H, J=8.8 Hz), 7.47 (d, 2H, J=9.1 Hz), 7.46 (d, 2H, J=9.2 Hz), 7.21 (d, 2H, J=8.8 Hz), 4.04 (q, 2H, J=7.1 Hz), 8.35 (s, 2H), 2.48–2.28 (m, 3H), 1.80–1.62 (m, 4H), 1.54–1.34 (m, 2H), 1.16 (t, 3H, J=7.2 Hz). MS (ESI) 545 (M+H), 568 (M+Na), 544 (M–H).

EXAMPLE 282

4-(formyl(hydroxy)amino)-4-(((4-(4-(trifluoromethoxy)phenoxy)phenyl)sulfonyl)methyl) cyclohexanecarboxylic acid Example 281 was converted to the title compound following the hydrolysis procedure of Example 154E.

mp 207° C. $^1$H NMR (d6-DMSO) δ 9.39 (s, 0.5H), 8.18 (s, 0.5H), 7.88 (d, 2H, J=8.8 Hz), 7.65 (d, 2H, J=9.1 Hz), 7.29 (d, 2H, J=9.2 Hz), 7.21 (d, 2H, J=8.8 Hz), 3.54 (s, 2H), 2.46–2.14 (m, 3H), 1.80–1.60 (m, 4H), 1.54–1.34 (m, 2H). MS (ESI) 518 (M+H), 540 (M+Na), 516 (M–H). Anal. Calcd for: $C_{22}H_{22}NO_8SF_3$ C, 51.06; H, 4.28; N, 2.71. Found: C, 51.07; H, 4.37; N 2.59.

EXAMPLE 283 hydroxy(4-hydroxy-1-methyl-1-(((4-(4-(trifluoromethoxy)phenoxy)phenyl)sulfonyl)methyl) butyl)formamide 5-tert-butyldimethylsilyloxy-pentan-2-one was converted to the title compound following the procedures of Examples 258A, 75C, 213B and 125B.

$^1$H NMR (d6-DMSO) δ 9.38 (s, 1H), 8.07 (s, 1H), 7.88 (dt, J=1,8 Hz, 2H), 7.47 (d, J=8 Hz, 2H), 7.37–7.25 (m, 2H), 7.22–7.15 (m, 2H), 4.44 (t, J=6 Hz, 1H), 3.70 (d, J=15 Hz, 1H), 3.56 (d, J=15 Hz, 1H), 4.45–3.30 (m, 2H), 1.85–1.60 (m, 2H), 1.56 (s, 3H), 1.45–1.20 (m, 2H). MS (ESI): 478 (M+H)$^+$. Anal. Calcd for: C20H22F3NO7S : C, 50.31; H, 4.64; N, 2.93, Found: C, 50.18; H, 4.64; N, 2.27).

EXAMPLE 284

4-cyano-4'-(((4-(formyl(hydroxy)amino)tetrahydro-2H-pyran-4-yl)methyl)sulfonyl-1,1-biphenyl

EXAMPLE 284A 4-(((4-bromophenyl)sulfonyl)methyl)tetrahydro-2H-pyran-4-ol

A –10° C. solution of diisopropylamine (0.35 mL) in THF (5 mL) was treated with n-BuLi (1 mL, 2.5M solution in hexanes), stiired for 15 min then added via canula to a –78 C solution of 4-bromophenyl methyl sulfone (534 mg) in THF (5 mL). Stirred for 1 h, then treated with tetrahydropyran-4H-pyran-4-one (0.21 mL) and stirred for an additional 1 h. The reaction was quenched with aq. NH₄Cl, diluted with water and extracted wth EtOAc (3×). The combined organics were washed with brine, dried (Na2SO4), filtered, concentrated and purified via silica gel chromatography eluting with 10% ethyl acetate/ dichloromethane to give 640 mg of the title compound.

MS (DCI): 357, 359 (M+NH4)$^+$.

EXAMPLE 284B 4-cyano-4'-(((4-(formyl(hydroxy)amino)tetrahydro-2H-pyran-4-yl)methyl)sulfonyl)-1,1'-biphenyl Example 284A was converted to the title compound following the procedures of Example 46B (substituting 4-(4,4,5,5-tetramethyl-1,3,2-dioxaborolan-2-yl) benzonitrile for 4-n-butyloxybenzeneboronic acid), 261B, 261C and 213B.

$^1$H NMR (DMSO) δ 9.53 (s(br), 1H), 8.27 (s(br), 1H), 8.06–7.96 (m, 8H), 3.74 (s(br), 2H), 3.68–3.62 (m, 2H), 3.54–3.52 (m, 2H), 2.21–2.15 (m, 2H), 2.05–1.97 (m, 2H). MS (ESI) 401 (M+1), 423 (M+23). Anal. Calcd for: $C_{20}H_{20}N_2O_5S$: C, 59.99; H, 5.03; N, 7.00. Found: C, 59.71; H, 5.12; N, 6.91.

EXAMPLE 285 hydroxy(4-(((4'-(trifluoromethyl)(1,1'-biphenyl)-4-yl)sulfonyl)methyl)tetrahydro-2H-pyran-4-yl) formamide Example 284A was conerted to the title compound following the procedures of Example 46B (substituting 4-trifluoromethylbenzeneboronic acid for 4-n-butyloxybenzeneboronic acid) 75B, 75C and 213B.

1H NMR (DMSO) δ 9.51 (bs, 1H), 8.27 (bs, 1H), 8.02–7.98 (m, 6H), 7.89 (d, 2H, J=8.7 Hz), 3.74 (bs, 2H), 3.69–3.63 (m, 2H), 3.55–3.47 (m, 2H), 2.22–2.16 (m, 2H), 2.06–1.97 (m, 2H). MS (ESI) 444 (M+H)$^+$. Anal. Calcd for: $C_{20}H_{20}F_3NO_5S$: C, 54.17; H, 4.55; N, 3.16. Found: C, 54.22; H, 4.40; N, 2.99.

EXAMPLE 286

(1R)-1-((4S)-5,5-dimethyl-2-oxo-1,3-thiazolidin-4-yl)-2-((4-(4-(trifluoromethoxy)phenoxy)phenyl) sulfonyl)ethyl(hydroxy)formamide The diastereomer of Example 257 was prepared from D-penicillamine methyl ester following the procedures of Examples 145 and 146 (separating the diasteromeric hydroxylamine intermediates).

$^1$H NMR (DMSO) δ 10.25 (s, 0.5H), 9.88 (s, 0.5H), 8.22 (s(br), 0.5H), 8.12 (s(br), 0.5H), 8.10 (s, 0.5H), 8.08 (s, 0.5H), 7.96–7.89 (m, 2H), 7.49–7.46 (m, 2H), 7.31–7.22 (m, 4H), 4.84–4.78 (m, 0.5H), 4.42–4.39 (m, 0.5H), 3.80–3.63 (m, 1H), 3.56–3.43 (m, 1H), 1.49 (s, 1.5H), 1.47 (s, 1.5H), 1.39 (s, 1.5H), 1.28 (s, 1.5H).

EXAMPLE 287 hydroxy(2-(1-piperidinylsulfonyl)-1-(((4-(4-(trifluoromethoxyvphenoxy)phenyl)sulfonyl)methyl) ethylyformamide The title compound was prepared from Example 236A following the procedures of Examples 236B and 236C, substituting N-methylsulfonylpiperidine for N-methylsulfonyl morpholine.

mp: 140–142.5. $^1$H NMR (DMSO-d6) δ 1.45–1.55 (6H), 3.02–3.11 (4H), 3.27–3.43 (m, 2H), 3.58–3.79 (m, 2H), 4.46–4.49 (m, 0.5H), 5.00–5.02 (m, 0.5H), 7.22–7.29 (m, 4H), 7.46–7.49 (dd, 2H, J=3, 8.5 Hz), 7.83 (s, 0.5H), 7.89–7.92 (dd, 2H, J=4, 9 Hz), 8.10 (s, 0.5H), 9.78 (s, 0.5H), 10.08 (s, 0.5H). MS (ESI) 567 (M+H)$^+$; Anal. Calcd for: C22H25F3N2O8S2C, 46.64; H, 4.45; N, 4.94. Found: C, 46.50; H, 4.41; N, 4.78.

EXAMPLE 288 hydroxy(2-(1-pyrrolidinylsulfonyl)-1-(((4-(4-(trifluoromethoxy)phenoxy)phenyl)sulfonyl)methyl) ethyl)formamide The title compound was prepared from 236A following the procedures of Examples 236B–C, substituting N-methylsulfonylpyrrolidine for N-methylsulfonyl morpholine.

mp: 120–123° C. $^1$H NMR (DMSO-d6) δ 1.76–1.83 (m, 4H), 3.12–3.20 (m, 4H), 3.41–3.51 (m, 1H), 3.59–3.82 (m, 2H), 4.45–4.55 (m, 0.5H), 4.97–5.08 (m, 0.5H), 7.21–7.30 (m, 4H), 7.46–7.49 (d, 2H, J=9 Hz), 7.84 (s, 0.5H), 7.88–7.92 (dd, 2H, J=3, 9 Hz), 8.10 (s, 0.5H), 9.78 (s, 0.5H), 10.09 (s, 0.5H). MS (ESI) 553 (M+H)$^+$; Anal. Calcd for: C, 45.65; H, 4.20; N, 5.07. Found: C, 45.68; H, 4.16; N, 4.96.

EXAMPLE 289

4-((3-(1,4-dioxaspiro[4.5]dec-8-yl)-2-(formyl (hydroxy)amino)propyl)sulfonyl)-4'-fluoro-1,1'-biphenyl Ethyl 1-cyclohexane 4-ethylene ketal-acetate (prepared from 1,4-dioxaspiro[4,5]decan-8-one following the procedures of Examples 219A and 219B) was converted to the title compound following the procedures of Example 213, substituting 4-(4'-fluorophenyl)-phenyl methyl sulfone for 4-(4'-trifluoromethoxyphenyl)-phenyl methyl sulfone.

mp: 172–174° C. $^1$H NMR (DMSO-d6) δ 0.92–1.67 (m, 11H), 3.44–3.50 (m, 2H), 3.57–3.67 (m, 1H), 3,79–3.80 (d, 4H, J=2.4 Hz), 4.03–4.16 (m, 0.5H), 4.60–4.71 (m, 0.5H), 7.33–7.39 (t, 2H, J=8.7 Hz), 7.79–7.86 (m, 2H), 7.91–7.99 (m, 4.5H), 8.12 (s, 0.5H), 9.51 (s, 0.5H), 9.84 (s, 0.5H). MS (ESI) 478 (m+H), 495 (m+NH4), 476 (m–H). Anal. Calcd for: $C_{24}H_{28}FNO_6S$: C, 60.36; H, 5.91; N, 2.93. Found: C, 60.23; H, 5.89; N, 2.66.

EXAMPLE 290

2-(formyl(hydroxy)amino)-N,N-dimethyl-3-((4-(4-(trifluoromethoxy)phenoxy)phenyl)sulfonyl)-1-propanesulfonamide The title compound was prepared following the procedures of Example 236, substituting methylsulfonyl (dimethyl) amine for N-Methylsulfonyl morpholine.

mp: 124.5–125.5° C. $^1$H NMR (300 MHz, DMSO-d6) δ 2.74–2.69 (2 s, 6H), 3.44–3.25 (m, 2H), 3.83–3.56 (m, 2H), 4.51 (m, 0.5H), 5.04 (m, 0.5H), 7.30–7.20 (m, 4H), 7.48 (d, 2H, J=9.0 Hz), 7.85 (s, 0.5H), 7.91 (dd, 2H, J=9.0, 3.0 Hz), 8.10 (s, 0.5H), 9.89 (s, bs, 0.5H), 10.08 (s, bs, 0.5H). MS (ESI, +Q1MS) 527 (M+H), 544 (M+NH4). Anal. Calcd for: $C_{19}H_{21}F_3N_2O_8S_2$: C, 43.34; H, 4.02; N, 5.32. Found: C, 43.51; H, 4.06; N, 5.25.

EXAMPLE 291

2-(1,4-dioxa-8-azaspiro[4.5]dec-8-ylsulfonyl)-1-(((4-(4-(trifluoromethoxy)phenoxy)phenyl)sulfonyl) methyl)ethyl(hydroxy)formamide The title compound was prepared following the procedures of Example 236, substituting 8-(methylsulfonyl)-1,4-dioxa-8-azaspiro[4.5]decane for N-methylsulfonyl morpholine.

mp: 178–179° C. $^1$H NMR (300 MHz, DMSO-d6) δ 1.70–1.60 (m, 4H), 3.25–3.15 (m, 4H), 3.34–3.38 (m, 1H), 3.85–3.44 (m, 3H), 4.48 (m, 0.5H), 5.02 (m, 0.5H), 7.32–7.20 (m, 4H), 7.52–7.45 (m, 2H), 7.84 (s, 0.5H), 7.94–7.86 (m, 2H), 8.09 (s, 0.5H), 9.75 (s, bs, 0.5H), 10.07 (s, bs, 0.5H). MS (ESI, +Q1MS) 625 (M+H), 642 (M+NH4). Anal. Calcd for: $C_{24}H_{27}F_3N_2O_{10}S_2$: C, 46.15; H, 4.36; N, 4.48. Found: C, 46.30; H, 4.35; N, 4.47.

EXAMPLE 292

1-(1,4-dioxaspiro[4.5]dec-8-yl)-2-((4-(4-(trifluoromethoxy)phenoxy)phenyl)sulfonyl)ethyl (hydroxy)formamide Ethyl 1,4-dioxaspiro[4.5]decane-8-carboxylate was converted to the title compound following the procedures of Example 213.

mp: 176–177° C. $^1$H NMR (DMSO-d6, 300 MHz) δ 1.68–0.90 (m, 9H), 3.77–3.47 (m, 3.6H), 3.84–3.841 (m, 4H), 4.25 (t, 0.4H), 7.30–7.18 (m, 4H), 7.50–7.44 (m, 2H), 7.79 (s, 0.6H), 7.95–7.85 (m, 2H), 8.13 (s, 0.4H), 9.54 (s, 0.6H), 10.01 (s, 0.4H). MS (ESI,+Q1MS) 545(M+H)$^+$,563 (M+NH$_4$)$^+$. Anal. Calcd for: $C_{24}H_{26}F_3NO_8S$: C, 52.84; H, 4.80; N, 2.57. Found: C, 53.04; H, 5.04; N, 2.46.

EXAMPLE 293

3-(cyanomethyl)-4'-(((4-(formyl(hydroxy)amino)tetrahydro-2H-pyran-4-yl)methyl)sulfonyl)-1,1'-biphenyl Example 284A was converted to the title compound following the procedures of Examples 261B, 261C, 46B (except substituting 3-(4,4,5,5-tetramethyl-1,3,2-dioxaborolan-2-yl)cyanomethyl benzene for 4-n-butyloxybenzeneboronic acid), and 213B.

mp 101° C. $^1$H NMR (d6-DMSO) δ 9.50 (s, 1H), 8.27 (s, 1H), 8.01–7.92 (m, 4H), 7.74–7.72 (m, 2H), 7.59–7.53 (m, 1H), 7.47–7.44 (m, 1H), 4.13 (s, 2H), 3.78–3.44 (m, 6H), 2.28–1.90 (m, 4H). MS (ESI) m/z 415 (M+H), 432 (M+NH$_4$), 413 (M−H). Anal. Calcd for: $C_{21}H_{22}N_2O_5S$·0.5H$_2$O C, 59.56; H, 5.47; N, 6.61. Found: C, 59.92; H, 5.63; N, 6.30.

EXAMPLE 294

2-(formyl(hydroxy)amino)-N-(4-(hydroxymethyl)phenyl)-N-methyl-3-((4-(4-(trifluoromethoxy)phenoxy)phenyl)sulfonyl)-1-propanesulfonamide Example 236B was converted to the title compound following the sequence of reactions described in Example 236C and 236D and 125B, substituting N-methyl-N-(4-((tert-butyldimethylsilyloxy)methyl)phenyl)methanesulfonamide for N-methylsulfonyl morpholine.

$^1$H NMR (300 MHz, DMSO-d$_6$) δ 3.16 (s, 0.5H), 3.20 (s, 0.5H), 3.30–3.81 (m, 4H), 4.48–4.54 (d+m, 2.5H, J=5.4 Hz), 5.07–5.17 (m, 0.5H), 5.24–5.28 (dt, 1H, J=2.1, 6 Hz), 7.20–7.33 (m, 4H), 7.46–7.49 (d, 2H, J=9 Hz), 7.73 (s, 0.5H), 7.87–7.90 (dd, 2H, J=2.1, 6.9 Hz), 8.09 (s, 0.5H), 9.81 (s, 0.5H), 10.13 (s, 0.5H), MS (ESI) m/e 636 (M+NH4)$^+$, 641 (M+Na)$^+$, 617 (M−H)$^−$, 653 M+Cl)$^−$. Anal. calcd for $C_{25}H_{25}N_2F_3O_9S_2$: C, 48.54; H, 4.07; N, 4.53. Found: C, 48.79; H, 4.38; N, 4.19.

EXAMPLE 295

N,N-diethyl-2-(formyl(hydroxy)amino)-3-((4-(4-(trifluoromethoxy)phenoxy)phenyl)sulfonyl)-1-propane sulfonamide

EXAMPLE 295A methyl (4-fluorophenyl)sulfanylacetate

A solution of 4-fluorothiophenol (10 g, 78 mmol) in ethanol(200 mL) was treated with powdered KOH (9.6 g), stirred for 30 min at rt, then treated with a solution of bromoacetic acid (10.84 g, 78 mmol) in ethanol (50 mL) and stirred at 80 C for 4 h. the reaction was cooled to rt, partitioned between 1N HCl and EtOAc and the organics were washed with water, dried (Na$_2$SO$_4$), filtered and concentrated. The crude product was dissolved in MeoH (250 mL), cooled to 0 C, treated with SOCl2 (8.5 mL) and stirred at rt overnight. The reaction was quenched with water, concentrated then partitioned between EtOAc (3 times) and water. The combined organics were washed with brine, dried (Na2SO4), filtered and concentrated to give 14.6 g of the title compound.

EXAMPLE 295B

Example 295A was converted to the title compound as follows: (a) reaction with diethyl(methylsulfonyl) amine as in 236A (b) ketone reduction as in 126B (c) sulfide oxidation as in 46D, (d) coupling with 4-trifluoromethoxyphenol as in 74A (e) elimination, Michael addition and formylation as in 75B, 75C and 213B.

1H NMR (300 MHz, DMSO-d$_6$) d 1.00–1.12 (m, 6H), 3.04–3.20 (m, 4H), 3.55–3.83 (m, 2H), 4.40–4.53 (m, 0.5H), 4.93–5.05 (m, 0.5H), 7.21–7.29 (m, 4H), 7.46–7.49 (d, 2H, J=8.7 Hz), 7.81–7.91 (m, 2.5H), 8.08 (s, 0.5H), 9.74 (s, 0.5H), 10.08 (s, 0.5H), MS (ESI) m/e 555 (M+H)$^+$, 572 (M+NH$_4$)$^+$, 553 (M−H)$^−$. Anal. calcd for $C_{21}H_{25}N_2F_3O_8S_2$: C, 45.48; H, 4.54; N, 5.05. Found: C, 45.52; H, 4.64; N, 4.89.

EXAMPLE 296 methyl (3-(2-(formyl(hydroxy)amino)-3-((4-(4-(trifluoromethoxy)phenoxy)phenyl)sulfonyl)propyl)phenyl)acetate Methyl [3-(2-methoxy-2-oxoethyl)phenyl]acetate was converted to the title compound following the procedures of Example 213.

mp 82–83 C. $^1$H NMR (DMSO-d6): δ 9.98 (bs, ½H), 9.63 (bs, ½H), 8.03 (s, ½H), 7.87 (s, 1H), 7.84 (s, 1H), 7.55 (s, ½H), 7.48 (s, 1H), 7.45 (s, 1H), 7.25–7.32 (m, 2H), 7.15–7.23 (m, 3H), 6.98–7.13 (m, 3H), 4.71–4.83 (m, ½H), 4.18–4.30 (m, ½H), 3.99–4.12 (m, ½H), 3.50–3.65 (m, 1½H), 3.36–3.50 (m, 2H), 3.33(s, 3H), 2.76–2.94 (m, 2H); MS ESI(+) m/z 568 (M+H), 585 (M+NH4); Anal. Calcd for: $C_{26}H_{24}F_3NO_8S$: C, 55.02; H, 4.26; N, 2.47;S, 5.65: F, 10.04. Found: C, 55.14; H, 4.25; N, 2.35; S, 5.73; F, 10.20.

EXAMPLE 297

(3-(2-(formyl(hydroxy)amino)-3-((4-(4-(trifluoromethoxy)phenoxy)phenyl)sulfonyl)propyl)phenyl)acetic acid Example 296 was converted to the title compound following the procedures of Example 251.

mp 138–140° C.; $^1$H NMR (DMSO-d6) δ 12.38 (bs, 1H), 9.98 (bs, ⅓H), 9.63 (bs, ⅔H), 8.01–8.08 (m, ½H), 7.82–7.89 (m, 2H), 7.55 (s, ½H), 7.43–7.52 (m, 2H), 7.25–7.32 (m, 2H), 7.41–7.22 (m, 3H), 7.05–7.12 (m, 2H), 6.95–7.05 (m, 1H), 4.71–4.82 (m, ⅓H), 4.19–4.34 (m, ⅔H), 3.65–3.81(m, 1H), 3.26–3.48(m, 3H), 2.75–2.92(2H). MS (ESI(+)) m/z 554 (M+H), 571 (M+NH4), 576 (M+Na); Anal. Calcd for: $C_{25}H_{22}F_3NO_8S$: C, 54.25; H, 4.01; N, 2.53;S, 5.79; F, 10.30. Found: C, 54.16; H, 4.02; N, 2.42;S, 6.12; F, 10.46.

EXAMPLE 298

1,2-dideoxy-2-(formyl(hydroxy)amino)-3,4-O-(1-methylethylidene)-1-((4-(4-(trifluoromethoxy)phenoxy)phenyl)sulfonyl)-L-threo-pentitol The desired product was prepared by substituting (2S, 3S)-2,3-O-isopropylidine-2,3,4-trihydroxybutanal tert-butyldimethylsilyl ether (prepared by the procedure described in J. Org. Chem. 1993, v. 58, p. 5153) for (R)-2,2-diethyl-1,3-dioxolane-4-carboxaldehyde in Example 6A, then substituting the resulting product for Example 6A in Example 6B and Example 16B.

MS (ESI) m/z 536 (M+H)$^+$, 553 (M+NH$_4$)$^+$; $^1$H NMR (400 MHz, DMSO-d$_6$): δ 9.96 (s, 0.5H), 9.62 (s, 0.5H), 8.14 (s, 0.5H), 7.94–7.88 (m, 2H), 7.81 (s, 0.5H), 7.48–7.45 (m, 2H), 7.29–7.20 (m, 4H), 5.18–5.12 (m, 1H), 4.72–4.62 (m, 1H), 4.10–3.92 (m, 2H), 3.80–3.62 (m, 2H), 3.60–3.30 (m, 4H), 1.29–1.22 (m, 6H).

What is claimed is:

1. A compound of formula (I),

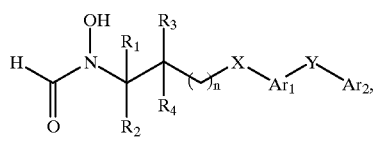
(I)

or a pharmaceutically acceptable salt or prodrug thereof, wherein n is zero;

R$_1$ is selected from the group consisting of
   (1) hydrogen and
   (2) alkyl of one to six carbon atoms;

R$_3$ and R$_4$ are hydrogen;

R$_2$ is selected from the group consisting of
   (1) alkyl of one to six carbon atoms,
   (2) alkoxyalkyl, wherein the alkoxyalkyl is substituted with hydroxy or silyloxy,
   (3) hydroxyalkyl, wherein the alkylene group is of one to six carbon atoms,
   (4) phenylalkyl, wherein the alkylene group is of one to six carbon atoms, and the phenyl can be optionally substituted with a substituent selected from the group consisting of
      (a) alkyl of one to six carbon atoms,
      (b) alkoxycarbonyl wherein the alkyl part is of one to six carbon atoms,
      (c) alkoxycarbonylalkyl, wherein the alkylene and alkyl groups are independently of one to six carbon atoms,
      (d) —C(O)OR$_5$ wherein R$_5$ is selected from the group consisting of hydrogen and alkyl of one to six carbon atoms, and
      (e) hydroxyalkyl of one to six carbon atoms,
   (5) -(alkylene)-S(O)$_p$-heterocycle, wherein p is two, the alkylene group is of one to six carbon atoms, and the heterogycle is piperidine, wherein the piperidine can be optionally substituted with dioxolanyl,
   (6) -(alkylene)-heterocycle, wherein the alkylene group is of one to six carbon atoms, and the heterocycle is selected from the group consisting of
      (a) thienyl,
      (b) tetrahydropyranyl,
      (c) tetrahydrothiopyranyl wherein the sulfur atom is oxidized, and (d)

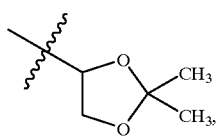

(7) -(alkylene)-NR$_6$R$_7$, wherein the alkylene group is of one to six carbon atoms, R$_6$ is hydrogen, and R$_7$ is alkanoyl of one to six carbon atoms wherein the alkanoyl group is substituted with alkoxncarbonyl, or R$_6$ and R$_7$, taken together with the nitrogen atom to which they are attached, define a group selected from the group consisting of
   (a) morpholinyl,
   (b) thiomorpholinyl,
   (c) piperidinyi,
   (d) piperazinyl substituted with a substituent selected from the group consisting of alkyl of one to six carbon atoms, alkanoyl of one to six carbon atoms, and —SO$_2$-alkyl wherein the alkyl is of one to six carbon atoms, (e)

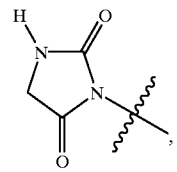
, (f)

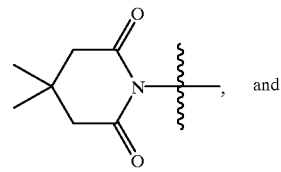
, and (g)

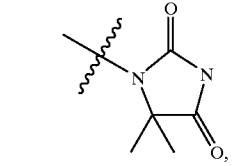
, (8) heterocycle selected from the group consisting of
   (a) oxazolidinonyl, wherein the oxazolidinonyl can be optionally substituted with alkyl of one to six carbon atoms,
   (b) tetrahydrofuranyl,
   (c) thiazolidinonyl, wherein the thiazolidinonyl can be optionally substituted with one or two alkyl of one to six carbon atom substituents,
   (d) pyrrolidinyl substituted with —SO$_2$-alkyl wherein the alkyl is of one to six carbon atoms,
   (e) piperidinyl substituted with a substituent selected from the group consisting of alkanoyl of one to ten carbons and —SO$_2$-alkyl wherein the alkyl is of one to six carbon atoms, (f)
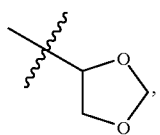

(g)
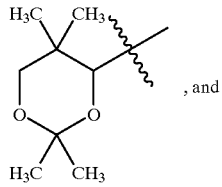, and (h)
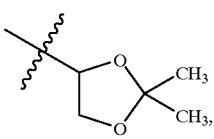

substituted with hydroxyalkyl of one to six carbon atoms, (9) -(alkylene)-$S(O)_p$-$NR_6R_7$, wherein p is 2, and $R_6$ and $R_7$ are selected from the group consisting of alkyl one to six carbon atoms and phenyl substituted with hydroxyalkyl of one to six carbon atoms, or $R_6$ and $R_7$ together with the nitrogen atom to which they are attached, define a group selected from the group consisting of morpholine and pyrrolidine,

(10) cycloalkyl, wherein the cycloalkyl can be optionally substituted with dioxolanyl,

(11) (cycloalkyl)alkyl, wherein the cycloalkyl part is substituted with dioxolanyl,

(12) -carbonyl-$NR_6R_7$, wherein $R_6$ and $R_7$ are alkyl of one to six carbon atoms or $R_6$ and $R_7$ together are morpholinyl,

(13) -(alkylene)-$S(O)_p$-phenyl, wherein the alkylene is of one to six carbon atoms, and the phenyl is substituted with halo,

(14) -(alkylene)-$N(R_5)SO_2$-alkyl, wherein the alkylene is of one to six carbon atoms, and $R_5$ is alkyl of one to five carbon atoms, and

(15) -(alkylene)-carbonyl-$NR_6R_7$, wherein $R_6$ and $R_7$, together with the nitrogen atom to which they are attached, are morpholinyl; or $R_1$ and $R_2$, taken together with the carbon atom to which they are attached form a ring selected from the group consisting of
(1) spiroalkyl of three to eight carbon atoms, wherein the spiroalkyl can be optionally substituted with dioxolanyl or —$CO_2R_5$,
(2) tetrahydropyranyl,
(3) tetrahydrothiopyranyl, wherein the sulfur atom is oxidized,
(4) piperidinyl, wherein the nitrogen group is substituted with alkanoyl or —$SO_p$-alkyl,
(5) dioxanyl, wherein the dioxanyl is substituted with alkyl, and
(6) dihydrobenzodioxepinyl;

X is selected from the group consisting of
(1) —O— and
(2) —$S(O)_p$—; and $Ar_1$ is unsubstituted phenyl;

Y is selected from the group consisting of
(1) a covalent bond and
(2) —O—; and $Ar_2$ is phenyl,
wherein the phenyl is substituted with one substituent selected from the group consisting of
(a) alkyl of one to six carbon atoms,
(b) alkoxy of one to six carbon atoms,
(c) alkoxy of one to six carbon atoms substituted with alkoxy of one to six carbon atoms,
(d) cyano,
(e) cyanoalkyl of one to six carbon atoms,
(f) halo,
(g) thioalkoxy of one to six carbon atoms,
(h) perfluoroalkyl of one to six carbon atoms, and
(i) perfluoroalkoxy, wherein the perfluoroalkyl part is of one to six carbon atoms.

2. A compound according to claim 1 wherein $R_3$ and $R_4$ are hydrogen.

3. A compound according to claim 2, wherein $R_1$ is alkyl of one to six carbon atoms and $R_2$ is alkyl of one to six carbon atoms or hydroxyalkyl, wherein the alkylene group is of one to six carbon atoms.

4. A compound according to claim 3 selected from the group consisting of
1,1-dimethyl-2-({4-[4-(trifluoromethoxy)phenoxy]phenyl}sulfonyl)ethyl(hydroxy)formamide and hydroxy(4-hydroxy-1-methyl-1-(((4-(4-(trifluoromethoxy)phenoxy)phenyl)sulfonyl)methyl)butyl)formamide.

5. A compound according to claim 2, wherein $R_1$ is hydrogen.

6. A compound according to claim 5, wherein $R_2$ is selected from the group consisting of
(1) -(alkylene)-$S(O)_p$-phenyl, wherein the alkylene group is of one to a six carbon atoms and the phenyl is substituted with halo,
(2) hydroxyalkyl, wherein the alkylene group is of one to six carbon atoms,
(3) -(alkylene)-heterocycle, wherein the alkylene group is of one to six carbon atoms, and the heterocycle is selected from the group consisting of
(a) thienyl,
(b) tetrahydropyranyl,
(c) tetrahydrothiopyranyl wherein the sulfur atom is oxidized, and (d)
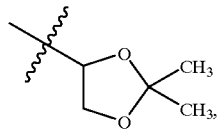

(4) alkoxyalkyl, wherein the alkoxyalkyl is substituted with hydroxy or silyloxy,
(5) -(alkylene)-$S(O)_p$-heterocycle, wherein the alkylene group is of one to six carbon atoms, and the heterocycle is piperidine, wherein the piperidine can be optionally substituted with dioxolanyl,
(6) heterocycle selected from the group consisting of
(a) oxazolidinonyl,
(b) tetrahydrofuranyl,
(c) thiazolidinonyl,
(d) pyrrolidinyl substituted with —$SO_2$-alkyl wherein the alkyl is of one to six carbon atoms, (e) piperidinyl substituted with a substituent selected from the group consisting of alkanoyl of one to ten carbons and —SO$_2$-alkyl wherein the alkyl is of one to six carbon atoms, (f) 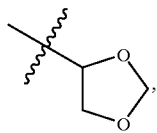

(g) 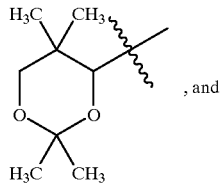, and (h) 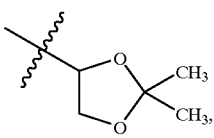

substituted with hydroxyalkyl of one to six carbon atoms, (7) -carbonyl-NR$_6$R$_7$, wherein R$_6$ and R$_7$ are alkyl of one to six carbon atoms or R$_6$ and R$_7$ together are morpholinyl, (8) -(alkylene)-N(R$_5$)SO$_2$-alkyl, wherein the alkylene is of one to six carbon atoms, (9) cycloalkyl, wherein the cycloalkyl can be optionally substituted with dioxolanyl,

(10) -(alkylene)-carbonyl-NR$_6$R$_7$, wherein R$_6$ and R$_7$, together with the nitrogen atom to which they are attached, are morpholinyl

(11) phenylalkyl, wherein the alkylene group is of one to six carbon atoms, and the phenyl can be optionally substituted with a substituent selected from the group consisting of
  (a) alkyl of one to six carbon atoms,
  (b) alkoxycarbonyl wherein the alkyl part is of one to six carbon atoms,
  (c) alkoxycarbonylalkyl, wherein the alkylene and alkyl groups are independently of one to six carbon atoms,
  (d) —C(O)OR$_5$ wherein R$_5$ is selected from the group consisting of hydrogen and alkyl of one to six carbon atoms, and hydroxyalkyl of one to six carbon atoms,

(12) (cycloalkyl)alkyl, wherein the cycloalkyl part is substituted with dioxolanyl, and

(13) -(alkylene)-S(O)$_p$-NR$_6$R$_7$wherein R$_6$ and R$_7$ are selected from the group consisting of alkyl one to six carbon atoms and phenyl substituted with hydroxmalkyl of one to six carbon atoms, or R$_6$ and R$_7$ together with the nitrogen atom to which they are attached, define a group selected from the group consisting of morpholine and pyyrrolidine, and

(14) alkyl of one to six carbon atoms.

7. A compound according to claim 6 selected from the group consisting of 4-fluoro-4'-({2-[formyl(hydroxy)amino]-4-hydroxybutyl}sulfonyl-1,1'-biphenyl;

4-chloro-4'-({2-[formyl(hydroxy)amino]-4-hydroxybutyl}sulfonyl-1,1'-biphenyl;

4-fluoro-4'-({2-[formyl(hydroxy)amino]-4-hydroxypentyl}sulfonyl-1,1'-biphenyl;

4-chloro-4'-({2-[formyl(hydroxy)amino]-4-hydroxypentyl}sulfonyl-1,1'-biphenyl;

hydroxy{2-tetrahydro-2H-pyran-4-yl-1-[({4-[4-(trifluoromethoxy)phenoxy]phenyl}sulfonyl)methyl]ethyl}formamide;

hydroxy[(1R)-1-(2R)-1-(methylsulfonyl)pyrrolidinyl]-2-({4-[4-(trifluoromethoxy)phenoxy]phenyl}sulfonyl)ethyl]formamide;

hydroxy[(1S)-1-(2R)-1-(methylsulfonyl)pyrrolidinyl]-2-({4-[4-(trifluoromethoxy)phenoxy]phenyl}sulfonyl)ethyl]formamide;

2-(1,1-dioxidotetrahydro-2H-thiopyran-4-yl)-1-[({4-[4-(trifluoromethoxy)phenoxy]phenyl}sulfonyl)methyl]ethyl(hydroxy)formamide;

1-cyclopropyl-2-({4-[4-(trifluoromethoxy)phenoxy]phenyl}sulfonyl)ethyl(hydroxy)formamide;

2-(1,4-dioxaspiro[4,5]dec-8-yl)-1-[({4-[4-(trifluoromethoxy)phenoxy]phenyl}sulfonyl)methyl]ethyl(hydroxy)formamide;

hydroxy[1-[(4S)-2-oxo-1,3-oxazolidin-4-yl]-2-({4-[4-(trifluoromethoxy)phenoxy]phenyl}sulfonyl)ethyl]formamide;

hydroxy[(1S)-1-[(2R)-tetrahydro-2-furanyl]-2-({4-[4-(trifluoromethoxy)phenoxy]phenyl}sulfonyl)ethyl]formamide;

hydroxy[(1R)-1-[(2R)-tetrahydro-2-furanyl]-2-({4-[4-(trifluoromethoxy)phenoxy]phenyl}sulfonyl)ethyl]formamide;

hydroxy[1-[(4S)-3-methyl-2-oxo-1,3-oxazolidin-4-yl]-2-({4-[4-(trifluoromethoxy)phenoxy]phenyl}sulfonyl)ethyl]formamide;

hydroxy[1-[1-(methylsulfonyl)-4-piperidinyl]-2-({4-[4-(trifluoromethoxy)phenoxy]phenyl}sulfonyl)ethyl]formamide;

hydroxy[1-(1-isobutyryl-4-piperidinyl)-2-({4-[4-(trifluoromethoxy)phenoxy]phenyl}sulfonyl)ethyl]formamide;

hydroxy{2-(4-morpholinylsulfonyl)-1-[({4-[4-(trifluoromethoxy)phenoxy]phenyl}sulfonyl)methyl]ethyl}formamide;

hydroxy{2-methyl-2-(4-morpholinylsulfonyl)-1-[({4-[4-(trifluoromethoxy)phenoxy]phenyl}sulfonyl)methyl]propyl}formamide;

hydroxy{2-(2-thienyl)-1-[({4-[4-(trifluoromethoxy)phenoxy]phenyl}sulfonyl)methyl]ethyl}formamide;

(1S)-1-[(4S)-2,2-dimethyl-1,3-dioxolan-4-yl]-2-{[4-(4-methoxyphenoxy)phenyl]sulfonyl}ethyl(hydroxy)formamide;

1,2,3-trideoxy-2-[formyl(hydroxy)amino]-4,5-O-(1-methylethylidene)-1-({4-[4-(trifluoromethoxy)phenoxy]phenyl}sulfonyl)-D-threo-pentitol;

(1S)-2-{[4-(4-chlorophenoxy)phenyl]sulfonyl}-1-[(4S)-2,2-dimethyl-1,3-dioxolan-4-yl]ethyl(hydroxy)formamide;

2-[formyl(hydroxy)amino]-N,N-dimethyl-3-({4-[4-(trifluoromethoxy)phenoxy]phenyl}sulfonyl)propanamide;

hydroxy{2-(4-morpholinyl)-2-oxo-1-[({4-[4-(trifluoromethoxy)phenoxy]phenyl}sulfonyl)methyl]ethyl}formamide;

N-[2-[formyl(hydroxy)amino]-3-({4-[4-(trifluoromethoxy)phenoxy]phenyl}sulfonyl)propyl]-N-methylmethanesulfonamide;

(1S)-1-[(4S)-2,2-dimethyl-1,3-dioxolan-4-yl]-2-({4-[4-(trifluoromethyl)phenoxy]phenyl}sulfonyl)ethyl(hydroxy)formamide;

(1S)-1-[(4S)-2,2-dimethyl-1,3-dioxolan-4-yl]-2-({4-[4-(methylphenoxy]phenyl}sulfonyl)ethyl(hydroxy)formamide;

4-({(2S)-2-[(4S)-2,2-dimethyl-1,3-dioxolan-4-yl]-2-[formyl(hydroxy)amino]ethyl}sulfonyl)-4'-(trifluoromethyl)-1,1'-biphenyl;

methyl 4-[3-[formyl(hydroxy)amino]-4-({4-[4-(tifluoromethoxy)phenoxy]phenyl}sulfonyl)butyl]benzoate;

4-[3-[formyl(hydroxy)amino]-4-({4-[4-(trifluoromethoxy)phenoxy]phenyl}sulfonyl)butyl]benzoic acid;

hydroxy{3-[4-(hydroxymethyl)phenyl]-1-[({4-[4-(trifluoromethoxy)phenoxy]phenyl}sulfonyl)methyl]propyl}formamide;

2-{[4-(4-chlorophenoxy)phenyl]sulfonyl}-1-{[(4-chlorophenyl)sulfonyl]methyl}ethyl(hydroxy)formamide;

hydroxy{(1S)-4-hydroxy-1-[({4-[4-(trifluoromethoxy)phenoxy]phenyl}sulfonyl)methyl]butyl}formamide;

hydroxy{(1R)-2-({4-[4-(trifluoromethoxy)phenoxy]phenyl}sulfonyl)-1-[(4S)-3,5,5-trimethyl-2-oxo-1,3-thiazolidin-4-yl]ethyl}formanide;

(1R)-1-[(4S)-5,5-dimethyl-2-oxo-1,3-thiazolidin-4-yl]-2-({4-[4-(trifluoromethoxy)phenoxy]phenyl}sulfonyl)ethyl(hydroxy)formamide;

(1S)-1-((4S)-1,3-dioxolan-4-yl)-2-((4-(4-(trifluoromethoxy)phenoxy)phenyl)sulfonyl)ethyl(hydroxy)formamide;

4-(((2S)-2-((4S)-2,2-dimethyl-1,3-dioxolan-4-yl)-2-(formyl(hydroxy)amino)ethyl)sulfonyl)-4'-(2-methoxyethoxy)-1,1'-biphenyl;

(1S)-1-((4S)-2,2-dimethyl-1,3-dioxolan-4-yl)-2-((4-(4-(2-methoxyethoxy)phenoxy)phenyl)sulfonyl)ethyl(hydroxy)formamide;

hydroxy(4-(4-morpholinyl)-4-oxo-1-(((4-(4-(trifluoromethoxy)phenoxy)phenyl)sulfonyl)methyl)butyl)formamide;

1,2,4-trideoxy-2-(formyl(hydroxy)amino)-4,4-dimethyl-3,5-O-(1-methylethylidene)-1-((4-(4-(trifluoromethoxy)phenoxy)phenyl)sulfonyl)-D-threopentitol;

hydroxy((2R)-2-phenyl-1-(((4-(4-(trifluoromethoxy)phenoxy)phenyl)sulfonyl)methyl)propyl)formamide;

1-(2-((tert0butyl(dimethyl)silyl)oxy)ethoxy)-1-(((4-(4-(trifluoromethoxy)phenoxy)phenyl)sulfonyl)methyl)ethyl(hydroxy)formamide;

hydroxy(2-(2-hydroxyethoxy)-1-(((4-(4-(trifluoromethoxy)phenoxy)phenyl)sulfonyl)methyl)ethyl)formamide;

hydroxy((1S,2S)-2-(4-isobutylphenyl)-1-(((4-(4-(trifluoromethoxy)phenoxy)phenyl)sulfonyl)methyl)propyl)formamide;

hydroxy(3-hydroxy-2,2-dimethyl-1-(((4-(4-(trifluoromethoxy)phenoxy)phenyl)sulfonyl)methyl)propyl)formamide;

1,2,3-trideoxy-2-(formyl(hydroxy)amino)-4,5-O-(1-methylethylidene)-1-((4-(4-(trifluoromethoxy)phenoxy)phenyl)sulfonyl)-D-erythro-pentitol;

hydroxy(4-hydroxy-1-methyl-1-(((4-(4-(trifluoromethoxy)phenoxy)phenyl)sulfonyl)methyl)butyl)formamide;

(1R)-1-((4S)-5,5-dimethyl-2-oxo-1,3-thiazolidin-4-yi)-2-((4-(4-(trifluoromethoxy)phenoxy)phenyl)sulfonyl)ethyl(hydroxy)formamide;

hydroxy(2-(1-piperidinyisulfonyl)-1-(((4-(4-(trifluoromethoxy)phenoxy)phenyl)sulfonyl)methyl)ethyl)formamide;

hydroxy(2-(1-pyrrolidinylsulfonyl)-1-(((4-(4-(trifluromethoxy)phenoxy)phenyl)sulfonyl)methyl)ethyl)formamide;

4-((3-(1,4-dioxaspiro[4.5]dec-8-yl)-2-formyl(hydroxy)amino)propyl)sulfonyl)-4'-fluoro-1,1'-biphenyl;

2-(formyl(hydroxy)amino)-N,N-dimethyl-3-((4-(4-(trifluoromethoxy)phenoxy)phenyl)sulfonyl)-1-propanesulfonamide;

2-(1,4-dioxa-8-azaspiro[4.5]dec-8-ylsulfonyl)-1-(((4-(4-(trifluoromethoxy)phenoxy)phenyl)sulfonyl)methyl)ethyl(hydroxy)formamide;

1-(1,4-dioxaspiro[4.5]dec-8-yl)-2-((4-(4-(trifluoromethoxy)phenoxy)phenyl)sulfonyl)ethyl(hydroxy)forrnamide;

2-(formyl(hydroxy)amino)-N-(4-(hydroxymethyl)phenyl)-N-methyl-3-((4-(4-(trifluoromethoxy)phenoxy)phenyl)sulfonyl)-1-propanesulfonamide;

N,N-diethyl-2-(formyl(hydroxy)amino)-3-((4-(4-(trifluoromethoxy)phenoxy)phenyl)sulfonyl)-1-propanesulfonamide;

methyl (3-(2-(formyl(hydroxy)amino)-3-((4-(4-(trifluoromethoxy)phenoxy)phenyl)sulfonyl)propyl)phenyl)acetate; and 1,2-dideoxy-2-(formyl(hydroxy)amino)-3,4-O-(1-methylethylidene)-1-((4-(4-(trifluoromethoxy)phenoxy)phenyl)sulfonyl)-L-threo-pentitol.

8. A compound according to claim 5 wherein $R_2$ is -(alkylene)-$NR_6R_7$, wherein the alkylene group is of one to six carbon atoms, $R_6$ is hydrogen and $R_7$ is alkanoyl of one to six carbon atoms wherein the alkanoyl group is substituted with alkoxycarbonyl, or $R_6$ and $R_7$, taken together with the nitrogen atom to which they are attached, define a group selected from the group consisting of (a) morpholinyl, (b) thiomorpholinyl, (c) piperidinyl, (d) piperazinyl substituted with a substituent selected from the group consisting of alkyl of one to six carbon atoms, alkanoyl of one to six carbon atoms, and —$SO_2$-alkyl wherein the alkyl is of one to six carbon atoms,

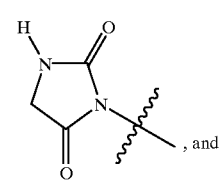
, and (e)

(f)

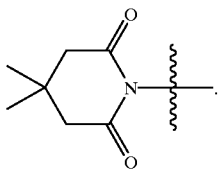

9. A compound according to claim 5 wherein $R_2$ is -(alkylene)-$NR_6R_7$, wherein $R_6$ and $R_7$, taken together with the nitrogen atom to which they are attached, are

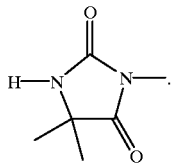

10. A compound according to claim 9 selected from the group consisting of
    3-(cyanomethyl)-4'-({3-(4,4-dimethyl-2,5-dioxo-1-imidazolidinyl)-2-[formyl(hydroxy)amino]propyl}sulfonyl)-1,1'-biphenyl;
    4-({3-(4,4-dimethyl-2,5-dioxo-1-imidazolidinyl)-2-[formyl(hydroxy)amino]propyl}sulfonyl)-4'-fluoro-1,1-biphenyl;
    4-({3-(4,4-dimethyl-2,5-dioxo-1-imidazolidinyl)-2-[formyl(hydroxy)amino]propyl}sulfonyl)-4'-(methylsulfanyl)-1,1-biphenyl;
    4-({3-(4,4-dimethyl-2,5-dioxo-1-imidazolidinyl)-2-[formyl(hydroxy)amino]propyl}sulfonyl)-4'-(methoxy)-1,1-biphenyl;
    (1S)-2-((4-(4-chlorophenoxy)phenyl)sulfonyl)-1-((4,4-dimethyl-2,5-dioxo-1-imidazolidinyl)methyl)ethyl(hydroxy)formamide;
    (1S)-2-(4,4-dimethyl-2,5-dioxo-1-imidazolidinyl)-1-(((4'-(trifluoromethyl)(1,1'-biphenyl)-4-yl)sulfonyl)methyl)ethyl(hydroxy)formamide;
    (1S)-2-(4,4-dimethyl-2,5-dioxo-1-imidazolidinyl)-1-(((4'-methoxy(1,1'-biphenyl)-4-yl)oxy)methyl)ethyl(hydroxy)formamide;
    (1S)-2-(4,4-dimethyl-2,5-dioxo-1-imidazolidinyl)-1-(((4'-methyl(1,1'-biphenyl)-4-yl)oxy)methyl)ethyl(hydroxy)formamide; and
    4-(((2S)-2-(formyl(hydroxy)amino)-3-(3,4,4-trimethyl-2,5-dioxo-1-imidazolidinyl)propyl)oxy)-4'-(trifluoromethoxyy-1,1'-biphenyl.

11. A compound according to claim 8 selected from the group consisting of
    hydroxy{3-(4-morpholinyl)-1-[({4-[4-(trifluoromethoxy)phenoxy]phenyl}sulfonyl)methyl]propyl}formamide;
    4-chloro-4'-({3-(4,4-dimethyl-2,6-dioxo-1-piperididnyl)-2-[formyl(hydroxy)amino]propyl}sulfonyl)-1,1-biphenyl;
    ethyl 5-({3-[4'-fluoro[1,1'-biphenyl]-4-yl)sulfonyl]-2-[formyl(hydroxy)amino]propyl}amino)-3,3-dimethyl-5-oxopentanoate;
    4-({3-(4,4-dimethyl-2,6-dioxo-1-piperidinyl)-2-[formyl(hydroxy)amino]propyl}sulfonyl)-4'-fluoro-1,1'-biphenyl;
    hydroxy[3-(4-morpholinyl)-1-({[4'-(trifluoromethyl)[1,1'-biphenyl]-4-yl]sulfonyl}methyl)propyl]formamide;
    4-chloro-4'-{[2-[formyl(hydroxy)amino]-4-(4-morpholinyl)butyl]sulfonyl}-1,1'-biphenyl;
    4-chloro-4'-{[2-[formyl(hydroxy)amino]-4-(1-piperidinyl)butyl]sulfonyl}-1,1'-biphenyl;
    hydroxy{3-(1-piperidinyl)-1-[({4-[4-(trifluoromethoxy)phenoxy]phenyl}sulfonyl)methyl]propyl}formamide;
    4-chloro-4'-{[2-[formyl(hydroxy)amino]-3-(1-piperidinyl)propyl]sulfonyl}-1,1'-biphenyl;
    hydroxy{2-(1-piperidinyl)-1-[({4-[4-(trifluoromethoxy)phenoxy]phenyl}sulfonyl)methyl]ethyl}formamide;
    3-(4-acetyl-1-piperazinyl)-1-[({4-[4-(trifluoromethoxy)phenoxy]phenyl}sulfonyl)methyl]propyl(hydroxy)formamide;
    hydroxy{3-(4-thiomorpholinyl)-1-[({4-[4-(trifluoromethoxy)phenoxy]phenyl}sulfonyl)methyl]propyl}formamide;
    hydroxy{3-(4-methyl-1-piperazinyl)-1-[({4-[4-(trifluoromethoxy)phenoxy]phenyl}sulfonyl)methyl]propyl}formamide;
    hydroxy{2-[4-(methylsulfonyl)-1-piperazinyl]-1-[({4-[4-(trifluoromethoxy)phenoxy]phenyl}sulfonyl)methyl]ethyl}formamide;
    hydroxy{3-[4-(methylsulfonyl)-1-piperazinyl]-1-[({4-[4-(trifluoromethoxy)phenoxy]phenyl}sulfonyl)methyl]propyl}formamide;
    2-[4-(2,2-dimethylpropanoyl)-1-piperazinyl]-1-[({4-[4-(trifluoromethoxy)phenoxy]phenyl}sulfonyl)methyl]ethyl(hydroxy)formamide, and
    (1S)-2-(2,5-dioxo-1-imidazolidinyl)-1-(((4-(4-(trifluoromethoxy)phenoxy)phenyl)sulfonyl)methyl)ethyl(hydroxy)formamide.

12. A compound according to claim 1, wherein $R_1$ and $R_2$, taken together with the carbon atom to which they are attached form a ring selected from
    (1) spiroalkyl of three to eight carbon atoms, wherein the spiroalkyl can be optionally substituted with dioxolanyl or —$CO_2R_5$,
    (2) tetrahydropyranyl,
    (3) tetrahydrothiopyranyl, wherein the sulfur atom is oxidized,
    (4) piperidinyl, wherein the nitrogen group is optionally substituted with alkanoyl or —$SO_p$-alkyl,
    (5) dioxanyl, wherein the dioxanyl can be optionally substituted with alkyl, and
    (6) dihydrobenzodioxepinyl.

13. A compound according to claim 12 selected from the group consisting of
    hydroxy{8-[({4-[4-(trifluoromethoxy)phenoxy]phenyl}sulfonyl)methyl]-1,4-dioxaspiro[4.5]dec-8-yl}formamide;
    hydroxy{1-[({4-[4-(trifluoromethoxy)phenoxy]phenyl}sulfonyl)methyl]cyclopentyl}formamide;
    1,1-dioxido-4-[({4-[4-(trifluoromethoxy)phenoxy]phenyl}sulfonyl)methyl]tetrahydro-2H-thiopyran-4-yl(hydroxy)formamide;
    hydroxy(4-(((4-(4-(trifluoromethoxy)phenoxy)phenyl)sulfonyl)methyl)tetrahydro-2H-pyran-4-yl)formamide;
    1-acetyl-4-(((4-(4-(trifluoromethoxy)phenoxy)phenyl)sulfonyl)methyl)-4-piperidinyl(hydroxy)formamide;
    hydroxy(1-methylsulfonyl)-4-(((4-(4-(trifluoromethoxy)phenoxy)phenyl)sulfonyl)methyl)-4-piperidinyl)formamide;
    2,2-dimethyl-5-(((4-(4-(trifluoromethoxy)phenoxy)phenyl)sulfonyl)methyl)-1,3-dioxan-5-yl(hydroxy)formamide;

hydroxy(3-(((4-(4-(trifluoromethoxy)phenoxy)phenyl)
  suffonyl)methyl)-3,4-dihydro-2H-1,5-benzodioxepin-
  3-yl)formamide;
ethyl 4-(formyl(hydroxy)amino)-4-(((4-(4-
  (trifluoromethoxy)phenoxy)phenyl)sulfonyl)methyl)
  cyclohexanecarboxylate;
4-(formyl(hydroxy)amino)-4-(((4-(4-(trifluoromethoxy)
  phenoxy)phenyl)sulfonyl)methyl)
  cyclohexanecarboxylic acid;
4-cyano-4'-(((4-(formyl(hydroxy)amino)tetrahydro-2H-
  pyran-4-yl)methyl)sulfonyl)-1,1'-biphenyl;
hydroxy(4-(((4'-(trifluoromethyl)(1,1'-biphenyl)-4-yl)
  sulfonyl)methyl)tetrahydro-2H-pyran-4-yl)formamide;
  and
3-(cyanomethyl)-4'-(((4-(formyl(hydroxy)amino)
  tetrahydro-2H-pyran-4-yl)methyl)sulfonyl)-1,1'-
  biphenyl.

14. A compound selected form the group consisting of
3-(cyanomethyl)-4'-({3-(4,4-dimethyl-2,5-dioxo-1-
  imidazolidinyl)-2-[formyl(hydroxy)amino]
  propyl}sulfonyl)-1,1'-biphenyl;
hydroxy{3-(4-morpholinyl)-1-[({4-[4-(trifluoromethoxy)
  phenoxy]phenyl}sulfonyl)methyl]propyl}formamide;
4-({3-(4,4-dimethyl-2,5-dioxo-1-imidazolidinyl)-2-
  [formyl(hydroxy)amino]propyl}sulfonyl)-4'-fluoro-1,
  1-biphenyl;
4-({3-(4,4-dimethyl-2,5-dioxo-1-imidazolidinyl)-2-
  [formyl(hydroxy)amino]propyl}sulfonyl)-4'-
  (methylsulfanyl)-1,1-biphenyl;
4-({3-(4,4-dimethyl-2,5-dioxo-1-imidazolidinyl)-2-
  [formyl(hydroxy)amino]propyl}sulfonyl)-4'-
  (methoxy)-1,1-biphenyl;
4-fluoro-4'-({2-[formyl(hydroxy)amino]-4-
  hydroxybutyl}sulfonyl-1,1'-biphenyl;
4-chloro-4'-({2-[fozmyl(hydroxy)amino]-4-
  hydroxybutyl}sulfonyl-1,1'-biphenyl;
4-fluoro-4'-({2-[formyl(hydroxy)amino]-4-
  hydroxypentyl}sulfonyl-1,1'-biphenyl;
4-chloro-4'-({2-[formyl(hydroxy)amino]-4-
  hydroxypentyl}sulfonyl-1,1'-biphenyl;
4-chloro-4'-({3-(4,4-dimethyl-2,6-dioxo-1-piperididnyl)-
  2-[formyl(hydroxy)amino]propyl}sulfonyl)-1,1-
  biphenyl;
ethyl 5-({3-[4'-fluoro[1,1'-biphenyl]-4-yl)sulfonyl]-2-
  [formyl(hydroxy)amino]propyl}amino)-3,3-dimethyl-
  5-oxopentanoate;
4-({3-(4,4-dimethyl-2,6-dioxo-1-piperidinyl)-2-[formyl
  (hydroxy)amino]propyl}sulfonyl)-4'-fluoro-1,1'-
  biphenyl;
hydroxy[3-(4-morpholinyl)-1-({[4'-(trifluoromethyl)[1,
  1'-biphenyl]-4-yl]sulfonyl}methyl)propyl]formamide;
4-chloro-4'-([2-[formyl(hydroxy)amino]-4-(4-
  morpholinyl)butyl]sulfonyl}-1,1'-biphenyl;
4-chloro-4'-{[2-[formyl(hydroxy)amino]-4-(1-
  piperidinyl)butyl]sulfonyl}-1,1'-biphenyl;
hydroxy{3-(1-piperidinyl)-1-[({4-[4-(trifluoromethoxy)
  phenoxy]phenyl}sulfonyl)methyl]propyl}formamide;
4-chloro-4'-{[2-[formyl(hydroxy)amino]-3-(1-
  piperidinyl)propyl]sulfonyl}-1,1'-biphenyl;
hydroxy{2-(1-piperidinyl)-1-[({4-[4-(trifluoromethoxy)
  phenoxy]phenyl}sulfonyl)methyl]ethyl}formamide;
3-(4-acetyl-1-piperazinyl)-1-[({4-[4-(trifluoromethoxy)
  phenoxy]phenyl}sulfonyl)methyl]propyl(hydroxy)
  formamide;
hydroxy{3-(4-thiomorpholinyl)-1-[({4-[4-
  (trifluoromethoxy)phenoxy]phenyl}sulfonyl)methyl]
  propyl}formamide;
hydroxy{3-(4-methyl-1-piperazinyl)-1-[({4-[4-
  (trifluoromethoxy)phenoxy]phenyl}sulfonyl)methyl]
  propyl}formamide;
hydroxy{2-tetrahydro-2H-pyran-4-yl-1-[({4-[4-
  (trifluoromethoxy)phenoxy]phenyl}sulfonyl)methyl]
  ethyl}formamide;
hydroxy[(1R)-1-(2R)-1-(methylsulfonyl)pyrrolidinyl]-2-
  ({4-[4-(trifluoromethoxy)phenoxy]phenyl}sulfonyl)
  ethyl]formarnmide;
hydroxy[(1S)-1-[(2R)-1-(methylsulfonyl)pyrrolidinyl]-2-
  ({4-[4-(trifluoromethoxy)phenoxy]phenyl}sulfonyl)
  ethyl]formamide;
2-(1,1-dioxidotetrahydro-2H-thiopyran-4-yl)-1-[({4-[4-
  (trifluoromethoxy)phenoxy]phenyl}sulfonyl)methyl]
  ethyl(hydroxy)formamide;
hydroxy{2-[4-(methylsulfonyl)-1-piperazinyl]-1-[({4-[4-
  (trifluoromethoxy)phenoxy]phenyl}sulfonyl)methyl]
  ethyl}formamide;
hydroxy{3-[4-(methylsulfonyl)-1-piperazinyl]-1-[({4-[4-
  (trifluoromethoxy)phenoxy]phenyl}sulfonyl)methyl]
  propyl}formamide;
2-[4-(2,2-dimethylpropanoyl)-1-piperazinyl]-1-[({4-[4-
  (trifluoromethoxy)phenoxy]phenyl}sulfonyl)methyl]
  ethyl(hydroxy)formamide;
2,2-dimethyl-1-[({4-[4-(trifluoromethoxy)phenoxy]
  phenyl}sulfonyl)methyl]propyl(hydroxy)formamide;
1-cyclopropyl-2-({4-[4-(trifluoromethoxy)phenoxy]
  phenyl}sulfonyl)ethyl(hydroxy)formamide;
2-(1,4-dioxaspiro[4.5]dec-8-yl)-1-[({4-[4-
  (trifluoromethoxy)phenoxy]phenyl}sulfonyl)methyl]
  ethyl(hydroxy)formamide;
hydroxy[1-[(4S)-2-oxo-1,3-oxazolidin-4-yl]-2-({4-[4-
  (trifluoromethoxy)phenoxy]phenyl}sulfonyl)ethyl]
  formamide;
hydroxy[(1S)-1-[(2R)-tetrahydro-2-furanyl]-2-({4-[4-
  (trifluoromethoxy)phenoxy]phenyl}sulfonyl)ethyl]
  formamide;
hydroxy[(1R)-1-[(2R)-tetrahydro-2-furanyl]-2-({4-[4-
  (trifluoromethoxy)phenoxy]phenyl}sulfonyl)ethyl]
  formamide;
hydroxy[1-[(4S)-3-methyl-2-oxo-1,3-oxazolidin-4-yl]-2-
  ({4-[4-(trifluoromethoxy)phenoxy]phenyl}sulfonyl)
  ethyl]formamide;
hydroxy[1-[(2R)-5-oxotetrahydro-2-furanyl]-2-({4-[4-
  (trifluoromethoxy)phenoxy]phenyl}sulfonyl)ethyl]
  formamide;
hydroxy[1-[1-(methylsulfonyl)-4-piperidinyl]-2-({4-[4-
  (trifluoromethoxy)phenoxy]phenyl}sulfonyl)ethyl]
  formamide;
hydroxy[1-(1-isobutyryl4-piperidinyl)-2-({4-[4-
  (trifluoromethoxy)phenoxy]phenyl}sulfonyl)ethyl]
  formamide;
hydroxy{2-(4-morpholinylsulfonyl)-1-[({4-[4-
  (trifluoromethoxy)phenoxy]phenyl}sulfonyl)methyl]
  ethyl}formamide;
hydroxy{2-methyl-2-(4-morpholinylsulfonyl)-1-[({4-[4-
  (trifluoromethoxy)phenoxy]phenyl}sulfonyl)methyl]
  propyl}formamide;
hydroxy{8-[({4-[4-(trifluoromethoxy)phenoxy]
  phenyl}sulfonyl)methyl]-1,4-dioxaspiro[4.5]dec-8-
  yl}formamide;

1,1-dimethyl-2-({4-[4-(trifluoromethoxy)phenoxy]phenyl}sulfonyl)ethyl(hydroxy)formamide;

hydroxy{2-(2-thienyl)-1-[({4-[4-(trifluoromethoxy)phenoxy]phenyl}sulfonyl)methyl]ethyl}formamide;

(1S)-1-[(4S)-2,2-dimethyl-1,3-dioxolan-4-yl]-2-{[4-(4-methoxyphenoxy)phenyl]sulfonyl}ethyl(hydroxy)formamide;

1,2,3-trideoxy-2-[formyl(hydroxy)amino]-4,5-O-(1-methylethylidene)-1-({4-[4-(trifluoromethoxy)phenoxy]phenyl}sulfonyl)-D-threo-pentitol;

(1S)-2-{[4-(4-chlorophenoxy)phenyl]sulfonyl}-1-[(4S)-2,2-dimethyl-1,3-yl]ethyl(hydroxy)formamide;

2-[formyl(hydroxy)amino]-N,N-dimethyl-3-({4-[4-(trifluoromethoxy)phenoxy]phenyl}sulfonyl)propanamide;

hydroxy{2-(4-morpholinyl)-2-oxo-1-[({4-[4-(trifluoromethoxy)phenoxy]phenyl}sulfonyl)methyl]ethyl}formamide;

N-[2-[formyl(hydroxy)amino]-3-({4-[4-(trifluoromethoxy)phenoxy]phenyl}sulfonyl)propyl]-N-methylmethanesulfonamide;

(1S)-1-[(4S)-2,2-dimethyl-1,3-dioxolan-4-yl]-2-({4-[4-(trifluoromethyl)phenoxy]phenyl}sulfonyl)ethyl(hydroxy)formamide;

(1S)-1-[(4S)-2,2-dimethyl-1,3-dioxolan-4-yl]-2-({4-[4-(methylphenoxy)phenyl]sulfonyl)ethyl(hydroxy)formamide;

4-({(2S)-2-[(4S)-2,2-dimethyl-1,3-dioxolan-4-yl]-2-[formyl(hydroxy)amino]ethyl}sulfonyl)-4'-(trifluoromethyl)-1,1'-biphenyl;

methyl 4-[3-[formyl(hydroxy)amino]-4-({4-[4-(trifluoromethoxy)phenoxy]phenyl}sulfonyl)butyl]benzoate;

4-[3-[formyl(hydroxy)amino]-4-({4-[4-(trifluoromethoxy)phenoxy]phenyl}sulfonyl)butyl]benzoic acid;

hydroxy{3-[4-(hydroxymethyl)phenyl]-1-[({4-[4-(trifluoromethoxy)phenoxy]phenyl}sulfonyl)methyl]propyl}formamide;

2-{[4-(4-chlorophenoxy)phenyl]sulfonyl}-1-{[(4-chlorophenyl)sulfonyl]methyl}ethyl(hydroxy)formamide;

hydroxy{(1S)-4-hydroxy-1-[({4-[4-(trifluoromethoxy)phenoxy]phenyl}sulfonyl)methyl]butyl}formamide;

hydroxy{(1R)-2-({4-[4-(trifluoromethoxy)phenoxy]phenyl}sulfonyl)-1-[(4S)-3,5,5-trimethyl-2-oxo-1,3-thiazolidin-4-yl]ethyl}formamide;

hydroxy{1-[({4-[4-(trifluoromethoxy)phenoxy]phenyl}sulfonyl)methyl]cyclopentyl}formamide;

(1R)-1-[(4S)-5,5-dimethyl-2-oxo-1,3-thiazolidin-4-yl]-2-({4-[4-(trifluoromethoxy)phenoxy]phenyl}sulfonyl)ethyl(hydroxy)formamide;

1,1-dioxido-4-[({4-[4-(trifluoromethoxy)phenoxy]phenyl}sulfonyl)methyl]tetrahydro-2H-thiopyran-4-yl(hydroxy)formamide;

(1S)-2-((4-(4-chlorophenoxy)phenyl)sulfonyl)-1-((4,4-dimethyl-2,5-dioxo-1-imidazolidinyl)methyl)ethyl(hydroxy)formamide;

(1S)-2-(4,4-dimethyl-2,5-dioxo-1-imidazolidinyl)-1-(((4'-(trifluoromethyl)(1,1'-biphenyl)-4-yl)sulfonyl)methyl)ethyl(hydroxy)formamide;

hydroxy(4-(((4-(4-(trifluoromethoxy)phenoxy)phenyl)sulfonyl)methyl)tetrahydro-2H-pyran-4-yl)formamide;

(1S)-2-(2,5-dioxo-1-imidazolidinyl)-1-(((4-(4-(trifluoromethoxy)phenoxy)phenyl)sulfonyl)methyl)ethyl(hydroxy)formamide;

1-acetyl-4-(((4-(4-(trifluoromethoxy)phenoxy)phenyl)sulfonyl)methyl)-4-piperidinyl(hydroxy)formamide;

hydroxy(1-(methylsulfonyl)-4-(((4-(4-(trifluoromethoxy)phenoxy)phenyl)sulfonyl)methyl)-4-piperidinyl)formamide;

2,2-dimethyl-5-(((4-(4-(trifluoromethoxy)phenoxy)phenyl)sulfonyl)methyl)-1,3-dioxan-5-yl(hydroxy)formamide;

(1S)-1-((4S)-1,3-dioxolan-4-yl)-2-((4-(4-(trifluoromethoxy)phenoxy)phenyl)sulfonyl)ethyl(hydroxy)formamide;

4-(((2S)-2-((4S)-2,2-dimethyl-1,3-dioxolan-4-yl)-2-(formyl(hydroxy)amino)ethyl)sulfonyl)-4'-(2-methoxyethoxy)-1,1'-biphenyl;

(1S)-1-((4S)-2,2-dimethyl-1,3-dioxolan-4-yl)-2-((4-(2-methoxyethoxy)phenoxy)phenyl)sulfonyl)ethyl(hydroxy)formamide;

hydroxy(4-(4-morpholinyl)-4-oxo-1-(((4-(4-(trifluoromethoxy)phenoxy)phenyl)sulfonyl)methyl)butyl)formamide;

1,2,4-trideoxy-2-(formyl(hydroxy)amino)-4,4-dimethyl-3,5-O-(1-methylethylidene)-1-((4-(4-(trifluoromethoxy)phenoxy)phenyl)sufonyl)-D-threo-pentitol;

hydroxy((2R)-2-phenyl-1-(((4-(4-(trifluoromethoxy)phenoxy)phenyl)sulfonyl)methyl)propyl)formamide;

2-(2-((tert-butyl(dimethyl)silyl)oxy)ethoxy)-1-(((4-(4-(trifluoromethoxy)phenoxy)phenyl)sulfonyl)methyl)ethyl(hydroxy)formamide;

hydroxy(2-(2-hydroxyethoxy)-1-(((4-(4-(trifluoromethoxy)phenoxy)phenyl)sulfonyl)methyl)ethyl)formamide;

(1S)-2-(4,4-dimethyl-2,5-dioxo-1-imidazolidinyl)-1-(((4'-methoxy(1,1'-biphenyl)-4-yl)oxy)methyl)ethyl(hydroxy)formamide;

(1S)-2-(4,4-dimethyl-2,5-dioxo-1-imidazolidinyl)-1-(((4'-methyl(1,1'-biphenyl)-4-yl)oxy)methyl)ethyl(hydroxy)formamide;

4-(((2S)-2-(formyl(hydroxy)amino)-3-(3,4,4-trimethyl-2,5-dioxo-1-imidazolidinyl)propyl)oxy)-4'-(trifluoromethoxy)-1,1'-biphenyl;

hydroxy((1S,2S)-2-(4-isobutylphenyl)-1-(((4-(4-(trifluoromethoxy)phenoxy)phenyl)sulfonyl)methyl)propyl)formamide;

hydroxy(3-hydroxy-2,2-dimethyl-1-(((4-(4-(trifluoromethoxy)phenoxy)phenyl)sulfonyl)methyl)propyl)formamide;

1,2,3-trideoxy-2-(formyl(hydroxy)amino)-4,5-O-(1-methylethylidene)-1-((4-(4-(trifluoromethoxy)phenoxy)phenyl)sulfonyl)-D-erythro-pentitol;

hydroxy(3-(((4-(4-(trifluoromethoxy)phenoxy)phenyl)sulfonyl)methyl)-3,4-dihydro-2H-1,5-benzodioxepin-3-yl)formamide;

ethyl 4-(formyl(hydroxy)amino)-4-(((4-(4-(trifluoromethoxy)phenoxy)phenyl)sulfonyl)methyl)cyclohexanecarboxylate;

4-(formyl(hydroxy)amino)-4-(((4-(4-(trifluoromethoxy)phenoxy)phenyl)sulfonyl)methyl)cyclohexanecarboxylic acid;

hydroxy(4-hydroxy-1-methyl-1-(((4-(4-(trifluoromethoxy)phenoxy)phenyl)sulfonyl)methyl)butyl)formamide;

4-cyano-4'-(((4-(forxyl(hydroxy)amino)tetrahydro-2H-pyran-4-yl)methyl)sulfonyl)-1,1'-biphenyl;

hydroxy(4-(((4'-(trifluoromethyl)(1,1'-biphenyl)-4-yl)sulfonyl)methyl)tetrahydro-2H-pyran-4-yl)formamide;

(1R)-1-((4S)-5,5-dimethyl-2-oxo-1,3-thiazolidin-4-yl)-2-((4-(4-(trifluoromethoxy)phenoxy)phenyl)sulfonyl)ethyl(hydroxy)formamide;

hydroxy(2-(1-piperidinylsulfonyl)-1-(((4-(4-(trifluoromethoxy)phenoxy)phenyl)sulfonyl)methyl)ethyl)formamide;

hydroxy(2-(1-pyrrolidinylsulfonyl)-1-(((4-(4-(trifluromethoxy)phenoxy)phenyl)sulfonyl)methyl)ethyl)formamide;

4-((3-(1,4-dioxaspiro[4.5]dec-8-yl)-2-formyl(hydroxy)amino)propyl)sulfonyl)-4'-fluoro-1,1'-biphenyl;

2-(formyl(hydroxy)amino)-N,N-dimethyl-3-((4-(4-(trifluoromethoxy)phenoxy)phenyl)sulfonyl)-1-propanesulfonamide;

2-(1,4-dioxa-8-azaspiro[4.5]dec-8-ylsulfonyl)-1-(((4-(4-(trifluoromethoxy)phenoxy)phenyl)sulfonyl)methyl)ethyl(hydroxy)formamide;

1-(1,4dioxaspiro[4.5]dec-8-yl)-2-((4-(4-(trifluoromethoxy)phenoxy)phenyl)sulfonyl)ethyl(hydroxy)formamide;

3-(cyanomethyl)-4'-(((4formyl(hydroxy)amino)tetrahydro-2H-pyran-4-yl)methyl)sulfonyl)-1,1'-biphenyl;

2-(formyl(hydroxy)amino)-N-(4-(hydroxymethyl)phenyl)-N-methyl-3-((4-(4-(trifluoromethoxy)phenoxy)phenyl)sulfonyl)-1-propanesulfonamide;

N,N-diethyl-2-(formyl(hydroxy)amino)-3-((4-(4-(trifluoromethoxy)phenoxy)phenyl)sulfonyl)-1-propanesulfonamide;

methyl (3-(2-(formyl(hydroxy)amino)-3-((4-(4-(trifluoromethoxy)phenoxy)phenyl)sulfonyl)propyl)phenyl)acetate;

(3-(2-(formyl(hydroxy)amino)-3-((4-(4-(trifluoromethoxy)phenoxy)phenyl)sulfonyl)propyl)phenyl)acetic acid; and 1,2-dideoxy-2-(formyl(hydroxy)amino)-3,4-O-(1-methylethylidene)-1-((4-(4-(trifluoromethoxy)phenoxy)phenyl)sulfonyl)-L-threo-pentitol.

15. A compound which is hydroxy[(1S)-1-[(2R)-tetrahydro-2-furanyl]-2-({4-[4-(trifluoromethoxy)phenoxy]phenyl}sulfonyl)ethyl]formamide.

16. A method for inhibiting matrix metalloproteinases in a mammal in need of such treatment, comprising administering to the mammal a therapeutically effective amount of a compound of claim 1.

17. A compound according to claim 1, wherein $R_1$ is hydrogen; X —$SO_2$—; Y is —O—; and $Ar_2$ is aryl substituted by perfluoroalkoxy.

* * * * *

UNITED STATES PATENT AND TRADEMARK OFFICE
CERTIFICATE OF CORRECTION

PATENT NO.   : 6,294,573 B1
DATED        : September 25, 2001
INVENTOR(S)  : Michael L. Curtin et al.

It is certified that error appears in the above-identified patent and that said Letters Patent is hereby corrected as shown below:

Column 157,
Line 58, replace "heterogycle" with -- heterocycle --.

Column 158,
Line 21, replace "(c) piperidinyi" with -- (c) piperidinyl --.

Column 161,
Line 58, replace "substituted with hydroxmalkyl" with -- substituted with hydroxyalkyl --.

Column 163,
Line 30, replace "formanide;" with -- formamide; --.

Column 164,
Line 4, replace "-4-yi)" with -- -4-yl) --.
Line 7, replace "(1- piperidinyisulfony1)" with -- (1-piperidinylsulfonyl). --.

Column 165,
Line 51, replace "(trifluoromethoxyy)" with -- (trifluoromethoxy) --.

Column 167,
Line 37, replace " fozmyl" with -- formyl --.
Line 54, replace "4-chloro-4'-({2-" with -- 4-chloro-4'-{[2- --.

Column 168,
Line 12, replace "formarnmide" with -- formamide --.
Line 56, replace "(1-isobutyrl4-" with -- (1-isobutyr-4-yl- --.

UNITED STATES PATENT AND TRADEMARK OFFICE
CERTIFICATE OF CORRECTION

PATENT NO. : 6,294,573 B1
DATED : September 25, 2001
INVENTOR(S) : Michael L. Curtin et al.

It is certified that error appears in the above-identified patent and that said Letters Patent is hereby corrected as shown below:

Column 169,
Line 12, replace "1,3-yl (ethy(hydroxy)formamide;" with -- 1,3-dioxolan-4-yl)ethyl (hydroxy)formamide; --.

Column 171,
Line 26, replace "(((4formyl" with -- (((4-(formyl --.

Signed and Sealed this

Eleventh Day of June, 2002

Attest:

JAMES E. ROGAN
Attesting Officer    Director of the United States Patent and Trademark Office